US012612387B2

(12) United States Patent

Belfield et al.

(10) Patent No.: US 12,612,387 B2

(45) Date of Patent: Apr. 28, 2026

(54) RAS INHIBITORS AND METHODS OF USING THE SAME

(71) Applicant: Jazz Pharmaceuticals Ireland Limited, Dublin (IE)

(72) Inventors: Andrew Belfield, Macclesfield (GB); Nicolas Emmanuel Stephane Guisot, Macclesfield (GB); Clifford David Jones, Macclesfield (GB); Chiara Colletto, Macclesfield (GB)

(73) Assignee: Jazz Pharmaceuticals Ireland Limited, Dublin (IE)

( * ) Notice: Subject to any disclaimer, the term of this patent is extended or adjusted under 35 U.S.C. 154(b) by 579 days.

(21) Appl. No.: 17/796,388

(22) PCT Filed: Jan. 29, 2021

(86) PCT No.: PCT/EP2021/052211

§ 371 (c)(1),
(2) Date: Jul. 29, 2022

(87) PCT Pub. No.: WO2021/152149

PCT Pub. Date: Aug. 5, 2021

(65) Prior Publication Data

US 2023/0339910 A1 Oct. 26, 2023

(30) Foreign Application Priority Data

Jan. 31, 2020 (GB) ...................................... 2001344

(51) Int. Cl.

| | |
|---|---|
| ***C07D 403/12*** | (2006.01) |
| ***C07D 239/42*** | (2006.01) |
| ***C07D 239/47*** | (2006.01) |
| ***C07D 239/48*** | (2006.01) |
| ***C07D 401/04*** | (2006.01) |
| ***C07D 401/14*** | (2006.01) |
| ***C07D 403/04*** | (2006.01) |
| ***C07D 403/14*** | (2006.01) |
| ***C07D 413/14*** | (2006.01) |
| ***C07D 487/08*** | (2006.01) |

(52) U.S. Cl.

CPC ......... *C07D 403/12* (2013.01); *C07D 239/42* (2013.01); *C07D 239/47* (2013.01); *C07D 239/48* (2013.01); *C07D 401/04* (2013.01); *C07D 401/14* (2013.01); *C07D 403/04* (2013.01); *C07D 403/14* (2013.01); *C07D 413/14* (2013.01); *C07D 487/08* (2013.01)

(58) Field of Classification Search

None

See application file for complete search history.

(56) References Cited

U.S. PATENT DOCUMENTS

2019/0248767 A1 8/2019 Planken et al.

FOREIGN PATENT DOCUMENTS

| | | | | |
|---|---|---|---|---|
| WO | WO-2015054572 A1 | 4/2015 | | |
| WO | WO-2016164675 A1 | 10/2016 | | |
| WO | WO-2016168540 A1 | 10/2016 | | |
| WO | WO-2017015562 A1 | 1/2017 | | |
| WO | WO-2017100546 A1 | 6/2017 | | |
| WO | WO-2017201161 A1 | * | 11/2017 | ........... A61K 31/519 |
| WO | WO-2018064510 A1 | 4/2018 | | |
| WO | WO-2018119183 A2 | 6/2018 | | |
| WO | WO-2018143315 A1 | 8/2018 | | |
| WO | WO-2018206539 A1 | 11/2018 | | |
| WO | WO-2018217651 A1 | 11/2018 | | |
| WO | WO-2018218069 A1 | 11/2018 | | |
| WO | WO-2018218070 A2 | 11/2018 | | |
| WO | WO-2018218071 A1 | 11/2018 | | |
| WO | WO-2019051291 A1 | 3/2019 | | |
| WO | WO-2019099524 A1 | 5/2019 | | |
| WO | WO-2019110751 A1 | 6/2019 | | |
| WO | WO-2020239123 A1 | 12/2020 | | |

OTHER PUBLICATIONS

Simanshu et al. "RAS Proteins and Their Regulators in Human Disease" Cell, 2017, 170, 1, 17â33. DOI: 10.1016/j.cell.2017.06.009. (Year: 2017).*

International Search Report and Written Opinion of the International Searching Authority for International Application No. PCT/EP2021/052211 dated Apr. 15, 2021, 8 pages.

* cited by examiner

*Primary Examiner* — Kortney L. Klinkel
*Assistant Examiner* — Sophia Reilly
(74) *Attorney, Agent, or Firm* — COOLEY LLP

(57) ABSTRACT

Provided herein are compounds identified as inhibitors of KRAS protein activity that can be used to treat various diseases and disorders, such as cancer.

18 Claims, No Drawings

RAS INHIBITORS AND METHODS OF USING THE SAME

CROSS REFERENCE TO RELATED APPLICATIONS

This application is a U.S. National Stage Application under 35 U.S.C. § 371 of International Application No. PCT/EP2021/052211, filed Jan. 29, 2021, which claims the benefit of and priority to GB Application No. 2001344.7, filed Jan. 31, 2020, which are herein incorporated by reference in their entireties.

FIELD OF INVENTION

The present disclosure relates to compounds and their methods of use. In particular, the disclosed compounds may be useful for inhibiting RAS proteins. More specifically, this disclosure relates to compounds for inhibiting $KRAS^{G12C}$ proteins. The compounds of the disclosure may therefore be used in treating conditions mediated by RAS proteins. For example, the compounds may be used in treating cancer.

BACKGROUND OF THE DISCLOSURE

RAS is the most commonly mutated oncogene in cancer (~30%), with KRAS the most commonly mutated isoform accounting for ~85% of RAS mutations. RAS proteins are a group of closely related monomeric globular proteins comprising 189 amino acids. These proteins are associated with the plasma membrane.

RAS proteins are small GTPases, known as G-proteins, that bind guanine nucleotides and hydrolyse GTP to GDP. They function as molecular switches, being 'on' when bound to GTP and 'off' when bound to GDP. When bound to GTP, the RAS protein can interact with other proteins. In order for the RAS proteins to be switched 'off' i.e. to hydrolyze GPT back to GDP, extrinsic proteins are required. These extrinsic proteins are called GTPase-activating proteins (GAPs) and increase the rate of conversion of GTP to GDP. In response to signals from receptor tyrosine kinases, guanine nucleotide exchange factors (GEFs) such as SOS1 and SOS2 facilitate nucleotide exchange converting RAS from GDP- to GTP-bound state. When GTP-bound, the intrinsic GTPase activity of RAS is stimulated by (GAPs) such as NF1, catalysing the conversion of RAS from GTP- to GDP-bound state. Thus, the intrinsic GTPase activity allows RAS to auto-inactivate downstream signalling. Mutations in RAS that reduce its intrinsic GTPase activity result in an accumulation of GTP-bound RAS leading to upregulation of effector pathways, causing increased cell proliferation. The most common oncogenic KRAS mutations are at amino acid position G12, G13 and Q61, with KRAS G12C being the most common activating mutation in lung cancer. KRAS mutations are also found in multiple other cancers including cervical cancer, multiple myeloma, stomach cancer, bladder cancer and uterine cancer. The role of $KRAS^{G12C}$ in multiple tumour types makes it a particularly attractive target for developing small molecule inhibitors against.

For these reasons, there have been a number of recent patent applications concerned with compounds which are capable of modulating G12C mutant KRAS. For example, see WO 2018/218069, WO 2018/218070, WO 2018/218071, WO 2017/100546, WO 2018/064510, WO 2016/168540, WO 2017/015562, WO 2016/164675, WO 2015/054572, WO 2019/099524, WO 2017/201161, WO 2018/119183, WO 2019/051291, WO 2018/217651, WO 2019/110751, WO 2018/206539, US20190248767, and WO 2018/143315.

There is a need in the art to provide alternative or improved compounds for inhibiting RAS proteins, specifically alternative or improved compounds for inhibiting KRAS proteins.

SUMMARY OF THE DISCLOSURE

Accordingly, in various aspects, the present disclosure provides a compound of formula (I), a pharmaceutically acceptable salt thereof, or a stereoisomer thereof:

(I)

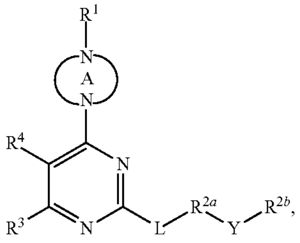

wherein:

ring A is a 4-12 membered heterocyclic ring, optionally substituted with one or more substituents selected from the group consisting of halo, hydroxyl, cyano, oxo, $C_{1-4}$-alkyl, $C_{2-4}$-alkynyl, $C_{1-4}$-heteroalkyl, $C_{3-8}$-cycloalkyl, —$C_{0-4}$-alkyl-C(O)N($R^{6d}$)$_2$, and —$C_{0-4}$-alkyl-C(O)O$R^{6d}$;

and/or wherein two substituents on the same atom of ring A may form a 3- to 5-membered ring together with the carbon atom on which they are attached;

and/or wherein two substituents on adjacent atoms of ring A may form a 3- to 6-membered ring together with the carbon atoms on which they are attached;

wherein the $C_{1-4}$-alkyl, $C_{2-4}$-alkynyl, $C_{1-4}$-heteroalkyl, and $C_{3-8}$-cycloalkyl are optionally substituted with one or more substituents selected from the group consisting of halo, hydroxy, —O$R^{6d}$, cyano and oxo;

$R^1$ is selected from the group consisting of

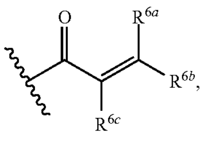

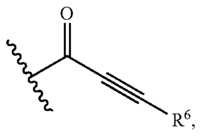

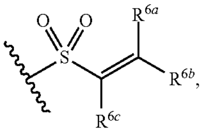

and

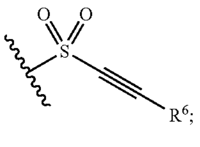

L is selected from the group consisting of a direct bond, —N($R^{6d}$)—, —C(O)N($R^{6d}$)—, —S($O_2$)N($R^{6d}$), and —O—;

$R^{2a}$ is a direct bond, $C_{1-4}$-alkylene, $C_{1-4}$-heteroalkyl, $C_{3-8}$-cycloalkylene, 3- to 8-membered heterocycloalkylene, 6- to 10-membered aryl, or 5- to 10-membered heteroaryl, each of which is optionally substituted with one or more substituents selected from the group consisting of halo, hydroxyl, carboxyl, —$OR^{6d}$, oxo, cyano, $C_{3-8}$-cycloalkyl, $C_{1-4}$-alkyl, $C_{1-4}$-heteroalkyl, 3- to 8-membered heterocycloalkyl;

Y is a direct bond, $C_{1-4}$-alkyl, $C_{1-4}$ alkylene, $C_{1-4}$-heteroalkyl, —$N(R^{6d})$—, —$NR^{6d}C(O)$—, —$C(O)NR^{6d}$, —$NR^{6d}C(O)NR^{6d}$—, —$S(O_2)NR^{6d}$—, or —$NR^{6d}S(O)_2$—;

$R^{2b}$ is H, $C_{1-4}$-alkyl, $C_{1-4}$-heteroalkyl, $C_{3-8}$-cycloalkyl, 3- to 8-membered heterocycloalkyl, 6- to 10-membered aryl, or 5- to 10-membered heteroaryl, each of which is optionally substituted with one or more substituents selected from halo, hydroxyl, carboxyl, —$OR^{6d}$, oxo, cyano, —$N(R^{6d})_2$, $C_{3-8}$-cycloalkyl, $C_{1-4}$-alkyl, $C_{1-4}$-heteroalkyl, and 3- to 8-membered heterocycloalkyl;

$R^3$ is

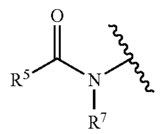

or

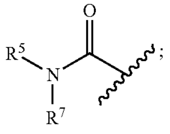

;

$R^4$ is H, $C_{1-6}$-alkyl, $C_{1-6}$-heteroalkyl, $C_{1-6}$-haloalkyl, $C_{3-8}$-cycloalkyl, 3- to 8-membered heterocycloalkyl, —$OC_{1-6}$-haloalkyl, —$NH(C_{1-6}$-alkyl) or —$N(C_{1-6}$-alkyl$)_2$; each of which is optionally substituted with one or more substituents selected from the group consisting of $C_{1-4}$-alkyl, $C_{1-4}$-heteroalkyl, halo, cyano, hydroxyl, ether, —$N(R^{6d})_2$, $C_{3-8}$-cycloalkyl, 3- to 8-membered heterocycloalkyl.

$R^5$ is H, $C_{1-6}$-alkyl, $C_{1-6}$-heteroalkyl, $C_{3-8}$-cycloalkyl, 3- to 8-membered heterocycloalkyl, 6- to 10-membered aryl, or 5-to-10 membered heteroaryl, each of which is optionally substituted with one or more substituents selected from the group consisting of halo, hydroxyl, carboxyl, cyano, —$OR^{6d}$, —$N(R^{6d})_2$, $C_{3-8}$-cycloalkyl, $C_{1-4}$-alkyl, $C_{1-4}$-heteroalkyl, 3- to 8-membered heterocycloalkyl, 6-membered aryl, and 5- to 6-membered heteroaryl, or an $R^5$ and $R^7$ taken together with the atom to which they are both attached form a 5- or 6-membered monocyclic ring system or a bicyclic system, wherein the bicyclic system is a 9- or 10-membered heterocyclic ring system;

$R^6$, $R^{6a}$ and $R^{6b}$ are each independently H, halo, cyano, $C_{1-6}$-alkyl, $C_{1-6}$-heteroalkyl, $C_{3-8}$-cycloalkyl, 3- to 8-membered heterocycloalkyl, $C_{3-8}$-aryl, or $C_{3-8}$-heteroaryl, each of which is optionally substituted with one or more substituents selected from the group consisting of halo, hydroxy, cyano, —$N(R^{6d})_2$, —$OR^{6d}$, $C_{1-4}$-alkyl, 3- to 8-membered heterocycloalkyl and $C_{1-4}$-heteroalkyl;

$R^{6c}$ is H, halo, cyano, $C_{1-6}$-alkyl, $C_{1-6}$-heteroalkyl, $C_{3-8}$-cycloalkyl, or 3- to 8-membered heterocycloalkyl, each of which is optionally substituted with one or more substituents selected from the group consisting of halo, cyano, —$OR^{6d}$, hydroxy and $C_{1-4}$-heteroalkyl;

$R^{6d}$ is independently at each occurrence selected from H, cyano, $C_{1-6}$-alkyl, $C_{1-6}$-heteroalkyl, $C_{3-8}$-cycloalkyl, and 3- to 8-membered heterocycloalkyl; and $R^7$ is H, $C_{1-6}$-alkyl, $C_{1-6}$-heteroalkyl, or $C_{3-8}$-cycloalkyl, each of which is optionally substituted with one or more substituents selected from halo, cyano, hydroxyl, carboxyl, —$OR^{6d}$, —$N(R^{6d})_2$, $C_{3-8}$-cycloalkyl, $C_{1-4}$-alkyl, $C_{1-4}$-heteroalkyl, and 3- to 8-membered heterocycloalkyl.

In some embodiments, the present disclosure provides a method for treating a condition modulated by RAS proteins in a subject in need thereof, the method comprising, administering to the subject a therapeutically effect amount of a compound disclosed herein (e.g., a compound of formula (I)), or a pharmaceutical composition thereof.

In some embodiments, the condition modulated by RAS proteins is cancer. In some embodiments, the cancer is selected from the group consisting of sarcoma, melanoma, skin cancer, haematological tumors, lymphoma, carcinoma, and leukemia.

In some embodiments, the compound of the present disclosure is an inhibitor of KRAS proteins. In some embodiments, the compounds have comparable activity to existing treatments. In some embodiments, the compounds have improved activity compared to existing treatments. In some embodiments, the compounds have improved solubility compared to known inhibitors of KRAS proteins and existing therapies.

In some embodiments, the present disclosure provides compounds that exhibit reduced cytotoxicity in normal cells relative to prior art compounds and existing therapies.

In some embodiments, the present disclosure provides compounds having a therapeutically effective pharmacokinetic profile and a suitable duration of action following administration. In some embodiments, the metabolised fragment or fragments of the disclosed compound after absorption are classified as Generally Regarded As Safe (GRAS).

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs The term "alkyl" refers to a linear or branched hydrocarbon chain. For example, the term "$C_{1-6}$ alkyl" or "$C_{1-4}$-alkyl" refers to a linear or branched hydrocarbon chain containing 1, 2, 3, 4, 5, or 6 carbon atoms, for example methyl, ethyl, n-propyl, iso-propyl, n-butyl, sec-butyl, tert-butyl, n-pentyl and n-hexyl. Where an alkyl group is indicated as being $C_{0-4}$alkyl, then it should be appreciated that this represents the possibility for the alkyl unit to be absent or 1, 2, 3, or 4 carbon atoms in length. Unless stated otherwise specifically in the specification, the alkyl groups may be optionally substituted by one or more substituents. Non-limiting examples of suitable substituents are described below. In some embodiments, substituents for the alkyl group include halogen, e.g. fluorine, chlorine, bromine and iodine, OH, $C_{1-6}$ alkoxy, and amino.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, and the like. The alkylene chain is attached to the rest of the molecule through a single bond and to a radical group (e.g., those described herein) through a single bond. The points of attachment of the alkylene chain to the rest of the molecule and to the radical group can be through one carbon or any two carbons within the chain. Unless stated otherwise specifically in the specification, an alkylene chain can be optionally substituted.

The term "alkoxy" refers to an alkyl group which is attached to a molecule via oxygen. For example, the term "$C_{1-6}$ alkoxy" refers to an alkyl group which is attached to a molecule via oxygen. This includes moieties where the alkyl part may be linear or branched and may contain 1, 2, 3, 4, 5, or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. Unless stated otherwise specifically in the specification, the alkyl moiety of the alkoxy group may be optionally substituted by one or more substituents. Non-limiting examples of suitable substituents are described below. In some embodiments, substituents for the alkyl group include halogen, e.g. fluorine, chlorine, bromine and iodine, OH, $C_{1-6}$ alkoxy, and amino.

The term "haloalkyl" refers to a hydrocarbon chain substituted with at least one halogen atom independently chosen at each occurrence, for example fluorine, chlorine, bromine and iodine. For example, the term "$C_{1-6}$ haloalkyl" refers to a linear or branched hydrocarbon chain containing 1, 2, 3, 4, 5 or 6 carbon atoms substituted with at least one halogen. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. Unless stated otherwise specifically in the specification, a haloalkyl chain can be optionally substituted.

The term "alkenyl" refers to a branched or linear hydrocarbon chain containing at least one double bond. For example, the term "$C_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl. Unless stated otherwise specifically in the specification, an alkenyl can be optionally substituted.

The term "alkynyl" refers to a branched or linear hydrocarbon chain containing at least one triple bond. For example, the term "$C_{2-6}$ alkynyl" refers to a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl. Unless stated otherwise specifically in the specification, alkynyl can be optionally substituted.

The term "heteroalkyl" refers to a branched or linear hydrocarbon chain containing at least one heteroatom selected from N, O and S positioned between any carbon in the chain or at an end of the chain. For example, the term "$C_{1-6}$ heteroalkyl" refers to a branched or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-6}$ heteroalkyl" may be $C_{1-6}$ N-alkyl, $C_{1-6}$ N,N-alkyl, or $C_{1-6}$ O-alkyl. Unless stated otherwise specifically in the specification, a heteroalkyl can be optionally substituted.

The term "carbocyclic" or "carbocyclic ring" refers to a saturated or unsaturated carbon containing ring system. A "carbocyclic" system may be monocyclic or a fused polycyclic ring system, for example, bicyclic or tricyclic. A "carbocyclic" moiety may contain from 3 to 14 carbon atoms, for example, 3 to 8 carbon atoms in a monocyclic system and 7 to 14 carbon atoms in a polycyclic system. "Carbocyclic" encompasses cycloalkyl moieties, cycloalkenyl moieties, aryl ring systems and fused ring systems including an aromatic portion. Unless stated otherwise specifically in the specification, a carbocyclic ring can be optionally substituted.

The term "heterocyclic" or "heterocyclic ring" refers to a saturated or unsaturated ring system containing at least one heteroatom selected from N, O or S. A "heterocyclic" system may contain 1, 2, 3 or 4 heteroatoms, for example 1 or 2 heteroatoms. A "heterocyclic" system may be monocyclic or a fused polycyclic ring system, for example, bicyclic or tricyclic. A "heterocyclic" moiety may contain from 3 to 14 atoms, for example, 3 to 8 atoms in a monocyclic system and 7 to 14 atoms in a polycyclic system. "Heterocyclic" encompasses heterocycloalkyl moieties, heterocycloalkenyl moieties and heteroaryl moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran. Unless stated otherwise specifically in the specification, a heterocyclic ring can be optionally substituted.

The term "heterocycloalkyl" refers to a saturated hydrocarbon ring system containing carbon atoms and at least one heteroatom within the ring selected from N, O and S. For example, there may be 1, 2 or 3 heteroatoms, optionally 1 or 2 heteroatoms. The "heterocycloalkyl" may be bonded to the rest of the molecule through any carbon atom or heteroatom. The "heterocycloalkyl" may have one or more, e.g. one or two, bonds to the rest of the molecule: these bonds may be through any of the atoms in the ring. For example, the "heterocycloalkyl" may be a "3- to 8-membered heterocycloalkyl". The term "3- to 8-membered heterocycloalkyl" refers to a saturated hydrocarbon ring system containing 3, 4, 5, 6, 7 or 8 atoms, including at least one heteroatom within the ring selected from N, O and S. For example, there may be 1, 2 or 3 heteroatoms, optionally 1 or 2. The "3- to 8-membered heterocycloalkyl" may be bonded to the rest of the molecule through any carbon atom or heteroatom. The "3- to 8-membered heterocycloalkyl" may have one or more, e.g. one or two, bonds to the rest of the molecule: these bonds may be through any of the atoms in the ring. For example, the "3- to 8-membered heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "heterocycloalkenyl" refers to an unsaturated hydrocarbon ring system that is not aromatic, containing carbon atoms and at least one heteroatom within the ring selected from N, O and S. For example, there may be 1, 2 or 3 heteroatoms, optionally 1 or 2 heteroatoms. The "heterocycloalkenyl" may be bonded to the rest of the molecule through any carbon atom or heteroatom. The "heterocycloalkenyl" may have one or more, e.g. one or two, bonds to the rest of the molecule: these bonds may be through any of the atoms in the ring. For example, the "heterocycloalkenyl" may be a "3- to 8-membered heterocycloalkenyl". The term "3- to 8-membered heterocycloalkenyl" refers to a saturated hydrocarbon ring system containing 3, 4, 5, 6, 7 or 8 atoms, wherein at least one of the atoms is a heteroatom within the ring selected from N, O and S. The "heterocycloalkenyl" may be tetrahydropyridine, dihydropyran, dihydrofuran, pyrroline.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl or naphthyl. Unless stated otherwise specifically in the specification, the "aryl" can be optionally substituted.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. For example, the "heteroaryl" may be imidazole, thiene, furane, thianthrene, pyrrole, benzimidazole, pyrazole, pyrazine, pyridine, pyrimidine and indole. Unless stated otherwise specifically in the specification, the "heteroaryl" can be optionally substituted.

The term "halo" or "halide", as used herein, refers to F, Cl, Br and I. In some embodiments, halo refers to fluoride or chloride.

By "acyl" is meant an organic radical derived from, for example, an organic acid by the removal of the hydroxyl group, e.g. A radical having the formula r-c(o)-, where r may be selected from h, $c_{1-6}$ alkyl, $c_{3-8}$ cycloalkyl, phenyl, benzyl or phenethyl group, eg r is h or $c_{1-3}$ alkyl. In one embodiment acyl is alkyl-carbonyl. Examples of acyl groups include, but are not limited to, formyl, acetyl, propionyl and butyryl. A particular acyl group is acetyl.

A bond terminating in a "" represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different. The substituent(s) may be selected from: OH, $NHR^{6d}$, —$N(R^{6d})_2$, amidino, guanidino, hydroxyguanidino, formamidino, isothioureido, ureido, mercapto, C(O)H, acyl, acyloxy, carboxy, sulfo, sulfamoyl, carbamoyl, cyano, azo, nitro, halo, $C_{1-6}$ alkyl, $C_{1-6}$ alkoxy, $C_{1-6}$ haloalkyl, $C_{3-8}$ cycloalkyl, $C_{2-6}$ alkenyl, $C_{2-6}$ alkynyl, aryl, heteroaryl or alkaryl. Where the group to be substituted is an alkyl group the substituent may be ═O. Where the moiety is substituted with two or more substituents and two of the substituents are adjacent the adjacent substituents may form a $C_{4-8}$ ring along with the atoms of the moiety on which the substituents are substituted, wherein the $C_{4-8}$ ring is a saturated or unsaturated hydrocarbon ring with 4, 5, 6, 7, or 8 carbon atoms or a saturated or unsaturated hydrocarbon ring with 4, 5, 6, 7, or 8 carbon atoms and 1, 2 or 3 heteroatoms.

Substituents are only present at positions where they are chemically possible, the person skilled in the art being able to decide (either experimentally or theoretically) without inappropriate effort which substitutions are chemically possible, and which are not.

Throughout the description and claims of this specification, the words "comprise" and "contain" and variations thereof mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. This disclosure is not restricted to the details of any foregoing embodiments. This disclosure extends to any novel one, or any novel combination, of the features disclosed in this specification (including any accompanying claims, abstract and drawings), or to any novel one, or any novel combination, of the steps of any method or process so disclosed.

DETAILED DESCRIPTION

Compounds of the Disclosure

In one aspect, the present disclosure provides a compound of formula (I), a pharmaceutically acceptable salt thereof, or a stereoisomer thereof:

(I)

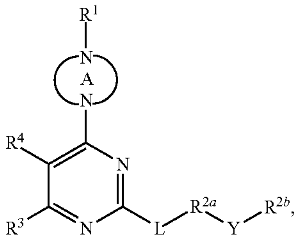

wherein:

ring A is a 4-12 membered heterocyclic ring, optionally substituted with one or more substituents selected from the group consisting of halo, hydroxyl, cyano, oxo, $C_{1-4}$-alkyl, $C_{2-4}$-alkynyl, $C_{1-4}$-heteroalkyl, $C_{3-8}$-cycloalkyl, —$C_{0-4}$-alkyl-$C(O)N(R^{6d})_2$, and —$C_{0-4}$-alkyl-$C(O)OR^{6d}$;

and/or wherein two substituents on the same atom of ring A may form a 3- to 5-membered ring together with the carbon atom on which they are attached;

and/or wherein two substituents on adjacent atoms of ring A may form a 3- to 6-membered ring together with the carbon atoms on which they are attached;

wherein the $C_{1-4}$-alkyl, $C_{2-4}$-alkynyl, $C_{1-4}$-heteroalkyl, and $C_{3-8}$-cycloalkyl are optionally substituted with one or more substituents selected from the group consisting of halo, hydroxy, —$OR^{6d}$, cyano and oxo;

$R^1$ is selected from the group consisting of

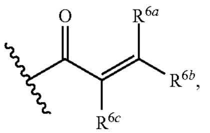

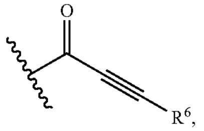

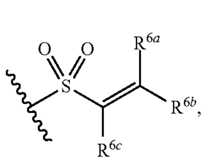

and

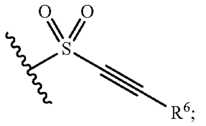

L is selected from the group consisting of a direct bond, —$N(R^{6d})$—, —$C(O)N(R^{6d})$—, —$S(O_2)N(R^{6d})$— and —O—;

$R^{2a}$ is a direct bond, $C_{1-4}$-alkylene, $C_{1-4}$-heteroalkylene, $C_{3-8}$-cycloalkylene, 3- to 8-membered heterocycloalkylene, 6- to 10-membered aryl, or 5- to 10-membered heteroaryl, each of which is optionally substituted with one or more substituents selected from the group consisting of halo, hydroxyl, carboxyl, —$OR^{6d}$, oxo, cyano, $C_{3-8}$-cycloalkyl, $C_{1-4}$-alkyl, $C_{1-4}$-heteroalkyl, 3- to 8-membered heterocycloalkyl;

Y is a direct bond, $C_{1-4}$-alkyl, $C_{1-4}$ alkylene, $C_{1-4}$-heteroalkyl, —$N(R^{6d})$—, —$NR^{6d}C(O)$—, —$C(O)NR^{6d}$—, —$NR^{6d}C(O)NR^{6d}$—, —$S(O_2)NR^{6d}$—, or —$NR^{6d}S(O)_2$—;

$R^{2b}$ is H, $C_{1-4}$-alkyl, $C_{1-4}$-heteroalkyl, $C_{3-8}$-cycloalkyl, 3- to 8-membered heterocycloalkyl, 6- to 10-membered aryl, or 5- to 10-membered heteroaryl, each of which is optionally substituted with one or more substituents selected from halo, hydroxyl, carboxyl, —$OR^{6d}$, oxo, cyano, —$N(R^{6d})_2$, $C_{3-8}$-cycloalkyl, $C_{1-4}$-alkyl, $C_{1-4}$-heteroalkyl, and 3- to 8-membered heterocycloalkyl;

$R^3$ is

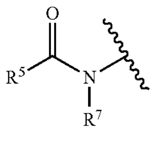

or

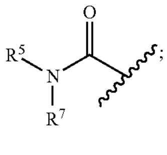

$R^4$ is H, $C_{1-6}$-alkyl, $C_{1-6}$-heteroalkyl, $C_{1-6}$-haloalkyl, $C_{3-8}$-cycloalkyl, 3- to 8-membered heterocycloalkyl, —$OC_{1-6}$-haloalkyl, —$NH(C_{1-6}$-alkyl) or —$N(C_{1-6}$-alkyl$)_2$; each of which is optionally substituted with one or more substituents selected from the group consisting of $C_{1-4}$-alkyl, $C_{1-4}$-heteroalkyl, halo, cyano, hydroxyl, ether, —$N(R^{6d})_2$, $C_{3-8}$-cycloalkyl, 3- to 8-membered heterocycloalkyl.

$R^5$ is H, $C_{1-6}$-alkyl, $C_{1-6}$-heteroalkyl, $C_{3-8}$-cycloalkyl, 3- to 8-membered heterocycloalkyl, 6- to 10-membered aryl, or 5-to-10 membered heteroaryl, each of which is optionally substituted with one or more substituents selected from the group consisting of halo, hydroxyl, carboxyl, cyano, —$OR^{6d}$, —$N(R^{6d})_2$, $C_{3-8}$-cycloalkyl, $C_{1-4}$-alkyl, $C_{1-4}$-heteroalkyl, 3- to 8-membered heterocycloalkyl, 6-membered aryl, and 5- to 6-membered heteroaryl, or an $R^5$ and $R^7$ taken together with the atom to which they are both attached form a 5- or 6-membered monocyclic ring system or a bicyclic system, wherein the bicyclic system is a 9- or 10-membered heterocyclic ring system;

$R^6$, $R^{6a}$ and $R^{6b}$ are each independently H, halo, cyano, $C_{1-6}$-alkyl, $C_{1-6}$-heteroalkyl, $C_{3-8}$-cycloalkyl, 3- to 8-membered heterocycloalkyl, $C_{3-8}$-aryl, or $C_{3-8}$-heteroaryl, each of which is optionally substituted with one or more substituents selected from the group consisting of halo, hydroxy, cyano, —$N(R^{6d})_2$, —$OR^{6d}$, $C_{1-4}$-alkyl, 3- to 8-membered heterocycloalkyl and $C_{1-4}$-heteroalkyl;

$R^{6c}$ is H, halo, cyano, $C_{1-6}$-alkyl, $C_{1-6}$-heteroalkyl, $C_{3-8}$-cycloalkyl, or 3- to 8-membered heterocycloalkyl, each of which is optionally substituted with one or more substituents selected from the group consisting of halo, cyano, —$OR^{6d}$, hydroxy and $C_{1-4}$-heteroalkyl;

$R^{6d}$ is independently at each occurrence selected from H, cyano, $C_{1-6}$-alkyl, $C_{1-6}$-heteroalkyl, $C_{3-8}$-cycloalkyl, and 3- to 8-membered heterocycloalkyl; and $R^7$ is H, $C_{1-6}$-alkyl, $C_{1-6}$-heteroalkyl, or $C_{3-8}$-cycloalkyl, each of which is optionally substituted with one or more substituents selected from halo, cyano, hydroxyl, carboxyl, —$OR^{6d}$, —$N(R^{6d})_2$, $C_{3-8}$-cycloalkyl, $C_{1-4}$-alkyl, $C_{1-4}$-heteroalkyl, and 3- to 8-membered heterocycloalkyl.

In some embodiments, ring A is a substituted or unsubstituted 4-8 membered heterocyclic ring. In some embodiments, ring A is a substituted or unsubstituted 5-7-membered heterocyclic ring. In some embodiments, ring A is a substituted or unsubstituted 6-membered heterocyclic ring. In some embodiments, ring A is a substituted or unsubstituted 6-membered heterocyclic ring, wherein the heterocyclic ring has 2 N atoms. In some embodiments, ring A is a substituted or unsubstituted 7-membered heterocyclic ring. In some embodiments, ring A is a substituted or unsubstituted 7-membered heterocyclic ring, wherein the heterocyclic ring has 2 N atoms. In some embodiments, ring A is diazepanyl. In some embodiments, ring A is piperazinyl. In some embodiments, ring A is unsubstituted except for $R^1$. In some embodiments, ring A is optionally substituted with $R^1$ and $R^8$ groups, as defined herein.

In some embodiments, ring A is optionally substituted with one or more substituents selected from halo, hydroxyl, unsubstituted or substituted $C_{1-4}$-alkyl, unsubstituted or substituted $C_{1-4}$-heteroalkyl, wherein when substituted, the $C_{1-4}$-alkyl or $C_{1-4}$-heteroalkyl is substituted with one or more substituents selected from the group consisting of halo, hydroxyl, and cyano. Where there are two or more substituents, the substituents may be the same or different. Thus, in some embodiments, ring A is substituted with substituted $C_{1-4}$-alkyl.

In some embodiments, ring A is optionally substituted with one or more substituents selected from the group consisting of halo, hydroxyl, cyano, —$(CH_2)_a$—OH, —$(CH_2)_a$—$N(R^{6d})_2$, —$(CH_2)_a$—CN, —$(CH_2)_a$—$C(O)N(R^{6d})_2$ and —$(CH_2)_a$—$CH_3$, wherein a is an integer selected from 0, 1, 2 and 3. In some embodiments, a is 1. In some embodiments, a is 0. In some embodiments, the one or more substituents of ring A is further substituted with one or more substituents selected from the group consisting of halo, hydroxy, and cyano. In some embodiments, ring A is optionally substituted with —$CH_2CN$ or —$CH_2CF_2$.

In some embodiments, ring A is selected from the group consisting of:
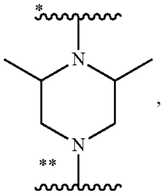, 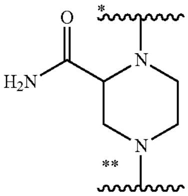, 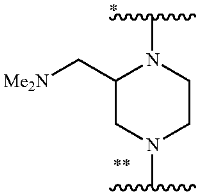, 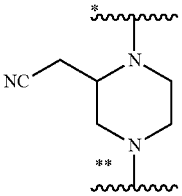, 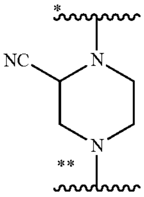, 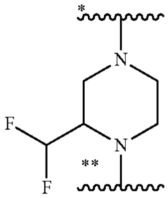, 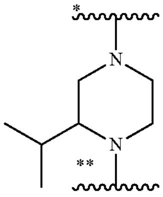, 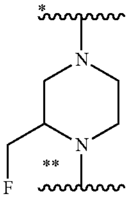, 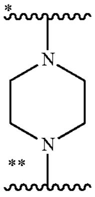, 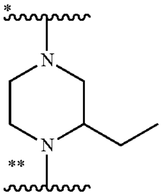, 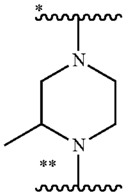, 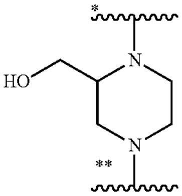, 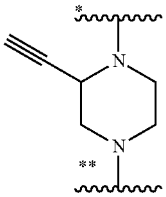, 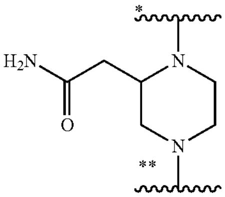, 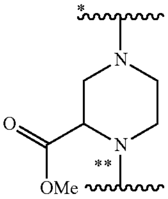, 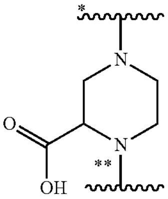, 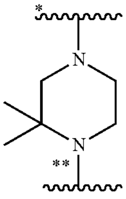, 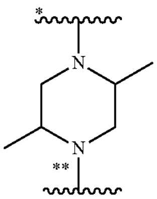, 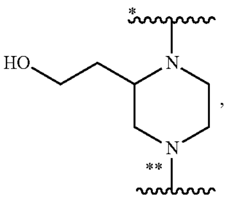,
-continued
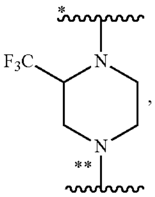, 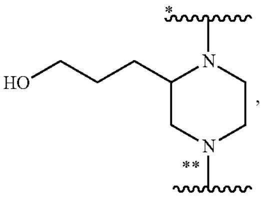, 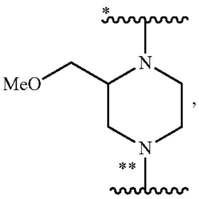, 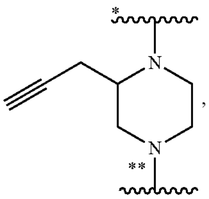, 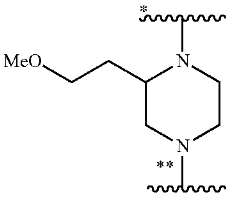, 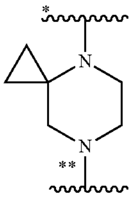, 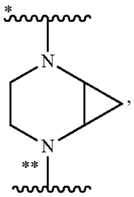, 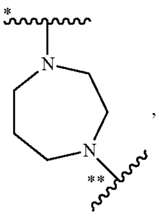, and 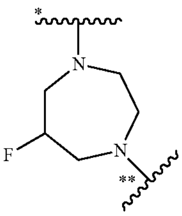.
In some embodiments, ring A is selected from the group consisting of:
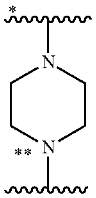, 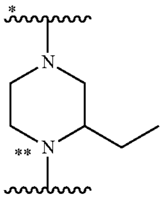, 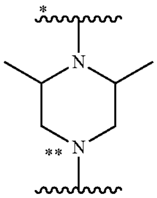, 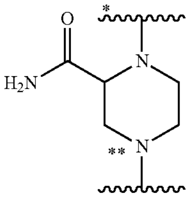, 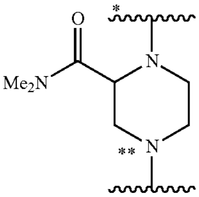, 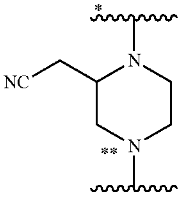, 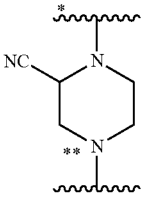, 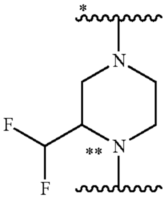, -continued

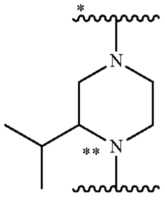,
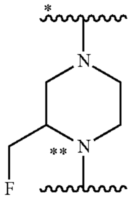,
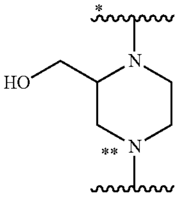,
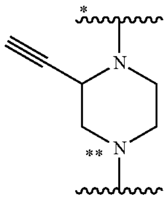,
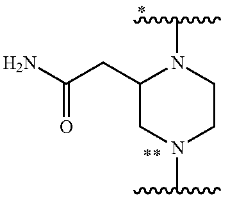,
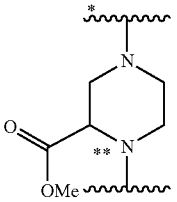,
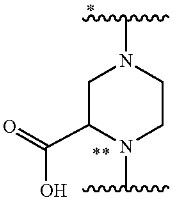,
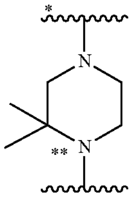,
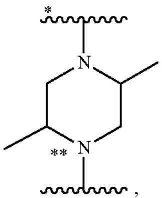,
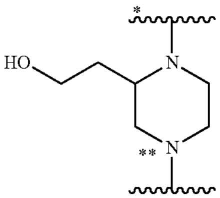,
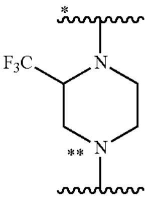,
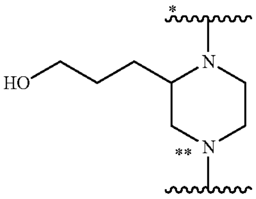,
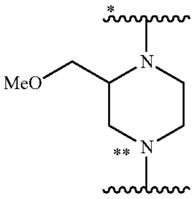,
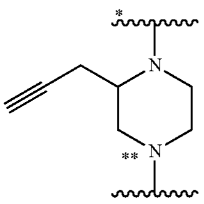, and
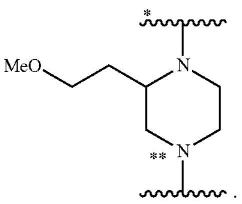.

The A rings represented in the preceding paragraphs may be oriented in the compound of the disclosure in any way that is evident to the person skilled in the art. In some embodiments, the * indicates a bond between the nitrogen atom of ring A and $R^1$; and the ** indicates a bond between the nitrogen atom of ring A and the pyrimidyl group of the remainder of the molecule. In other embodiments, the * indicates a bond between the nitrogen atom of ring A and the pyrimidyl group of the remainder of the molecule; and the ** indicates a bond between the nitrogen atom of ring A and $R^1$.

In some embodiments, ring A is

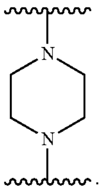.

In some embodiments, ring A is

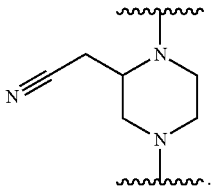 [SMILES: *N1CCN(*)C(CC#N)C1].

In some embodiments, ring A is

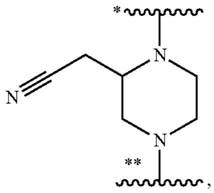, wherein * indicates a bond between the nitrogen atom of ring A and $R^1$; and the ** indicates a bond between the nitrogen atom of ring A and the pyrimidyl group of the remainder of the molecule.

In some embodiments, $R^1$ is selected from the group consisting of:

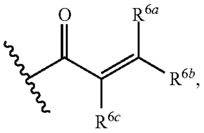
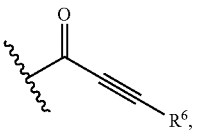
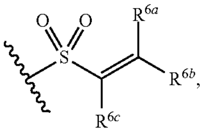 and
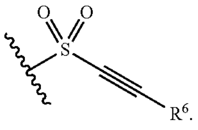

In some embodiments, $R^1$ is

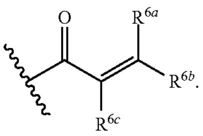

In some embodiments, $R^1$ is

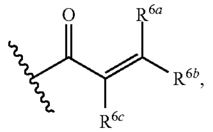

wherein $R^{6a}$, $R^{6b}$ and $R^{6c}$ are H.

Accordingly, in some embodiments, $R^1$ is

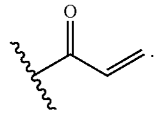 [SMILES: *C(=O)C=C]

In some embodiments, $R^1$ is

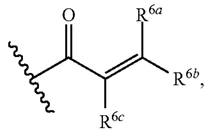

wherein $R^{6a}$ and $R^{6b}$ are H, and $R^{6c}$ is an electron withdrawing group. In some embodiments, $R^1$ is

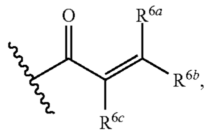

wherein $R^{6a}$ and $R^{6b}$ are H, and $R^{6c}$ is F.

In some embodiments, L is selected from the group consisting of a direct bond, —N($R^{6d}$)—, and —O—. In some embodiments, L is a direct bond or —O—. In some embodiments, L is —N($R^{6d}$)— or —O—. In some embodiments, L is a direct bond. In some embodiments, L is —O—. In some embodiments, L is —N($R^{6d}$).

In some embodiments, Y is selected from the group consisting of a direct bond, —N($R^{6d}$)—, and —O—. In some embodiments, Y is a direct bond or —O—. In some embodiments, Y is a direct bond. In some embodiments, Y is —O—. In some embodiments, Y is —N($R^{6d}$).

In some embodiments, $R^{2a}$ is $C_{1-4}$-alkylene, $C_{1-4}$-heteroalkylene, $C_{3-8}$-cycloalkylene, 3- to 8-membered heterocycloalkylene, 6- to 10-membered aryl, or 5- to 10-membered heteroaryl, each of which is optionally substituted with one or more substituents selected from the group consisting of halo, hydroxyl, carboxyl, —$OR^{6d}$, oxo, cyano, $C_{3-8}$-cycloalkyl, $C_{1-4}$-alkyl, $C_{1-4}$-heteroalkyl, and 3- to 8-membered heterocycloalkyl. In some embodiments, $R^{2a}$ is 3- to 8-membered heterocycloalkylene and heteroaryl. In some embodiments, $R^{2a}$ is a direct bond. In some embodiments, $R^{2a}$ is a $C_{1-4}$-alkylene. In some embodiments, the $C_{1-4}$-alkylene is methylene (—$CH_2$—) or ethylene (—$CH_2CH_2$—).

In some embodiments, $R^{2b}$ is H, $C_{1-4}$-alkyl, $C_{1-4}$-heteroalkyl, $C_{3-8}$-cycloalkyl, 3- to 8-membered heterocycloalkyl, 6- to 10-membered aryl, or 5- to 10-membered heteroaryl, each of which is optionally substituted with one or more substituents selected from the group consisting of halo, hydroxyl, carboxyl, —$OR^{6d}$, oxo, cyano, —N($R^{6d}$)$_2$, $C_{3-8}$-cycloalkyl, $C_{1-4}$-alkyl, $C_{1-4}$-heteroalkyl, and 3- to 8-membered heterocycloalkyl. In some embodiments, $R^{2b}$ is H, $C_{1-4}$-alkylene, or $C_{1-4}$-heteroalkylene. In some embodiments, $R^{2b}$ is H.

In some embodiments, L is —N($R^{6d}$) and Y is —N($R^{6d}$)—. In some embodiments, L is O, $R^{2a}$ is $C_{1-4}$-alkylene and $R^{2b}$ is unsubstituted or substituted $C_{1-4}$-heteroalkyl. In some embodiments, each of L, $R^{2a}$ and Y are direct bonds, and $R^{2b}$ is unsubstituted or substituted heteroaryl. In some embodiments, the heteroaryl is pyridyl, pyrazolyl, or indazolyl. In some embodiments, L is O or —N($R^{6d}$), $R^{2a}$ is $C_{1-4}$-alkylene, Y is a direct bond, and $R^{2b}$ is heterocycloalkyl or heteroaryl. In some embodiments, L is O or —N($R^{6d}$), $R^{2a}$ is $C_{1-4}$-alkylene, Y is a direct bond, and $R^{2b}$ is heterocycloalkyl. In some embodiments, $R^{2a}$ is methylene (—$CH_2$—) or ethylene (—$CH_2CH_2$—). In some embodiments, $R^{2a}$ is methylene. In some embodiments, $R^{2b}$ is a 5- or 6-membered heterocycloalkyl with 1 or 2 heteroatoms selected from the group consisting of N, O, or S. In some embodiments, the heterocyclyl is a pyrrolidinyl, piperidinyl, or morpholinyl, each of which is optionally substituted. In some embodiments, $R^{2b}$ is a 5-membered heteroaryl with 1, 2, or 3 heteroatoms selected from the group consisting of N, O, or S. In some embodiments, the heteroaryl is an optionally substituted pyrazole.

In some embodiments, -L-$R^{2a}$—Y—$R^{2b}$ is selected from the group consisting of:

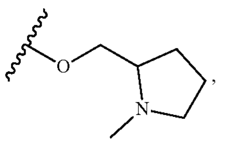

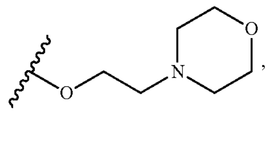

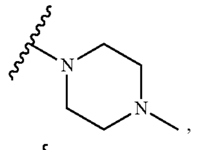

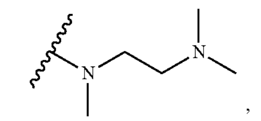

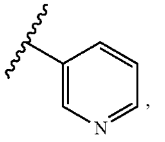

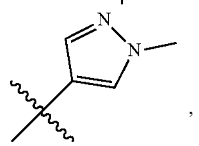

and

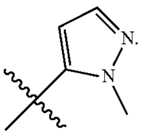

In some embodiments, $R^3$ is

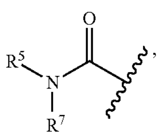

wherein:

$R^5$ is $C_{1-6}$-alkyl, 6- to 10-membered aryl or 6- to 10-membered heteroaryl, each of which is optionally substituted with one or more substituents selected from halo, hydroxyl, carboxyl, cyano, —$OR^{6d}$, —$N(R^{6d})_2$, $C_{3-8}$-cycloalkyl, $C_{1-4}$-alkyl, $C_{1-4}$-heteroalkyl, 3- to 8-membered heterocycloalkyl, 6-membered aryl, 5- to 6-membered heteroaryl; and $R^7$ is H or $C_{1-6}$-alkyl; or $R^5$ and $R^7$ taken together with the atom to which they are attached form a bicyclic system, wherein the bicyclic system is a 9- or 10-membered heterocyclic ring system.

In some embodiments, $R^3$ is

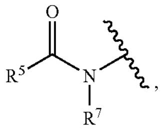, wherein:

$R^5$ is $C_{1-6}$-alkyl, 6- to 10-membered aryl or 6- to 10-membered heteroaryl, each of which is optionally substituted with one or more substituents selected from halo, hydroxyl, carboxyl, cyano, —$OR^{6d}$, —$N(R^{6d})_2$, $C_{3-8}$-cycloalkyl, $C_{1-4}$-alkyl, $C_{1-4}$-heteroalkyl, 3- to 8-membered heterocycloalkyl, 6-membered aryl, 5 to 6 membered heteroaryl; and $R^7$ is H or $C_{1-6}$-alkyl; or $R^5$ and $R^7$ taken together with the atom to which they are attached form a bicyclic system, wherein the bicyclic system is a 9- or 10-membered heterocyclic ring system.

In some embodiments, $R^5$ is $C_{1-6}$-heteroalkyl, $C_{3-8}$-cycloalkyl, 3- to 8-membered heterocycloalkyl, 6- to 10-membered aryl, or 6- to 10-membered heteroaryl, each of which is optionally substituted with one or more substituents selected from the group consisting of halo, hydroxyl, carboxyl, cyano, —$OR^{6d}$, —$N(R^{6d})_2$, $C_{3-8}$-cycloalkyl, $C_{1-4}$-alkyl, $C_{1-4}$-heteroalkyl, 3- to 8-membered heterocycloalkyl, 6-membered aryl, or 5- to 6-membered heteroaryl. In some embodiments, $R^5$ is 6- to 10-membered aryl or 6- to 10-membered heteroaryl, optionally substituted with one or more substituents selected from halo, hydroxyl, carboxyl, cyano, —$OR^{6d}$, —$N(R^{6d})_2$, and $C_{1-4}$-alkyl. In some embodiments, $R^5$ is 6- to 10-membered aryl, optionally substituted with one or more substituents selected from halo, hydroxyl, carboxyl, cyano, —$OR^{6d}$, —$N(R^{6d})_2$, and $C_{1-4}$-alkyl. In some embodiments, $R^5$ is naphthyl, pyridyl, isoquinolyl, or indazolyl, each of which is optionally substituted. In some embodiments, $R^5$ is naphthyl or indazolyl, each of which is optionally substituted. In some embodiments, $R^5$ is unsubstituted naphthyl. In some embodiments, $R^5$ is naphthyl substituted with hydroxyl. In some embodiments, $R^5$ is pyridyl substituted with an amino group. In some embodiments, $R^5$ is isoquinolyl substituted with an amino group. In some embodiments, $R^5$ is selected from the group consisting of:

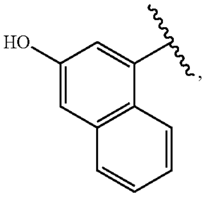,

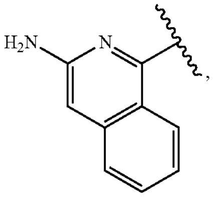,

-continued

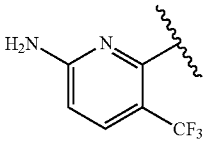, and

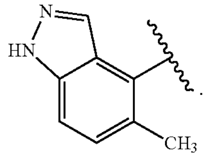.

In some embodiments, $R^5$ is

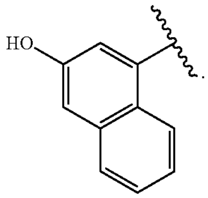.

In some embodiments, $R^7$ is H, $C_{1-6}$-alkyl, $C_{1-6}$-heteroalkyl, or $C_{3-8}$-cycloalkyl, wherein the $C_{1-6}$-alkyl, $C_{1-6}$-heteroalkyl, or $C_{3-8}$-cycloalkyl each are optionally substituted with one or more substituents selected from the group consisting of halo, cyano, hydroxyl, carboxyl, —$OR^{6d}$, —$N(R^{6d})_2$, $C_{3-8}$-cycloalkyl, $C_{1-4}$-alkyl, $C_{1-4}$-heteroalkyl, and 3- to 8-membered heterocycloalkyl, or wherein $R^5$ and $R^7$ taken together with the atom to which they are attached form a bicyclic system, wherein the bicyclic system is a 9- or 10-membered heterocyclic ring system. In some embodiments, $R^7$ is H or $C_{1-6}$-alkyl. In some embodiments, $R^7$ is H.

In some embodiments, $R^3$ is selected from the group consisting of:

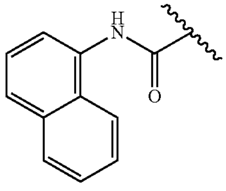,

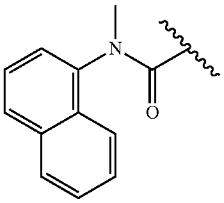,

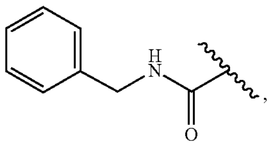,

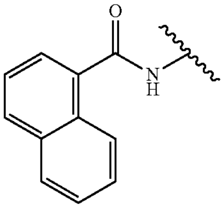,

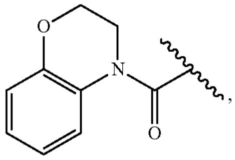,

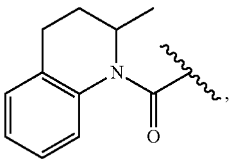,

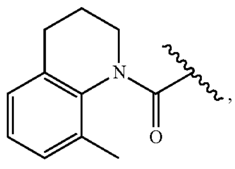,

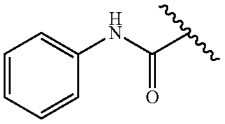,

-continued

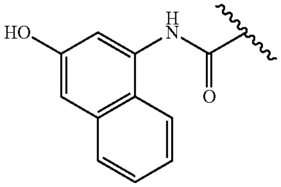

,

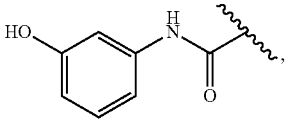

,

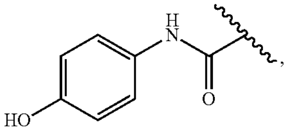

,

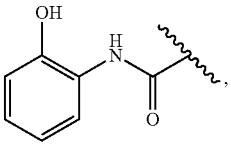

,

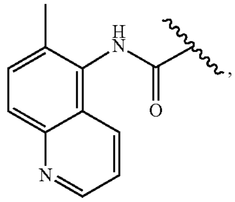

, and

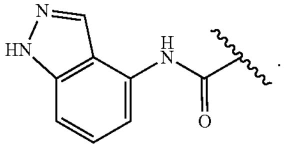

.

In some embodiments, $R^4$ is H, halo, $C_{1-6}$-alkyl, $C_{1-3}$ haloalkyl, —$OC_{1-6}$ alkyl, —$OC_{1-3}$ haloalkyl, —$CH_2$—$OC_{1-6}$ alkyl, —NH($C_{1-6}$-alkyl) or —N($C_{1-6}$-alkyl)$_2$. In some embodiments, $R^4$ is H, halo, $C_{1-6}$-alkyl, $C_{1-3}$ haloalkyl, —$OC_{1-6}$ alkyl, —$OC_{1-3}$ haloalkyl, or —$CH_2$—$OC_{1-6}$ alkyl. In some embodiments, $R^4$ is H, halo or $C_{1-6}$-alkyl. In some embodiments, $R^4$ is H. In some embodiments, $R^4$ is halo, $C_{1-3}$ haloalkyl, —$OC_{1-6}$ alkyl, —$OC_{1-3}$ haloalkyl, —$CH_2O$—$C_{1-6}$ alkyl, —NH($C_{1-6}$-alkyl) or —N($C_{1-6}$-alkyl)$_2$. In some embodiments, the halo is F or Cl. In some embodiments, the —$OC_{1-6}$ alkyl is —OMe or —OEt. In some embodiments, the —$OC_{1-6}$ alkyl is —OMe. In some embodiments, the $C_{1-3}$ haloalkyl is —$CF_2H$. In some embodiments, the —$CH_2O$—$C_{1-6}$ alkyl is —$CH_2OMe$. In some embodiments, the $C_{1-3}$ haloalkyl is $CF_3$, $CHF_2$, or $CH_2F$. In some embodiments, the $C_{1-6}$-alkyl is $CH_3$. In some embodiments, the —$OC_{1-3}$ haloalkyl is —$OCF_3$. In some embodiments, the —N($C_{1-6}$-alkyl)$_2$ is —$NMe_2$. In some embodiments, the —NH($C_{1-6}$-alkyl) is —NHMe.

In some embodiments, $R^6$, $R^{6a}$ and $R^{6b}$ are independently at each occurrence selected from the group consisting of H, halo, cyano, $C_{1-6}$-alkyl and $C_{1-6}$-heteroalkyl. In some embodiments, $R^6$, $R^{6a}$ and $R^{6b}$ are independently at each occurrence H or $C_{1-4}$-alkyl, wherein the $C_{1-4}$ alkyl is optionally substituted with one or more substituents selected from the group consisting of halo, cyano, hydroxy, —N($R^{6d}$)$_2$, —$OR^{6d}$, $C_{1-4}$-alkyl, 3- to 8-membered heterocycloalkyl and $C_{1-4}$-heteroalkyl. In some embodiments, $R^6$, $R^{6a}$ and $R^{6b}$ are each H.

In some embodiments, $R^{6c}$ is selected from the group consisting of H, halo, cyano, $C_{1-6}$-alkyl and $C_{1-6}$-heteroalkyl, optionally wherein the $C_{1-6}$-alkyl and $C_{1-6}$-heteroalkyl is optionally substituted with one or more substituents selected from the group consisting of halo, cyano, hydroxy, —$OR^{6d}$ and $C_{1-4}$-heteroalkyl.

In some embodiments, $R^{6a}$, $R^{6b}$ and $R^{6c}$ are each H. In some embodiments, $R^{6a}$ and $R^{6b}$ are each H, and $R^{6c}$ is F.

In some embodiments, $R^{6d}$ is independently at each occurrence selected from the group consisting of H, halo, cyano, $C_{1-6}$-alkyl, and $C_{1-6}$-heteroalkyl. In some embodiments, $R^{6d}$ is H. In some embodiments, $R^{6d}$ is selected from $C_{1-4}$-alkyl and $C_{1-4}$-heteroalkyl.

In some embodiments, the compound of formula (I) is a compound of formula (Ia):

(Ia)

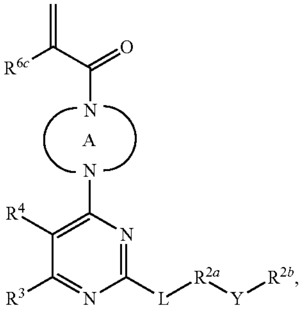

wherein A, $R^{2a}$, $R^{2b}$, $R^3$, $R^4$, $R^{6d}$, L and Y are as defined above in formula (I).

In some embodiments, $R^{6c}$ is H or F. In some embodiments, $R^{6c}$ is H.

In some embodiments, the compound of formula (I) is a compound of formula (II):

(II)

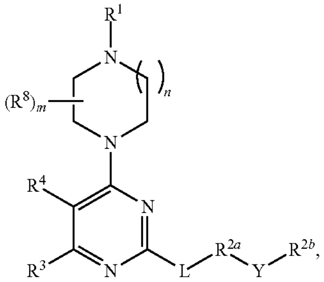

wherein:

$R^1$, $R^{2a}$, $R^{2b}$, $R^3$, $R^4$, L and Y are as defined above in formula (I);

$R^8$ is halo, hydroxyl, unsubstituted or substituted $C_{1-4}$-alkyl, or unsubstituted or substituted $C_{1-4}$-heteroalkyl, wherein when substituted, the $C_{1-4}$-alkyl or $C_{1-4}$-heteroalkyl is substituted with one or more substituents selected from the group consisting of halo, hydroxyl, and cyano;

m is 1, 2, or 3; and n is 1 or 2.

In some embodiments, $R^8$ is halo, hydroxyl, cyano, —$(CH_2)_a$—OH, —$(CH_2)_a$—N($R^{6d}$)$_2$, —$(CH_2)_a$—CN, —$(CH_2)_a$—C(O)N($R^{6d}$)$_2$ and —$(CH_2)_a$—$CH_3$, wherein a is an integer selected from 0, 1, 2 and 3. In some embodiments, $R^8$ is halo, hydroxyl, cyano, —$(CH_2)_a$—OH, —$(CH_2)_a$—N($R^{6d}$)$_2$, —$(CH_2)_a$—CN, and —$(CH_2)_a$—C(O)N($R^{6d}$)$_2$, wherein a is an integer selected from 0, 1, 2 and 3. In some embodiments, a is 1. In some embodiments, a is 0. In some embodiments, the one or more substituents is substituted with one or more substituents selected from the group consisting of halo, hydroxy, and cyano. Thus, in some embodiments ring A is unsubstituted or substituted with —$CH_2CN$, —$CH_2CF_3$, or —$CH_2CHF_2$.

In some embodiments, m is 1 or 2. In some embodiments, m is 1. In some embodiments, m is 2. In some embodiments, m is 3.

In some embodiments, n is 1. In some embodiments, n is 2.

In some embodiments, the compound of formula (II) is a compound of formula (IIa):

(IIa)

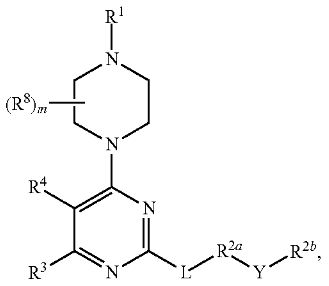

wherein: $R^1$, $R^{2a}$, $R^{2b}$, $R^3$, $R^4$, L and Y are as defined above in formula (I); and $R^8$ and m are as defined in formula (II).

In some embodiments, the compound of formula (II) is a compound of formula (IIa1):

(IIa1)

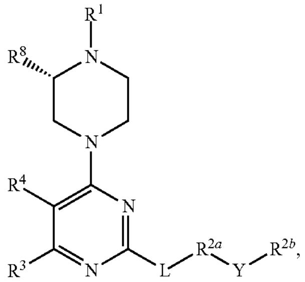

wherein: $R^1$, $R^{2a}$, $R^{2b}$, $R^3$, $R^4$, L and Y are as defined above in formula (I); and $R^8$ is as defined in formula (II).

In some embodiments, the compound of formula (II) is a compound of formula (IIb):

(IIb)

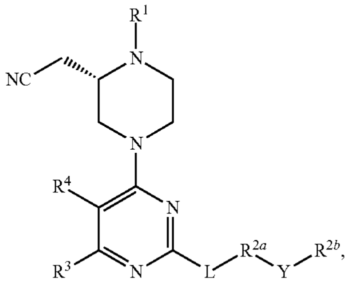

wherein $R^1$, $R^{2a}$, $R^{2b}$, $R^3$, $R^4$, L and Y are as defined above in formula (I).

In some embodiments, the compound of formula (I) is a compound of formula (IIc):

(IIc)

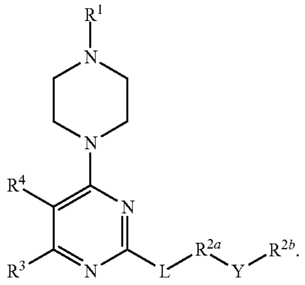

In some embodiments, the compound of formula (I) is a compound of formula (III):

(III)

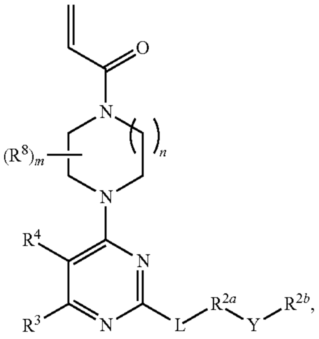

wherein $R^1$, $R^{2a}$, $R^{2b}$, $R^3$, $R^4$, L and Y are as defined above in formula (I);

$R^8$ is halo, hydroxyl, unsubstituted or substituted $C_{1-4}$-alkyl, or unsubstituted or substituted $C_{1-4}$-heteroalkyl, wherein when substituted, the $C_{1-4}$-alkyl or $C_{1-4}$-heteroalkyl is substituted with one or more substituents selected from the group consisting of halo, hydroxyl, and cyano;

m is 1, 2, or, 3; and n is 1 or 2.

In some embodiments, $R^3$ is halo, hydroxyl, cyano, $-(CH_2)_a-OH$, $-(CH_2)_a-N(R^{6d})_2$, $-(CH_2)_a-CN$, $-(CH_2)_a-C(O)N(R^{6d})_2$ and $-(CH_2)_a-CH_3$, wherein a is an integer selected from 0, 1, 2 and 3. In some embodiments, a is 1. In some embodiments, a is 0. In some embodiments, the one or more substituents is substituted with one or more substituents selected from the group consisting of halo, hydroxy, and cyano. Thus, in some embodiments ring A is unsubstituted or substituted with $-CH_2CN$ or $-CH_2CHF_2$.

In some embodiments, m is 1 or 2. In some embodiments, m is 1. In some embodiments, m is 2. In some embodiments, m is 3.

In some embodiments, n is 1. In some embodiments, n is 2.

In some embodiments, the compound of formula (III) is a compound of formula (IIIa):

(IIIa)

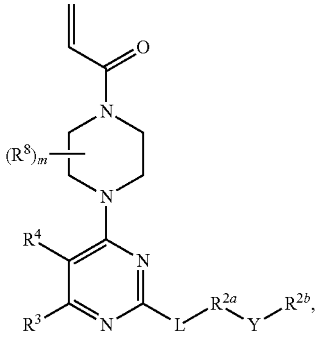

wherein $R^1$, $R^{2a}$, $R^{2b}$, $R^3$, $R^4$, L and Y are as defined above in formula (I); and $R^8$ and m are as defined above in formula (III).

In some embodiments, the compound of formula (III) is a compound of formula (IIIa1):

(IIIa1)

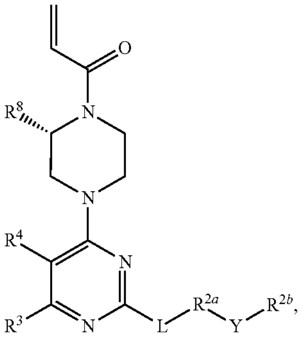

wherein $R^1$, $R^{2a}$, $R^{2b}$, $R^3$, $R^4$, L and Y are as defined above in formula (I); and $R^8$ is as defined above in formula (III).

In some embodiments, the compound of formula (III) is a compound of formula (IIIb):

(IIIb)

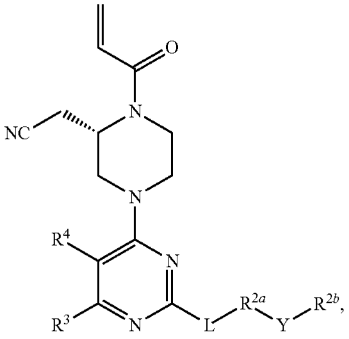

wherein $R^{2a}$, $R^{2b}$, $R^3$, $R^4$, L and Y are as defined above in formula (I).

In some embodiments, the compound of formula (I) is a compound of formula (IIIc):

(IIIc)

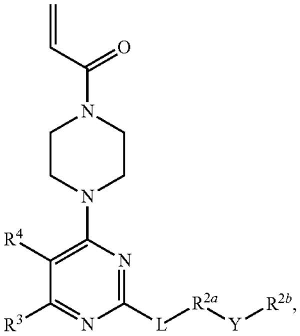

wherein $R^{2a}$, $R^{2b}$, $R^3$, $R^4$, L and Y are as defined above in formula (I).

In some embodiments, the compound of formula (I) is a compound of formula (IV):

(IV)

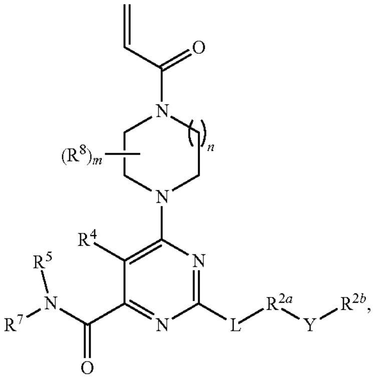

wherein $R^{2a}$, $R^{2b}$, $R^4$, $R^5$, $R^7$, L and Y are as defined above in formula (I);

$R^8$ is halo, hydroxyl, unsubstituted or substituted $C_{1-4}$-alkyl, or unsubstituted or substituted $C_{1-4}$-heteroalkyl, wherein when substituted, the $C_{1-4}$-alkyl or $C_{1-4}$-heteroalkyl is substituted with one or more substituents selected from the group consisting of halo, hydroxyl, and cyano;

m is 1, 2, or 3; and n is 1 or 2.

In some embodiments, $R^8$ is halo, hydroxyl, cyano, $—(CH_2)_a—OH$, $—(CH_2)_a—N(R^{6d})_2$, $—(CH_2)_a—CN$, $—(CH_2)_a—C(O)N(R^{6d})_2$ and $—(CH_2)_a—CH_3$, wherein a is an integer selected from 0, 1, 2 and 3. In some embodiments, a is 1. In some embodiments, a is 0. In some embodiments, the one or more substituents is substituted with one or more substituents selected from the group consisting of halo, hydroxy, and cyano. Thus, in some embodiments ring A is unsubstituted or substituted with $—CH_2CN$ or $—CH_2CHF_2$.

In some embodiments, m is 1 or 2. In some embodiments, m is 1. In some embodiments, m is 2. In some embodiments, m is 3.

In some embodiments, n is 1. In some embodiments, n is 2.

In some embodiments, the compound of formula (IV) is a compound of formula (IVa):

(IVa)

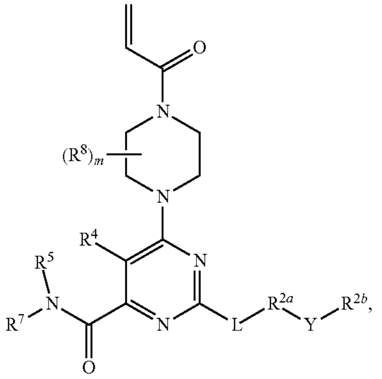

wherein $R^{2a}$, $R^{2b}$, $R^4$, $R^5$, $R^7$, L and Y are as defined above in formula (I); and $R^8$ and m are as defined above in formula (IV).

In some embodiments, the compound of formula (IV) is a compound of formula (IVa1):

(IVa1)

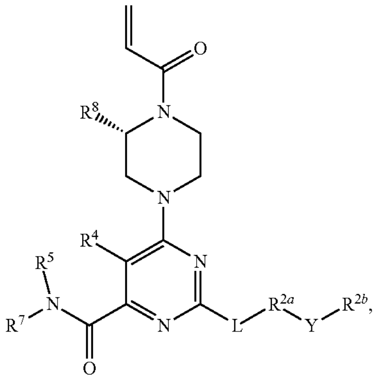

wherein $R^{2a}$, $R^{2b}$, $R^4$, $R^5$, $R^7$, L and Y are as defined above in formula (I); and $R^8$ is as defined above in formula (IV).

In some embodiments, the compound of formula (IV) is a compound of formula (IVb):

(IVb)

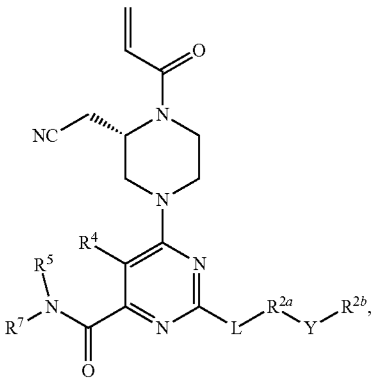

wherein $R^2$, $R^{2b}$, $R^4$, $R^5$, $R^7$, L and Y are as defined above in formula (I).

In some embodiments, the compound of formula (I) is a compound of formula (IVc):

(IVc)

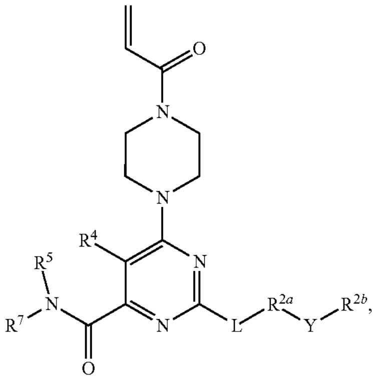

wherein $R^2$, $R^{2b}$, $R^4$, $R^5$, $R^7$, L and Y are as defined above in formula (I).

In some embodiments, the compound of formula (I) is selected from the group consisting of:

| Cmpd No. | Structure |
| --- | --- |
| 1 | 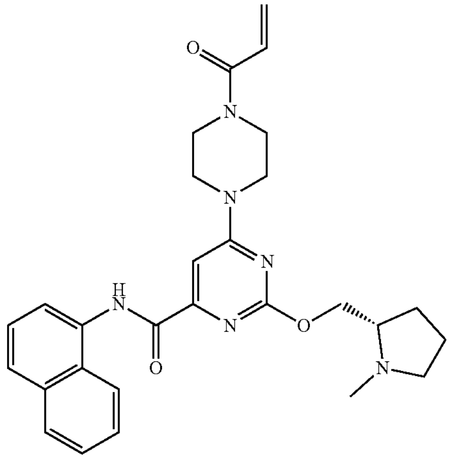 [SMILES: C=CC(=O)N1CCN(c2cc(C(=O)Nc3cccc4ccccc34)nc(OC[C@@H]3CCCN3C)n2)CC1] |
| 2 | 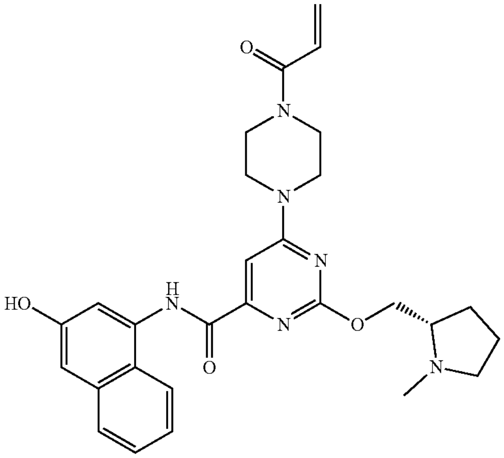 [SMILES: C=CC(=O)N1CCN(c2cc(C(=O)Nc3cc(O)cc4ccccc34)nc(OC[C@@H]3CCCN3C)n2)CC1] |

-continued
| Cmpd No. | Structure |
|---|---|
| 4 | 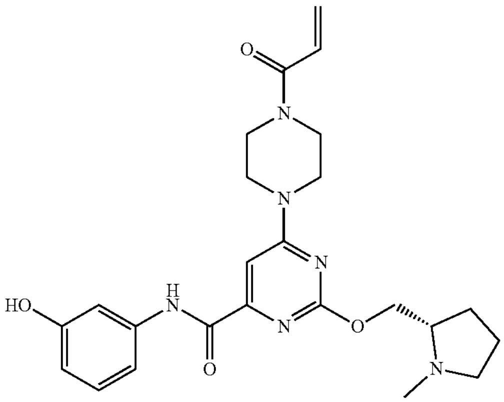 [SMILES: C=CC(=O)N1CCN(c2cc(C(=O)Nc3cccc(O)c3)nc(OC[C@@H]3CCCN3C)n2)CC1] |
| 5 | 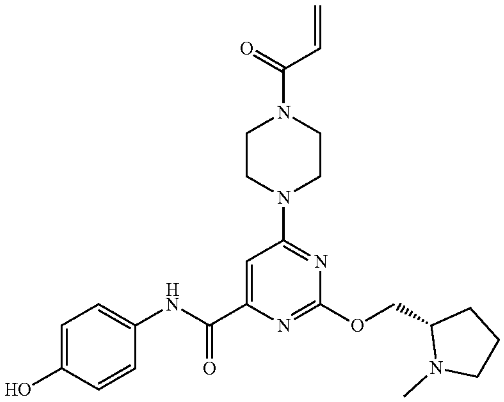 [SMILES: C=CC(=O)N1CCN(c2cc(C(=O)Nc3ccc(O)cc3)nc(OC[C@@H]3CCCN3C)n2)CC1] |
| 6 | 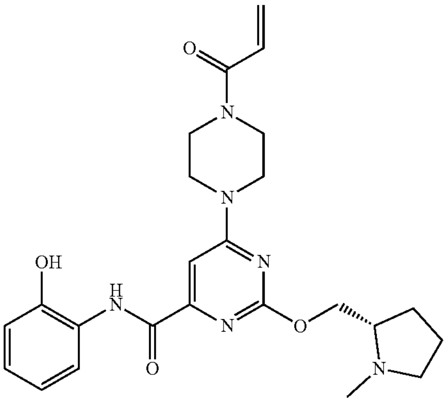 [SMILES: C=CC(=O)N1CCN(c2cc(C(=O)Nc3ccccc3O)nc(OC[C@@H]3CCCN3C)n2)CC1] |
-continued
| Cmpd No. | Structure |
|---|---|
| 7 | 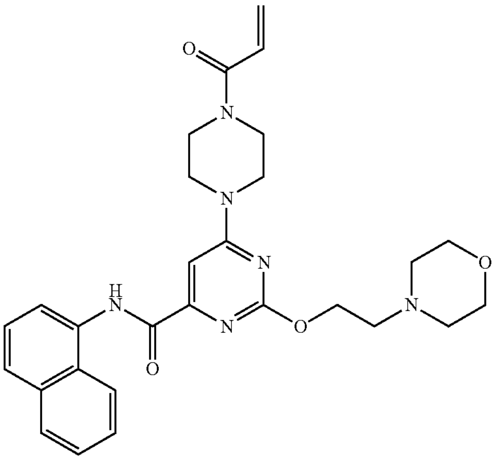 [SMILES: C=CC(=O)N1CCN(c2cc(C(=O)Nc3cccc4ccccc34)nc(OCCN3CCOCC3)n2)CC1] |
| 9 | 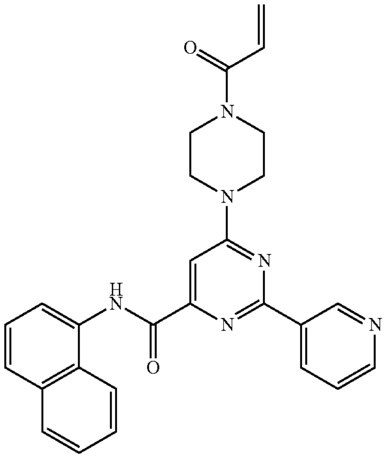 [SMILES: C=CC(=O)N1CCN(c2cc(C(=O)Nc3cccc4ccccc34)nc(-c3cccnc3)n2)CC1] |
| 10 | 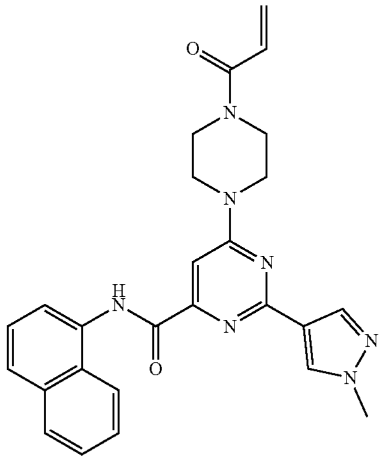 [SMILES: C=CC(=O)N1CCN(c2cc(C(=O)Nc3cccc4ccccc34)nc(-c3cnn(C)c3)n2)CC1] |

-continued
| Cmpd No. | Structure |
|---|---|
| 11 | 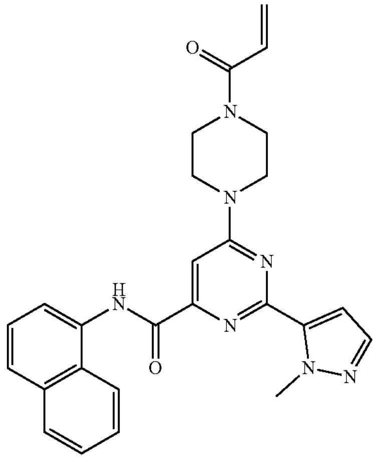 [SMILES: C=CC(=O)N1CCN(c2cc(C(=O)Nc3cccc4ccccc34)nc(-c3ccnn3C)n2)CC1] |
| 12 | 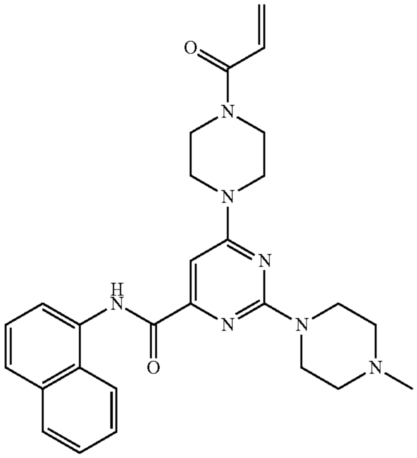 [SMILES: C=CC(=O)N1CCN(c2cc(C(=O)Nc3cccc4ccccc34)nc(N3CCN(C)CC3)n2)CC1] |
| 13 | 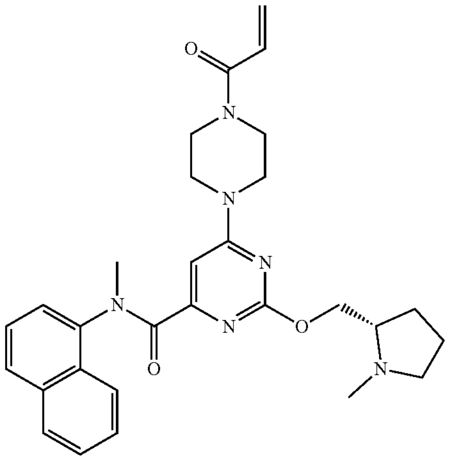 [SMILES: C=CC(=O)N1CCN(c2cc(C(=O)N(C)c3cccc4ccccc34)nc(OC[C@@H]3CCCN3C)n2)CC1] |
-continued
| Cmpd No. | Structure |
|---|---|
| 14 | 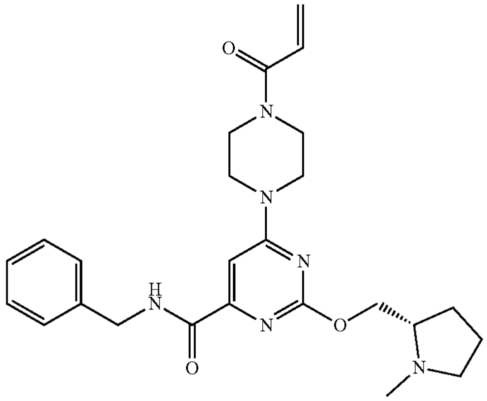 [SMILES: C=CC(=O)N1CCN(c2cc(C(=O)NCc3ccccc3)nc(OC[C@@H]3CCCN3C)n2)CC1] |
| 15 | 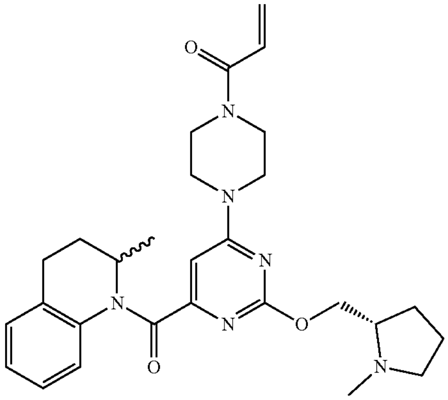 [SMILES: C=CC(=O)N1CCN(c2cc(C(=O)N3c4ccccc4CCC3C)nc(OC[C@@H]3CCCN3C)n2)CC1] |
| 16 | 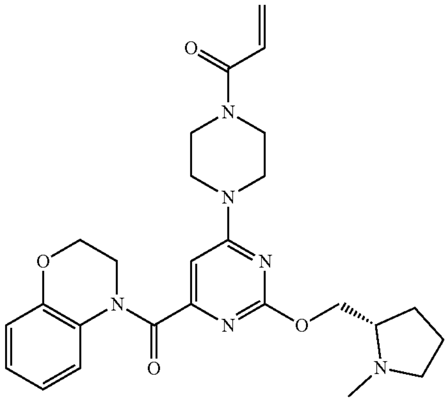 [SMILES: C=CC(=O)N1CCN(c2cc(C(=O)N3CCOc4ccccc43)nc(OC[C@@H]3CCCN3C)n2)CC1] |

-continued
| Cmpd No. | Structure |
| --- | --- |
| 17 | 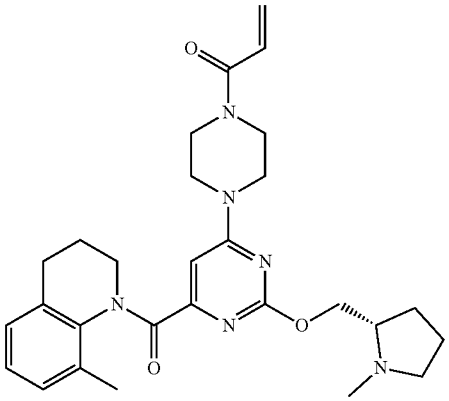 [SMILES: C=CC(=O)N1CCN(c2cc(C(=O)N3CCCc4cccc(C)c43)nc(OC[C@@H]3CCCN3C)n2)CC1] |
| 18 | 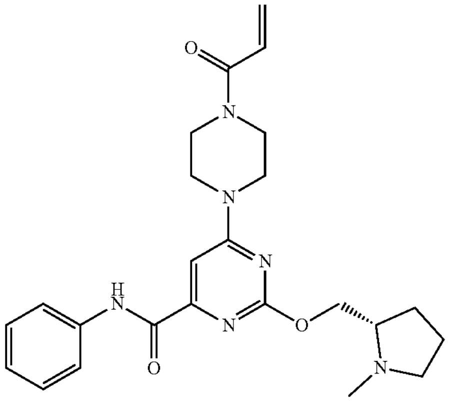 [SMILES: C=CC(=O)N1CCN(c2cc(C(=O)Nc3ccccc3)nc(OC[C@@H]3CCCN3C)n2)CC1] |
| 19 | 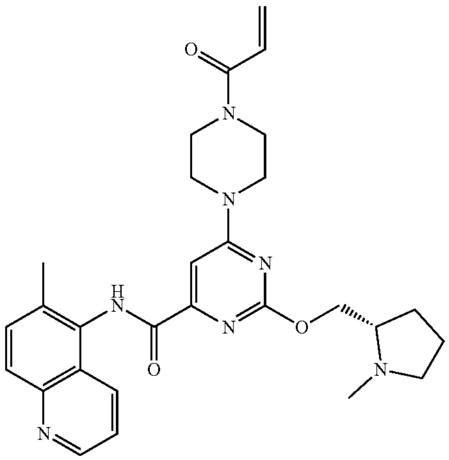 [SMILES: C=CC(=O)N1CCN(c2cc(C(=O)Nc3c(C)ccc4ncccc34)nc(OC[C@@H]3CCCN3C)n2)CC1] |
-continued
| Cmpd No. | Structure |
| --- | --- |
| 20 | 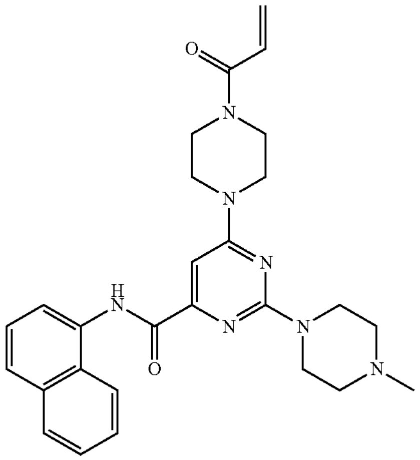 [SMILES: C=CC(=O)N1CCN(c2cc(C(=O)Nc3cccc4ccccc34)nc(N3CCN(C)CC3)n2)CC1] |
| 21 | 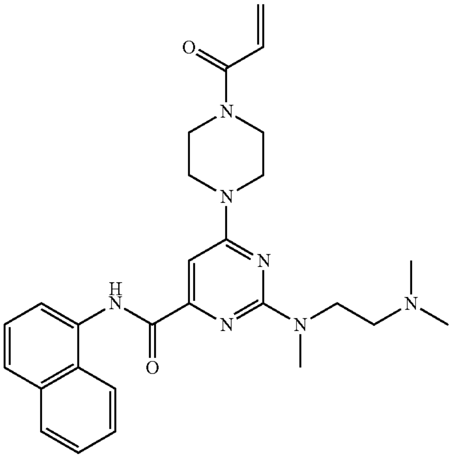 and |
| 22 | 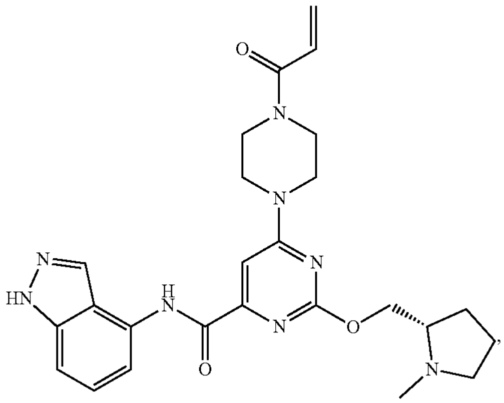 [SMILES: C=CC(=O)N1CCN(c2cc(C(=O)Nc3cccc4[nH]ncc34)nc(OC[C@@H]3CCCN3C)n2)CC1] |
or a pharmaceutically acceptable salt thereof.

In some embodiments, the compound of formula (I) is selected from the group consisting of:
| Cmpd No. | Structure |
| --- | --- |
| 2 | 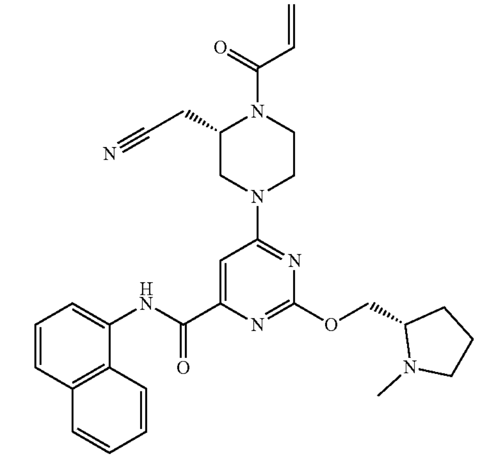 [SMILES: C=CC(=O)N1CCN(c2cc(C(=O)Nc3cccc4ccccc34)nc(OC[C@@H]3CCCN3C)n2)C[C@@H]1CC#N] |
| 8 | 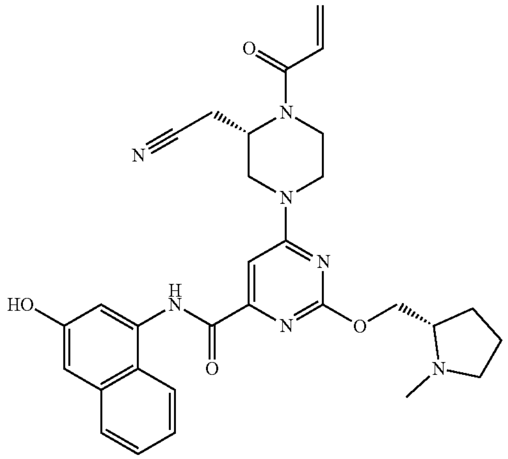 [SMILES: C=CC(=O)N1CCN(c2cc(C(=O)Nc3cc(O)cc4ccccc34)nc(OC[C@@H]3CCCN3C)n2)C[C@@H]1CC#N] |
| 23 | 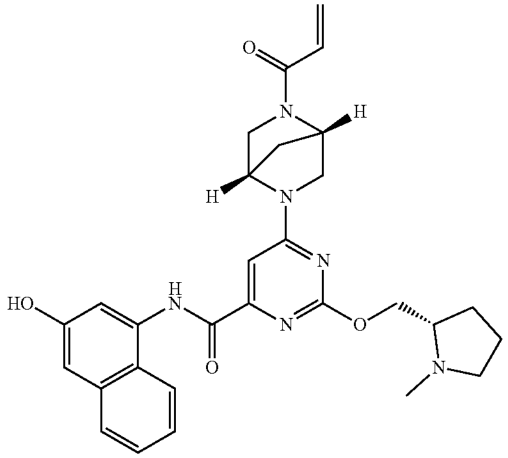 [SMILES: C=CC(=O)N1C[C@@H]2C[C@H]1CN2c1cc(C(=O)Nc2cc(O)cc3ccccc23)nc(OC[C@@H]2CCCN2C)n1] |

-continued
| Cmpd No. | Structure |
|---|---|
| 24 | 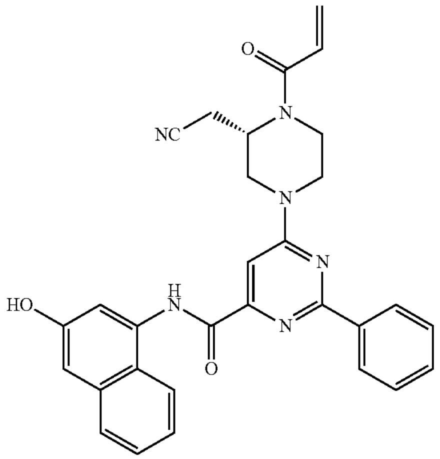 [SMILES: C=CC(=O)N1CCN(c2cc(C(=O)Nc3cc(O)cc4ccccc34)nc(-c3ccccc3)n2)C[C@@H]1CC#N] |
| 25 | 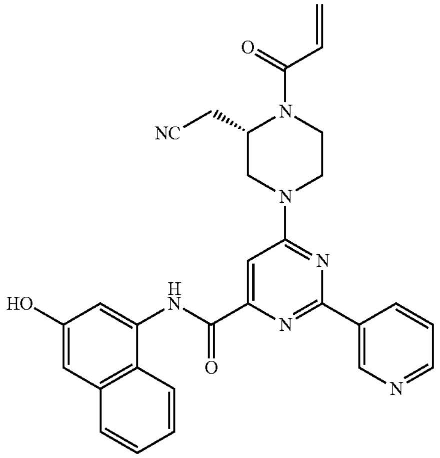 [SMILES: C=CC(=O)N1CCN(c2cc(C(=O)Nc3cc(O)cc4ccccc34)nc(-c3cccnc3)n2)C[C@@H]1CC#N] |
| 26 | 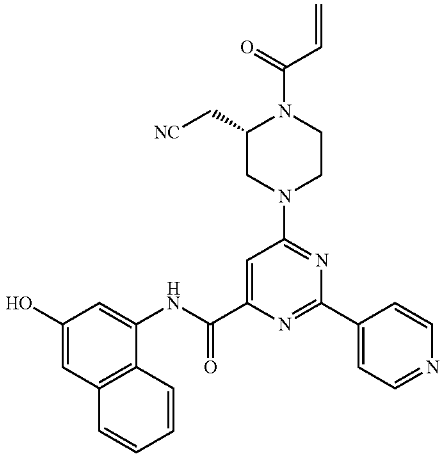 [SMILES: C=CC(=O)N1CCN(c2cc(C(=O)Nc3cc(O)cc4ccccc34)nc(-c3ccncc3)n2)C[C@@H]1CC#N] |

-continued
| Cmpd No. | Structure |
|---|---|
| 27 | 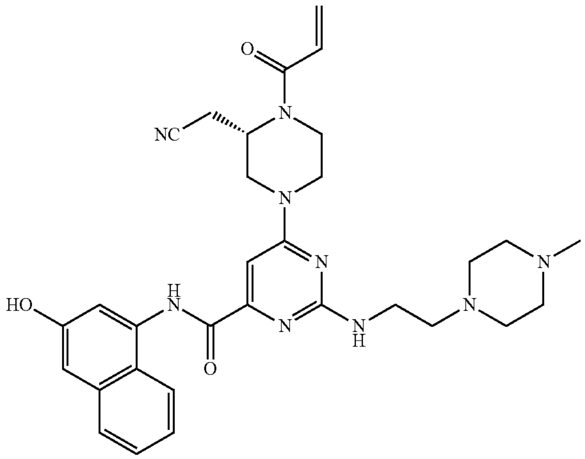 [SMILES: C=CC(=O)N1CCN(c2cc(C(=O)Nc3cc(O)cc4ccccc34)nc(NCCN3CCN(C)CC3)n2)C[C@@H]1CC#N] |
| 28 | 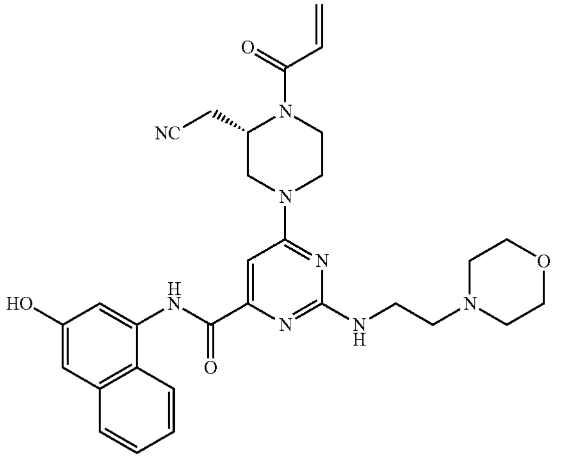 [SMILES: C=CC(=O)N1CCN(c2cc(C(=O)Nc3cc(O)cc4ccccc34)nc(NCCN3CCOCC3)n2)C[C@@H]1CC#N] |
| 29 | 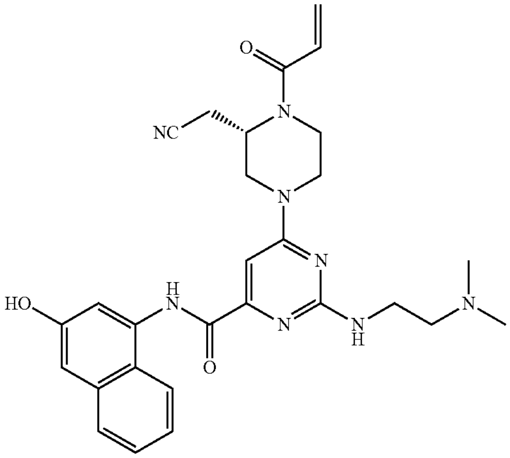 [SMILES: C=CC(=O)N1CCN(c2cc(C(=O)Nc3cc(O)cc4ccccc34)nc(NCCN(C)C)n2)C[C@@H]1CC#N] |

-continued
| Cmpd No. | Structure |
| --- | --- |
| 30 | 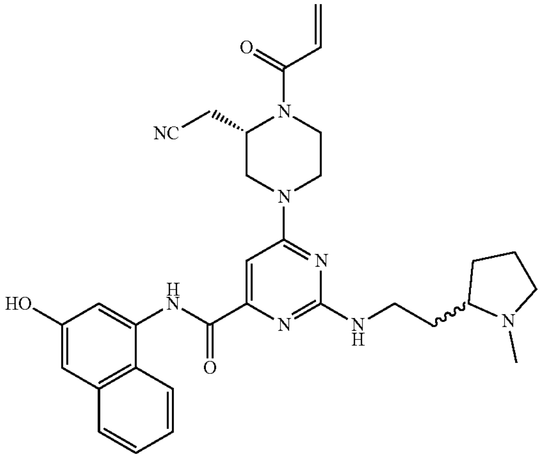 [SMILES: C=CC(=O)N1CCN(c2cc(C(=O)Nc3cc(O)cc4ccccc34)nc(NCCC3CCCN3C)n2)C[C@@H]1CC#N] |
| 31 | 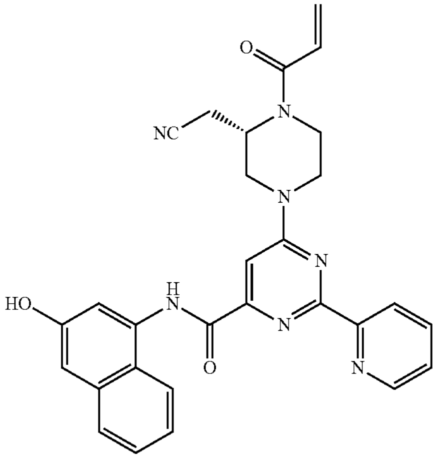 |
| 32 | 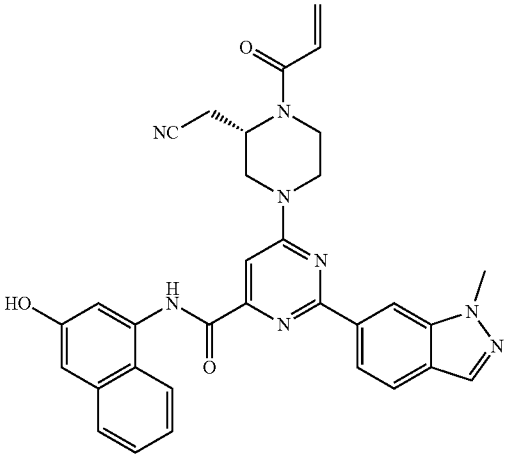 [SMILES: C=CC(=O)N1CCN(c2cc(C(=O)Nc3cc(O)cc4ccccc34)nc(-c3ccc4cnn(C)c4c3)n2)C[C@@H]1CC#N] |

-continued
| Cmpd No. | Structure |
|---|---|
| 33 | 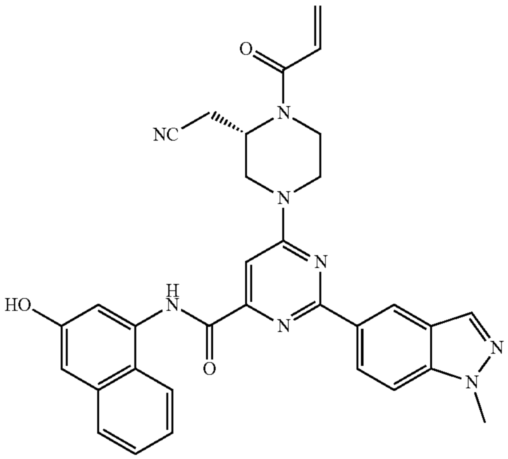 [SMILES: C=CC(=O)N1CCN(c2cc(C(=O)Nc3cc(O)cc4ccccc34)nc(-c3ccc4c(cnn4C)c3)n2)C[C@@H]1CC#N] |
| 34 | 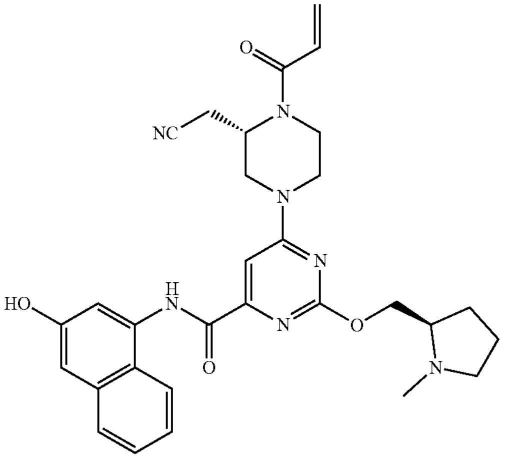 [SMILES: C=CC(=O)N1CCN(c2cc(C(=O)Nc3cc(O)cc4ccccc34)nc(OC[C@H]3CCCN3C)n2)C[C@@H]1CC#N] |
| 35 | 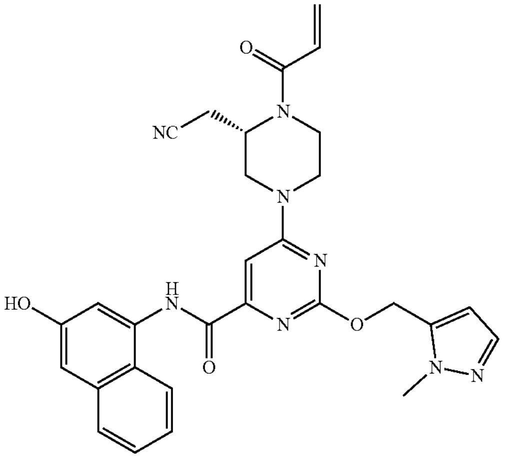 |

-continued
| Cmpd No. | Structure |
|---|---|
| 36 | 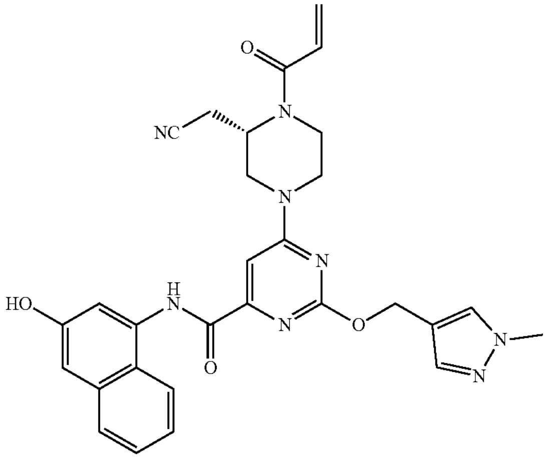 [SMILES: C=CC(=O)N1CCN(c2cc(C(=O)Nc3cc(O)cc4ccccc34)nc(OCc3cnn(C)c3)n2)C[C@@H]1CC#N] |
| 37 | 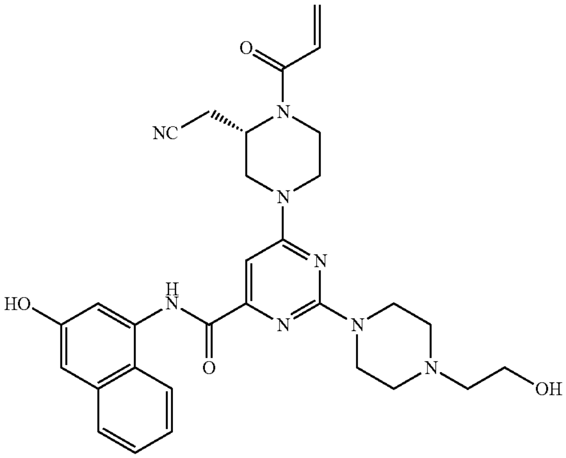 [SMILES: C=CC(=O)N1CCN(c2cc(C(=O)Nc3cc(O)cc4ccccc34)nc(N3CCN(CCO)CC3)n2)C[C@@H]1CC#N] |
| 38 | 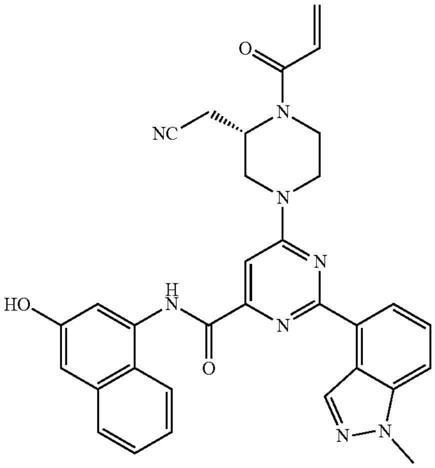 [SMILES: C=CC(=O)N1CCN(c2cc(C(=O)Nc3cc(O)cc4ccccc34)nc(-c3cccc4c3cnn4C)n2)C[C@@H]1CC#N] |

-continued
| Cmpd No. | Structure |
|---|---|
| 39 | 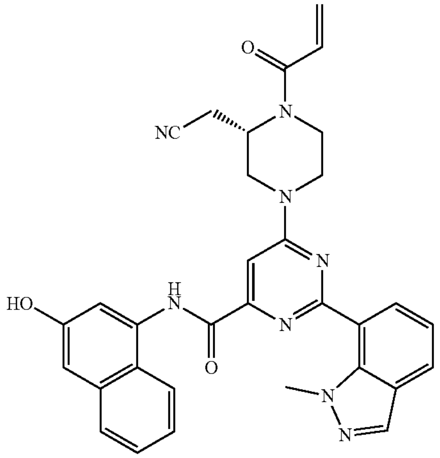 [SMILES: C=CC(=O)N1CCN(c2cc(C(=O)Nc3cc(O)cc4ccccc34)nc(-c3cccc4cnn(C)c34)n2)C[C@@H]1CC#N] |
| 40 | 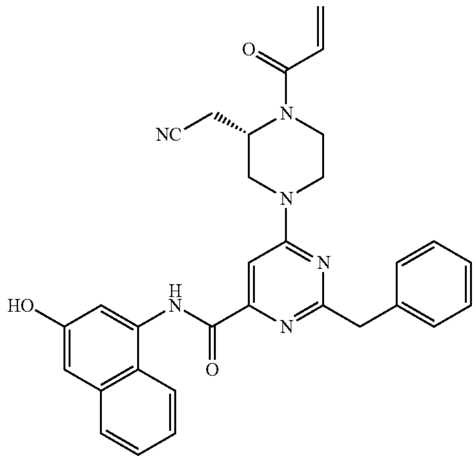 [SMILES: C=CC(=O)N1CCN(c2cc(C(=O)Nc3cc(O)cc4ccccc34)nc(Cc3ccccc3)n2)C[C@@H]1CC#N] |
| 41 | 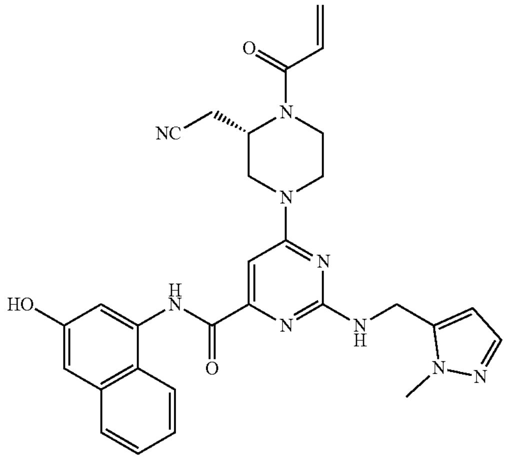 [SMILES: C=CC(=O)N1CCN(c2cc(C(=O)Nc3cc(O)cc4ccccc34)nc(NCc3ccnn3C)n2)C[C@@H]1CC#N] |

-continued
| Cmpd No. | Structure |
|---|---|
| 42 | 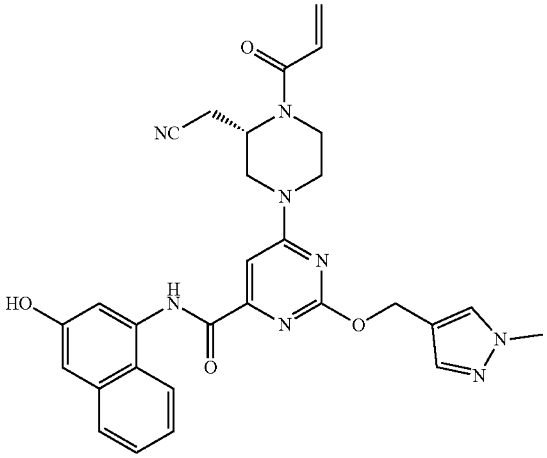 [SMILES: C=CC(=O)N1CCN(c2cc(C(=O)Nc3cc(O)cc4ccccc34)nc(OCc3cnn(C)c3)n2)C[C@@H]1CC#N] |
| 43 | 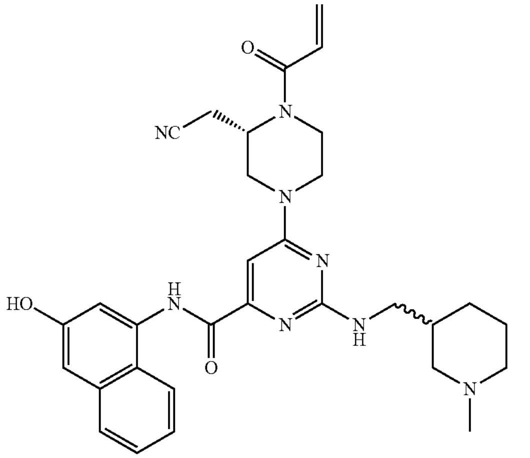 [SMILES: C=CC(=O)N1CCN(c2cc(C(=O)Nc3cc(O)cc4ccccc34)nc(NCC3CCCN(C)C3)n2)C[C@@H]1CC#N] |
| 44 | 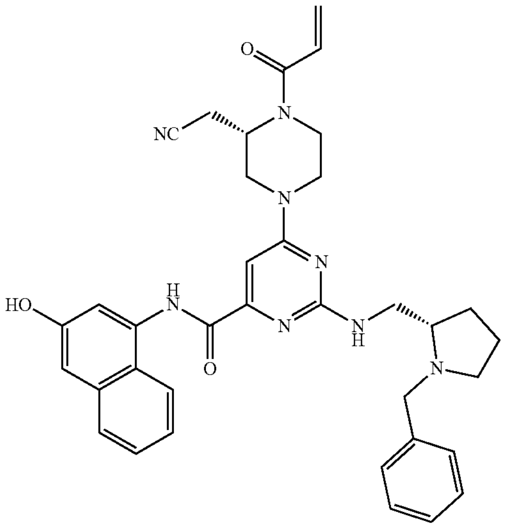 [SMILES: C=CC(=O)N1CCN(c2cc(C(=O)Nc3cc(O)cc4ccccc34)nc(NC[C@@H]3CCCN3Cc3ccccc3)n2)C[C@@H]1CC#N] |

-continued
| Cmpd No. | Structure |
| --- | --- |
| 45 | 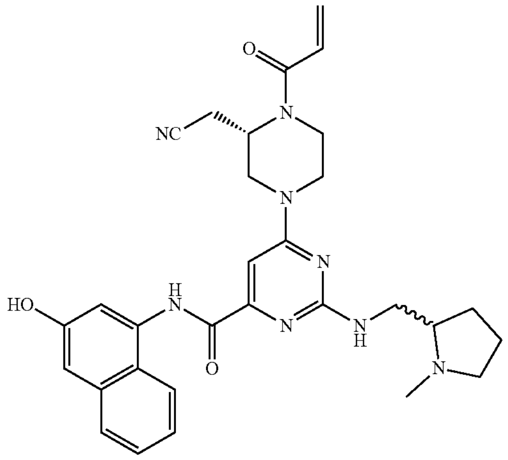 [SMILES: C=CC(=O)N1CCN(c2cc(C(=O)Nc3cc(O)cc4ccccc34)nc(NCC3CCCN3C)n2)C[C@@H]1CC#N] |
| 46 | 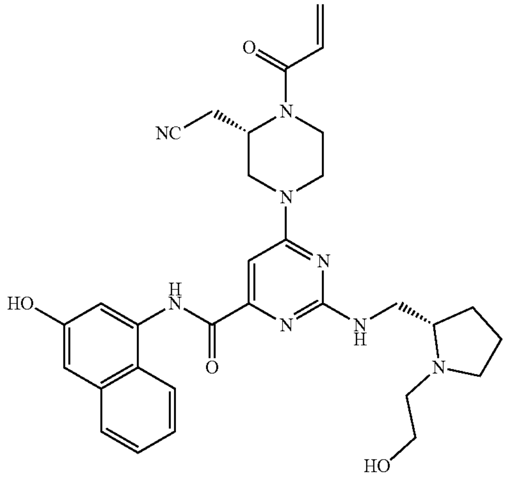 [SMILES: C=CC(=O)N1CCN(c2cc(C(=O)Nc3cc(O)cc4ccccc34)nc(NC[C@@H]3CCCN3CCO)n2)C[C@@H]1CC#N] |
| 47 | 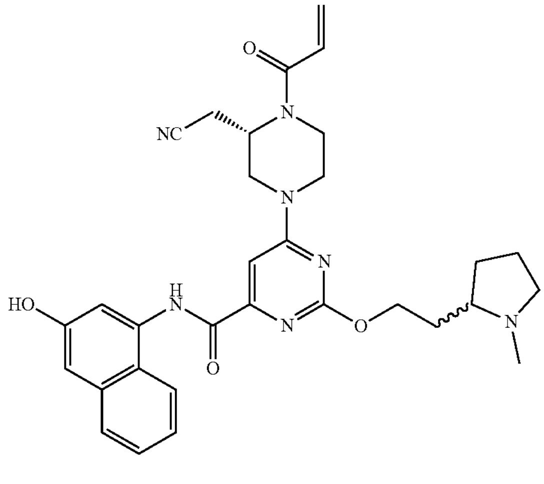 [SMILES: C=CC(=O)N1CCN(c2cc(C(=O)Nc3cc(O)cc4ccccc34)nc(OCCC3CCCN3C)n2)C[C@@H]1CC#N] |

-continued
| Cmpd No. | Structure |
| --- | --- |
| 48 | 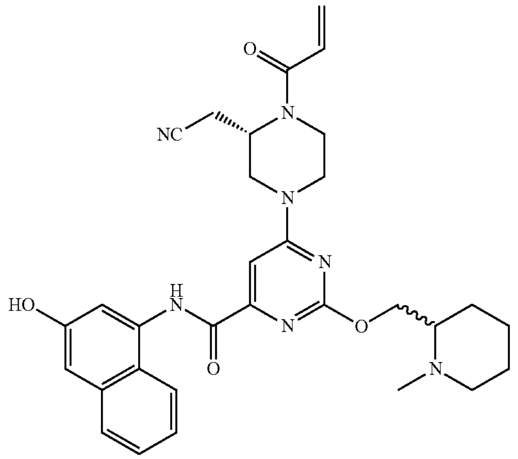 [SMILES: C=CC(=O)N1CCN(c2cc(C(=O)Nc3cc(O)cc4ccccc34)nc(OCC3CCCCN3C)n2)C[C@@H]1CC#N] |
| 49 | 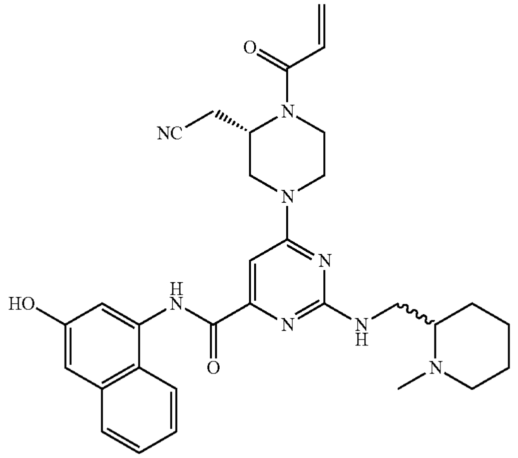 [SMILES: C=CC(=O)N1CCN(c2cc(C(=O)Nc3cc(O)cc4ccccc34)nc(NCC3CCCCN3C)n2)C[C@@H]1CC#N] |
| 50 | 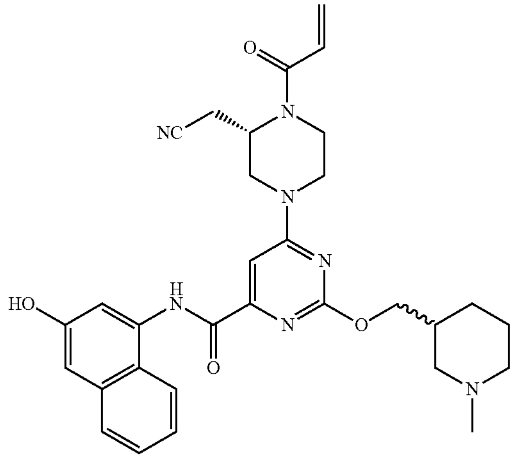 [SMILES: C=CC(=O)N1CCN(c2cc(C(=O)Nc3cc(O)cc4ccccc34)nc(OCC3CCCN(C)C3)n2)C[C@@H]1CC#N] |

-continued
| Cmpd No. | Structure |
| --- | --- |
| 51 | 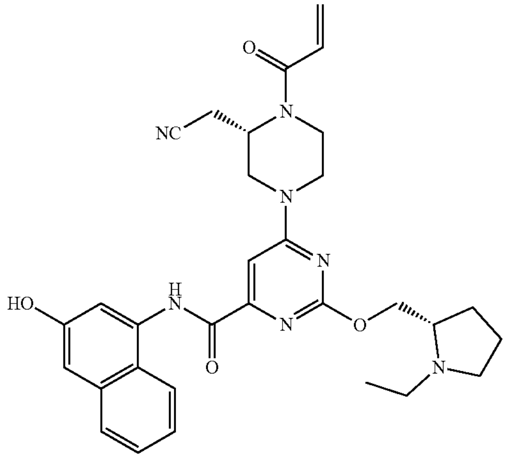 [SMILES: C=CC(=O)N1CCN(c2cc(C(=O)Nc3cc(O)cc4ccccc34)nc(OC[C@@H]3CCCN3CC)n2)C[C@@H]1CC#N] |
| 52 | 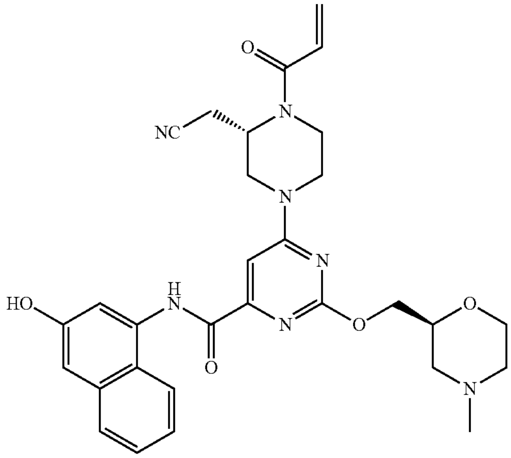 [SMILES: C=CC(=O)N1CCN(c2cc(C(=O)Nc3cc(O)cc4ccccc34)nc(OC[C@@H]3CN(C)CCO3)n2)C[C@@H]1CC#N] |
| 53 | 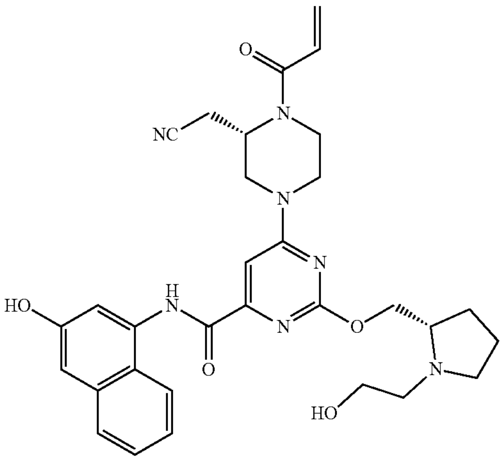 and |

-continued
| Cmpd No. | Structure |
|---|---|
| 54 | 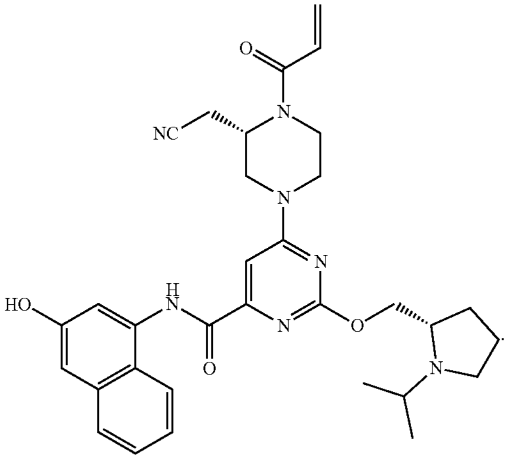 [SMILES: C=CC(=O)N1CCN(c2cc(C(=O)Nc3cc(O)cc4ccccc34)nc(OC[C@@H]3CCCN3C(C)C)n2)C[C@@H]1CC#N] |
or a pharmaceutically acceptable salt thereof.
In some embodiments, the compound of formula (I) is selected from the group consisting of:
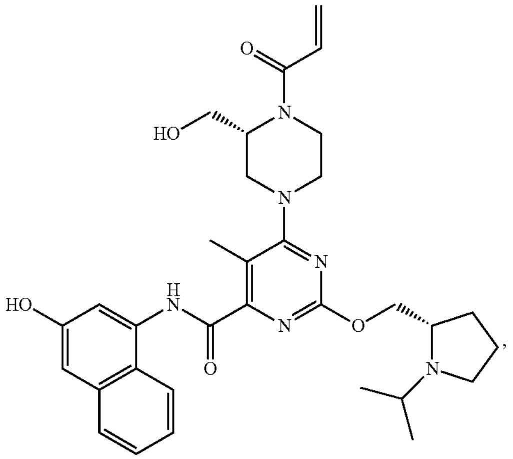
,
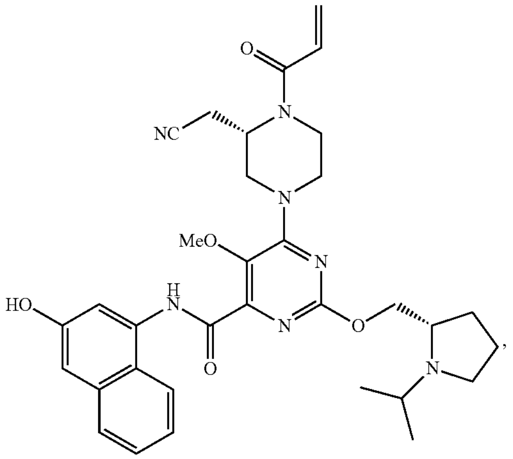
,
-continued
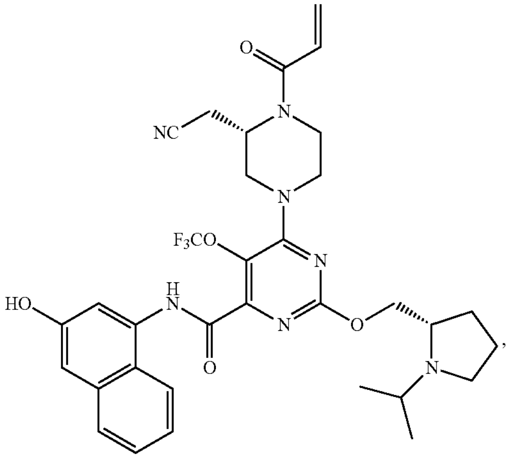
,
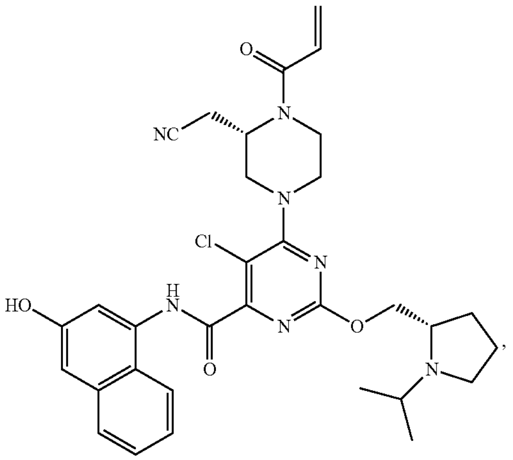
, -continued

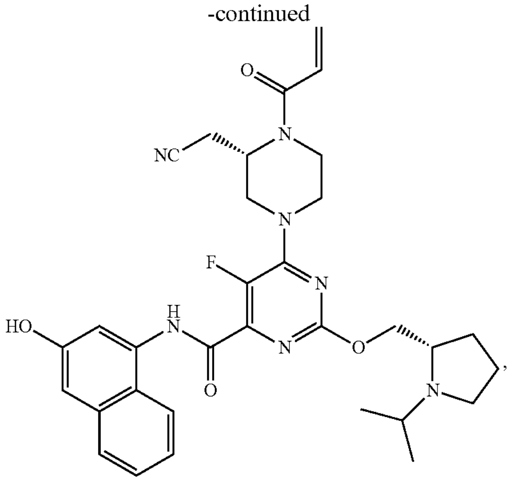

,

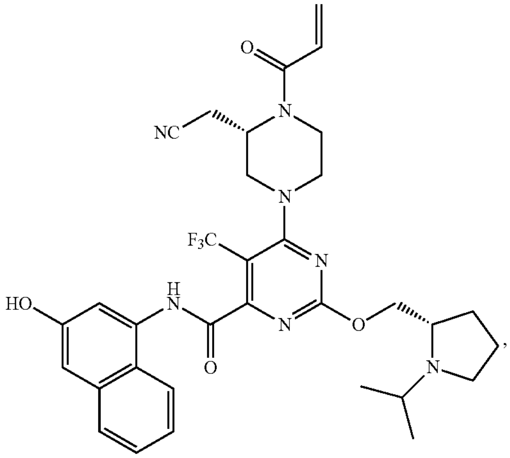

,

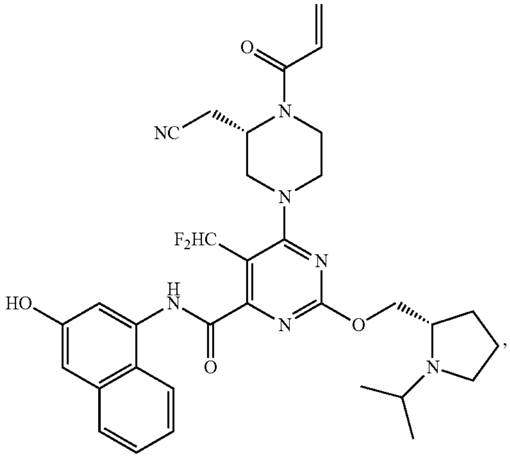

,

-continued

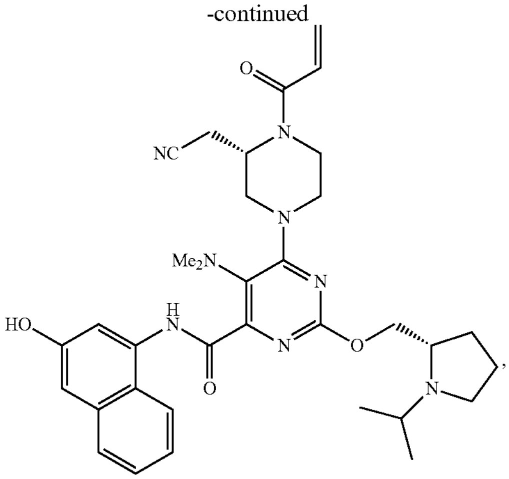

,

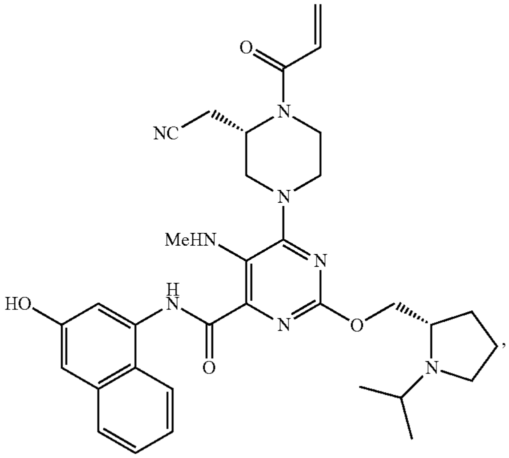

, and

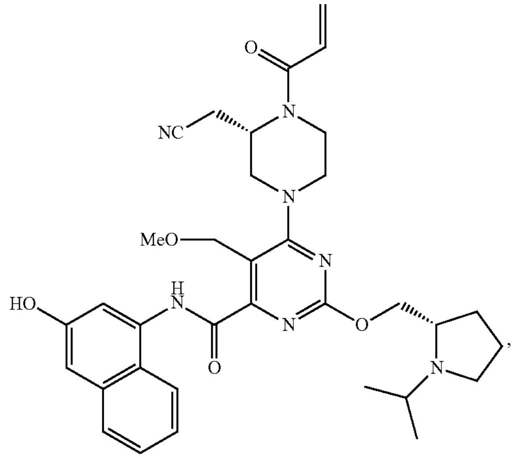 [SMILES: C=CC(=O)N1CCN(c2nc(OC[C@@H]3CCCN3C(C)C)nc(C(=O)Nc3cc(O)cc4ccccc34)c2COC)C[C@@H]1CC#N]

, or a pharmaceutically acceptable salt thereof.

As described herein, the compounds of the present disclosure include pharmaceutically acceptable salts, solvates and/or stereoisomers thereof. Where a compound has a stereocentre, both (R) and (S) stereoisomers are contemplated by the invention, equally mixtures of stereoisomers or a racemic mixture are completed by the present application. Where a compound of the disclosure has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100%, but could have an e.e. or d.e. of about at least 85%, at least 60% or less. For example, the e.e. or d.e. may be 95% or more, 90% or more, 80% or more, 70% or more, 60% or more, 50% or more, 40% or more, 30% or more, 20% or more, or 10% or more.

The present disclosure also contemplates pharmaceutically acceptable salts of the compounds described herein. These may include the acid addition and base salts of the compounds. These may be acid addition and base salts of the compounds. In addition, the invention contemplates solvates of the compounds. These may be hydrates or other solvated forms of the compound.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds disclosed herein (e.g., the compounds of formula (I)) may be prepared by one or more of three methods:

(i) by reacting the compound of the disclosure with the desired acid or base;

(ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the disclosure may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the disclosure are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the present disclosure include compounds of a number of formulae as herein defined, including all polymorphs and crystal habits thereof, prodrugs and isomers thereof (including optical, geometric and tautomeric isomers) as hereinafter defined and isotopically-labelled compounds of the invention.

The present disclosure also includes all pharmaceutically acceptable isotopically-labelled compounds of the invention wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Before purification, the compounds of the present disclosure may exist as a mixture of enantiomers depending on the synthetic procedure used. The enantiomers can be separated by conventional techniques known in the art. Thus, the present disclosure covers individual enantiomers as well as mixtures thereof.

For some of the steps of the process of preparation of the compounds of the disclosure, it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present disclosure as well as intermediates for the preparation thereof can be purified according to various well-known methods, such as for example crystallization or chromatography.

Pharmaceutical Compositions

In some embodiments, the present disclosure also provides pharmaceutical compositions comprising one or more compounds disclosed herein, e.g., a compound of formula (I), formula (Ia), formula (II), formula (IIa)-(IIc), formula (III), formula (IIIa)-(IIIc), formula (IV), and/or formula (IVa)-(IVc), or a pharmaceutically acceptable solvate, hydrate, tautomer, or salt thereof; and a pharmaceutically acceptable excipient or adjuvant.

In some embodiments, a pharmaceutical composition comprising one or more compounds disclosed herein, or a pharmaceutically acceptable solvate, hydrate, tautomer, or salt thereof, further comprises a pharmaceutically acceptable carrier. In some embodiments, a pharmaceutically acceptable carrier includes a pharmaceutically acceptable excipient, binder, and/or diluent. In some embodiments, suitable pharmaceutically acceptable excipients include, but are not limited to, acacia, animal oils, benzyl alcohol, benzyl benzoate, calcium stearate, carbomers, cetostearyl alcohol, cetyl alcohol, cholesterol, cyclodextrins, dextrose, diethanolamine, emulsifying wax, ethylene glycol palmitostearate, glycerin, glycerin monostearate, glycerol stearate, glyceryl monooleate, glyceryl monostearate, hydrous, histidine, hydrochloric acid, hydroxypropyl cellulose, hydroxypropyl-β-cyclodextrin (HPBCD), hypromellose (hydroxypropyl methylcellulose (HPMC)), lanolin, lanolin alcohols, lecithin, medium-chain triglycerides, metallic soaps, methylcellulose, mineral oil, monobasic sodium phosphate, monoethanolamine, oleic acid, polyethylene glycols (PEG 3350, PEG 4000, PEG 6000), polyoxyethylene-polyoxypropylene copolymer (poloxamer), polyoxyethylene alkyl ethers, polyoxyethylene castor oil, polyoxyethylene castor oil derivatives, polyoxyethylene sorbitan fatty acid esters, polyoxyethylene stearates, polysorbate, polyoxyethylene (20) sorbitan monolaurate (Tween 20, Polysorbate 20), polyoxyethylene (20) sorbitan monooleate (Tween 80, Polysorbate 80), povidone, propylene glycol alginate, saline, sodium chloride, sodium citrate, sodium citrate dihydrate, sodium hydroxide, sodium lauryl sulfate, sodium phosphate monobasic, sodium phosphate dibasic, sorbitan esters, stearic acid, stearyl alcohol, sunflower oil, tragacanth, triethanolamine, vegetable oils, water, xanthan gum, or a combinations thereof.

In some embodiments, the pharmaceutical composition further comprises an additional pharmaceutically active agent. In some embodiments, the additional pharmaceutically active is an anti-inflammatory agent, an anti-fibrotic agent, a chemotherapeutic, an anti-cancer agent, an immunosuppressant, an anti-tumour vaccine, a cytokine therapy, or a tyrosine kinase inhibitor. Non-limiting examples of additional active active agents suitable for use in a pharmaceutical composition disclosed herein are provided below.

Methods of Treatment

In some embodiments, the present disclosure provides a method for treating a condition modulated by RAS proteins in a subject in need thereof, the method comprising, administering to the subject a therapeutically effect amount of a compound disclosed herein (e.g., a compound of formula (I)), or a pharmaceutically acceptable salt thereof.

In some embodiments, the compound of the present disclosure is an inhibitor of KRAS proteins.

In some embodiments, the present disclosure provides a method for treating a condition modulated by RAS proteins in a subject in need thereof, the method comprising, administering to the subject a pharmaceutical composition disclosed herein.

In some embodiments, the condition modulated by RAS proteins is cancer. In some embodiments, the cancer is selected from the group consisting of sarcoma, melanoma, skin cancer, haematological tumors, lymphoma, carcinoma, and leukemia.

As discussed above, RAS signalling is instrumental in a number of conditions. In some embodiments, the condition is treatable by inhibiting RAS. In some embodiments, the condition treatable by the inhibition of RAS is cancer. In some embodiments, the cancer is sarcoma, melanoma, skin cancer, haematological tumors, lymphoma, carcinoma, or leukemia. In some embodiments, the cancer is cervical cancer, multiple myeloma, stomach cancer, bladder cancer, uterine cancer, esophageal squamous cell carcinoma, gastric cancer, glioblastomas, astrocytomas; retinoblastoma, osteosarcoma, chondosarcoma, Ewing's sarcoma, rabdomysarcoma, Wilm's tumor, basal cell carcinoma, non-small cell lung cancer, brain tumour, hormone refractory prostate cancer, prostate cancer, metastatic breast cancer, breast cancer, metastatic pancreatic cancer, pancreatic cancer, colorectal cancer, head and neck squamous cell carcinoma or cancer of the head and neck. In some embodiments, the condition is lung cancer, esophageal cancer, colorectal cancer, stomach cancer, bladder cancer, hepatocellular cancer, uterine cancer, cervical cancer, pancreatic cancer or ovarian cancer.

In some embodiments, the present disclosure provides a compound having a RAS binding affinity within category A, B or C as defined below. In some embodiments, the present disclosure provides compounds having a RAS G12C binding such that ≥70% of the compound remains at the indicated timepoint (category A). In some embodiments, is the present disclosure provides compounds having a RAS G12C binding such that 30%-70% of the compound remains at the indicated timepoint (category B). In some embodiments, the present disclosure provides compounds having a RAS G12C binding such that ≤30% of the compound remains at the indicated timepoint (category C). Optionally, the binding activity is determined using the assay for RAS inhibition defined in the examples.

In some embodiments, one or more compounds of the present disclosure is combined with one or more additional pharmaceutical agents, for example anti-inflammatory agents, anti-fibrotic agents, chemotherapeutics, anti-cancer agents, immunosuppressants, anti-tumour vaccines, cytokine therapy, or tyrosine kinase inhibitors, for the treatment of conditions modulated by the inhibition of RAS proteins, for example cancer, sarcoma, melanoma, skin cancer, haematological tumors, lymphoma, carcinoma, and leukemia.

In some embodiments, the present disclosure provides compounds for use as a medicament.

In some embodiments, the present disclosure provides a method of treating a condition modulated by inhibition of KRAS proteins in a subject in need thereof, the method comprising administering a therapeutically effective amount of a compound disclosed herein or a pharmaceutical composition to the subject.

In some embodiments, the present disclosure provides a pharmaceutical formulation comprising a compound disclosed herein and a pharmaceutically acceptable excipient.

In some embodiments, the present disclosure provides a compound for use in the treatment of a condition which is modulated by RAS. In some embodiments, conditions that are modulated by RAS are conditions that are treatable by the inhibition of RAS using a compound of the present disclosure. A compound of any formula disclosed herein may be for use in the treatment of a condition treatable by the inhibition of RAS.

In some embodiments, the condition treatable by a compound disclosed herein is associated with a KRAS mutation. In some embodiments, the KRAS mutation is a G12C mutation.

The method of treatment or the compound for use in the treatment of cancer, sarcoma, melanoma, skin cancer, haematological tumors, lymphoma, carcinoma, and leukemia as defined herein may be applied as a sole therapy or be a combination therapy with an additional active agent.

In some embodiments, the method of treatment or the compound for use in the treatment of cancer, sarcoma, melanoma, skin cancer, haematological tumors, lymphoma, carcinoma, and leukemia comprises, in addition to the compound of disclosed herein (e.g., a compound of formula (I)), comprises one or more additional active agents. The additional active agents may be one or more active agents used to treat the condition being treated by the compound of the disclosure. In some embodiments, the additional active agent is one or more of the following active agents:

(i) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(ii) TNF inhibitors for example etanercept; monoclonal antibodies (e.g. infliximab (Remicade), adalimumab (Humira), certolizumab pegol (Cimzia), golimumab (Simponi)); fusion proteins (e.g. etanercept (Enbrel)); and 5-HT2A agonists (e.g. 2,5-dimethoxy-4-iodoamphetamine, TCB-2, lysergic acid diethylamide (LSD), lysergic acid dimethylazetidine);

(iii) anti-inflammatory drugs, for example non-steroidal anti-inflammatory drugs;

(iv) dihydrofolate reductase inhibitors/antifolates, for example methotrexate, trimethoprim, brodimoprim, tetroxoprim, iclaprim, pemetrexed, raltitrexed and pralatrexate; and (v) immunosuppressants for example cyclosporins, tacrolimus, sirolimus pimecrolimus, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides.

(vi) anti-fibrotic agents for example: Pirfenidone, Nintedanib, Anti-IL-13 monoclonal antibodies (e.g. Tralokinumab, QAX576, Lebrikizumab), simtuzumab, FG-3019, lysophosphatidic acid receptor antagonists (e.g. BMS-986020, AM966), LOXL2 inhibitors, BET bromodomain inhibitors (e.g. JQ1), HDAC inhibitors (e.g. Vorinostat), thrombin inhibitors (e.g. Dabigatran), FactorXa inhibitors (e.g. Apixban, Rivaroxaban) 15PGDH inhibitors, anti-αvβ6 monoclonal antibodies (e.g. BG00011), Anti-CTGF monoclonal antibodies (e.g. FG-3019), PAR1 inhibitors, Nox4 inhibitors and PAI-1 inhibitors.

(vii) CNS therapies, for example: Levodopa, Dopamine agonists, Apomorphine, Glutamate antagonist, Anticholinergics, COMT inhibitors, MAO-B inhibitors, riluzole (Rilutek), Tetrabenazine (Xenazine), haloperidol (Haldol), chlorpromazine, risperidone (Risperdal), quetiapine (Seroquel), amantadine, levetiracetam (Keppra), clonazepam (Klonopin), Donepezil (Aricept), Galantamine (Razadyne), Rivastigmine (Exelon)), Memantine (Ebixa, Axura), Aducanumab, Ocrelizumab, interferon beta-1a (Avonex, Rebif), peginterferon beta-1a (Plegridy), teriflunomide (Aubagio), fingolimod (Gilenya), mitoxantrone (Novantrone), dimethyl fumarate (Tecfidera), natalizumab (Tysabri)

The method of treatment or the compound for use in the treatment of cancer, such as sarcoma, melanoma, skin cancer, haematological tumors, lymphoma, carcinoma, leukemia, and central nervous system disorders may involve, in addition to administering a compound disclosed herein or pharmaceutical composition thereof, conventional surgery or radiotherapy or chemotherapy. Such chemotherapy may include one or more of the following categories of anti-tumor agents:

(i) antiproliferative/antineoplastic drugs and combinations thereof, such as alkylating agents (for example cis platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5 fluorouracil and tegafur, raltitrexed, methotrexate, pemetrexed, cytosine arabinoside, floxuridine, cytarabine, 6-mercaptopurine, 6-thioguanine, fludarabine phosphate, pentostatine, and gemcitabine and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin); bleomcin, dactinomycin, daunorubicin, doxorubicin, epirubicin, idarubicin, ara-C, paclitaxel (Taxol™), nabpaclitaxel, docetaxel, mithramycin, deoxyco-formycin, mitomycin-C, L-asparaginase, interferons (especially IFN-a), etoposide, and teniposide;

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride; and navelbene, CPT-II, anastrazole, letrazole, capecitabine, reloxafme, cyclophosphamide, ifosamide, and droloxafine;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti erbB2 antibody trastuzumab [Herceptin™], the anti-EGFR antibody panitumumab, the anti erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (Cl 1033), erbB2 tyrosine kinase inhibitors such as lapatinib) and antibodies to costimulatory molecules such as CTLA-4, 4-IBB and PD-I, or antibodies to cytokines (IL-I0, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors; and CCR2, CCR4 or CCR6 modulator;

(v) antiangiogenic agents such as those which inhibit the effects of vascular endothelial growth factor, for example the anti vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); and toll-like receptor modulators for example TLR-7 or TLR-9 agonists; and (viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine; PD-1, PD-L1, PD-L2 and CTL4-A modulators, antibodies and vaccines; other IDO inhibitors (such as indoximod); anti-PD-1 monoclonal antibodies (such as MK-3475 and nivolumab); anti-PD-L1 monoclonal antibodies (such as MEDI-4736 and RG-7446); anti-PD-L2 monoclonal antibodies; and anti-CTLA-4 antibodies (such as ipilimumab);

(xii) chimeric antigen receptors, anticancer vaccines and arginase inhibitors.

Such combination treatment may be achieved by way of the simultaneous, sequential or separate dosing of the individual components of the treatment. Such combination products employ the compounds of the present disclosure within a therapeutically effective dosage range described herein and the additional pharmaceutically-active agent within its approved dosage range.

Compounds of the disclosure may exist in a single crystal form or in a mixture of crystal forms or they may be amorphous. Thus, compounds of the disclosure intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

Administration

For the above-mentioned compounds of the present disclosure, the dosage administered will vary with the compound employed, the mode of administration, the treatment desired and the disorder indicated. For example, if the compound of the disclosure is administered orally, then the daily dosage of the compound of the disclosure may be in the range from 0.01 micrograms per kilogram body weight (μg/kg) to 100 milligrams per kilogram body weight (mg/kg).

A compound of the present disclosure, or pharmaceutically acceptable salt thereof, may be used on its own, but in some embodiments is administered in the form of a pharmaceutical composition in which the compounds of the disclosure, or pharmaceutically acceptable salt thereof, is provided with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds disclosed herein, the pharmaceutical composition, which is used to administer the compound, comprises from 0.05 to 99% by weight of compound, from 0.05 to 80% by weight of compound, from 0.10 to 70% by weight of compound, or from 0.10 to 50% by weight, with all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration, the compounds of the disclosure may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the disclosure may be admixed with, for example, a vegetable oil or polyethylene glycol. Hard gelatine capsules may contain granules of the compound using either the above-mentioned excipients for tablets. Also, liquid or semisolid formulations of the compound of the disclosure may be filled into hard gelatine capsules. Liquid preparations for oral application may be in the form of syrups or suspensions, for example, solutions containing the compound of the disclosure, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration, the compounds of the disclosure may be administered as a sterile aqueous or oily solution.

The size of the dose for therapeutic purposes of compounds of the disclosure will naturally vary according to the nature and severity of the conditions, the age and sex of the animal or patient and the route of administration, according to well-known principles of medicine.

Dosage levels, dose frequency, and treatment durations of compounds of the disclosure are expected to differ depending on the formulation and clinical indication, age, and co-morbid medical conditions of the patient.

EXAMPLES

As used herein the following terms have the meanings given: "Boc" refers to tert-butyloxycarbonyl; "Cbz" refers to carboxybenzyl; "dba" refers to dibenzylideneacetone; "DCM" refers to dichloromethane; "DIPEA" refers to N,N-diisopropylethylamine; "DMA" refers to dimethylacetamide; "DMF" refers to N,N-dimethylformamide; "DMSO" refers to dimethyl sulfoxide; "dppf" refers to 1,1'-bis(diphenylphosphino)ferrocene; "EtOAc" refers to ethyl acetate; "EtOH" refers to ethanol; "$Et_2O$" refers to diethyl ether; "IPA" refers to isopropyl alcohol; "LiHMDS" refers to lithium bis(trimethylsilyl)amide; "mCPBA" refers to meta-chloroperoxybenzoic acid; "MeCN" refers to acetonitrile; "MeOH" refers to methanol; "min" refers to minutes; "NMR" refers to nuclear magnetic resonance; "PhMe" refers to toluene; "pTsOH" refers to p-toluenesulfonic acid; "py" refers to pyridine; "r.t." refers to room temperature; "SCX" refers to strong cation exchange; "T3P" refers to propylphosphonic anhydride; "$Tf_2O$" refers to trifluoromethanesulfonic anhydride; "THF" refers to tetrahydrofuran; "THP" refers to 2-tetrahydropyranyl; "(UP)LC-MS" refers to (ultra performance) liquid chromatography/mass spectrometry. Solvents, reagents and starting materials were purchased from commercial vendors and used as received unless otherwise described. All reactions were performed at room temperature unless otherwise stated. Compound identity and purity confirmations were performed by LC-MS UV using a Waters Acquity SQ Detector 2 (ACQ-SQD2 #LCA081). The diode array detector wavelength was 254 nM and the MS was in positive and negative electrospray mode (m/z: 150-800). A 2 μL aliquot was injected onto a guard column (0.2 μm×2 mm filters) and UPLC column (C18, 50×2.1 mm, <2 μm) in sequence maintained at 40° C. The samples were eluted at a flow rate of 0.6 mL/min with a mobile phase system composed of A (0.1% (v/v) formic acid in water) and B (0.1% (v/v) formic acid in MeCN) according to the gradients outlined below. Retention times RT are reported in minutes.

| Time (min) | % A | % B |
|---|---|---|
| Method 1 | | |
| 0 | 95 | 5 |
| 1.1 | 95 | 5 |
| 6.1 | 5 | 95 |
| 7 | 5 | 95 |
| 7.5 | 95 | 5 |
| 8 | 95 | 5 |

-continued

| Time (min) | % A | % B |
|---|---|---|
| Method 2 | | |
| 0 | 95 | 5 |
| 0.3 | 95 | 5 |
| 2 | 5 | 95 |
| 2.6 | 95 | 5 |
| 3 | 95 | 5 |

NMR was also used to characterise final compounds. $^1$H NMR Spectra were recorded at 400 MHz using a Bruker AVANCE 400 MHz spectrometer.

Optionally, compound Rf values on silica thin layer chromatography (TLC) plates were measured.

Compound purification was performed by flash column chromatography on silica or by preparative LC-MS. LC-MS purification was performed using a Waters 3100 Mass detector in positive and negative electrospray mode (m/z: 150-800) with a Waters 2489 UV/Vis detector.

Alternatively, compound identity and purity confirmations were performed by the following LCMS equipment and conditions:

Method A

LC: Agilent Technologies 1290 series; Binary Pump; Diode Array Detector; Column: Agilent Eclipse Plus RRHD C18, 1.8 μm, 3.0×50 mm; Column Temperature: 40° C.; Acquisition wavelength: 214 nm, 254 nm; Mobile phase: A: 0.05% Formic acid in water (v/v), B: 0.05% Formic acid in MeCN (v/v); Run time: 3.0 min; Flow Rate: 0.8 mL/min Gradient:

| T (min) | A (%) | B (%) |
|---|---|---|
| 0.00 | 60 | 40 |
| 2.65 | 0 | 100 |
| 3.00 | 0 | 100 |

MS: G6120A, Quadrupole LC/MS; Ion Source: ESI; Signal: positive; TIC: 70~1000 m/z; Fragmentor: 60; Threshold: 5; Gain: 1; Drying gas flow: 10 L/min; Nebulizer pressure: 35 psi Method B LC: Agilent Technologies 1290 series; Binary Pump; Diode Array Detector; Column: Agilent Eclipse Plus RRHD C18, 1.8 μm, 3.0×50 mm; Column Temperature: 40° C.; Acquisition wavelength: 214 nm, 254 nm; Mobile phase: A: 0.05% Formic acid in water (v/v), B: 0.05% Formic acid in MeCN (v/v); Run time: 3.0 min; Flow Rate: 0.8 mL/min Gradient:

| T (min) | A(%) | B(%) |
|---|---|---|
| 0.00 | 80 | 20 |
| 2.65 | 20 | 80 |
| 3.00 | 20 | 80 |

MS: G6120A, Quadrupole LC/MS; Ion Source: ESI; Signal: positive; TIC: 70~1000 m/z; Fragmentor: 60; Threshold: 5; Gain: 1; Drying gas flow: 10 L/min; Nebulizer pressure: 35 psi Method C LC: Agilent Technologies 1290 series; Binary Pump; Diode Array Detector; Column: Agilent Eclipse Plus RRHD C18, 1.8 μm, 3.0×50 mm; Column Temperature: 40° C.; Acquisition wavelength: 214 nm, 254 nm; Mobile phase: A: 0.05% Formic acid in water (v/v), B: 0.05% Formic acid in MeCN (v/v); Run time: 3.0 min; Flow Rate: 0.8 mL/min Gradient:

| T (min) | A (%) | B (%) |
|---|---|---|
| 0.00 | 92 | 8 |
| 2.50 | 40 | 60 |
| 3.00 | 20 | 80 |

MS: G6120A, Quadrupole LC/MS; Ion Source: ESI; Signal: positive; TIC: 70~1000 m/z; Fragmentor: 60; Threshold: 5; Gain: 1; Drying gas flow: 10 L/min; Nebulizer pressure: 35 psi Method D LC: Shimadzu 2020 series; Binary Pump; Diode Array Detector; Column: Agilent Poroshell 120 EC-C18, 2.7 μm, 4.6×50 mm; Column Temperature: 35° C.; Acquisition wavelength: 214 nm, 254 nm; Mobile Phase: A: 0.05% Formic acid in water (v/v), B: 0.05% Formic acid in ACN (v/v); Run time: 5.0 min; Flow rate: 1.0 mL/min Gradient:

| T (min) | A (%) | B (%) |
|---|---|---|
| 0.00 | 50 | 50 |
| 0.50 | 50 | 50 |
| 4.00 | 0 | 100 |
| 4.50 | 0 | 100 |
| 4.51 | 50 | 50 |
| 5.00 | 50 | 50 |

MS: Ion Source: ESI; Signal: positive and negative

TIC: 100~900 m/z; Fragmentor: 60; Threshold: 5; Gain: 1; Drying gas: 20 L/min;

Nebulizing Gas: 1.5 L/min

Method E

LC: Shimadzu 2020 series; Binary Pump; Diode Array Detector; Column: Agilent Poroshell 120 EC-C18, 2.7 μm, 4.6×50 mm; Column Temperature: 35° C.; Acquisition wavelength: 214 nm, 254 nm; Mobile Phase: A: 0.05% Formic acid in water (v/v), B: 0.05% Formic acid in ACN (v/v); Run time: 5.0 min; Flow rate: 1.0 mL/min Gradient:

| T (min) | A (%) | B (%) |
|---|---|---|
| 0.01 | 85 | 15 |
| 1.0 | 85 | 15 |
| 4.0 | 0 | 100 |
| 4.5 | 0 | 100 |
| 4.51 | 85 | 15 |
| 5.0 | 85 | 15 |

MS: Ion Source: ESI; Signal: positive and negative; TIC: 100~900 m/z; Fragmentor: 60; Threshold: 5; Gain: 1; Drying gas: 20 L/min; Nebulizing Gas: 1.5 L/min Method F LC: Shimadzu LC-20XR series; Binary Pump; Diode Array Detector; Column: Waters ACQUITY UPLC HSS C18, 1.8 μm, 3.0×50 mm; Column Temperature: 25° C.; Acquisition wavelength: 214 nm, 254 nm; Mobile phase: A: 0.05% Formic acid in water (v/v), B: 0.05% Formic acid in ACN (v/v); Run time: 3.0 min; Flow Rate: 0.5 mL/min Gradient:

| T (min) | A (%) | B (%) |
|---|---|---|
| 0.01 | 70 | 30 |
| 2.00 | 5 | 95 |
| 2.50 | 5 | 95 |
| 2.51 | 70 | 30 |
| 3.00 | 70 | 30 |

MS: 2020, Quadrupole LC/MS, Ion Source: API-ESI; TIC: 100~900 m/z; Drying gas flow: 15 L/min; Nebulizer pressure: 1.5 L/min; Drying gas temperature: 250° C.; Vcap: 4500V.

Method G

LC: Shimadzu 2020 series; Binary Pump; Diode Array Detector; Column: Agilent Poroshell 120 EC-C18, 2.7 μm, 4.6×50 mm; Column Temperature: 35° C.; Acquisition wavelength: 214 nm, 254 nm; Mobile Phase: A: 0.05% Formic acid in water (v/v), B: 0.05% Formic acid in ACN (v/v); Run time: 5.0 min; Flow rate: 1.0 ml/min Gradient:

| T (min) | A (%) | B (%) |
|---|---|---|
| 0.01 | 97 | 3 |
| 1.0 | 97 | 3 |
| 4.0 | 30 | 70 |
| 4.01 | 0 | 100 |
| 4.5 | 0 | 100 |
| 4.51 | 97 | 3 |
| 5.0 | 97 | 3 |

MS: Ion Source: ESI; Signal: positive and negative; TIC: 100~900 m/z; Fragmentor: 60 Threshold: 5; Gain: 1; Drying gas: 20 L/min; Nebulizing Gas: 1.5 L/min Chemical names in this document were generated using mol2nam—Structure to Name Conversion by OpenEye Scientific Software. Starting materials were purchased from commercial sources or synthesised according to literature procedures.

Synthesis of Intermediates

Intermediate 1—2,6-dichloropyrimidine-4-carboxylic acid

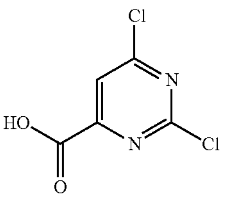 [SMILES: O=C(O)c1cc(Cl)nc(Cl)n1]

Orotic acid (1.00 g, 6.41 mmol) was dissolved in $POCl_3$ (5.97 mL, 64.06 mmol) and dimethylaniline (0.89 mL, 7.05 mmol) and the mixture stirred and heated at 110° C. for 4.5 hours. The reaction was cooled to room temperature and solvent removed in vacuo. The reaction was then poured into ice-water (250 mL) and extracted with $Et_2O$ (3×250 mL). The combined organic layers were dried over $Na_2SO_4$ and concentrated in vacuo to give 2,6-dichloropyrimidine-4-carboxylic acid (Intermediate 1) (1.23 g, 6.37 mmol, 99% yield) as yellow solid. The compound was used without further purification.

UPLC-MS (ES+, Method 2): 0.94 min, m/z 192.4, 194.9, 196.7 $[M+H]^+$.

$^1$H-NMR (400 MHz, DMSO-$d_6$) δ/ppm: 8.16 (1H, s), exchangeable proton not seen.

Intermediate 2—Ethyl 2,6-dichloropyrimidine-4-carboxylate

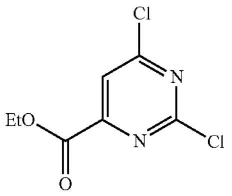 [SMILES: CCOC(=O)c1cc(Cl)nc(Cl)n1]

Orotic acid (9.00 g, 57.66 mmol) was added to a stirring solution of $POCl_3$ (5.37 mL, 57.66 mmol) and dimethylaniline (7.31 mL, 57.66 mmol) at room temperature under a nitrogen atmosphere. The reaction was heated to 110° C. for 18 hours, after which time EtOH quench of a sample showed desired product. The reaction was cooled to room temperature and excess $POCl_3$ removed in vacuo. The residue was taken up in DCM (100 mL) and loaded into a dropping funnel. This was added slowly to a stirring solution of DCM (100 mL), EtOH (10 mL) and DIPEA (10.04 mL, 57.66 mmol). After stirring for 5 minutes the mixture was poured into sat. aq. $NaHCO_3$ (500 mL) and DCM (500 mL) was added. The organic layer was separated, dried over $Na_2SO_4$ and solvent removed in vacuo. The residue was purified by column chromatography using an eluent of 0-60% EtOAc in petroleum ether reached via a gradient to give ethyl 2,6-dichloropyrimidine-4-carboxylate (Intermediate 2) (9.48 g, 43.00 mmol, 74% yield) as a yellow oil.

UPLCMS (ES+, Method 2): 1.55 min, m/z 220.9, 222.9, 224.9 $[M+H]^+$.

$^1$H NMR (400 MHz, $CDCl_3$) δ/ppm: 7.99 (1H, s), 4.54 (2H, q, J=7.2 Hz), 1.46 (3H, t, J=7.2 Hz).

Intermediate 3—benzyl (2S)-2-(cyanomethyl)piperazine-1-carboxylate hydrochloride

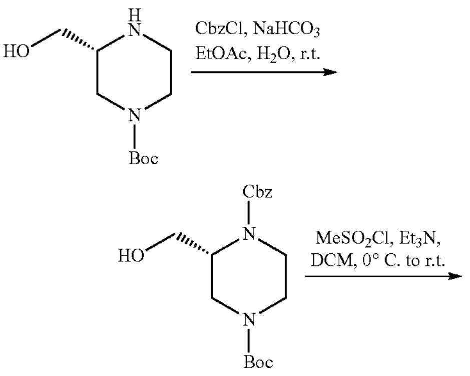

-continued

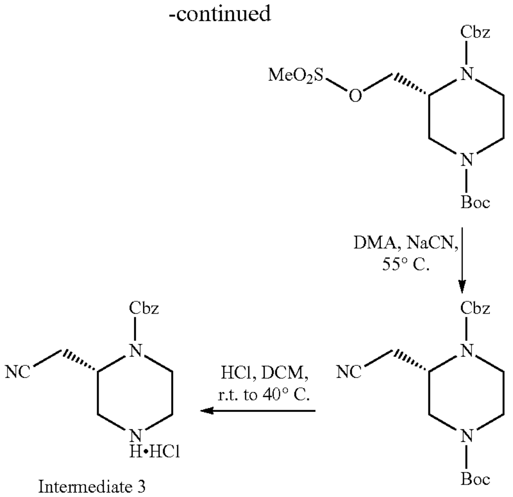

Intermediate 3

Step 1—O1-benzyl O4-tert-butyl (2R)-2-(hydroxymethyl)piperazine-1,4-dicarboxylate To a stirred biphasic solution of tert-butyl (3R)-3-(hydroxymethyl)piperazine-1-carboxylate (1.00 g, 4.62 mmol) and $NaHCO_3$ (1.16 g, 13.87 mmol) in EtOAc (10 mL) and water (10 mL) at 0° C. was added benzyl chloroformate (0.99 mL, 6.94 mmol) dropwise. The reaction mixture was stirred at room temperature overnight. The reaction mixture was then diluted with EtOAc (250 mL) and the organic layer separated, dried over $Na_2SO_4$ and concentrated in vacuo. The crude material was purified by column chromatography using an eluent of 0-50% EtOAc in petroleum ether reached via a gradient to give O1-benzyl O4-tert-butyl (2R)-2-(hydroxymethyl)piperazine-1,4-dicarboxylate (1.60 g, 4.57 mmol, 99% yield) as a colourless oil.

UPLC-MS (ES+, Method 2): 1.65 min, m/z 251.2 $[M\text{-}Boc+H]^+$.

$^1$H-NMR (400 MHz, $CDCl_3$) δ/ppm: 7.41-7.30 (5H, m), 5.15 (2H, d, J=2.8 Hz), 4.38-4.16 (2H, m), 4.08-3.83 (2H, m), 3.78-3.47 (2H, m), 3.22-2.60 (4H, m), 1.47 (9H, s).

Step 2—O1-benzyl O4-tert-butyl (2R)-2-(methylsulfonyloxymethyl)piperazine-1,4-dicarboxylate O1-benzyl O4-tert-butyl (2R)-2-(hydroxymethyl)piperazine-1,4-dicarboxylate (1.60 g, 4.57 mmol) and $Et_3N$ (0.95 mL, 6.85 mmol) were dissolved in DCM (30 mL) and cooled to 0° C. Methanesulfonyl chloride (0.53 mL, 6.85 mmol) was added dropwise and the reaction was left stirring at room temperature for 20 minutes. The reaction mixture was then diluted with DCM (250 mL), washed with 1M aq. HCl (250 mL), water (250 mL), sat. aq. $NaHCO_3$ (250 mL), and brine (250 mL), dried over $Na_2SO_4$ and concentrated in vacuo to give O1-benzyl O4-tert-butyl (2R)-2-(methylsulfonyloxymethyl)piperazine-1,4-dicarboxylate (1.95 g, 4.55 mmol, 100% yield) as a colourless oil.

UPLC-MS (ES+, Method 2): 1.77 min, m/z 373.7 $[M\text{-}^tBu+H]^+$.

$^1$H-NMR (400 MHz, DMSO-$d_6$) δ/ppm: 7.45-7.28 (5H, m), 5.11 (2H, s), 4.37 (1H, br s), 4.30-4.13 (2H, m), 3.99-3.76 (3H, m), 3.26-2.71 (6H, m), 1.40 (9H, s).

Step 3—O1-benzyl O4-tert-butyl (2S)-2-(cyanomethyl)piperazine-1,4-dicarboxylate

O1-benzyl O4-tert-butyl (2R)-2-(methylsulfonyloxymethyl)piperazine-1,4-dicarboxylate (1.95 g, 4.55 mmol) was dissolved in DMA (46 mL) followed by the addition of NaCN (446 mg, 9.10 mmol). The reaction was stirred at 55° C. for 48 hours. A second portion of NaCN (111 mg, 2.28 mmol) was added and the reaction was left to stir for 72 hours. The mixture was then partitioned between EtOAc (250 mL) and brine (250 mL), and the organic layer washed with brine (3×250 mL), dried over $Na_2SO_4$ and solvent removed in vacuo. The residue was purified by column chromatography using an eluent of 0-100% EtOAc in petroleum ether reached via a gradient to give O1-benzyl O4-tert-butyl (2S)-2-(cyanomethyl)piperazine-1,4-dicarboxylate (1.2 g, 3.34 mmol, 73% yield) as a colourless oil.

UPLC-MS ($ES^+$, Method 2): 1.77 min, m/z 304.3 $[M\text{-}^tBu+H]^+$.

$^1$H-NMR (400 MHz, $CDCl_3$) δ/ppm: 7.41-7.33 (5H, m), 5.17 (2H, s), 4.55 (1H, brs), 4.06 (3H, br s), 3.25-2.96 (2H, m), 2.95-2.76 (1H, m), 2.74-2.44 (2H, m), 1.48 (9H, s).

Step 4—benzyl (2S)-2-(cyanomethyl)piperazine-1-carboxylate hydrochloride

O1-benzyl O4-tert-butyl (2S)-2-(cyanomethyl)piperazine-1,4-dicarboxylate (600 mg, 1.67 mmol) was dissolved in DCM (15 mL) followed by the addition of HCl (4M in 1,4-dioxane-2.00 mL, 8.00 mmol) and the reaction was stirred for 3 hours at room temperature. A second portion of HCl (4M in 1,4-dioxane-1.3 mL, 5.2 mmol,) was added and the reaction heated to 40° C. for 45 minutes. The solvent was then removed in vacuo to give benzyl (2S)-2-(cyanomethyl)piperazine-1-carboxylate hydrochloride (Intermediate 3) (494 mg, 1.67 mmol, 100% yield) as white foam which was used in the next step without further purification.

UPLC-MS ($ES^+$, Method 2): 1.04 min, m/z 260.3 $[M+H]^+$.

$^1$H-NMR (400 MHz, $CDCl_3$) δ/ppm: 10.05 (1H, br s), 7.50-7.30 (5H, m), 5.17 (2H, s), 4.80 (1H, br s), 4.35-4.15 (1H, m), 3.82-3.74 (1H, m), 3.58-3.29 (3H, m), 3.19 (1H, br s), 3.06-2.88 (2H, m).

Intermediate 4—3-methoxynaphthalen-1-amine

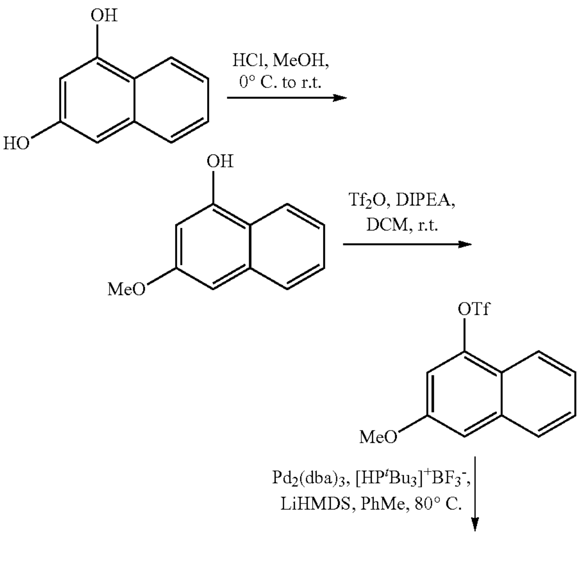

-continued

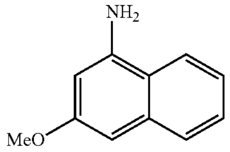

Intermediate 4

Step 1 —3-methoxynaphthalen-1-ol

To a solution of 1,3-dihydroxynaphthalene (25 g, 156.08 mmol) in MeOH (400 mL) at 0° C. was added conc. HCl (65.04 mL, 780.42 mmol). The reaction was left to stir for 48 hours and then solvent removed in vacuo. The residue was partitioned between water (200 mL) and DCM (200 mL). The organic layer was separated, dried over $Na_2SO_4$ and solvent removed in vacuo. The residue was purified by column chromatography using as eluent of 0-30% EtOAc in petroleum ether reached via a gradient to give 3-methoxynaphthalen-1-ol (19.10 g, 109.64 mmol, 70% yield) as a yellow oil.

UPLC-MS (ES+, Method 2): 1.58 min, m/z 175.0 $[M+H]^+$.

$^1$H-NMR (400 MHz, $CDCl_3$) δ/ppm: 8.08 (1H, d, J=8.4 Hz), 7.71 (1H, d, J=8.4 Hz), 7.49-7.45 (1H, m), 7.38-7.33 (1H, m), 6.79 (1H, d, J=2.0 Hz), 6.54 (1H, d, J=2.0 Hz), 5.43 (1H, s), 3.93 (3H, s).

Step 2—(3-methoxy-1-naphthyl) trifluoromethanesulfonate 3-methoxynaphthalen-1-ol (19.10 g, 109.64 mmol) was dissolved in DCM (500 mL), stirred at room temperature, followed by the addition of DIPEA (38.2 mL, 219.29 mmol) and then trifluoromethanesulfonic anhydride (22.1 mL, 131.57 mmol) was added slowly. The reaction was stirred at room temperature for 18 hours. Water (400 mL) was then slowly added and the organic layer was separated and the aqueous extracted with DCM (200 mL). The combined organic layers were washed with brine (300 mL), dried over $Na_2SO_4$ and the solvent removed in vacuo. The residue was purified by column chromatography using an eluent of 0-30% EtOAc in petroleum ether reached via a gradient to give (3-methoxy-1-naphthyl) trifluoromethanesulfonate (27.60 g, 90.12 mmol, 82% yield) as a light yellow oil.

UPLC-MS (ES+, Method 2): 2.07 min, m/z 307.0 $[M+H]^+$; m/z 305.1 $[M-H]^-$.

$^1$H-NMR (400 MHz, $CDCl_3$) δ/ppm: 7.99 (1H, d, J=8.4 Hz), 7.78 (1H, d, J=8.4 Hz), 7.60-7.55 (1H, m), 7.53-7.48 (1H, m), 7.21-7.18 (2H, m), 3.98 (3H, s).

Step 3—3-methoxynaphthalen-1-amine (3-methoxy-1-naphthyl) trifluoromethanesulfonate (1.02 g, 3.34 mmol), $Pd_2(dba)_3$ (153 mg, 0.17 mmol) and tri-tert-butylphosphonium tetrafluoroborate (194 mg, 0.67 mmol) were dissolved in toluene (15 mL) followed by the addition of LiHMDS (1M in toluene-6.67 mL, 6.67 mmol). The reaction was left stirring under a nitrogen atmosphere at 80° C. for 18 hours. 1M aq. HCl (20 mL) and DCM (20 mL) were added and the reaction was left stirring at room temperature for 3 hours. The crude material was filtered over a plug of celite and the two phases were separated. The organic layer was dried over $Na_2SO_4$ and solvent removed in vacuo. The residue was purified by column chromatography using only DCM as eluent. The product containing fractions were concentrated in vacuo and then dissolved in a small amount of MeOH and loaded onto an SCX-2 column. The column was flushed with MeOH followed by $NH_3$ in MeOH to elute the product which gave 3-methoxynaphthalen-1-amine (Intermediate 4) (116 mg, 0.67 mmol, 20% yield) as a yellow oil.

UPLC-MS (ES+, Method 2): 1.42 min, m/z 174.1 $[M+H]^+$.

$^1$H-NMR (400 MHz, DMSO-$d_6$) δ/ppm: 7.94 (1H, d, J=8.4 Hz), 7.61 (1H, d, J=8.4 Hz), 7.33 (1H, t, J=7.6 Hz), 7.17 (1H, t, J=7.6 Hz), 6.53 (1H, d, J=2.4 Hz), 6.31 (1H, d, J=2.4 Hz), 5.73 (2H, br s), 3.77 (3H, s).

Intermediate 5—6-(4-benzyloxycarbonylpiperazin-1-yl)-2-chloro-pyrimidine-4-carboxylic acid Method A

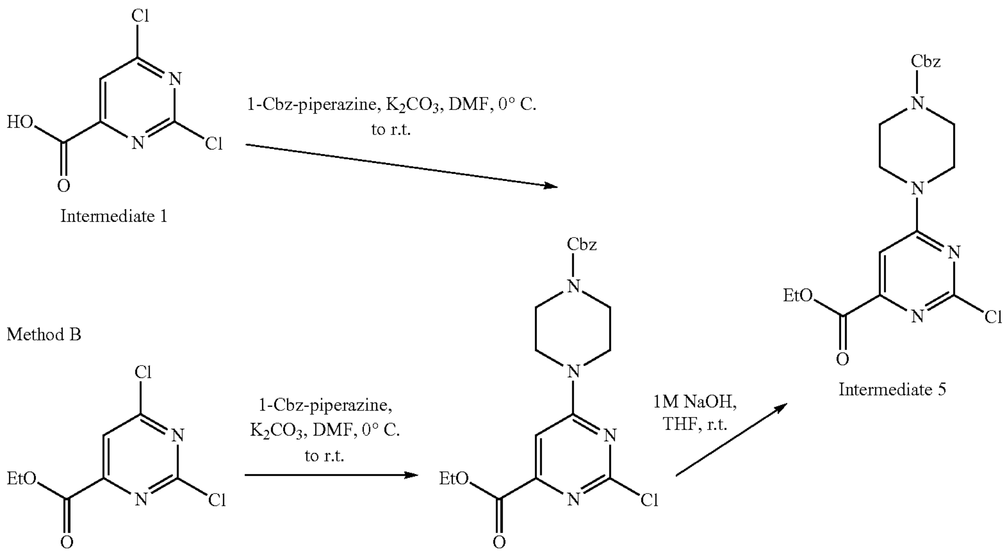

Intermediate 5

Method A—Step 1—6-(4-benzyloxycarbonylpiperazin-1-yl)-2-chloro-pyrimidine-4-carboxylic acid (Intermediate 5)

Intermediate 1 (1.73 g, 8.98 mmol) and $K_2CO_3$ (8.68 g, 62.87 mmol) were stirred in DMF (40 mL) and 1-Cbz-piperazine (1.38 mL, 7.18 mmol) added at 0° C. and stirred. The reaction was warmed to room temperature and stirred for 18 hours. Solvent was then removed in vacuo. Water was added and the pH adjust to 1-2 by addition of 1M aq. HCl followed by extraction with EtOAc (3×300 mL). The combined organic phases were dried over $Na_2SO_4$ and the solvent removed in vacuo. The residue was purified by column chromatography using an eluent of 0-20% MeOH in DCM reached via a gradient followed by reverse phase column chromatography using an eluent 5-100% of MeCN (+0.1% formic acid) in water (+0.1% formic acid) reached via a gradient to give 6-(4-benzyloxycarbonylpiperazin-1-yl)-2-chloro-pyrimidine-4-carboxylic acid (Intermediate 5) (1.36 g, 3.61 mmol, 40% yield).

UPLC-MS (ES+, Method 2): 1.53 min, m/z 377.1, 379.1 $[M+H]^+$.

$^1$H-NMR (400 MHz, DMSO-$d_6$) δ/ppm: 7.40-7.31 (5H, m), 7.30 (1H, s), 5.12 (2H, s), 3.88-3.61 (4H, m), 3.52 (4H, br s), exchangeable proton not seen.

Method B—Step 1—ethyl 6-(4-benzyloxycarbonylpiperazin-1-yl)-2-chloro-pyrimidine-4-carboxylate Intermediate 2 (2.05 g, 9.25 mmol) and $K_2CO_3$ (8.95 g, 64.77 mmol) were dissolved in DMF (40 mL) and stirred at 0° C. followed by the addition of 1-Cbz-piperazine (1.42 mL, 7.4 mmol). The reaction was allowed to warm to room temperature and stir for 72 hours. Solvent was then removed in vacuo. Brine (300 mL) was added followed by extraction with EtOAc (3×400 mL). The combined organic phases were washed with brine (300 mL), dried over $Na_2SO_4$ and solvent removed in vacuo. The residue was purified by column chromatography using an eluent of petroleum ether to give ethyl 6-(4-benzyloxycarbonylpiperazin-1-yl)-2-chloro-pyrimidine-4-carboxylate (2.78 g, 6.87 mmol, 74% yield) as a yellow oil.

UPLC-MS (ES+, Method 2): 1.78 min, m/z 405.3, 407.1 $[M+H]^+$.

$^1$H-NMR (400 MHz, DMSO-$d_6$) δ/ppm: 7.39-7.31 (5H, m), 7.17 (1H, s), 5.18 (2H, s), 4.44 (2H, q, J=7.2 Hz), 3.91-3.58 (8H, m), 1.41 (3H, t, J=7.2 Hz).

Method B—Step 2-6-(4-benzyloxycarbonylpiperazin-1-yl)-2-chloro-pyrimidine-4-carboxylic acid Ethyl 6-(4-benzyloxycarbonylpiperazin-1-yl)-2-chloro-pyrimidine-4-carboxylate (2.78 g, 6.87 mmol) was dissolved in THF (30 mL) and NaOH (1M in water-30 mL, 30 mmol) was added. The reaction was left to stir at room temperature for 45 minutes. Solvent was then removed in vacuo. The pH was adjusted to ~1-2 by addition of 1M aq. HCl followed by extraction with EtOAc (3×300 mL). The organic phases were combined, dried over $Na_2SO_4$ and the solvent removed in vacuo to give 6-(4-benzyloxycarbonylpiperazin-1-yl)-2-chloro-pyrimidine-4-carboxylic acid (Intermediate 5) (2.59 g, 6.87 mmol, 100% yield) as a yellow solid which was used in the next step without further purification.

UPLC-MS (ES+, Method 2): 1.53 min, m/z 377.1, 379.0 $[M+H]^+$.

$^1$H-NMR (400 MHz, DMSO-$d_6$) δ/ppm: 7.40-7.31 (5H, m), 7.30 (1H, s), 5.12 (2H, s), 3.88-3.61 (4H, m), 3.52 (4H, br s), exchangeable proton not seen.

Intermediate 6—1-tetrahydropyran-2-ylindazol-4-amine

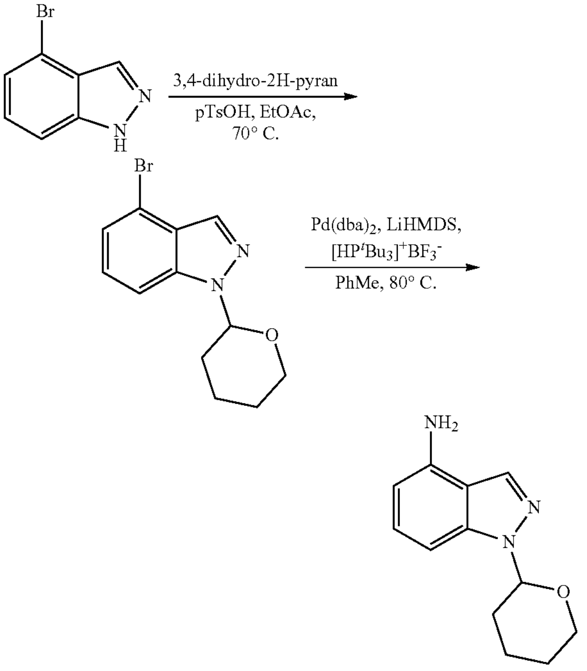

Intermediate 6

Step 1—4-bromo-1-tetrahydropyran-2-yl-indazole 3,4-Dihydro-2H-pyran (2.32 mL, 25.38 mmol) was added to a stirred solution of 4-bromo-1H-indazole (2.5 g, 12.69 mmol) and p-toluenesulfonic acid monohydrate (121 mg, 0.63 mmol) in EtOAc (50 mL) and the mixture was heated at 70° C. for 16 hours. The mixture was the cooled to room temperature and poured into sat. aq. $NaHCO_3$ (50 mL) and the phases were separated. The aqueous phase was extracted with EtOAc (50 mL) and the combined organic layers were dried over $Na_2SO_4$, filtered and concentrated in vacuo. The residue was purified by column chromatography using an eluent of 0-50% EtOAc in petroleum ether reached via a gradient to give 4-bromo-1-tetrahydropyran-2-yl-indazole (3.42 g, 12.16 mmol, 96% yield) as a white solid.

UPLC-MS (ES+, Method 2): 1.89 min, m/z 280.4, 282.4 $[M+H]^+$; 197.0, 199.0 $[M-THP]^+$.

$^1$H NMR (400 MHz, $CDCl_3$) δ/ppm: 8.04 (1H, s), 7.55 (1H, d, J=8.4 Hz), 7.32 (1H, d, J=12.0 Hz), 7.23 (1H, d, J=12.0 Hz), 5.71 (1H, dd, J=9.2 Hz, 2.8 Hz), 4.05-3.97 (1H, m), 3.79-3.70 (1H, m), 2.61-2.49 (1H, m), 2.21-2.04 (2H, m), 1.85-1.59 (3H, m).

Step 2—1-tetrahydropyran-2-ylindazol-4-amine 4-bromo-1-tetrahydropyran-2-yl-indazole (500 mg, 1.78 mmol), $Pd(dba)_2$ (65 mg, 0.07 mmol) and tri-tert-butylphosphonium tetrafluoroborate (82 mg, 0.28 mmol) were dissolved in toluene (6 mL) followed by the addition of LiHMDS (1M in THF-2.86 mL, 2.86 mmol). The reaction was left stirring under inert atmosphere at 80° C. for 18 hours. A second portion of tri-tert-butylphosphonium tetrafluoroborate (414 mg, 1.43 mmol), LiHMDS (1M in THF-7.14 mL, 7.14 mmol), $Pd(dba)_2$ (327 mg, 0.36 mmol) were added and the reaction was stirred at 80° C. for 18 hours. MeOH (10 mL) was added to quench remaining LiHMDS and solvent removed in vacuo. The residue was purified by column chromatography using an eluent of 0-50% EtOAc in petroleum ether reached via a gradient. Product containing fractions were concentrated in vacuo and then dissolved in MeOH and loaded onto an SCX-2 column. The column was flushed with MeOH followed by $NH_3$ in MeOH to elute the product which gave 1-tetrahydropyran-2-ylindazol-4-amine (Intermediate 6) (117 mg, 0.54 mmol, 30% yield) as a yellow oil.

UPLC-MS (ES+, Method 2): 1.30 min, m/z 218.3 $[M+H]^+$.

$^1$H-NMR (400 MHz, DMSO-$d_6$): δ/ppm: 8.11 (1H, s), 7.03 (1H, dd, J=8.4 Hz, 7.6 Hz), 6.74 (1H, d, J=8.4 Hz), 6.18 (1H, dd, J=7.6 Hz, 0.8 Hz), 5.78 (2H, s), 5.66-5.63 (1H, m), 3.91-3.82 (1H, m), 3.73-3.64 (1H, m), 2.44-2.30 (1H, m), 2.05-1.97 (1H, m), 1.94-1.86 (1H, m), 1.77-1.65 (1H, m), 1.52 (2H, m).

Example 1—2-[[(2S)-1-methylpyrrolidin-2-yl]methoxy]-N-(1-naphthyl)-6-(4-prop-2-enoylpiperazin-1-yl)pyrimidine-4-carboxamide

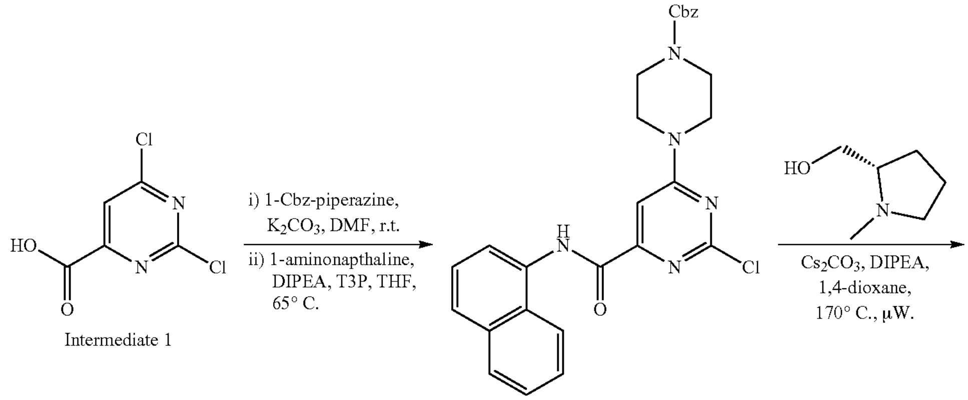

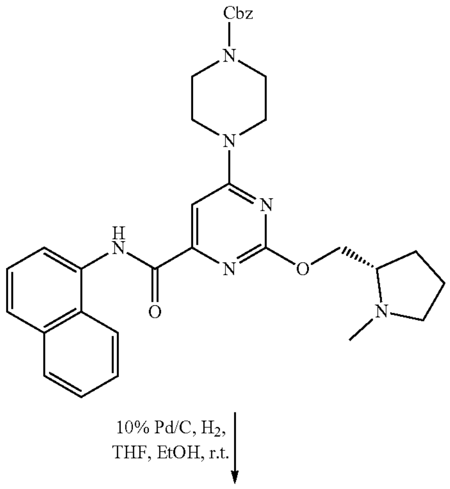

-continued

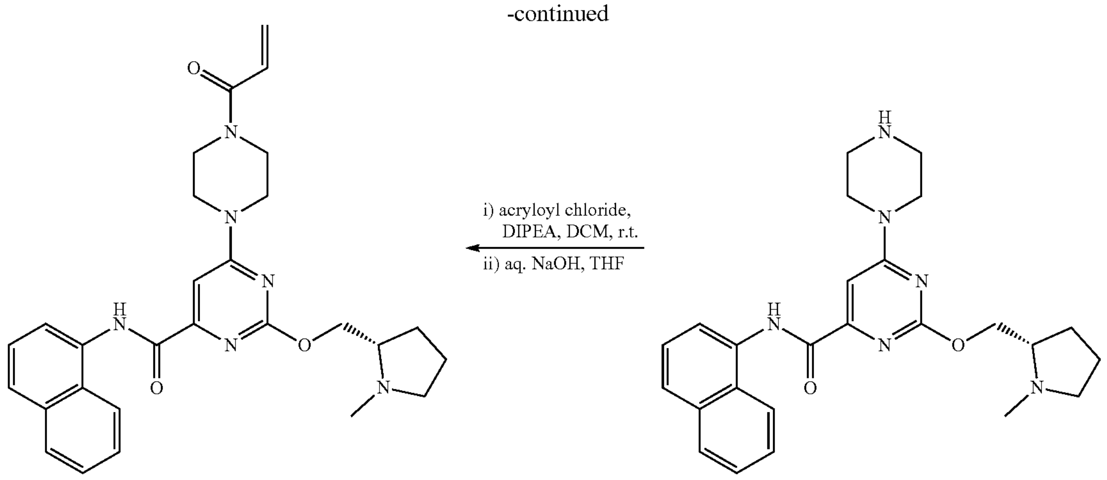

Example 1

Step 1—benzyl 4-[2-chloro-6-(1-naphthylcarbamoyl)pyrimidin-4-yl]piperazine-1-carboxylate Intermediate 1 (729 mg, 3.78 mmol) and $K_2CO_3$ (3.65 g, 26.44 mmol) were dissolved in DMF (20 mL) followed by the addition of 1-Cbz-piperazine (0.58 mL, 3.02 mmol). The reaction was left stirring at room temperature for 5 hours and then solvent removed in vacuo. The residue was dissolved in THF (20 mL) followed by the addition of DIPEA (1.98 mL, 11.37 mmol), T3P (3.37 mL, 5.66 mmol, 50% volume in EtOAc) and 1-aminonaphthalene (1.62 g, 11.33 mmol). The reaction was stirred at 65° C. for 1.5 hours and the solvent removed in vacuo. The residue was dissolved in DCM (200 mL) and washed with water (2×200 mL). The organic phase was dried over $Na_2SO_4$ and the solvent removed in vacuo. The residue was purified by column chromatography using an eluent of 0-50% EtOAc in petroleum ether reached via a gradient to give benzyl 4-[2-chloro-6-(1-naphthylcarbamoyl)pyrimidin-4-yl]piperazine-1-carboxylate (352 mg, 0.70 mmol, 17% yield) as a yellow oil.

UPLC-MS (ES+, Method 2): 2.16 min, m/z 502.2, 504.1 $[M+H]^+$.

$^1$H-NMR (400 MHz, $CDCl_3$) δ/ppm: 10.30 (1H, s), 8.26 (1H, d, J=7.2 Hz), 8.01 (1H, d, J=8.8 Hz), 7.91 (1H, d, J=8.0 Hz), 7.74 (1H, d, J=8.0 Hz), 7.64-7.59 (1H, m), 7.57-7.51 (2H, m), 7.42 (1H, s), 7.41-7.33 (5H, m), 5.20 (2H, s), 3.81 (4H, br s), 3.69-3.59 (4H, m).

Step 2—benzyl 4-[2-[[(2S)-1-methylpyrrolidin-2-yl]methoxy]-6-(1-naphthylcarbamoyl)pyrimidin-4-yl]piperazine-1-carboxylate Benzyl 4-[2-chloro-6-(1-naphthylcarbamoyl)pyrimidin-4-yl]piperazine-1-carboxylate (302 mg, 0.60 mmol) was dissolved in 1,4-dioxane (11 mL) in a microwave vial followed by the addition of (S)-(−)-1-methyl-2-pyrrolidinemethanol (0.50 mL, 4.2 mmol), $Cs_2CO_3$ (588 mg, 1.80 mmol) and DIPEA (1.05 mL, 6.03 mmol). The reaction was heated in the microwave at 170° C. for 2 hours. Solvent was then removed in vacuo and the residue dissolved in EtOAc (100 mL) and washed with brine (100 mL). The organic layer was dried over $Na_2SO_4$ and solvent removed in vacuo. The residue was purified by column chromatography using an eluent of 0-5% MeOH in DCM reached via a gradient to give benzyl 4-[2-[[(2S)-1-methylpyrrolidin-2-yl]methoxy]-6-(1-naphthylcarbamoyl)pyrimidin-4-yl]piperazine-1-carboxylate (164 mg, 0.28 mmol, 40% yield) as a yellow oil.

UPLC-MS (ES+, Method 2): 1.56 min, m/z 581.5 $[M+H]^+$.

$^1$H-NMR (400 MHz, DMSO-$d_6$) δ/ppm: 10.66 (1H, s), 8.02-7.97 (1H, m), 7.95-7.90 (1H, m), 7.89-7.82 (2H, m), 7.61-7.55 (3H, m), 7.40-7.39 (4H, m), 7.37-7.31 (1H, m), 7.14 (1H, s), 5.13 (2H, s), 4.52-4.44 (1H, m), 4.32-4.22 (1H, m), 3.77 (4H, br s), 3.54 (4H, br s), 3.03-2.94 (1H, m), 2.63-2.55 (1H, m), 2.39 (3H, s), 2.26-2.16 (1H, m), 2.04-1.92 (1H, m), 1.78-1.62 (3H, m).

Step 3—2-[[(2S)-1-methylpyrrolidin-2-yl]methoxy]-N-(1-naphthyl)-6-piperazin-1-yl-pyrimidine-4-carboxamide Benzyl 4-[2-[[(2S)-1-methylpyrrolidin-2-yl]methoxy]-6-(1-naphthylcarbamoyl)pyrimidin-4-yl]piperazine-1-carboxylate (164 mg, 0.28 mmol) was dissolved in THF (7 mL) and EtOH (3 mL) followed by the addition of palladium, 10 wt. % on carbon powder, (21 mg, 0.20 mmol) under a nitrogen atmosphere. The reaction was fitted with a $H_2$ balloon and subjected to 3×vacuum/$H_2$ cycles and then left to stir under a $H_2$ atmosphere for 72 hours. The reaction was then filtered through celite, washed with $NH_3$ in MeOH (10 mL) and the solvent removed in vacuo to give 2-[[(2S)-1-methylpyrrolidin-2-yl]methoxy]-N-(1-naphthyl)-6-piperazin-1-yl-pyrimidine-4-carboxamide (120 mg, 0.27 mmol, 95% yield) as a yellow oil, which was used in the next step without further purification.

UPLC-MS (ES+, Method 2): 1.09 min, m/z 447.2 $[M+H]^+$.

Step 4—2-[[(2S)-1-methylpyrrolidin-2-yl]methoxy]-N-(1-naphthyl)-6-(4-prop-2-enoylpiperazin-1-yl)pyrimidine-4-carboxamide DIPEA (0.38 mL, 2.15 mmol) was added to a stirred solution of acryloyl chloride (0.09 mL, 1.07 mmol), 2-[[(2S)-1-methylpyrrolidin-2-yl]methoxy]-N-(1-naphthyl)-6-piperazin-1-yl-pyrimidine-4-carboxamide (120 mg, 0.27 mmol) in DCM (5 mL) at room temperature. After 5 minutes a solution of 2M $K_2CO_3$ (10 mL) was added to the crude and the mixture allowed to stir for 30 minutes. DCM (10 mL) was added and the organic layer separated, dried over $Na_2SO_4$ and solvent removed in vacuo. The residue was purified by column chromatography using an eluent of 0-5% MeOH in DCM reached via a gradient to give the di-substituted product. This intermediate was stirred in a mixture 1:1 of THF (5 mL) and 1M aq. NaOH (5 mL) at room temperature for 20 minutes. DCM (20 mL) was then added to the mixture and the organic phase was separated, dried over $Na_2SO_4$ and the solvent removed in vacuo. The residue was purified by preparative LC-MS to give 2-[[(2S)-1-methylpyrrolidin-2-yl]methoxy]-N-(1-naphthyl)-6-(4-prop-2-enoylpiperazin-1-yl)pyrimidine-4-carboxamide (Example 1) (4 mg, 0.01 mmol, 3% yield) as a white solid.

UPLC-MS (ES+, Method 1): 2.90 min, m/z 501.4 $[M+H]^+$.

$^1H$-NMR (400 MHz, $CD_3OD$) δ/ppm: 8.04-7.97 (2H, m), 7.96-7.92 (1H, m), 7.81-7.79 (1H, m), 7.61-7.50 (3H, m), 7.24 (1H, s), 6.80 (1H, dd, J=16.8 Hz, 10.8 Hz), 6.25 (1H, dd, J=16.8 Hz, 2.0 Hz), 5.79 (1H, dd, J=10.8 Hz, 2.0 Hz), 4.61-4.47 (3H, m), 3.90-3.74 (8H, m), 3.22-3.14 (1H, m), 2.98-2.88 (1H, m), 2.59 (3H, s), 2.54-2.43 (1H, m), 2.23-2.10 (1H, m), 1.96-1.77 (3H, m).

Example 2—6-[(3S)-3-(cyanomethyl)-4-prop-2-enoyl-piperazin-1-yl]-2-[[(2S)-1-methylpyrrolidin-2-yl]methoxy]-N-(1-naphthyl)pyrimidine-4-carboxamide

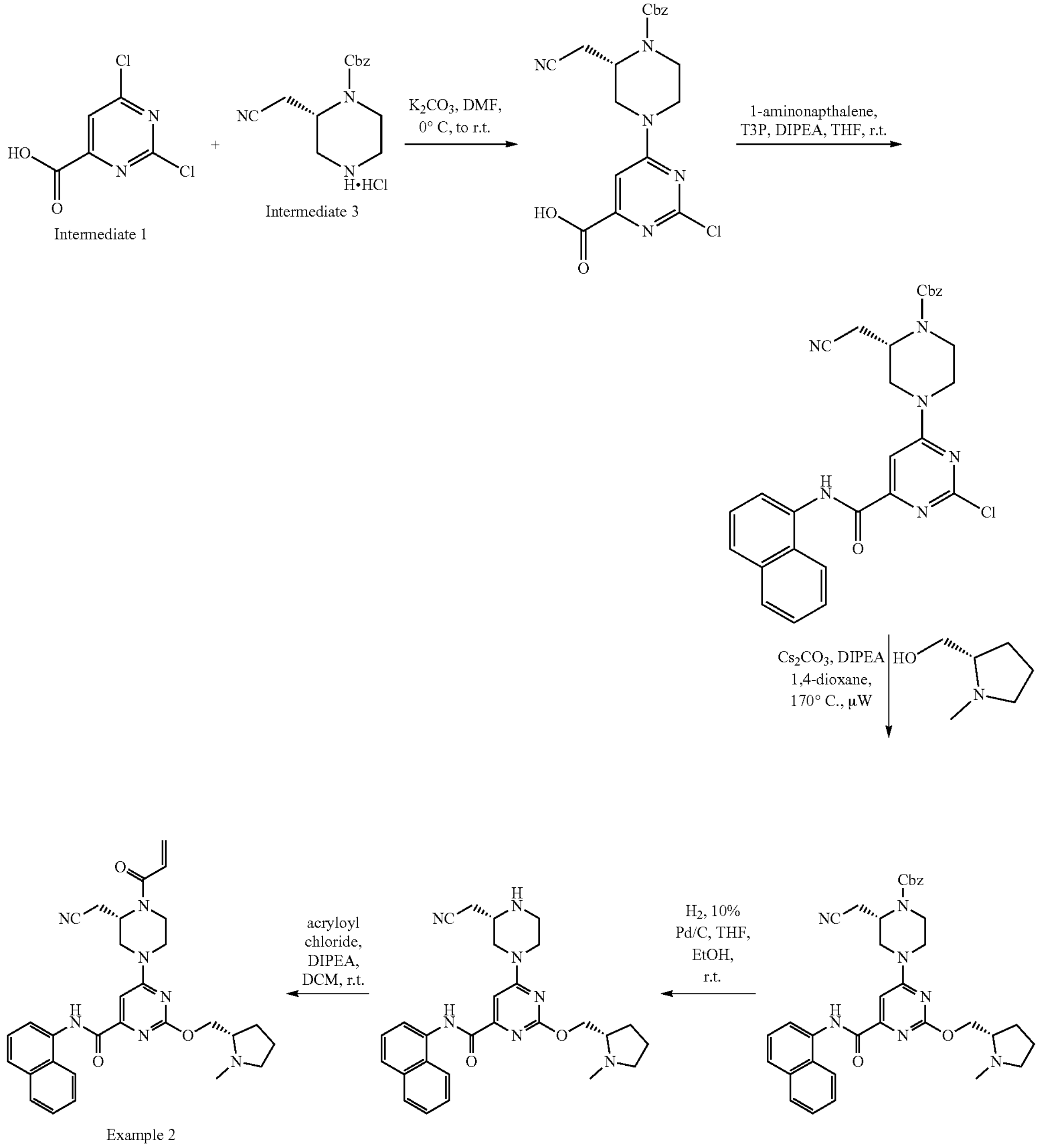

Intermediate 1

Intermediate 3

Example 2

Step 1—6-[(3S)-4-benzyloxycarbonyl-3-(cyanomethyl)piperazin-1-yl]-2-chloro-pyrimidine-4-carboxylic acid Intermediate 1 (400 mg, 2.07 mmol) and $K_2CO_3$ (2.00 g, 14.51 mmol) were stirred in DMF (10 mL) at 0° C. and Intermediate 3 (494 mg, 1.67 mmol) added. The reaction was allowed to warm to room temperature stir for 18 hours. Solvent was then removed in vacuo. Water (100 mL) was added and the pH was brought to ~1-2 using 1M aq. HCl and the mixture extracted with EtOAc (3×100 mL). The organic phases were combined, dried over $Na_2SO_4$ and the solvent removed in vacuo. The residue was then purified by reverse column chromatography using as eluent a gradient 5-100% of MeCN (+0.1% formic acid) in water (+0.1% formic acid) reached via a gradient to give 6-[(3S)-4-benzyloxycarbonyl-3-(cyanomethyl)piperazin-1-yl]-2-chloro-pyrimidine-4-carboxylic acid (304 mg, 0.73 mmol, 35% yield) as a pale yellow solid.

UPLC-MS (ES+, Method 2): 1.49 min, m/z 416.1, 418.0 $[M+H]^+$.

$^1$H-NMR (400 MHz, DMSO-$d_6$): δ/ppm: 13.80 (1H, brs), 7.44-7.31 (5H, m), 7.29 (1H, s), 5.19-5.09 (2H, m), 4.58 (1H, br s), 3.97 (1H, d, J=13.2 Hz), 3.45-3.38 (2H, m, (underwater peak)), 3.19-3.08 (1H, m), 3.03-2.82 (2H, m), 2.55-2.45 (2H, m).

Step 2—benzyl (2S)-4-[2-chloro-6-(1-naphthylcarbamoyl)pyrimidin-4-yl]-2-(cyanomethyl)piperazine-1-carboxylate 6-[(3S)-4-benzyloxycarbonyl-3-(cyanomethyl)piperazin-1-yl]-2-chloro-pyrimidine-4-carboxylic acid (163 mg, 0.39 mmol) was dissolved in THF (5 mL) followed by the addition of 1-aminonaphthalene (67 mg, 0.47 mmol), T3P (0.35 mL, 0.59 mmol, 50% volume in EtOAc) and DIPEA (0.21 mL, 1.18 mmol). The reaction was stirred at room temperature for 18 hours. A second portion of 1-aminonaphthalene (28 mg, 0.20 mmol), T3P (0.08 mL, 0.28 mmol, 50% volume in EtOAc) and DIPEA (0.1 mL, 0.59 mmol) were added and the reaction was left to stir for a further 18 hours. Solvent was then removed in vacuo. The residue was dissolved in DCM (50 mL) and washed with water (2×50 mL). The organic phase was dried over $Na_2SO_4$ and concentrated in vacuo. The residue was purified by column chromatography using an eluent of 0-50% EtOAc in petroleum ether reached via a gradient to give benzyl (2S)-4-[2-chloro-6-(1-naphthylcarbamoyl)pyrimidin-4-yl]-2-(cyanomethyl)piperazine-1-carboxylate (128 mg, 0.24 mmol, 60% yield) as a pale brown oil.

UPLC-MS (ES+, Method 2): 2.05 min, m/z 541.2, 543.1 $[M+H]^+$.

$^1$H-NMR (400 MHz, $CDCl_3$) δ/ppm: 10.29 (1H, s), 8.25 (1H, d, J=7.6 Hz), 8.01 (1H, d, J=8.4 Hz), 7.91 (1H, d, J=8.0 Hz), 7.75 (1H, d, J=8.4 Hz), 7.65-7.59 (1H, m), 7.58-7.51 (2H, m), 7.43-7.36 (6H, m), 5.21 (2H, s), 4.68-4.58 (1H, m), 4.46 (1H, br s), 4.21 (2H, br s), 3.74 (1H, br s), 3.56-3.31 (2H, m), 2.92-2.58 (2H, m).

Step 3—benzyl (2S)-2-(cyanomethyl)-4-[2-[[(2S)-1-methylpyrrolidin-2-yl]methoxy]-6-(1-naphthylcarbamoyl)pyrimidin-4-yl]piperazine-1-carboxylate To benzyl (2S)-4-[2-chloro-6-(1-naphthylcarbamoyl)pyrimidin-4-yl]-2-(cyanomethyl)piperazine-1-carboxylate (128 mg, 0.24 mmol) in a microwave vial was added 1,4-dioxane (5 mL) followed by (S)-(−)-1-methyl-2-pyrrolidinemethanol (0.14 mL, 1.18 mmol), $Cs_2CO_3$ (231 mg, 0.71 mmol) and DIPEA (0.33 mL, 1.89 mmol). The reaction was heated in the microwave at 170° C. for 3 hours. Solvent was then removed in vacuo. The residue was dissolved in EtOAc (50 mL) and washed with brine (50 mL). The organic layer was dried over $Na_2SO_4$ and the solvent removed in vacuo. The residue was purified by column chromatography using an eluent of 0-10% MeOH in DCM reached via a gradient to give benzyl (2S)-2-(cyanomethyl)-4-[2-[[(2S)-1-methylpyrrolidin-2-yl]methoxy]-6-(1-naphthylcarbamoyl)pyrimidin-4-yl]piperazine-1-carboxylate (25 mg, 0.04 mmol, 17% yield) as a brown oil.

UPLC-MS (ES+, Method 2): 1.56 min, m/z 620.4 $[M+H]^+$.

Step 4—6-[(3S)-3-(cyanomethyl)piperazin-1-yl]-2-[[(2S)-1-methylpyrrolidin-2-yl]methoxy]-N-(1-naphthyl)pyrimidine-4-carboxamide Benzyl (2S)-2-(cyanomethyl)-4-[2-[[(2S)-1-methylpyrrolidin-2-yl]methoxy]-6-(1-naphthylcarbamoyl)pyrimidin-4-yl]piperazine-1-carboxylate (25 mg, 0.04 mmol) was dissolved in THF (3 mL) and EtOH (1 mL) followed by the addition of palladium, 10 wt. % on carbon powder, (10 mg, 0.09 mmol) under a nitrogen atmosphere. The reaction was fitted with a $H_2$ balloon and subjected to 3×vacuum/$H_2$ cycles and then left to stir under a $H_2$ atmosphere for 72 hours. The reaction was then filtered over celite, washed with $NH_3$ in MeOH (10 mL) and the solvent removed in vacuo to give 6-[(3S)-3-(cyanomethyl)piperazin-1-yl]-2-[[(2S)-1-methylpyrrolidin-2-yl]methoxy]-N-(1-naphthyl)pyrimidine-4-carboxamide (19 mg, 0.04 mmol, 100% yield) as a pale yellow oil.

UPLC-MS (ES+, Method 2): 1.22 min, m/z 486.3 $[M+H]^+$.

Step 5—6-[(3S)-3-(cyanomethyl)-4-prop-2-enoyl-piperazin-1-yl]-2-[[(2S)-1-methylpyrrolidin-2-yl]methoxy]-N-(1-naphthyl)pyrimidine-4-carboxamide DIPEA (0.02 mL, 0.12 mmol) was added to a stirred solution of 6-[(3S)-3-(cyanomethyl)piperazin-1-yl]-2-[[(2S)-1-methylpyrrolidin-2-yl]methoxy]-N-(1-naphthyl)pyrimidine-4-carboxamide (19 mg, 0.04 mmol), acryloyl chloride (3.3 μL, 0.04 mmol) in DCM (2 mL) at room temperature for 10 minutes. A solution 2M $K_2CO_3$ (5 mL) was added to the reaction and the mixture allowed to stir for 20 minutes. DCM (10 mL) was added and the organic layer separated, dried over $Na_2SO_4$ and solvent removed in vacuo. The residue was purified by preparative LC-MS to give 6-[(3S)-3-(cyanomethyl)-4-prop-2-enoyl-piperazin-1-yl]-2-[[(2S)-1-methylpyrrolidin-2-yl]methoxy]-N-(1-naphthyl)pyrimidine-4-carboxamide (Example 2) (4 mg, 0.01 mmol, 18% yield) as a white solid.

UPLC-MS (ES+, Method 1): 2.91 min, m/z 540.4 $[M+H]^+$.

$^1$H-NMR (400 MHz, DMSO-$d_6$) δ/ppm: 10.67 (1H, s), 8.05-7.98 (1H, m), 7.95-7.90 (1H, m), 7.89-7.81 (2H, m), 7.65-7.54 (3H, m), 7.24-7.13 (1H, m), 6.98-6.79 (1H, m), 6.20 (1H, d, J=18.8 Hz), 5.79 (1H, d, J=11.2 Hz), 4.99-4.72 (1H, m), 4.55-4.23 (4H, m), 4.17-4.00 (1H, m), 3.64-3.51 (2H, m, (underwater peak)), 3.18-3.05 (1H, m), 3.03-2.85 (2H, m), 2.72-2.59 (2H, m), 2.39 (3H, s), 2.28-2.15 (1H, m), 2.06-1.90 (1H, m), 1.79-1.58 (3H, m).

Example 3—N-(3-hydroxy-1-naphthyl)-2-[[(2S)-1-methylpyrrolidin-2-yl]methoxy]-6-(4-prop-2-enoylpiperazin-1-yl)pyrimidine-4-carboxamide

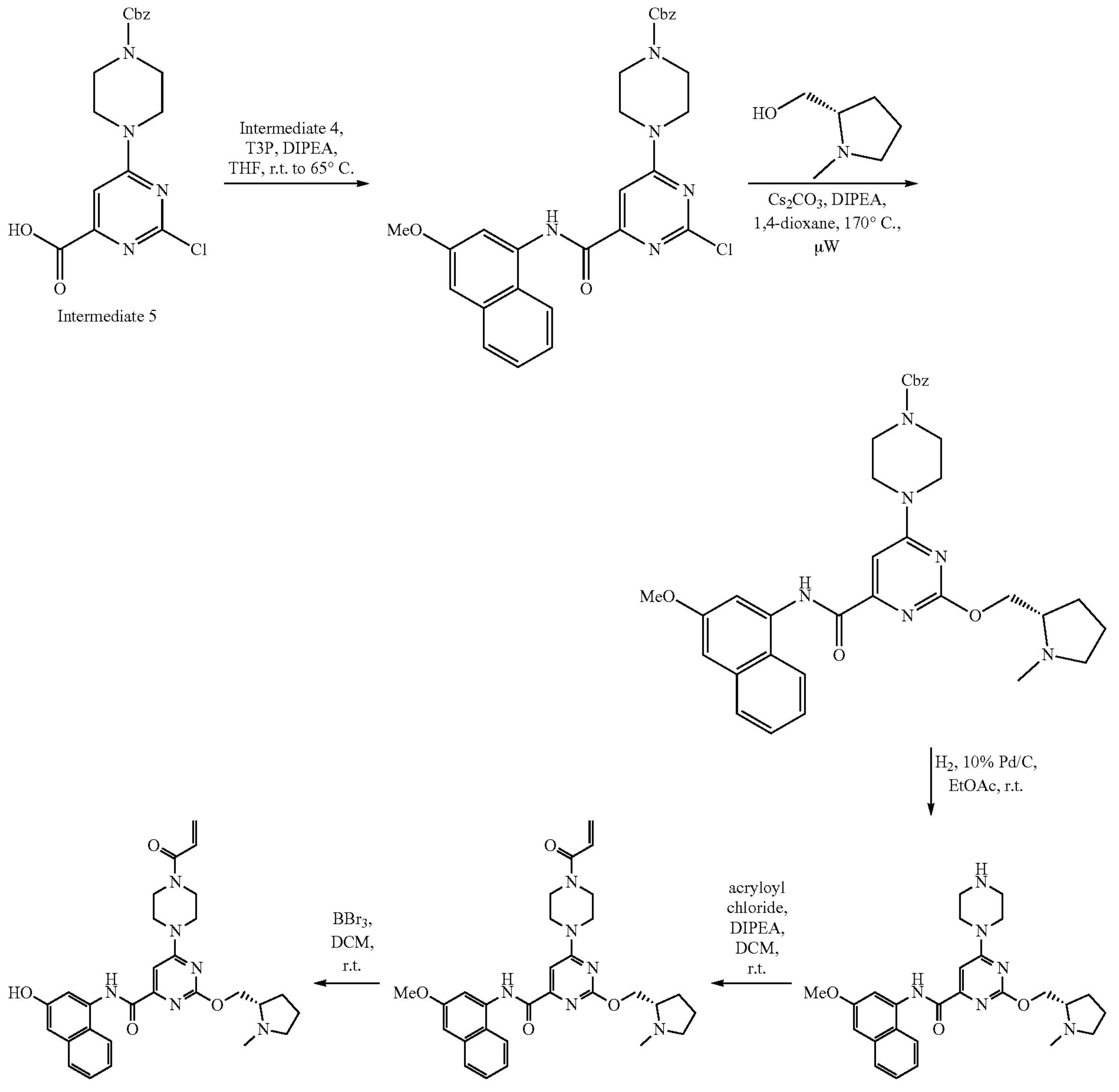

Intermediate 5

Example 3

Step 1—benzyl 4-[2-chloro-6-[(3-methoxy-1-naphthyl)carbamoyl]pyrimidin-4-yl]piperazine-1-carboxylate Intermediate 5 (229 mg, 0.61 mmol) was dissolved in THF (6 mL) and stirred at room temperature. T3P (0.54 mL, 0.91 mmol, 50% volume in EtOAc), DIPEA (0.32 mL, 1.82 mmol) and Intermediate 4 (116 mg, 0.67 mmol) were then added and the reaction stirred for 18 hours. A second portion of DIPEA (0.32 mL, 1.82 mmol) and T3P (0.54 mL, 0.91 mmol, 50% volume in EtOAc) were added and the reaction was stirred at 65° C. for 6 hours. Solvent was then removed in vacuo. The residue was dissolved in DCM (50 mL) and washed with water (2×50 mL). The organic layer was dried over $Na_2SO_4$ and solvent removed in vacuo. The residue was purified by column chromatography using an eluent of 0-100% EtOAc in petroleum ether reached via a gradient to give benzyl 4-[2-chloro-6-[(3-methoxy-1-naphthyl)carbamoyl]pyrimidin-4-yl]piperazine-1-carboxylate (162 mg, 0.30 mmol, 50% yield) as a brown oil.

UPLC-MS (ES+, Method 2): 2.19 min, m/z 532.2, 534.2 $[M+H]^+$.

$^1$H-NMR (400 MHz, $CDCl_3$) δ/ppm: 10.34 (1H, br s), 8.08 (1H, d, J=2.4 Hz), 7.90 (1H, d, J=8.0 Hz), 7.77 (1H, d, J=8.0 Hz), 7.52-7.42 (2H, m), 7.40 (1H, s), 7.40-7.33 (5H, m), 7.04 (1H, d, J=2.0 Hz), 5.19 (2H, s), 3.95 (3H, s), 3.81 (4H, br s), 3.70-3.59 (4H, m).

Step 2—benzyl 4-[6-[(3-methoxy-1-naphthyl)carbamoyl]-2-[[(2S)-1-methylpyrrolidin-2-yl]methoxy]pyrimidin-4-yl]piperazine-1-carboxylate To benzyl 4-[2-chloro-6-[(3-methoxy-1-naphthyl)carbamoyl]pyrimidin-4-yl]piperazine-1-carboxylate (162 mg, 0.30 mmol) in a microwave vial was added 1,4-dioxane (5 mL) followed by the addition of (S)-(−)-1-methyl-2-pyrrolidinemethanol (0.18 mL, 1.52 mmol), $Cs_2CO_3$ (298 mg, 0.91 mmol) and DIPEA (0.42 mL, 2.44 mmol). The reaction was heated at the microwave at 170° C. for 3.5 hours. Solvent was then removed in vacuo and the residue dissolved in EtOAc (50 mL) and washed with brine (50 mL). The organic layer was dried over $Na_2SO_4$ and solvent removed in vacuo. The residue was purified by column chromatography using an eluent of 0-5% MeOH in DCM reached via a gradient to give benzyl 4-[6-[(3-methoxy-1-naphthyl)carbamoyl]-2-[[(2S)-1-methylpyrrolidin-2-yl]methoxy]pyrimidin-4-yl]piperazine-1-carboxylate (109 mg, 0.18 mmol, 58% yield) as a pale yellow solid.

UPLC-MS (ES+, Method 2): 1.65 min, m/z 611.4 $[M+H]^+$.

$^1$H-NMR (400 MHz, DMSO-$d_6$) δ/ppm: 10.66 (1H, s), 7.88 (1H, d, J=8.0 Hz), 7.83 (1H, d, J=8.4 Hz), 7.65 (1H, d, J=2.4 Hz), 7.55-7.50 (1H, m), 7.44-7.31 (6H, m), 7.28 (1H, d, J=2.4 Hz), 7.15 (1H, s), 5.13 (2H, s), 4.48 (1H, dd, J=10.8 Hz, 4.8 Hz), 4.27 (1H, dd, J=10.8 Hz, 6.4 Hz), 3.90 (3H, s), 3.77 (4H, br s), 3.53 (4H, br s), 3.03-2.92 (1H, m), 2.64-2.59 (1H, m), 2.39 (3H, s), 2.23-2.16 (1H, m), 2.05-1.94 (1H, m), 1.77-1.55 (3H, m).

Step 3—N-(3-methoxy-1-naphthyl)-2-[[(2S)-1-methylpyrrolidin-2-yl]methoxy]-6-piperazin-1-yl-pyrimidine-4-carboxamide Benzyl 4-[6-[(3-methoxy-1-naphthyl)carbamoyl]-2-[[(2S)-1-methylpyrrolidin-2-yl]methoxy]pyrimidin-4-yl]piperazine-1-carboxylate (92 mg, 0.15 mmol) was dissolved in EtOAc (7 mL), stirred and palladium, 10 wt. % on carbon powder, (31 mg, 0.29 mmol) added under an inert atmosphere. The reaction was fitted with a $H_2$ balloon and subjected to 3×vacuum/$H_2$ cycles and then left to stir under an $H_2$ atmosphere for 18 hours. The reaction was filtered through celite, washed with $NH_3$ in MeOH (10 mL) and the solvent removed in vacuo to give N-(3-methoxy-1-naphthyl)-2-[[(2S)-1-methylpyrrolidin-2-yl]methoxy]-6-piperazin-1-yl-pyrimidine-4-carboxamide (67 mg, 0.14 mmol, 93% yield) as a yellow solid.

UPLC-MS (ES+, Method 2): 1.45 min, m/z 477.2 $[M+H]^+$.

Step 4—N-(3-methoxy-1-naphthyl)-2-[[(2S)-1-methylpyrrolidin-2-yl]methoxy]-6-(4-prop-2-enoylpiperazin-1-yl)pyrimidine-4-carboxamide DIPEA (0.07 mL, 0.42 mmol) was added to a stirred solution of N-(3-methoxy-1-naphthyl)-2-[[(2S)-1-methylpyrrolidin-2-yl]methoxy]-6-piperazin-1-yl-pyrimidine-4-carboxamide (67 mg, 0.14 mmol), acryloyl chloride (0.01 mL, 0.14 mmol) and DCM (4 mL) at room temperature. After 20 minutes a solution 2M $K_2CO_3$ (10 mL) was added to the reaction and the mixture allowed to stir for 20 minutes. DCM was added and the organic layer separated, dried over $Na_2SO_4$ and the solvent removed in vacuo. The residue was purified by column chromatography using an eluent of 0-5% MeOH in DCM reached via a gradient to give N-(3-methoxy-1-naphthyl)-2-[[(2S)-1-methylpyrrolidin-2-yl]methoxy]-6-(4-prop-2-enoylpiperazin-1-yl)pyrimidine-4-carboxamide (22 mg, 0.04 mmol, 29% yield) as a colourless oil.

UPLC-MS (ES+, Method 2): 1.37 min, m/z 531.4 $[M+H]^+$.

Step 5—N-(3-hydroxy-1-naphthyl)-2-[[(2S)-1-methylpyrrolidin-2-yl]methoxy]-6-(4-prop-2-enoylpiperazin-1-yl)pyrimidine-4-carboxamide N-(3-methoxy-1-naphthyl)-2-[[(2S)-1-methylpyrrolidin-2-yl]methoxy]-6-(4-prop-2-enoylpiperazin-1-yl)pyrimidine-4-carboxamide (22 mg, 0.04 mmol) was dissolved in DCM (4 mL) followed by the addition of $BBr_3$ (0.02 mL, 0.12 mmol). The reaction was left stirring for 30 min and a second portion of $BBr_3$ (0.01 mL, 0.04 mmol) was added and the reaction was left stirring for 20 minutes. MeOH (5 mL) was added and the solvent removed in vacuo. The residue was purified by preparative LC-MS to give N-(3-hydroxy-1-naphthyl)-2-[[(2S)-1-methylpyrrolidin-2-yl]methoxy]-6-(4-prop-2-enoylpiperazin-1-yl)pyrimidine-4-carboxamide (Example 3) (18 mg, 0.03 mmol, 84% yield) as a yellow solid.

UPLC-MS (ES+, Method 1): 2.63 min, m/z 517.5 $[M+H]^+$.

$^1$H-NMR (400 MHz, DMSO-$d_6$) δ/ppm: 10.63 (1H, s), 7.79-7.74 (2H, m), 7.63 (1H, d, J=2.4 Hz), 7.45 (1H, t, J=7.2 Hz), 7.32 (1H, t, J=7.2 Hz), 7.16 (1H, s), 7.05 (1H, d, J=2.0 Hz), 6.84 (1H, dd, J=16.8 Hz, 10.4 Hz), 6.16 (1H, dd, J=16.8 Hz, 2.4 Hz), 5.74 (1H, dd, J=10.4 Hz, 2.4 Hz), 4.48 (1H, dd, J=10.8 Hz, 4.8 Hz), 4.28 (1H, dd, J=10.8 Hz, 6.8 Hz), 3.85-3.61 (8H, m), 3.03-2.96 (1H, m), 2.64-2.58 (1H, m), 2.40 (3H, s), 2.26-2.17 (1H, m), 2.06-1.92 (1H, m), 1.77-1.60 (3H, m), exchangeable proton not seen.

The compounds in the table below were made in an analogous manner to Example 3, using the appropriate commercial methoxyanilines in place of Intermediate 4:

| Compound | Name | Data |
| --- | --- | --- |
| Example 4 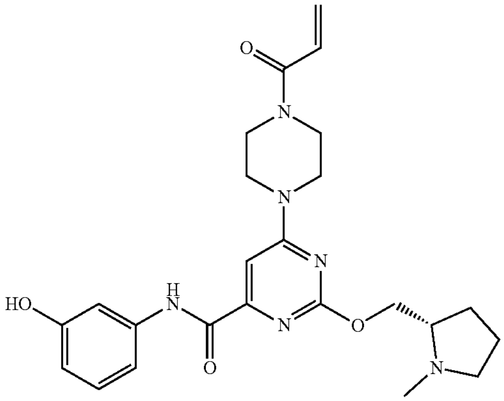 | N-(3-hydroxyphenyl)-2-[[(2S)-1-methylpyrrolidin-2-yl]methoxy]-6-(4-prop-2-enoylpiperazin-1-yl)pyrimidine-4-carboxamide | UPLC-MS (ES+, Method 1): 2.37 min, m/z 467.4 $[M + H]^+$. $^1$H-NMR (400 MHz, DMSO-$d_6$) δ/ppm: 10.06 (1H, s), 7.38 (1H, s), 7.22-7.10 (2H, m), 7.09 (1H, s), 6.84 (1H, dd, J = 16.4 Hz, 10.4 Hz), 6.54 (1H, dt, J = 7.6 Hz, 1.2 Hz), 6.19-6.12 (1H, m), 5.76-5.70 (1H, m), 4.43 (1H, dd, J = 10.8 Hz, 4.4 Hz), 4.17 (1H, dd, J = 10.8 Hz, 6.4 Hz), 3.82-3.59 (8H, m), 2.99-2.91 (1H, m), 2.63-2.57 (1H, m), 2.38 (3H, s), 2.24-2.17 (1H, m), 2.05-1.89 (1H, m), 1.76-1.59 (3H, m), exchangeable proton not seen. |
| Example 5 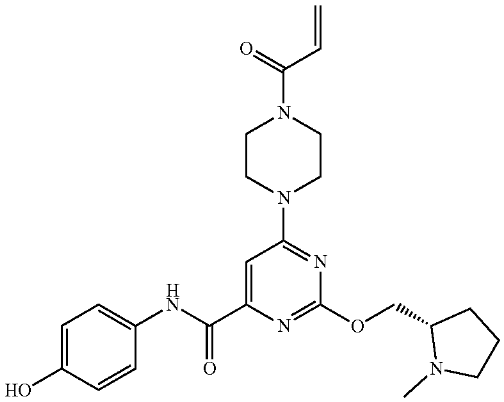 | N-(4-hydroxyphenyl)-2-[[(2S)-1-methylpyrrolidin-2-yl]methoxy]-6-(4-prop-2-yl)pyrimidine-4-carboxamide | UPLC-MS (ES+, Method 1): 2.27 min, m/z 467.5 $[M + H]^+$. $^1$H-NMR (400 MHz, DMSO-$d_6$) δ/ppm: 10.02 (1H, s), 7.58 (2H, d, J = 8.8 Hz), 7.07 (1H, s), 6.83 (1H, dd, J = 16.4 Hz, 10.4 Hz), 6.74 (2H, d, J = 8.8 Hz), 6.15 (1H, dd, J = 16.4 Hz, 2.4 Hz), 5.73 (1H, dd, J = 10.4 Hz, 2.4 Hz), 4.43 (1H, dd, J = 10.8 Hz, 4.8 Hz), 4.17 (1H, dd, J = 10.8 Hz, 6.4 Hz), 3.82-3.56 (8H, m), 3.01-2.93 (1H, m), 2.62-2.56 (1H, m), 2.38 (3H, s), 2.25-2.14 (1H, m), 2.03-1.91 (1H, m), 1.75-1.57 (3H, m), exchangeable proton not seen. |
| Example 6 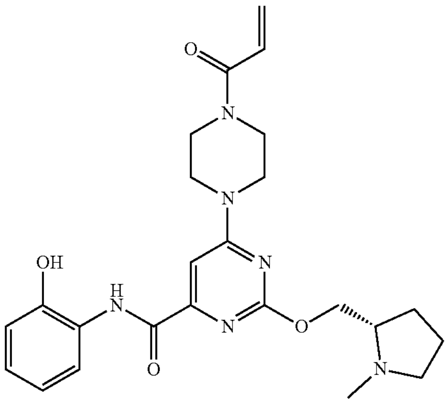 | N-(2-hydroxyphenyl)-2-[[(2S)-1-methylpyrrolidin-2-yl]methoxy]-6-(4-prop-2-enoylpiperazin-1-yl)pyrimidine-4-carboxamide | UPLC-MS (ES+, Method 1): 2.56 min, m/z 467.4 $[M + H]^+$. $^1$H-NMR (400 MHz, DMSO-$d_6$) δ/ppm: 10.30 (1H, s), 8.33 (1H, dd, J = 8.0 Hz, 1.6 Hz), 7.14 (1H, s), 7.00-6.92 (2H, m), 6.88-6.79 (2H, m), 6.16 (1H, dd, J = 16.4 Hz, 2.4 Hz), 5.73 (1H, dd, J = 10.4 Hz, 2.4 Hz), 4.37 (1H, dd, J = 10.8 Hz, 4.8 Hz), 4.18 (1H, dd, J = 10.8 Hz, 6.4 Hz), 3.85-3.58 (8H, m), 3.00-2.93 (1H, m), 2.62-2.55 (1H, m), 2.37 (3H, s), 2.19 (1H, q, J = 8.4 Hz), 2.04-1.92 (1H, m), 1.77-1.55 (3H, m), exchangeable proton not seen. |

Example 7—2-(2-morpholinoethoxy)-N-(1-naphthyl)-6-(4-prop-2-enoylpiperazin-1-yl)pyrimidine-4-carboxamide

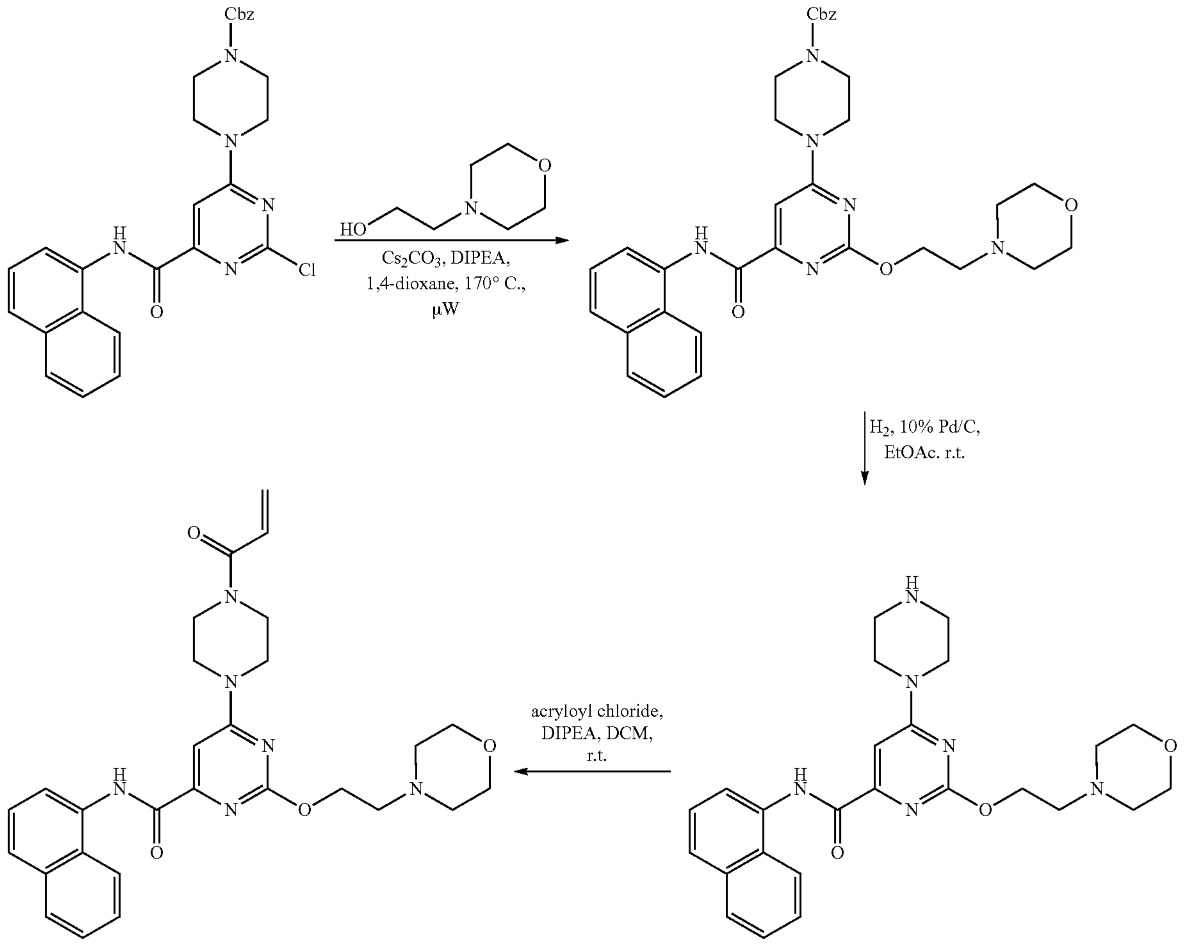

Example 7

Step 1—benzyl 4-[2-(2-morpholinoethoxy)-6-(1-naphthylcarbamoyl)pyrimidin-4-yl]piperazine-1-carboxylate To benzyl 4-[2-chloro-6-(1-naphthylcarbamoyl)pyrimidin-4-yl]piperazine-1-carboxylate (130 mg, 0.26 mmol) (Step 1, Example 1) was added 1,4-dioxane (5 mL) followed by the addition of 2-morpholinoethanol (0.16 mL, 1.3 mmol), $Cs_2CO_3$ (253 mg, 0.78 mmol) and DIPEA (0.36 mL, 2.07 mmol). The reaction was stirred at 170° C. for 4 hours in the microwave. Solvent was removed in vacuo and the residue dissolved in EtOAc (50 mL) and washed with brine (50 mL). The organic phase was separated, dried over $Na_2SO_4$ and solvent removed in vacuo. The residue was purified by column chromatography using an eluent of 0-5% MeOH in DCM reached via a gradient to give benzyl 4-[2-(2-morpholinoethoxy)-6-(1-naphthylcarbamoyl)pyrimidin-4-yl]piperazine-1-carboxylate (56 mg, 0.09 mmol, 36% yield) as a yellow oil.

UPLC-MS ($ES^+$, Method 2): 1.59 min, m/z 597.4 $[M+H]^+$ $^1$H-NMR (400 MHz, $CDCl_3$) δ/ppm: 10.42 (1H, s), 8.31-8.27 (1H, m), 8.04-7.99 (1H, m), 7.94-7.90 (1H, m), 7.74 (1H, d, J=8.0 Hz), 7.61-7.52 (3H, m), 7.45-7.34 (5H, m), 7.23 (1H, s), 5.20 (2H, s), 4.60 (2H, t, J=6.4 Hz), 3.84-3.73 (8H, m), 3.68-3.60 (4H, m), 2.91 (2H, t, J=6.4 Hz), 2.69-2.60 (4H, m).

Step 2—2-(2-morpholinoethoxy)-N-(1-naphthyl)-6-piperazin-1-yl-pyrimidine-4-carboxamide Benzyl 4-[2-(2-morpholinoethoxy)-6-(1-naphthylcarbamoyl)pyrimidin-4-yl]piperazine-1-carboxylate (56 mg, 0.09 mmol) was dissolved in EtOAc (7 mL) followed by the addition of palladium, 10 wt. % on carbon powder, (20 mg, 0.19 mmol) under inert atmosphere. The reaction was fitted with a $H_2$ balloon and subjected to 3×vacuum/$H_2$ cycles and then left to stir under an $H_2$ atmosphere for 4 hours. The reaction was filtered through celite, washed with $NH_3$ in MeOH (10 mL) and the solvent removed in vacuo to give 2-(2-morpholinoethoxy)-N-(1-naphthyl)-6-piperazin-1-yl-pyrimidine-4-carboxamide (36 mg, 0.08 mmol, 83% yield) as a pale yellow oil.

UPLC-MS (ES+, Method 2): 1.20 min, m/z 463.3 $[M+H]^+$.

Step 3—2-(2-morpholinoethoxy)-N-(1-naphthyl)-6-(4-prop-2-enoylpiperazin-1-yl)pyrimidine-4-carboxamide Acryloyl chloride (0.01 mL, 0.09 mmol) and 2-(2-morpholinoethoxy)-N-(1-naphthyl)-6-piperazin-1-yl-pyrimidine-4-carboxamide (36 mg, 0.08 mmol) were dissolved in DCM (4 mL) and stirred followed by the addition of DIPEA (0.04 mL, 0.23 mmol). After 5 minutes a solution 2M $K_2CO_3$ (5 mL) was added and the mixture allowed to stir for 20 minutes. DCM (10 mL) was added and the organic layer separated, dried over $Na_2SO_4$ and the solvent removed in vacuo. The residue was purified by preparative LC-MS to give 2-(2-morpholinoethoxy)-N-(1-naphthyl)-6-(4-prop-2-enoylpiperazin-1-yl)pyrimidine-4-carboxamide (Example 7) (13 mg, 0.02 mmol, 32% yield) as a white solid.

UPLC-MS ($ES^+$, Method 1): 2.80 min, m/z 517.5 $[M+H]^+$.

$^1$H-NMR (400 MHz, DMSO-$d_6$) δ/ppm: 10.66 (1H, s), 8.03-7.97 (1H, m), 7.95-7.89 (1H, m), 7.88-7.82 (2H, m), 7.62-7.53 (3H, m), 7.15 (1H, s), 6.84 (1H, dd, J=16.4 Hz, 10.4 Hz), 6.16 (1H, dd, J=16.4 Hz, 2.4 Hz), 5.74 (1H, dd, J=10.4 Hz, 2.4 Hz), 4.56 (2H, t, J=6.0 Hz), 3.88-3.62 (8H, m), 3.58 (4H, t, J=4.8 Hz), 2.73 (2H, t, J=6.0 Hz), 2.54-2.44 (4H, m).

Example 8—6-[(3S)-3-(cyanomethyl)-4-prop-2-enoyl-piperazin-1-yl]-N-(3-hydroxy-1-naphthyl)-2-[[(2S)-1-methylpyrrolidin-2-yl]methoxy]pyrimidine-4-carboxamide

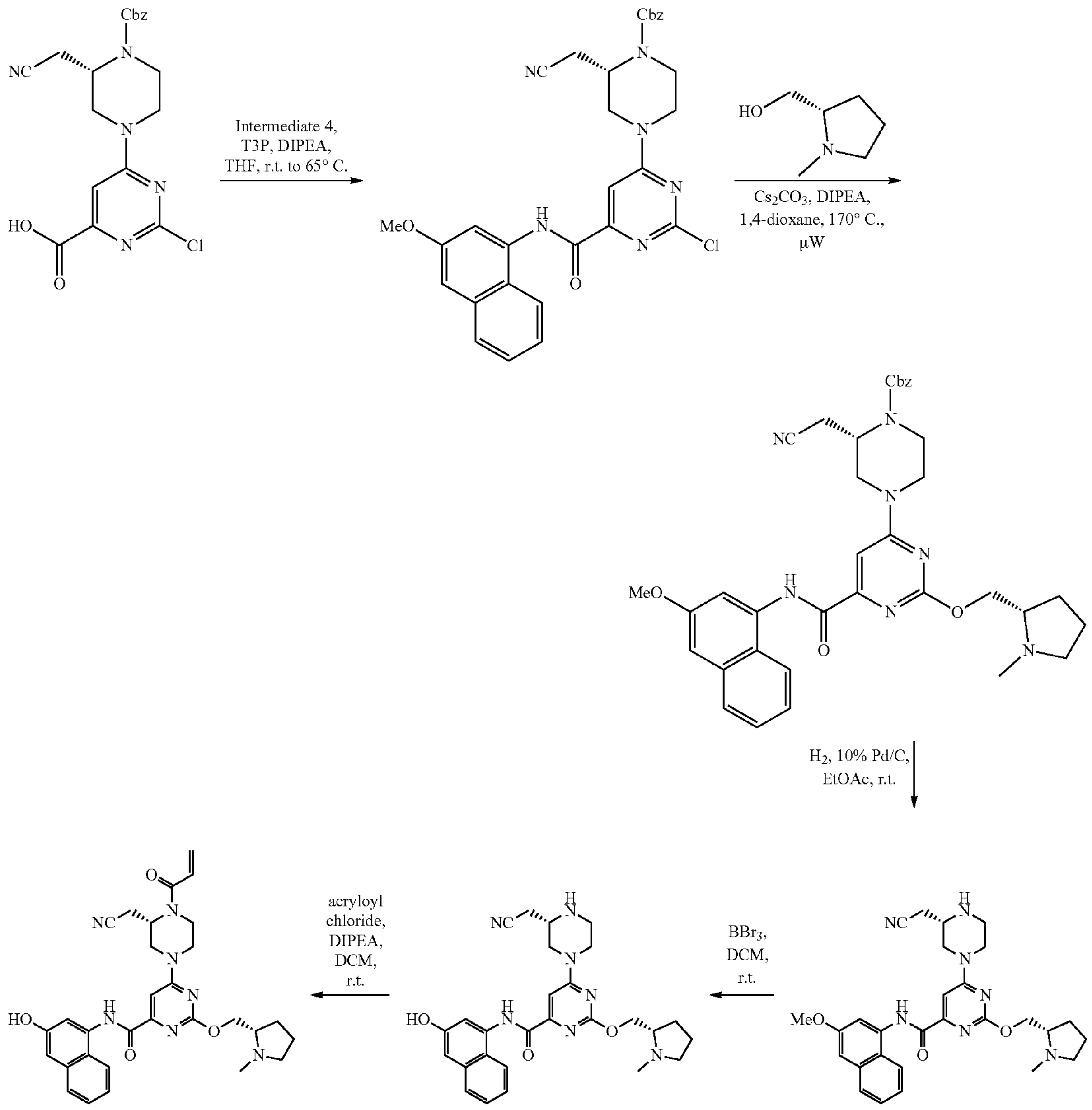

Example 8

Step 1—benzyl (2S)-4-[2-chloro-6-[(3-methoxy-1-naphthyl)carbamoyl]pyrimidin-4-yl]-2-(cyanomethyl)piperazine-1-carboxylate Intermediate 4 (76 mg, 0.44 mmol) and 6-[(3S)-4-benzyloxycarbonyl-3-(cyanomethyl)piperazin-1-yl]-2-chloro-pyrimidine-4-carboxylic acid (Step 1, Example 2) (170 mg, 0.41 mmol) were dissolved in THF (5 mL) and stirred. T3P (0.36 mL, 0.61 mmol, 50% volume in EtOAc) and DIPEA (0.21 mL, 1.23 mmol) were added and the reaction was left to stir at room temperature for 18 hours and then heated to 65° C. for 1 hour. Solvent was then removed in vacuo. The residue was dissolved in DCM (100 mL) and washed with water (2×100 mL). The organic phase was dried over $Na_2SO_4$ and solvent removed in vacuo. The residue was purified by column chromatography using an eluent of 0-50% EtOAc in petroleum ether reached via a gradient to give benzyl (2S)-4-[2-chloro-6-[(3-methoxy-1-naphthyl)carbamoyl]pyrimidin-4-yl]-2-(cyanomethyl)piperazine-1-carboxylate (200 mg, 0.35 mmol, 85% yield) as a yellow oil.

UPLC-MS (ES+, Method 2): 2.08 min, m/z 573.2 $[M+H]^+$.

$^1$H-NMR (400 MHz, $CDCl_3$) δ/ppm: 10.33 (1H, s), 8.09 (1H, d, J=2.4 Hz), 7.90 (1H, d, J=8.0 Hz), 7.78 (1H, d, J=8.0 Hz), 7.53-7.43 (2H, m), 7.42-7.33 (6H, m), 7.05 (1H, d, J=2.4 Hz), 5.21 (2H, s), 4.63 (1H, br s), 4.46 (1H, br s), 4.20 (2H, br s), 3.95 (3H, s), 3.83-3.63 (1H, m), 3.51-3.29 (2H, m), 2.94-2.65 (2H, m).

Step 2—benzyl (2S)-2-(cyanomethyl)-4-[6-[(3-methoxy-1-naphthyl)carbamoyl]-2-[[(2S)-1-methylpyrrolidin-2-yl]methoxy]pyrimidin-4-yl]piperazine-1-carboxylate To benzyl (2S)-4-[2-chloro-6-[(3-methoxy-1-naphthyl)carbamoyl]pyrimidin-4-yl]-2-(cyanomethyl)piperazine-1-carboxylate (200 mg, 0.35 mmol) in a microwave vial was added 1,4-dioxane (5 mL) followed by the addition of (S)-(−)-1-methyl-2-pyrrolidinemethanol (0.21 mL, 1.77 mmol), $Cs_2CO_3$ (342 mg, 1.05 mmol) and DIPEA (0.5 mL, 2.87 mmol). The reaction was heated at the microwave at 170° C. for 2 hours. The solvent was then removed in vacuo and the residue was dissolved in EtOAc (100 mL) and washed with brine (100 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[6-[(3-methoxy-1-naphthyl)carbamoyl]-2-[[(2S)-1-methylpyrrolidin-2-yl]methoxy]pyrimidin-4-yl]piperazine-1-carboxylate (70 mg, 0.11 mmol, 31% yield) as a dark yellow oil.

UPLC-MS (ES+, Method 2): 1.59 min, m/z 650.6 $[M+H]^+$.

Step 3—6-[(3S)-3-(cyanomethyl)piperazin-1-yl]-N-(3-methoxy-1-naphthyl)-2-[[(2S)-1-methylpyrrolidin-2-yl]methoxy]pyrimidine-4-carboxamide Benzyl (2S)-2-(cyanomethyl)-4-[6-[(3-methoxy-1-naphthyl)carbamoyl]-2-[[(2S)-1-methylpyrrolidin-2-yl]methoxy]pyrimidin-4-yl]piperazine-1-carboxylate (70 mg, 0.11 mmol) was dissolved in EtOAc (7 mL) followed by the addition of palladium, 10 wt. % on carbon powder, (10 mg, 0.09 mmol) under a nitrogen atmosphere. The reaction was fitted with a $H_2$ balloon and subjected to 3×vacuum/$H_2$ cycles and then left to stir under an $H_2$ atmosphere for 72 hours. The reaction was filtered through celite, washed with $NH_3$ in MeOH (10 mL) and solvent removed in vacuo to give 6-[(3S)-3-(cyanomethyl)piperazin-1-yl]-N-(3-methoxy-1-naphthyl)-2-[[(2S)-1-methylpyrrolidin-2-yl]methoxy]pyrimidine-4-carboxamide (45 mg, 0.08 mmol, 81% yield) as a pale yellow solid.

UPLC-MS (ES+, Method 2): 1.30 min, m/z 516.5 $[M+H]^+$.

Step 4—6-[(3S)-3-(cyanomethyl)piperazin-1-yl]-N-(3-hydroxy-1-naphthyl)-2-[[(2S)-1-methylpyrrolidin-2-yl]methoxy]pyrimidine-4-carboxamide 6-[(3S)-3-(cyanomethyl)piperazin-1-yl]-N-(3-methoxy-1-naphthyl)-2-[[(2S)-1-methylpyrrolidin-2-yl]methoxy]pyrimidine-4-carboxamide (45 mg, 0.09 mmol) was dissolved in DCM (4 mL) followed by the addition of boron tribromide (0.06 mL, 0.35 mmol). After 1 hour MeOH (5 mL) was added and solvent removed in vacuo. The residue was loaded into an SCX-2 column and flushed at first with MeOH (10 mL) and then $NH_3$ in MeOH (10 mL) to elute the product. Fractions containing the products were combined and the solvent removed in vacuo to give 6-[(3S)-3-(cyanomethyl)piperazin-1-yl]-N-(3-hydroxy-1-naphthyl)-2-[[(2S)-1-methylpyrrolidin-2-yl]methoxy]pyrimidine-4-carboxamide (30 mg, 0.06 mmol, 68% yield) as a dark yellow oil.

UPLC-MS (ES+, Method 2): 1.12 min, m/z 502.4 $[M+H]^+$.

Step 5—6-[(3S)-3-(cyanomethyl)-4-prop-2-enoyl-piperazin-1-yl]-N-(3-hydroxy-1-naphthyl)-2-[[(2S)-1-methylpyrrolidin-2-yl]methoxy]pyrimidine-4-carboxamide Acryloyl chloride (0.01 mL, 0.06 mmol) and 6-[(3S)-3-(cyanomethyl)piperazin-1-yl]-N-(3-hydroxy-1-naphthyl)-2-[[(2S)-1-methylpyrrolidin-2-yl]methoxy]pyrimidine-4-carboxamide (30 mg, 0.06 mmol) were dissolved in DCM (4 mL) followed by the addition of DIPEA (0.03 mL, 0.18 mmol). The reaction was left stirring for 5 min. A solution 2M $K_2CO_3$ (5 mL) added and the mixture allowed to stir for 20 minutes. DCM (10 mL) was then added and the organic layer separated, dried over $Na_2SO_4$ and solvent removed in vacuo. The residue was purified by preparative LC-MS to give 6-[(3S)-3-(cyanomethyl)-4-prop-2-enoyl-piperazin-1-yl]-N-(3-hydroxy-1-naphthyl)-2-[[(2S)-1-methylpyrrolidin-2-yl]methoxy]pyrimidine-4-carboxamide (Example 8) (3 mg, 0.01 mmol, 9% yield) as a pale yellow solid.

UPLC-MS (ES+, Method 1): 2.66 min, m/z 556.4 $[M+H]^+$.

$^1$H-NMR (400 MHz, DMSO-$d_6$) δ/ppm: 10.64 (1H, s), 7.81-7.71 (2H, m), 7.61 (1H, d, J=2.4 Hz), 7.48-7.43 (1H, m), 7.36-7.30 (1H, m), 7.20-7.12 (1H, m), 7.06 (1H, d, J=2.4 Hz), 6.95-6.80 (1H, m), 6.25-6.17 (1H, m), 5.82-5.77 (1H, m), 4.99-4.78 (1H, m), 4.54-4.22 (4H, m), 4.16-4.06 (1H, m), 3.62-3.54 (2H, m), 3.11-2.87 (4H, m), 2.65-2.58 (1H, m), 2.40 (3H, s), 2.26-2.15 (1H, m), 2.05-1.93 (1H, m), 1.78-1.60 (3H, m), exchangeable proton not seen.

Example 9—N-(1-naphthyl)-6-(4-prop-2-enoylpiperazin-1-yl)-2-(3-pyridyl)pyrimidine-4-carboxamide

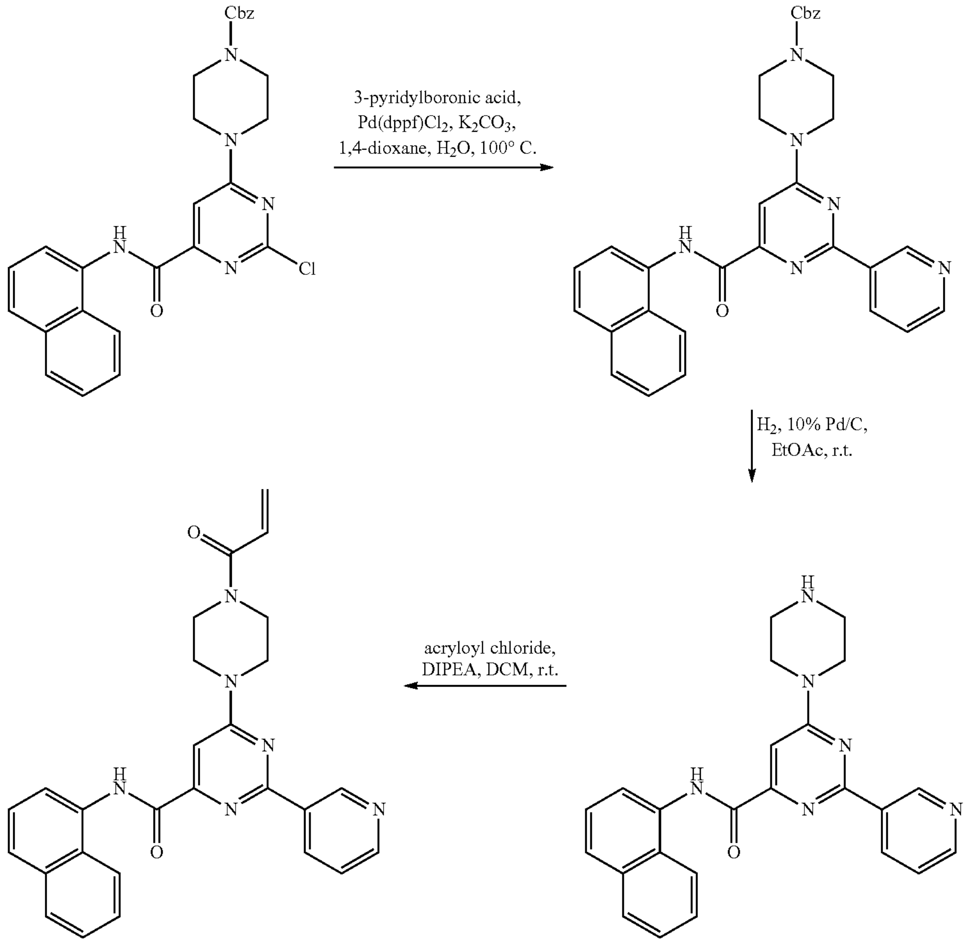

Example 9

Step 1—benzyl 4-[6-(1-naphthylcarbamoyl)-2-(3-pyridyl)pyrimidin-4-yl]piperazine-1-carboxylate 3-Pyridylboronic acid (48 mg, 0.39 mmol), benzyl 4-[2-chloro-6-(1-naphthylcarbamoyl)pyrimidin-4-yl]piperazine-1-carboxylate (Step 1, Example 1) (130 mg, 0.26 mmol), $Pd(dppf)Cl_2 \cdot CH_2Cl_2$ (31 mg, 0.04 mmol) and $K_2CO_3$ (160 mg, 1.16 mmol) were dissolved in 1,4-dioxane (4 mL) and water (1 mL). The flask was evacuated and flushed 3 times with nitrogen and then stirred under a nitrogen atmosphere at 100° C. for 18 hours. Solvent was then removed in vacuo. The residue was purified by column chromatography using an eluent of 0-60% EtOAc in petroleum ether reached via a gradient to give benzyl 4-[6-(1-naphthylcarbamoyl)-2-(3-pyridyl)pyrimidin-4-yl]piperazine-1-carboxylate (83 mg, 0.15 mmol, 59% yield) as a pale yellow oil.

UPLC-MS ($ES^+$, Method 2): 1.95 min, m/z 545.4 $[M+H]^+$.

$^1$H-NMR (400 MHz, $CDCl_3$) δ/ppm: 10.66 (1H, s), 9.73 (1H, s), 8.87 (1H, d, J=7.6 Hz), 8.78 (1H, d, J=4.0 Hz), 8.36 (1H, dd, J=7.6 Hz, 0.8 Hz), 8.07 (1H, d, J=8.4 Hz), 7.92 (1H, d, J=8.0 Hz), 7.75 (1H, d, J=8.4 Hz), 7.66 (1H, app dt, J=7.2 Hz, 0.8 Hz), 7.62-7.50 (4H, m), 7.42-7.32 (5H, m), 5.20 (2H, s), 3.93 (4H, br s), 3.74-3.67 (4H, m).

Step 2—N-(1-naphthyl)-6-piperazin-1-yl-2-(3-pyridyl)pyrimidine-4-carboxamide

Benzyl 4-[6-(1-naphthylcarbamoyl)-2-(3-pyridyl)pyrimidin-4-yl]piperazine-1-carboxylate (83 mg, 0.15 mmol) was dissolved in EtOAc (7 mL) followed by the addition of palladium, 10 wt. % on carbon powder, (20 mg, 0.19 mmol) under inert atmosphere. The reaction was fitted with a $H_2$ balloon and subjected to 3×vacuum/$H_2$ cycles and then left to stir under a $H_2$ atmosphere for 4 hours. The reaction was filtered through celite, washed with $NH_3$ in MeOH (10 mL) and solvent removed in vacuo to give N-(1-naphthyl)-6-piperazin-1-yl-2-(3-pyridyl)pyrimidine-4-carboxamide (54 mg, 0.13 mmol, 86% yield) as a yellow solid. UPLC-MS ($ES^+$, Method 2): 1.29 min, m/z 411.2 $[M+H]^+$.

Step 3—N-(1-naphthyl)-6-(4-prop-2-enoylpiperazin-1-yl)-2-(3-pyridyl)pyrimidine-4-carboxamide Acryloyl chloride (0.01 mL, 0.14 mmol) and N-(1-naphthyl)-6-piperazin-1-yl-2-(3-pyridyl)pyrimidine-4-carboxamide (54 mg, 0.13 mmol) were dissolved in DCM (4 mL) followed by the addition of DIPEA (0.07 mL, 0.40 mmol). The reaction was left stirring for 5 minutes and then a solution 2M $K_2CO_3$ (5 mL) was added and the mixture allowed to stir for 20 minutes. DCM (10 mL) was then added and the organic layer separated, dried over $Na_2SO_4$ and solvent removed in vacuo. The residue was purified by column chromatography using an eluent of 0-3% MeOH in DCM reached via a gradient followed by preparative LC-MS to give N-(1-naphthyl)-6-(4-prop-2-enoylpiperazin-1-yl)-2-(3-pyridyl)pyrimidine-4-carboxamide (Example 9) (17 mg, 0.04 mmol, 28% yield) as a pale yellow solid.

UPLC-MS (ES+, Method 1): 3.49 min, m/z 465.4 $[M+H]^+$.

$^1$H-NMR (400 MHz, DMSO-$d_6$) δ/ppm: 11.05 (1H, s), 9.84 (1H, dd, J=2.0 Hz, 0.8 Hz), 8.98 (1H, dt, J=8.0 Hz, 1.6 Hz), 8.73 (1H, dd, J=4.8 Hz, 1.6 Hz), 8.04-7.95 (2H, m), 7.91 (1H, d, J=8.4 Hz), 7.76 (1H, d, J=7.2 Hz), 7.64-7.55 (4H, m), 7.46 (1H, s), 6.87 (H, dd, J=16.4 Hz, 10.4 Hz), 6.18 (1H, dd, J=16.4 Hz, 2.4 Hz), 5.75 (1H, dd, J=10.4 Hz, 2.4 Hz), 3.93 (4H, br s), 3.81-3.69 (4H, m).

The compounds below were made in an analogous manner to Example 9, using the appropriate boronic ester in place of 3-pyridylboronic acid in the first step:

| Compound | Name | Data |
| --- | --- | --- |
| Example 10 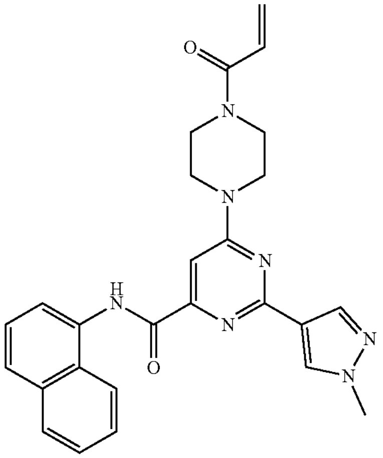 | 2-(1-methylpyrazol-4-yl)-N-(1-naphthyl)-6-(4-prop-2-enoylpiperazin-1-yl)pyrimidine-4-carboxamide | UPLC-MS (ES+, Method 1): 3.86 min, m/z 468.4 $[M + H]^+$. $^1$H-NMR (400 MHz, DMSO-$d_6$,) δ/ppm: 10.91 (1H, s), 8.58 (1H, s), 8.27 (1H, s), 8.03-8.00 (1H, m), 7.98-7.94 (1H, m), 7.90 (1H, d, J = 8.4 Hz), 7.82 (1H, d, J = 7.2 Hz), 7.66-7.56 (3H, m), 7.25 (1H, s), 6.86 (1H, dd, J = 16.8 Hz, 10.4 Hz), 6.17 (1H, dd, J = 16.8 Hz, 2.4 Hz), 5.74 (1H, dd, J = 10.4 Hz, 2.4 Hz), 3.92 (3H, s), 3.85 (4H, br s), 3.77-3.66 (4H, m). |
| Example 11 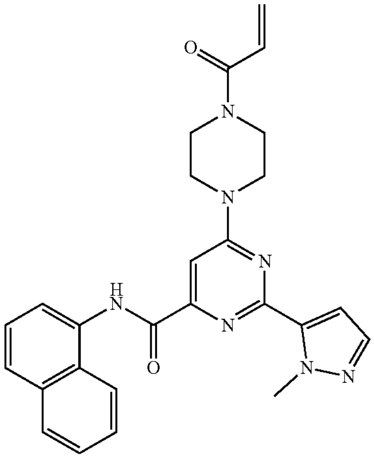 | 2-(2-methylpyrazol-3-yl)-N-(1-naphthyl)-6-(4-prop-2-enoylpiperazin-1-yl)pyrimidine-4-carboxamide | UPLC-MS (ES+, Method 1): 4.05 min, m/z 468.3 $[M + H]^+$. $^1$H-NMR (400 MHz, DMSO-$d_6$) δ/ppm: 10.75 (s, 1H), 8.04-7.99 (1H, m), 7.99-7.95 (1H, m), 7.91-7.86 (2H, m), 7.65-7.56 (3H, m), 7.54 (1H, d, J = 2.0 Hz), 7.40 (1H, s), 7.34 (1H, d, J = 2.0 Hz), 6.86 (1H, dd, J = 16.8 Hz, 10.4 Hz), 6.17 (1H, dd, J = 16.8 Hz, 2.4 Hz), 5.74 (1H, dd, J = 10.4 Hz, 2.4 Hz), 4.35 (3H, s), 4.87 (4H, br s), 3.80-3.69 (4H, m). |

Example 12—N-[2-(4-methylpiperazin-1-yl)-6-(4-prop-2-enoylpiperazin-1-yl)pyrimidin-4-yl]naphthalene-1-carboxamide

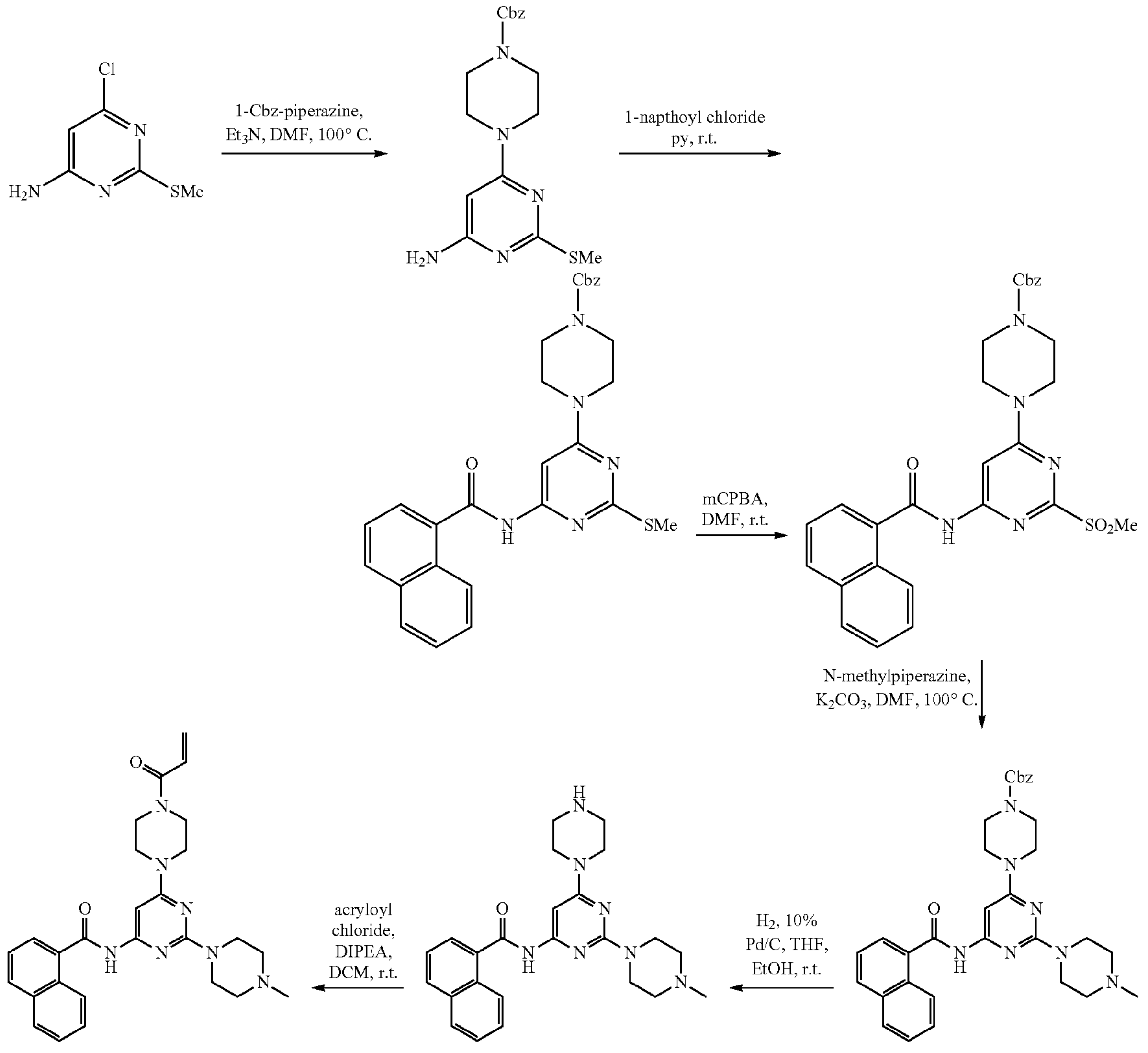

Example 12

Step 1—benzyl 4-(6-amino-2-methylsulfanyl-pyrimidin-4-yl)piperazine-1-carboxylate 1-Cbz-piperazine (4.19 mL, 21.87 mmol) was added to a stirred solution of 6-chloro-2-(methylsulfanyl)-4-pyrimidinamine (1.93 g, 10.93 mmol), $Et_3N$ (3.05 mL, 21.87 mmol) and DMF (10 mL) at room temperature under a nitrogen atmosphere. The reaction was heated to 100° C. and allowed to stir for 18 hours. The reaction was then cooled to room temperature and solvent removed in vacuo. The residue was partitioned between water (100 mL) and DCM (100 mL). The organic layer separated and washed with sat. aq. $NH_4Cl$ (100 mL), sat. aq. $NaHCO_3$ (100 mL), dried over $Na_2SO_4$ and solvent removed in vacuo. The residue was purified by column chromatography using an eluent of 0-100% EtOAc in petroleum ether reached via a gradient to give benzyl 4-(6-amino-2-methylsulfanyl-pyrimidin-4-yl)piperazine-1-carboxylate (3.10 g, 8.62 mmol, 78% yield) as a waxy brown solid.

UPLCMS (ES+, Method 2): 1.34 min, m/z 360.5 $[M+H]^+$. $^1H$ NMR (400 MHz, DMSO-$d_6$) δ/ppm: 7.41-7.30 (5H, m), 6.30 (1H, s), 5.12 (2H, s), 3.50-3.35 (8H, m), 2.36 (3H, s), exchangeable protons not seen.

Step 2—benzyl 4-[2-methylsulfanyl-6-(naphthalene-1-carbonylamino)pyrimidin-4-yl]piperazine-1-carboxylate 1-Naphthoyl chloride (0.32 mL, 2.08 mmol) was added to a stirred solution of benzyl 4-(6-amino-2-methylsulfanyl-pyrimidin-4-yl)piperazine-1-carboxylate (500 mg, 1.40 mmol) and pyridine (5 mL) at room temperature under a nitrogen atmosphere. After stirring for 1 hour solvent was removed in vacuo and the residue partitioned between water (50 mL) and DCM (50 mL). The organic layer was separated, dried over $Na_2SO_4$ and solvent removed in vacuo. The residue was purified by column chromatography using an eluent of 0-50% EtOAc in petroleum ether reached via a gradient to give benzyl 4-[2-methylsulfanyl-6-(naphthalene-1-carbonylamino)pyrimidin-4-yl]piperazine-1-carboxylate (350 mg, 0.68 mmol, 48% yield) as an orange oil.

UPLCMS (ES+, Method 2): 2.10 min, m/z 514.3 $[M+H]^+$.

$^1$H NMR (400 MHz, DMSO-$d_6$) δ/ppm: 9.01-8.99 (1H, m), 8.69-8.63 (1H, m), 8.42-8.36 (1H, m), 8.11-8.08 (1H, m), 8.04-8.02 (1H, m), 7.96-7.91 (2H, m), 7.82-7.80 (1H, m), 7.67-7.50 (4H, m), 7.43-7.32 (2H, m), 5.21 (2H, s), 3.83-3.76 (4H, m), 3.70-3.63 (4H, m), 2.51 (3H, s).

Step 3—benzyl 4-[2-methylsulfonyl-6-(naphthalene-1-carbonylamino)pyrimidin-4-yl]piperazine-1-carboxylate m-Chloroperbenzoic acid (353 mg, 2.04 mmol) was added to a stirred solution of benzyl 4-[2-methylsulfanyl-6-(naphthalene-1-carbonylamino)pyrimidin-4-yl]piperazine-1-carboxylate (350 mg, 0.68 mmol) and DCM (10 mL) at room temperature under a nitrogen atmosphere. The reaction was allowed to stir for 2 hours. Solvent was removed in vacuo and the residue purified by column chromatography using an eluent of 0-100% EtOAc in petroleum ether reached via a gradient to give benzyl 4-[2-methylsulfonyl-6-(naphthalene-1-carbonylamino)pyrimidin-4-yl]piperazine-1-carboxylate (310 mg, 0.57 mmol, 83% yield) as a white solid.

UPLCMS (ES+, Method 2): 1.86 min, m/z 546.2 $[M+H]^+$.

$^1$H NMR (400 MHz, $CDCl_3$) δ/ppm: 8.59-8.54 (1H, m), 8.41-8.36 (1H, m), 8.08-8.03 (1H, m), 7.98-7.93 (1H, m), 7.90-7.87 (1H, m), 7.82-7.78 (1H, m), 7.66-7.53 (3H, m), 7.43-7.35 (4H, m), 5.22 (2H, s), 3.96-3.66 (8H, m), 3.28 (3H, s), exchangeable proton not seen.

Step 4—benzyl 4-[2-(4-methylpiperazin-1-yl)-6-(naphthalene-1-carbonylamino)pyrimidin-4-yl]piperazine-1-carboxylate Benzyl 4-[2-methylsulfonyl-6-(naphthalene-1-carbonylamino)pyrimidin-4-yl]piperazine-1-carboxylate (155 mg, 0.28 mmol), 1-methylpiperazine (0.11 mL, 0.85 mmol), $K_2CO_3$ (118 mg, 0.85 mmol) and DMF (5 mL) were combined and stirred under a nitrogen atmosphere. The reaction was heated to 100° C. for 18 hours and then cooled to room temperature. Solvent was removed in vacuo and the residue partitioned between water (50 mL) and DCM (50 mL). The organic layer was separated, dried over $Na_2SO_4$ and solvent removed in vacuo. The residue was purified by column chromatography using an eluent of 0-5% MeOH in DCM reached via a gradient to give benzyl 4-[2-(4-methylpiperazin-1-yl)-6-(naphthalene-1-carbonylamino)pyrimidin-4-yl]piperazine-1-carboxylate (67 mg, 0.12 mmol, 42% yield) as a yellow oil.

UPLCMS (ES+, Method 2): 1.65 min, m/z 566.3 $[M+H]^+$.

Step 5—N-[2-(4-methylpiperazin-1-yl)-6-piperazin-1-yl-pyrimidin-4-yl]naphthalene-1-carboxamide Palladium, 10 wt. % on carbon powder, (20 mg) was added to a stirred solution of benzyl 4-[2-(4-methylpiperazin-1-yl)-6-(naphthalene-1-carbonylamino)pyrimidin-4-yl]piperazine-1-carboxylate (67 mg, 0.12 mmol) and EtOAc (5 mL) at room temperature under a nitrogen atmosphere. The reaction was fitted with a $H_2$ balloon and subjected to 3×vacuum/$H_2$ cycles and then allowed to stir for 48 hours under a $H_2$ atmosphere. The reaction was then filtered through celite and the filter cake washed with MeOH (10 mL) and $NH_3$ in MeOH (10 mL). The filtrate was concentrated in vacuo to give N-[2-(4-methylpiperazin-1-yl)-6-piperazin-1-yl-pyrimidin-4-yl]naphthalene-1-carboxamide (50 mg, 0.12 mmol, 98% yield) as a yellow oil which was used in the next step without further purification.

UPLCMS (ES+, Method 2): 1.12 min, m/z 432.2 $[M+H]^+$.

Step 6—N-[2-(4-methylpiperazin-1-yl)-6-(4-prop-2-enoylpiperazin-1-yl)pyrimidin-4-yl]naphthalene-1-carboxamide Acryloyl chloride (14 μL, 0.1738 mmol) was added to a stirred solution of N-[2-(4-methylpiperazin-1-yl)-6-piperazin-1-yl-pyrimidin-4-yl]naphthalene-1-carboxamide (50 mg, 0.12 mmol), DIPEA (0.03 mL, 0.17 mmol) and DCM (5 mL) at room temperature. After 5 minutes a solution of 2M $K_2CO_3$ (20 mL) was added and the resulting mixture stirred for 10 minutes. DCM (50 mL) was then added and the organic layer separated, dried over $Na_2SO_4$ and solvent removed in vacuo. The residue was purified by column chromatography using an eluent of 0-5% MeOH in DCM reached via a gradient to give N-[2-(4-methylpiperazin-1-yl)-6-(4-prop-2-enoylpiperazin-1-yl)pyrimidin-4-yl]naphthalene-1-carboxamide (Example 12) (4 mg, 0.01 mmol, 7% yield) as a white solid.

UPLCMS (ES+, Method 1): 2.85 min, m/z 486.3 $[M+H]^+$.

$^1$H NMR (400 MHz, $CD_3OD$) δ/ppm: 8.27-8.21 (1H, m), 8.06-8.04 (1H, m), 7.99-7.95 (1H, m), 7.74-7.73 (1H, m), 7.63-7.54 (3H, m), 7.18-7.05 (1H, m), 6.84 (1H, dd, J=16.8 Hz, 10.8 Hz), 6.27 (1H, dd, J=16.8 Hz, 2.0 Hz), 5.81 (1H, dd, J=10.8 Hz, 2.0 Hz), 3.83-3.71 (12H, m), 2.51-2.44 (4H, m), 2.34 (3H, s), exchangeable proton not seen.

Example 13—N-methyl-2-[[(2S)-1-methylpyrrolidin-2-yl]methoxy]-N-(1-naphthyl)-6-(4-prop-2-enoylpiperazin-1-yl)pyrimidine-4-carboxamide

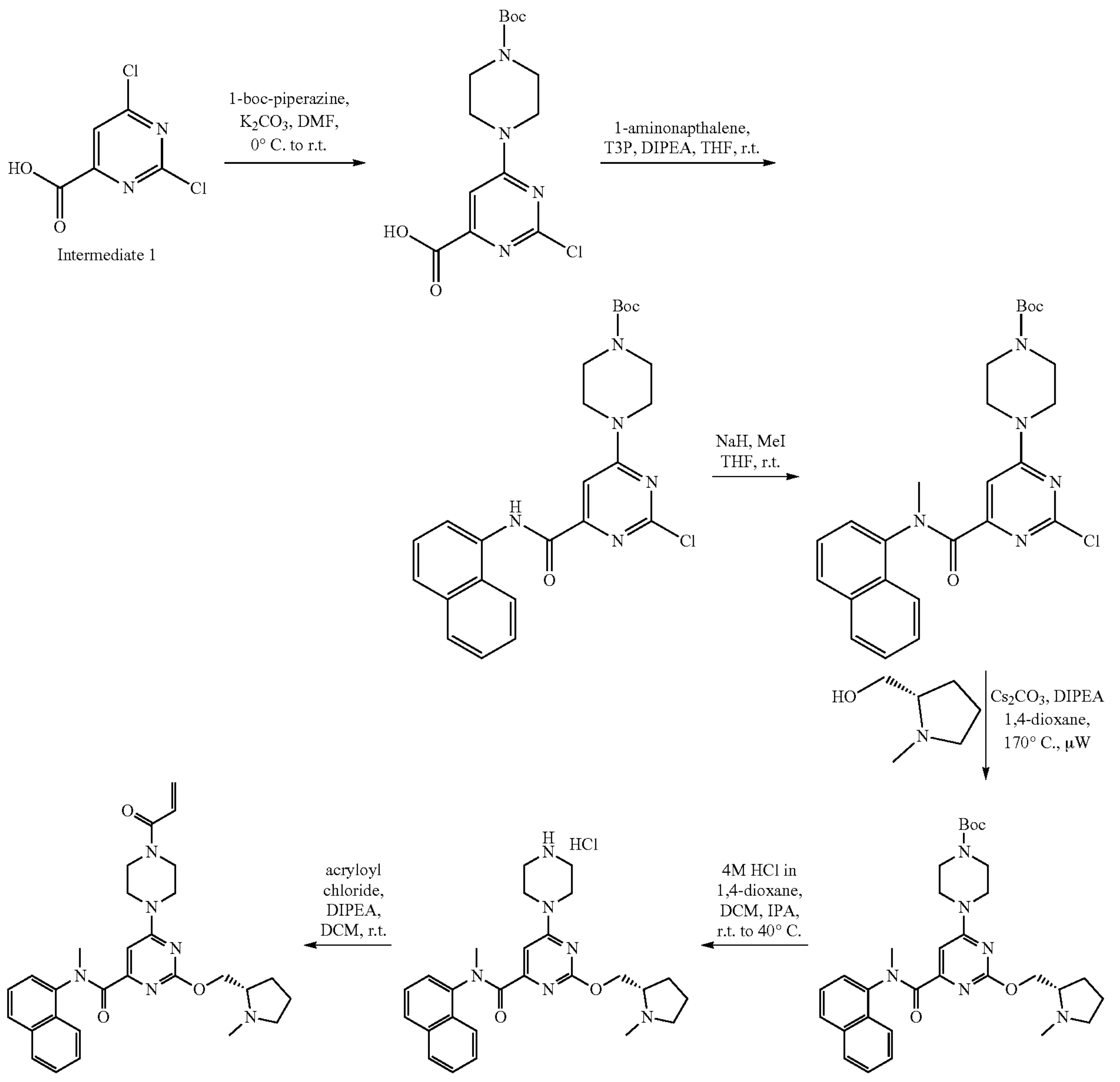

Example 13

Step 1—6-(4-tert-butoxycarbonylpiperazin-1-yl)-2-chloro-pyrimidine-4-carboxylic acid Intermediate 1 (729 mg, 3.78 mmol), $K_2CO_3$ (3.65 g, 26.44 mmol) were stirred in DMF (20 mL) at 0° C. followed by the addition of 1-boc-piperazine (0.58 mL, 3.02 mmol). The reaction was allowed to warm to room temperature and stir for 18 hours. The volatiles were removed in vacuo. Water (100 mL) was added and the pH adjusted ~2 by addition of 1M aq. HCl followed by extraction with EtOAc (3×200 mL). The organic phases were combined, dried over $Na_2SO_4$ and the solvent removed under vacuo. The material was purified by column chromatography using an eluent of 0-20% MeOH in DCM reached via a gradient to give 6-(4-tert-butoxycarbonylpiperazin-1-yl)-2-chloro-pyrimidine-4-carboxylic acid (805 mg, 2.35 mmol, 62% yield) as a pale yellow solid.

UPLC-MS (ES+, Method 2): 1.50 min, m/z 343.1, 345.0 $[M+H]^+$.

$^1$H-NMR (400 MHz, DMSO-$d_6$) δ/ppm: 7.12-6.91 (2H, m), 3.64-3.56 (4H, m), 3.45-3.37 (4H, m), 1.43 (9H, s).

Step 2—tert-butyl 4-[2-chloro-6-(1-naphthylcarbamoyl)pyrimidin-4-yl]piperazine-1-carboxylate 6-(4-tert-butoxycarbonylpiperazin-1-yl)-2-chloro-pyrimidine-4-carboxylic acid (315 mg, 0.92 mmol) was dissolved in THF (10 mL) followed by the addition of 1-aminonaphthalene (157.91 mg, 1.10 mmol), T3P (0.82 mL, 1.38 mmol, 50% volume in EtOAc) and DIPEA (0.48 mL, 2.76 mmol). The reaction was stirred at room temperature for 18 hours and then solvent was removed in vacuo. The residue was dissolved in DCM (100 mL) and washed with water (2×100 mL). The organic phase was separated, dried over $Na_2SO_4$ and solvent removed in vacuo. The residue was purified by column chromatography using an eluent of 0-40% EtOAc in petroleum ether reached via a gradient to give tert-butyl 4-[2-chloro-6-(1-naphthylcarbamoyl)pyrimidin-4-yl]piperazine-1-carboxylate (236 mg, 0.50 mmol, 55% yield) as a pale yellow foam.

UPLC-MS (ES+, Method 2): 2.19 min, m/z 468.3, 470.2 $[M+H]^+$.

$^1$H-NMR (400 MHz, $CDCl_3$) δ/ppm: 10.31 (1H, s), 8.25 (1H, dd, J=7.6 Hz, 0.4 Hz), 8.01 (1H, dd, J=8.4 Hz, 0.8 Hz), 7.90 (1H, dt, J=8.0 Hz, 0.8 Hz), 7.74 (1H, d, J=8.4 Hz), 7.64-7.51 (3H, m), 7.42 (1H, s), 3.80 (4H, br s), 3.61-3.54 (4H, m), 1.50 (9H, s).

Step 3—tert-butyl 4-[2-chloro-6-[methyl(1-naphthyl)carbamoyl]pyrimidin-4-yl]piperazine-1-carboxylate tert-Butyl 4-[2-chloro-6-(1-naphthylcarbamoyl)pyrimidin-4-yl]piperazine-1-carboxylate (115 mg, 0.25 mmol) was dissolved in THF (4 mL) followed by the addition of NaH (60% dispersed in mineral oil-20 mg, 0.50 mmol) under a nitrogen atmosphere. After stirring for 20 minutes iodomethane (0.02 mL, 0.29 mmol) was added. The reaction was stirred for 18 hours after which time DCM (50 mL) and brine (50 mL) were added, the phases separated and the aqueous further extracted with DCM (3×50 mL). The organic phases were combined, dried over $Na_2SO_4$ and solvent removed in vacuo. The residue was purified by column chromatography using an eluent of 0-80% EtOAc in petroleum ether reached via a gradient to give tert-butyl 4-[2-chloro-6-[methyl(1-naphthyl)carbamoyl]pyrimidin-4-yl]piperazine-1-carboxylate (65 mg, 0.14 mmol, 55% yield) as a colourless oil.

UPLC-MS (ES+, Method 2): 1.93 min, m/z 482.3, 484.1 $[M+H]^+$.

Step 4—tert-butyl 4-[6-[methyl(1-naphthyl)carbamoyl]-2-[[(2S)-1-methylpyrrolidin-2-yl]methoxy]pyrimidin-4-yl]piperazine-1-carboxylate To tert-butyl 4-[2-chloro-6-[methyl(1-naphthyl)carbamoyl]pyrimidin-4-yl]piperazine-1-carboxylate (65 mg, 0.14 mmol) in a microwave vial was added 1,4-dioxane (5 mL) followed by the addition of (S)-(−)-1-methyl-2-pyrrolidinemethanol (0.08 mL, 0.68 mmol), $Cs_2CO_3$ (133 mg, 0.41 mmol) and DIPEA (0.19 mL, 1.09 mmol). The reaction was heated at the microwave at 170° C. for 3 hours. Solvent was then removed under reduce pressure and the residue dissolved in EtOAc (50 mL) and washed with brine (50 mL). The organic phase was separated, dried over $Na_2SO_4$ and the solvent removed in vacuo. The residue was purified by column chromatography using an eluent of 0-10% MeOH in DCM reached via a gradient to give tert-butyl 4-[6-[methyl(1-naphthyl)carbamoyl]-2-[[(2S)-1-methylpyrrolidin-2-yl]methoxy]pyrimidin-4-yl]piperazine-1-carboxylate (32 mg, 0.06 mmol, 42% yield) as a colourless oil.

UPLC-MS (ES+, Method 2): 1.48 min, m/z 561.4 $[M+H]^+$.

Step 5—N-methyl-2-[[(2S)-1-methylpyrrolidin-2-yl]methoxy]-N-(1-naphthyl)-6-piperazin-1-yl-pyrimidine-4-carboxamide hydrochloride tert-Butyl 4-[6-[methyl(1-naphthyl)carbamoyl]-2-[[(2S)-1-methylpyrrolidin-2-yl]methoxy]pyrimidin-4-yl]piperazine-1-carboxylate (32 mg, 0.06 mmol) was dissolved in DCM (5 mL) and IPA (1 mL) followed by the addition of HCl (4M in 1,4-dioxane-0.14 mL, 0.57 mmol). The reaction stirred at room temperature for 72 hours and then a second portion of HCl (4M in 1,4-dioxane-0.14 mL, 0.57 mmol) was added and the reaction was stirred at 40° C. for 24 hours. Solvent was then removed in vacuo to give N-methyl-2-[[(2S)-1-methylpyrrolidin-2-yl]methoxy]-N-(1-naphthyl)-6-piperazin-1-yl-pyrimidine-4-carboxamide hydrochloride (25 mg, 0.05 mmol, 90% yield) as a white solid, which was used in the next step without further purification.

UPLC-MS (ES+, Method 2): 1.04 min, m/z 461.2 $[M+H]^+$.

Step 6—N-methyl-2-[[(2S)-1-methylpyrrolidin-2-yl]methoxy]-N-(1-naphthyl)-6-(4-prop-2-enoylpiperazin-1-yl)pyrimidine-4-carboxamide DIPEA (0.04 mL, 0.21 mmol) was added to a stirred solution of N-methyl-2-[[(2S)-1-methylpyrrolidin-2-yl]methoxy]-N-(1-naphthyl)-6-piperazin-1-yl-pyrimidine-4-carboxamide hydrochloride (26 mg, 0.05 mmol), acryloyl chloride (0.01 mL, 0.08 mmol) in DCM (3 mL) at room temperature. After 5 minutes a solution of 2M $K_2CO_3$ (5 mL) was added and the mixture allowed to stir for 20 minutes. DCM (10 mL) was added and the organic layer separated, dried over $Na_2SO_4$ and solvent removed in vacuo. The residue was purified by column chromatography using an eluent of 0-8% MeOH in DCM reached via a gradient to give N-methyl-2-[[(2S)-1-methylpyrrolidin-2-yl]methoxy]-N-(1-naphthyl)-6-(4-prop-2-enoylpiperazin-1-yl)pyrimidine-4-carboxamide (Example 13) (24 mg, 0.05 mmol, 89% yield) as a white solid.

UPLC-MS (ES+, Method 1): 2.68 min, m/z 515.6 $[M+H]^+$.

$^1$H-NMR (400 MHz, DMSO-$d_6$) δ/ppm: 8.07-7.90 (2H, m), 7.83 (1H, d, J=8.4 Hz), 7.66-7.52 (2H, m), 7.39-7.33 (1H, m), 7.27 (1H, d, J=7.6 Hz), 6.77 (1H, dd, J=16.4 Hz, 10.4 Hz), 6.69 (1H, d, J=1.6 Hz), 6.13 (1H, dd, J=16.8 Hz, 2.4 Hz), 5.71 (1H, dd, J=10.4 Hz, 2.4 Hz), 3.81-3.63 (1H, m), 3.58-3.43 (9H, m), 3.39 (3H, s), 3.07-2.82 (2H, m), 2.31-1.96 (5H, m), 1.83-1.50 (3H, m).

Example 14—N-benzyl-2-[[(2S)-1-methylpyrrolidin-2-yl]methoxy]-6-(4-prop-2-enoylpiperazin-1-yl)pyrimidine-4-carboxamide

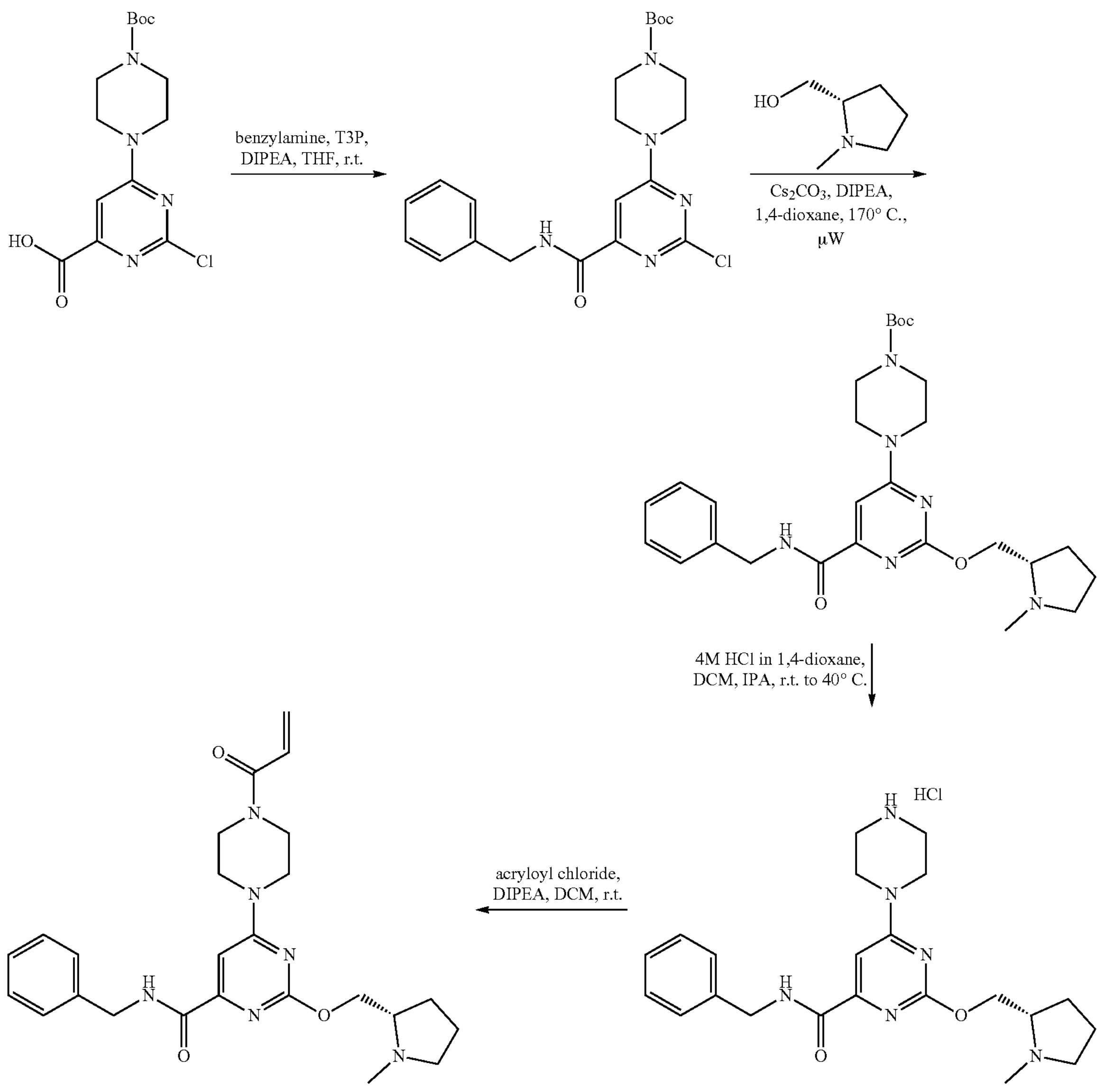

Example 14

Step 1—tert-butyl 4-[6-(benzylcarbamoyl)-2-chloro-pyrimidin-4-yl]piperazine-1-carboxylate 6-(4-tert-butoxycarbonylpiperazin-1-yl)-2-chloro-pyrimidine-4-carboxylic acid (Step 1, Example 13) (300 mg, 0.88 mmol) was dissolved in THF (10 mL) followed by the addition of benzylamine (0.11 mL, 1.05 mmol), T3P (0.78 mL, 1.31 mmol, 50% volume in EtOAc) and DIPEA (0.46 mL, 2.63 mmol). The reaction was stirred at room temperature for 18 hours and then solvent was removed in vacuo. The residue was dissolved in DCM (50 mL) and washed with water (2×50 mL). The organic phase was separated, dried over $Na_2SO_4$ and solvent removed in vacuo. The residue was purified by column chromatography using an eluent of 0-40% EtOAc in petroleum ether reached via a gradient to give tert-butyl 4-[6-(benzylcarbamoyl)-2-chloro-pyrimidin-4-yl]piperazine-1-carboxylate (155 mg, 0.36 mmol, 41% yield) as a pale yellow foam.

UPLC-MS (ES+, Method 2): 1.97 min, m/z 432.3, 434.1 $[M+H]^+$.

$^1$H-NMR (400 MHz, $CDCl_3$) δ/ppm: 8.12 (1H, t, J=6.4 Hz), 7.38-7.28 (6H, m), 4.62 (2H, d, J=6.4 Hz), 3.74 (4H, br s), 3.59-3.49 (4H, m), 1.49 (9H, s).

Step 2—tert-butyl 4-[6-(benzylcarbamoyl)-2-[[(2S)-1-methylpyrrolidin-2-yl]methoxy]pyrimidin-4-yl]piperazine-1-carboxylate To tert-butyl 4-[6-(benzylcarbamoyl)-2-chloro-pyrimidin-4-yl]piperazine-1-carboxylate (155 mg, 0.36 mmol) in a microwave vial was added 1,4-dioxane (5 mL) followed by the addition of (S)-(−)-1-methyl-2-pyrrolidinemethanol (0.21 mL, 1.77 mmol), $Cs_2CO_3$ (350 mg, 0.41 mmol) and DIPEA (0.50 mL, 2.87 mmol). The reaction was heated at the microwave at 170° C. for 3 hours. Solvent was then removed under reduce pressure and the residue dissolved in EtOAc (50 mL) and washed with brine (50 mL). The organic phase was separated, dried over $Na_2SO_4$ and the solvent removed in vacuo. The residue was purified by column chromatography using an eluent of 0-10% MeOH in DCM reached via a gradient to give tert-butyl 4-[6-(benzylcarbamoyl)-2-[[(2S)-1-methylpyrrolidin-2-yl]methoxy]pyrimidin-4-yl]piperazine-1-carboxylate (115 mg, 0.23 mmol, 63% yield) as a colourless oil.

UPLC-MS (ES+, Method 2): 1.44 min, m/z 511.4 $[M+H]^+$.

Step 3—N-benzyl-2-[[(2S)-1-methylpyrrolidin-2-yl]methoxy]-6-piperazin-1-yl-pyrimidine-4-carboxamide hydrochloride tert-Butyl 4-[6-(benzylcarbamoyl)-2-[[(2S)-1-methylpyrrolidin-2-yl]methoxy]pyrimidin-4-yl]piperazine-1-carboxylate (115 mg, 0.23 mmol) was dissolved in DCM (5 mL) and IPA (1 mL) followed by the addition of HCl (4M in 1,4-dioxane-0.56 mL, 2.25 mmol). The reaction was stirred at room temperature for 72 hours and then a second portion of HCl (4M in 1,4-dioxane-0.56 mL, 2.25 mmol) was added and the reaction was stirred at 40° C. for 24 hours. Solvent was then removed in vacuo to give N-benzyl-2-[[(2S)-1-methylpyrrolidin-2-yl]methoxy]-6-piperazin-1-yl-pyrimidine-4-carboxamide hydrochloride (66 mg, 0.16 mmol, 71% yield) as a white solid, which was used in the next step without further purification.

UPLC-MS (ES+, Method 2): 0.98 min, m/z 411.2 $[M+H]^+$.

Step 4—N-benzyl-2-[[(2S)-1-methylpyrrolidin-2-yl]methoxy]-6-(4-prop-2-enoylpiperazin-1-yl)pyrimidine-4-carboxamide DIPEA (0.11 mL, 0.64 mmol) was added to a stirred solution of (N-benzyl-2-[[(2S)-1-methylpyrrolidin-2-yl]methoxy]-6-piperazin-1-yl-pyrimidine-4-carboxamide hydrochloride (66 mg, 0.16 mmol) and acryloyl chloride (0.01 mL, 0.16 mmol) in DCM (3 mL) at room temperature. After 5 minutes a solution 2M $K_2CO_3$ (5 mL) was added and the mixture allowed to stir for 20 minutes. DCM (10 mL) was added and the organic layer separated, dried over $Na_2SO_4$ and solvent removed in vacuo. The residue was purified by column chromatography using an eluent of 0-8% MeOH in DCM reached via a gradient to give N-benzyl-2-[[(2S)-1-methylpyrrolidin-2-yl]methoxy]-6-(4-prop-2-enoylpiperazin-1-yl)pyrimidine-4-carboxamide (Example 14) (32 mg, 0.07 mmol, 43% yield) as a white solid.

UPLC-MS (ES+, Method 1): 2.55 min, m/z 465.6 $[M+H]^+$.

$^1$H-NMR (400 MHz, DMSO-$d_6$) δ/ppm: 9.14 (1H, t, J=6.4 Hz), 7.34-7.27 (4H, m), 7.26-7.20 (1H, m), 7.01 (1H, s), 6.83 (1H, dd, J=16.4 Hz, 10.4 Hz), 6.15 (1H, dd, J=16.4 Hz, 2.4 Hz), 5.72 (1H, dd, J=10.4 Hz, 2.4 Hz), 4.46 (2H, d, J=6.4 Hz), 4.35 (1H, dd, J=10.8 Hz, 4.4 Hz), 4.13 (1H, dd, J=10.8 Hz, 6.8 Hz), 3.80-3.58 (8H, m), 2.98-2.91 (1H, m), 2.57-2.53 (1H, m), 2.33 (3H, s), 2.21-2.12 (1H, m), 1.97-1.88 (1H, m), 1.73-1.56 (3H, m).

Example 15—1-[4-[6-(2-methyl-3,4-dihydro-2H-quinoline-1-carbonyl)-2-[[(2S)-1-methylpyrrolidin-2-yl]methoxy]pyrimidin-4-yl]piperazin-1-yl]prop-2-en-1-one

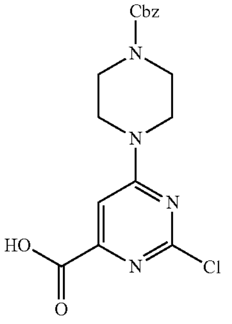

Intermediate 5

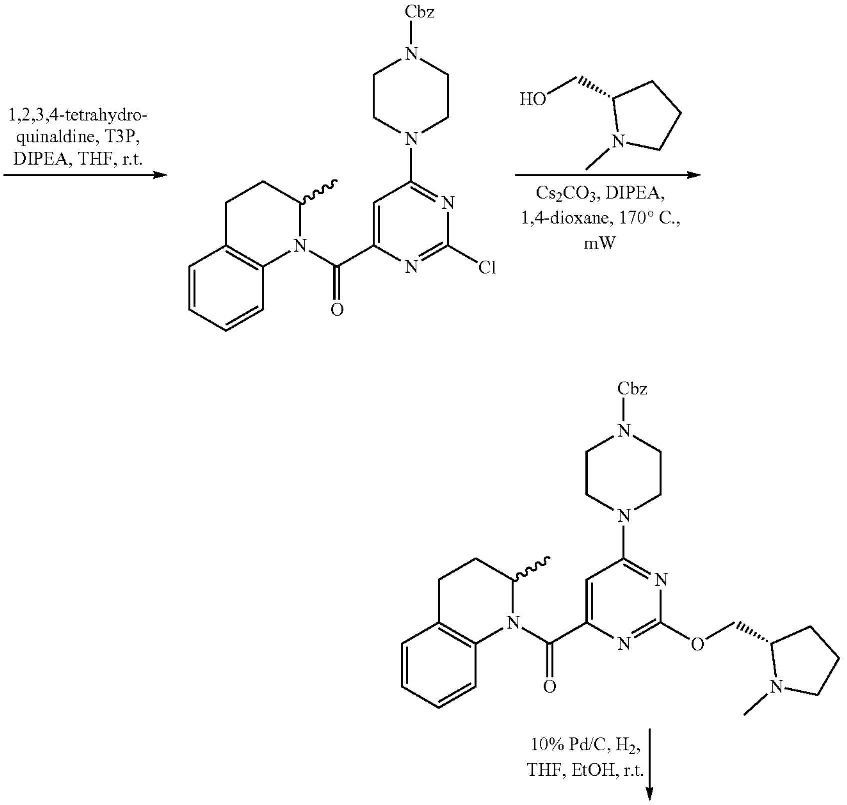

-continued

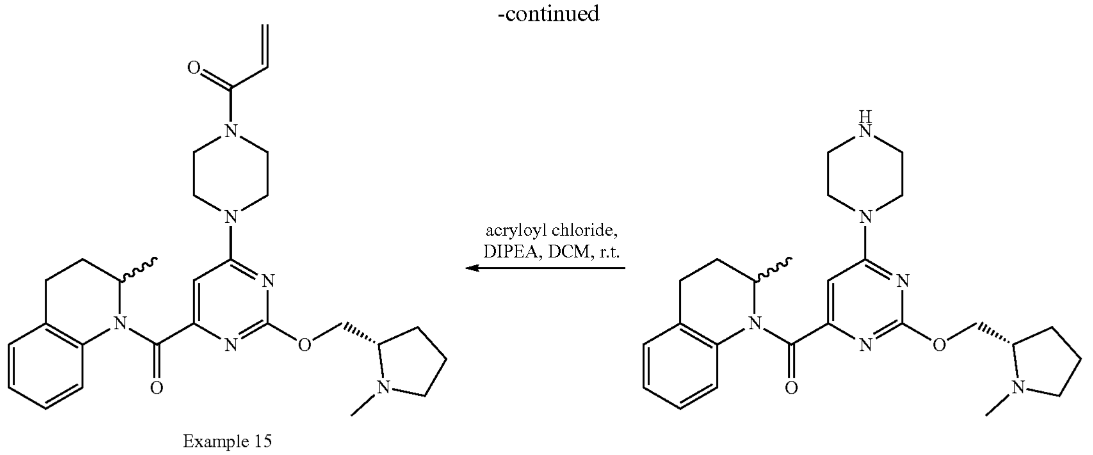

Example 15

Step 1—benzyl 4-[2-chloro-6-(2-methyl-3,4-dihydro-2H-quinoline-1-carbonyl)pyrimidin-4-yl]piperazine-1-carboxylate Intermediate 5 (190 mg, 0.50 mmol) was dissolved in THF (10 mL) followed by the addition of 1,2,3,4-tetrahydroquinaldine (0.09 mL, 0.61 mmol), T3P (0.45 mL, 0.76 mmol, 50% volume in EtOAc) and DIPEA (0.26 mL, 1.52 mmol). The reaction was stirred at room temperature for 18 hours and then solvent was removed in vacuo. The residue was dissolved in DCM (50 mL) and washed with water (2×50 mL). The organic phase was separated, dried over $Na_2SO_4$ and solvent removed in vacuo. The residue was purified by column chromatography using an eluent of 0-40% EtOAc in petroleum ether reached via a gradient to give benzyl 4-[2-chloro-6-(2-methyl-3,4-dihydro-2H-quinoline-1-carbonyl)pyrimidin-4-yl]piperazine-1-carboxylate (119 mg, 0.24 mmol, 47% yield) as pale yellow crystalline solid.

UPLC-MS (ES+, Method 2): 1.99 min, m/z 506.3, 508.1 $[M+H]^+$.

Step 2—benzyl 4-[6-(2-methyl-3,4-dihydro-2H-quinoline-1-carbonyl)-2-[[(2S)-1-methylpyrrolidin-2-yl]methoxy]pyrimidin-4-yl]piperazine-1-carboxylate To benzyl 4-[2-chloro-6-(2-methyl-3,4-dihydro-2H-quinoline-1-carbonyl)pyrimidin-4-yl]piperazine-1-carboxylate (119 mg, 0.24 mmol) in a microwave vial was added 1,4-dioxane (5 mL) followed by the addition of (S)-(−)-1-methyl-2-pyrrolidinemethanol (0.14 mL, 1.18 mmol), $Cs_2CO_3$ (230 mg, 0.71 mmol) and DIPEA (0.33 mL, 1.88 mmol). The reaction was heated at the microwave at 170° C. for 3 hours. Solvent was then removed under reduce pressure and the residue dissolved in EtOAc (50 mL) and washed with brine (50 mL). The organic phase was separated, dried over $Na_2SO_4$ and the solvent removed in vacuo. The residue was purified by column chromatography using an eluent of 0-10% MeOH in DCM reached via a gradient to give benzyl 4-[6-(2-methyl-3,4-dihydro-2H-quinoline-1-carbonyl)-2-[[(2S)-1-methylpyrrolidin-2-yl]methoxy]pyrimidin-4-yl]piperazine-1-carboxylate (69 mg, 0.12 mmol, 50% yield) as a colourless oil.

UPLC-MS (ES+, Method 2): 1.53 min, m/z 585.5 $[M+H]^+$.

Step 3—(2-methyl-3,4-dihydro-2H-quinolin-1-yl)-[2-[[(2S)-1-methylpyrrolidin-2-yl]methoxy]-6-piperazin-1-yl-pyrimidin-4-yl]methanone Palladium, 10 wt. % on carbon powder, (30 mg) was added to a stirred solution of benzyl 4-[6-(2-methyl-3,4-dihydro-2H-quinoline-1-carbonyl)-2-[[(2S)-1-methylpyrrolidin-2-yl]methoxy]pyrimidin-4-yl]piperazine-1-carboxylate (69 mg, 0.12 mmol), THF (7 mL) and EtOH (3 mL) at room temperature under a nitrogen atmosphere. The reaction was fitted with a $H_2$ balloon and subjected to 3×vacuum/$H_2$ cycles and then allowed to stir for 48 hours under a $H_2$ atmosphere. The reaction was then filtered through celite and the filter cake washed with MeOH (10 mL) and $NH_3$ in MeOH (10 mL). The filtrate was concentrated in vacuo to give (2-methyl-3,4-dihydro-2H-quinolin-1-yl)-[2-[[(2S)-1-methylpyrrolidin-2-yl]methoxy]-6-piperazin-1-yl-pyrimidin-4-yl]methanone (50 mg, 0.11 mmol, 94% yield) as a yellow oil which was used in the next step without further purification.

UPLCMS (ES+, Method 2): 1.09 min, m/z 451.3 $[M+H]^+$.

Step 4—1-[4-[6-(2-methyl-3,4-dihydro-2H-quinoline-1-carbonyl)-2-[[(2S)-1-methylpyrrolidin-2-yl]methoxy]pyrimidin-4-yl]piperazin-1-yl]prop-2-en-1-one DIPEA (0.06 mL, 0.33 mmol) was added to a stirred solution of (2-methyl-3,4-dihydro-2H-quinolin-1-yl)-[2-[[(2S)-1-methylpyrrolidin-2-yl]methoxy]-6-piperazin-1-yl-pyrimidin-4-yl]methanone (50 mg, 0.11 mmol), acryloyl chloride (0.01 mL, 0.13 mmol) and DCM (4 mL) at room temperature. After 10 minutes a solution of 2M $K_2CO_3$ (10 mL) was added and the mixture allowed to stir for 20 minutes. DCM (10 mL) was added and the organic layer separated, dried over $Na_2SO_4$ and the solvent removed in vacuo. The residue was purified by column chromatography using an eluent of 0-10% MeOH in DCM reached via a gradient followed by further purification by preparative LC-MS to give 1-[4-[6-(2-methyl-3,4-dihydro-2H-quinoline-1-carbonyl)-2-[[(2S)-1-methylpyrrolidin-2-yl]methoxy]pyrimidin-4-yl]piperazin-1-yl]prop-2-en-1-one (Example 15) (7 mg, 0.01 mmol, 12% yield) as a white solid.

UPLC-MS (ES+, Method 1): 2.73 min, m/z 505.4 $[M+H]^+$.

$^1$H-NMR (400 MHz, $CD_3OD$) δ/ppm: 7.26-7.20 (1H, m), 7.14-7.06 (1H, m), 6.98 (1H, br s), 6.89-6.67 (2H, m), 6.52 (1H, br s), 6.25 (1H, dd, J=16.8 Hz, 2.0 Hz), 5.79 (1H, dd, J=10.8 Hz, 2.0 Hz), 4.81-4.69 (2H, m), 4.31-4.02 (2H, m), 3.81-3.58 (8H, m), 3.18-2.92 (1H, m), 2.83-2.60 (6H, m), 2.59-2.43 (1H, m), 2.20-2.03 (1H, m), 2.01-1.88 (2H, m), 1.72 (1H, br s), 1.47 (1H, br s), 1.23 (3H, d, J=6.4 Hz).

The following compounds were made in an analogous manner to Example 15, using the appropriate amine in place of 1,2,3,4-tetrahydroquinaldine in the first step:

| Compound | Name | Data |
|---|---|---|
| Example 16 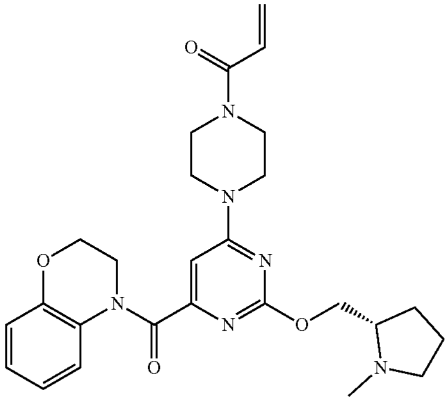 | 1-[4-[6-(2,3-dihydro-1,4-benzoxazine-4-carbonyl)-2-[[(2S)-1-methylpyrrolidin-2-yl]methoxy]pyrimidin-4-yl]piperazin-1-yl]prop-2-en-1-one | UPLC-MS (ES+, Method 1): 2.49 min, m/z 493.6 $[M + H]^+$. $^1$H-NMR (400 MHz, DMSO-$d_6$) δ/ppm: 8.07 (1H, br s), 7.09-7.00 (1H, m), 6.95-6.79 (3H, m), 6.77 (1H, s), 6.15 (1H, dd, J = 16.8 Hz, 2.0 Hz), 5.72 (1H, dd, J = 10.0 Hz, 2.0 Hz), 4.35-4.14 (3H, m), 4.09-3.78 (3H, m), 3.75-3.57 (8H, m), 2.97-2.86 (1H, m), 2.30 (3H, s), 2.19-2.08 (1H, m), 1.94-1.79 (2H, m), 1.70-1.43 (3H, m). |
| Example 17 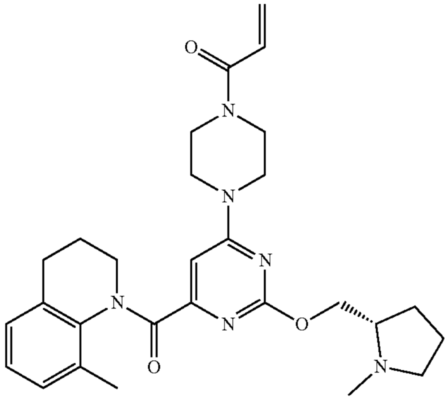 | 1-[4-[6-(8-methyl-3,4-dihydro-2H-quinoline-1-carbonyl)-2-[[(2S)-1-methylpyrrolidin-2-yl]methoxy]pyrimidin-4-yl]piperazin-1-yl]prop-2-en-1-one | UPLC-MS (ES+, Method 1): 2.69 min, m/z 505.5 $[M + H]^+$. $^1$H-NMR (400 MHz, DMSO-$d_6$) δ/ppm: 7.17-6.98 (3H, m), 6.94-6.63 (2H, m), 6.21-6.10 (1H, m), 5.79-5.68 (1H, m), 4.63-4.52 (0.4H, m), 4.37-4.25 (0.6H, m), 4.12-4.05 (0.6H, m), 3.91-3.51 (10.4H, m), 3.06-2.86 (1H, m), 2.80-2.63 (2H, m), 2.35 (3H, s), 2.31-2.19 (2H, m), 2.15 (1.8H, s), 2.13-2.01 (1.2H, m), 1.97-1.90 (0.8H, m), 1.87 (1.2H, s), 1.80-1.56 (4H, m). |
| Example 18 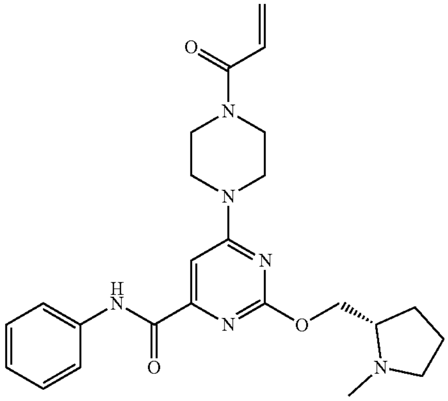 | 2-[[(2S)-1-methylpyrrolidin-2-yl]methoxy]-N-phenyl-6-(4-prop-2-enoylpiperazin-1-yl)pyrimidine-4-carboxamide | UPLC-MS (ES+, Method 1): 2.63 min, m/z 451.4 $[M + H]^+$. $^1$H-NMR (400 MHz, DMSO-$d_6$) δ/ppm: 10.23 (1H, s), 7.83 (2H, d, J = 8.0 Hz), 7.37 (2H, t, J = 8.0 Hz), 7.14 (1H, t, J = 7.6 Hz), 7.10 (1H, s), 6.84 (1H, dd, J = 16.8 Hz, 10.4 Hz), 6.16 (1H, dd, J = 16.8 Hz, 2.0 Hz), 5.73 (1H, dd, J = 10.4 Hz, 2.0 Hz), 4.44 (1H, dd, J = 11.2 Hz, 4.4 Hz), 4.17 (1H, dd, J = 10.8 Hz, 6.4 Hz), 3.86-3.61 (8H, m), 3.00-2.92 (1H, m), 2.62-2.57 (1H, m), 2.37 (3H, s), 2.22-2.14 (1H, m), 2.00-1.90 (1H, m), 1.75-1.61 (3H, m). |

-continued

| Compound | Name | Data |
|---|---|---|
| Example 19 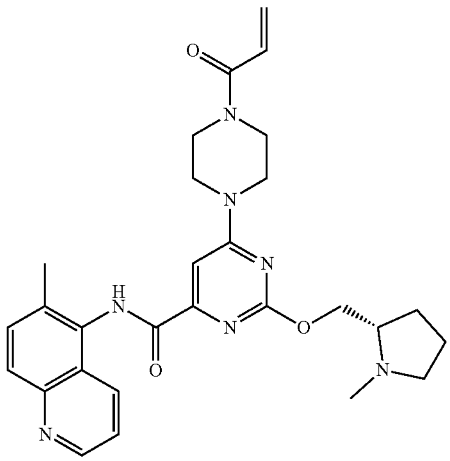 | 2-[[(2S)-1-methylpyrrolidin-2-yl]methoxy]-N-(6-methyl-5-quinolyl)-6-(4-prop-2-enoylpiperazin-1-yl)pyrimidine-4-carboxamide | UPLC-MS (ES+, Method 1): 2.07 min, m/z 516.4 $[M + H]^+$. $^1$H-NMR (400 MHz, DMSO-$d_6$) δ/ppm: 10.51 (1H, s), 8.86 (1H, dd, J = 4.4 Hz, 2.0 Hz), 8.17-8.14 (1H, m), 7.95 (1H, d, J = 8.8 Hz), 7.73 (1H, d, J = 8.8 Hz), 7.52 (1H, dd, J = 8.4 Hz, 4.4 Hz), 7.10 (1H, s), 6.84 (1H, dd, J = 16.8 Hz, 10.4 Hz), 6.16 (1H, dd, J = 16.8 Hz, 2.4 Hz), 5.73 (1H, dd, J = 10.4 Hz, 2.4 Hz), 4.45 (1H, dd, J = 11.2 Hz, 4.4 Hz), 4.25 (1H, dd, J = 10.8 Hz, 6.4 Hz), 3.83-3.60 (8H, m), 3.00-2.93 (1H, m), 2.55-2.53 (1H, m), 2.39-2.35 (6H, m), 2.23-2.14 (1H, m), 2.04-1.92 (1H, m), 1.75-1.64 (3H, m). |

Example 20 —2-(4-methylpiperazin-1-yl)-N-(1-naphthyl)-6-(4-prop-2-enoylpiperazin-1-yl)pyrimidine-4-carboxamide

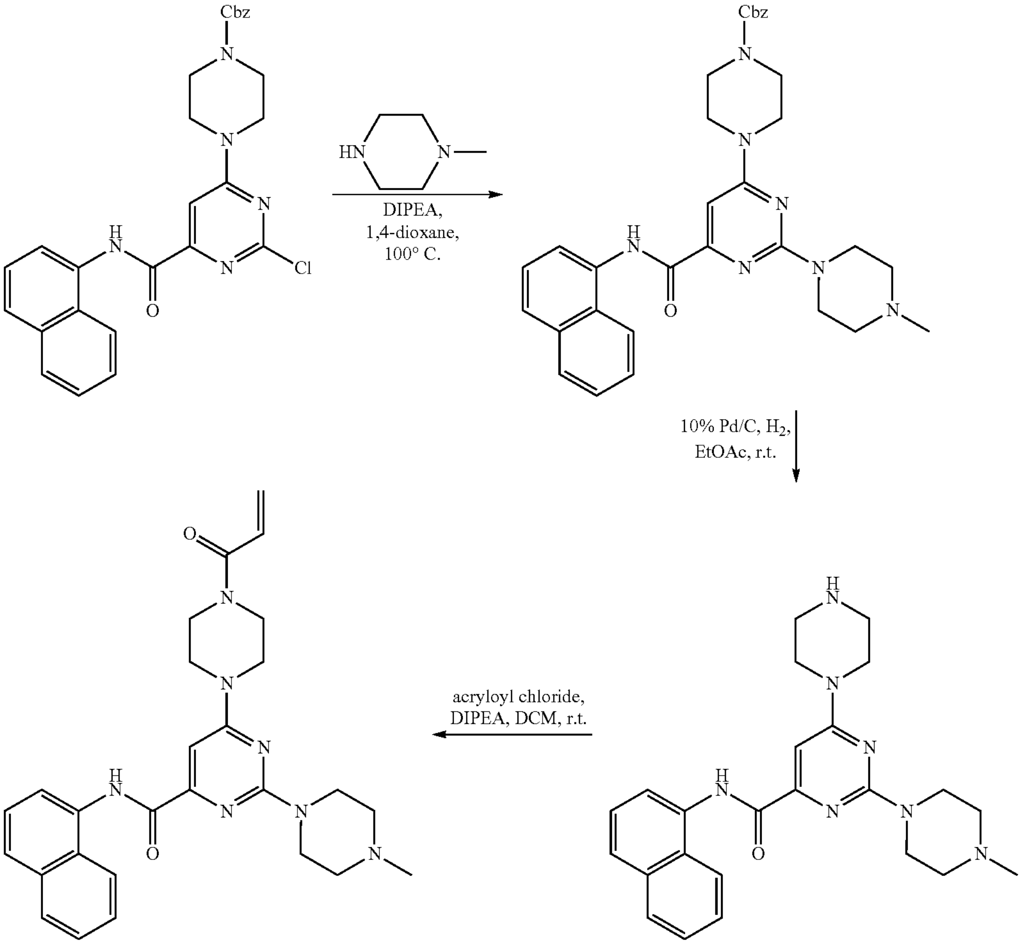

Example 20

Step 1—benzyl 4-[2-(4-methylpiperazin-1-yl)-6-(1-naphthylcarbamoyl)pyrimidin-4-yl]piperazine-1-carboxylate To benzyl 4-[2-chloro-6-(1-naphthylcarbamoyl)pyrimidin-4-yl]piperazine-1-carboxylate (Step 1, Example 1) (130 mg, 0.26 mmol) was added 1,4-dioxane (5 mL) followed by the addition of 1-methylpiperazine (0.12 mL, 1.29 mmol) and DIPEA (0.36 mL, 2.07 mmol). The reaction was stirred at 100° C. for 18 hours and then solvent removed in vacuo. The residue was dissolved in EtOAc (50 mL) and washed with brine (50 mL). The organic phase was separated, dried over $Na_2SO_4$ and solvent removed in vacuo. The residue was purified by column chromatography using an eluent of 0-5% MeOH in DCM reached via a gradient to give benzyl 4-[2-(4-methylpiperazin-1-yl)-6-(1-naphthylcarbamoyl)pyrimidin-4-yl]piperazine-1-carboxylate (120 mg, 0.21 mmol, 82% yield) as a pale yellow solid.

UPLC-MS (ES+, Method 2): 1.64 min, m/z 566.3 $[M+H]^+$.

$^1$H-NMR (400 MHz, DMSO-$d_6$) δ/ppm: 10.68 (1H, s), 8.03-7.98 (1H, m), 7.94-7.82 (3H, m), 7.64-7.56 (3H, m), 7.39 (4H, d, J=4.4 Hz), 7.38-7.30 (1H, m), 6.78 (1H, s), 5.13 (2H, s), 3.85 (4H, br s), 3.71 (4H, br s), 3.53 (4H, br s), 2.41 (4H, br s), 2.24 (3H, s).

Step 2 —2-(4-methylpiperazin-1-yl)-N-(1-naphthyl)-6-piperazin-1-yl-pyrimidine-4-carboxamide Benzyl 4-[2-(4-methylpiperazin-1-yl)-6-(1-naphthylcarbamoyl)pyrimidin-4-yl]piperazine-1-carboxylate (120 mg, 0.21 mmol) was dissolved in EtOAc (7 mL) followed by the addition of palladium, 10 wt. % on carbon powder, (30 mg) under a nitrogen atmosphere. The reaction was fitted with a $H_2$ balloon and subjected to 3×vacuum/$H_2$ cycles and then allowed to stir for 72 hours under a $H_2$ atmosphere. The reaction was filtered over celite, and the filter cake washed with $NH_3$ in MeOH (10 mL) and solvent removed in vacuo to give 2-(4-methylpiperazin-1-yl)-N-(1-naphthyl)-6-piperazin-1-yl-pyrimidine-4-carboxamide (89 mg, 0.21 mmol, 97% yield) as a pale yellow oil.

UPLC-MS (ES+, Method 2): 1.17 min, m/z 432.3 $[M+H]^+$.

Step 3 —2-(4-methylpiperazin-1-yl)-N-(1-naphthyl)-6-(4-prop-2-enoylpiperazin-1-yl)pyrimidine-4-carboxamide Acryloyl chloride (0.02 mL, 0.21 mmol) and 2-(4-methylpiperazin-1-yl)-N-(1-naphthyl)-6-piperazin-1-yl-pyrimidine-4-carboxamide (89 mg, 0.21 mmol) were dissolved in DCM (4 mL) followed by the addition of DIPEA (0.11 mL, 0.63 mmol). The reaction was left stirring for 5 minutes. A solution 2M $K_2CO_3$ (5 mL) was then added to the reaction and the mixture allowed to stir for 20 minutes. DCM (10 mL) was added and the organic layer separated, dried over $Na_2SO_4$ and solvent removed in vacuo. The residue was purified by preparative LC-MS to give 2-(4-methylpiperazin-1-yl)-N-(1-naphthyl)-6-(4-prop-2-enoylpiperazin-1-yl)pyrimidine-4-carboxamide (Example 20) (10 mg, 0.02 mmol, 10% yield) as a white solid.

UPLC-MS (ES+, Method 1): 2.86 min, m/z 486.6 $[M+H]^+$.

$^1$H-NMR (400 MHz, DMSO-$d_6$) δ/ppm: 10.68 (1H, s), 8.03-7.97 (1H, m), 7.92-7.80 (3H, m), 7.63-7.54 (3H, m), 6.90-6.77 (2H, m), 6.16 (1H, dd, J=16.8 Hz, 2.4 Hz), 5.73 (1H, dd, J=10.4 Hz, 2.4 Hz), 3.95-3.57 (12H, m), 2.43-2.37 (4H, m), 2.24 (3H, s).

The following compound was made in an analogous manner to Example 20, using N,N,N-trimethylethylenediamine in place of 1-methylpiperazine in the first step:

| Compound | Name | Data |
|---|---|---|
| Example 21 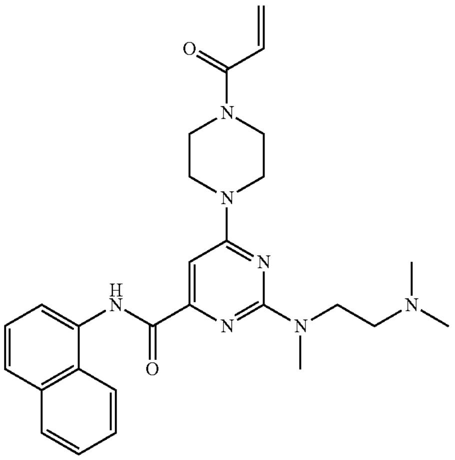 | 2-[2-(dimethylamino)ethyl-methyl-amino]-N-(1-naphthyl)-6-(4-prop-2-enoylpiperazin-1-yl)pyrimidine-4-carboxamide | UPLC-MS (ES+, Method 1): 3.01 min, m/z 488.6 $[M + H]^+$. $^1$H-NMR (400 MHz, DMSO-$d_6$) δ/ppm: 10.74 (1H, s), 8.03-7.95 (2H, m), 7.82 (1H, d, J = 8.0 Hz), 7.64-7.55 (4H, m), 6.89-6.76 (2H, m), 6.16 (1H, dd, J = 16.8 Hz, 2.4 Hz), 5.73 (1H, dd, J = 10.4 Hz, 2.4 Hz), 3.82-3.56 (8H, m), 3.31-3.12 (3H, m), 2.60-2.40 (4H, m), 2.24 (6H, s). |

Example 22—N-(1H-indazol-4-yl)-2-[[(2S)-1-methylpyrrolidin-2-yl]methoxy]-6-(4-prop-2-enoylpiperazin-1-yl)pyrimidine-4-carboxamide

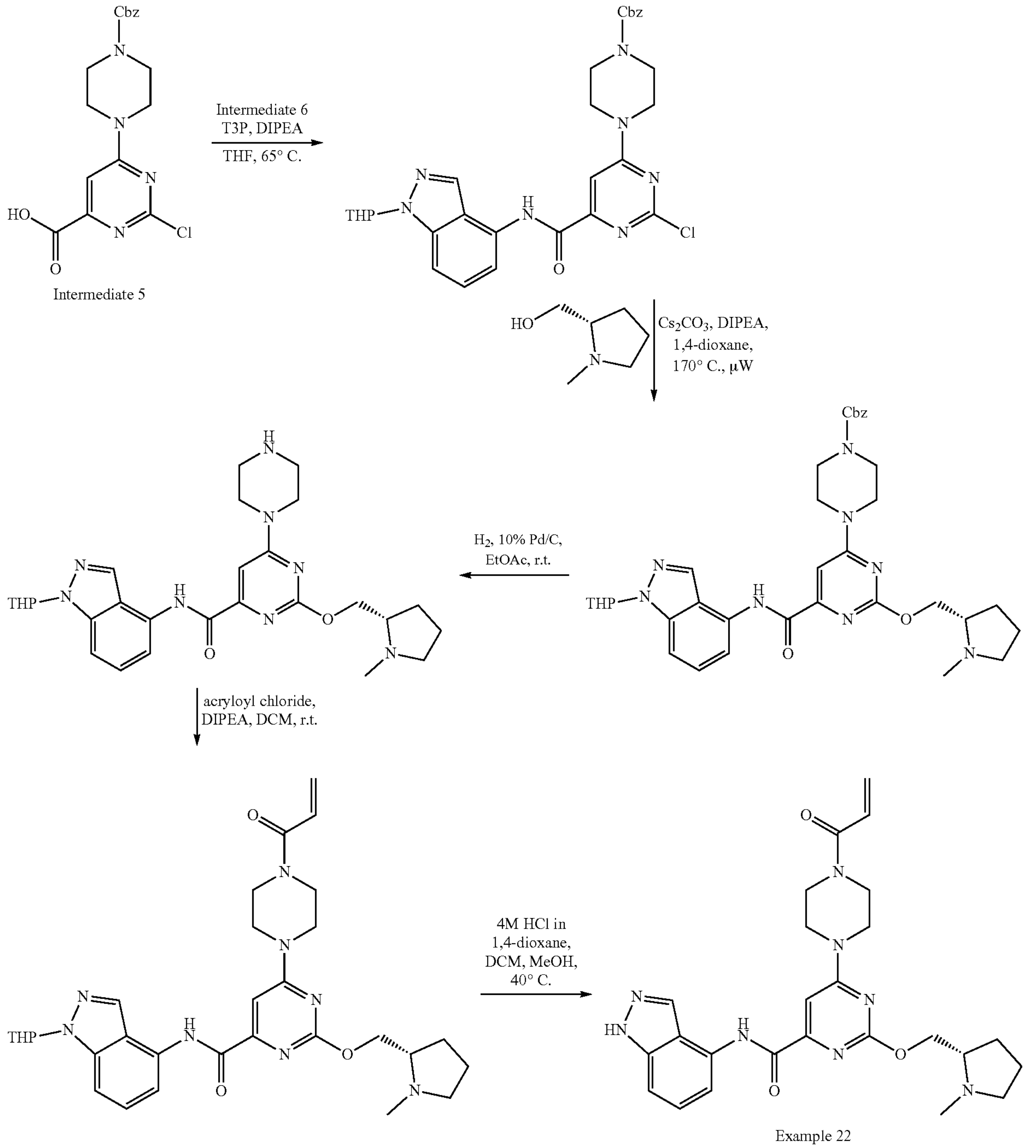

Step 1—benzyl 4-[2-chloro-6-[(1-tetrahydropyran-2-ylindazol-4-yl)carbamoyl]pyrimidin-4-yl]piperazine-1-carboxylate Intermediate 6 (116 mg, 0.53 mmol) was dissolved in THF (6 mL) followed by the addition of T3P (0.45 mL, 0.76 mmol, 50% volume in EtOAc), DIPEA (0.26 mL, 1.51 mmol) and Intermediate 5 (190 mg, 0.50 mmol). The reaction stirred at 65° C. for 4 hours. Solvent was removed in vacuo, the residue dissolved in DCM (50 mL) and washed with water (2×50 mL). The organic phase was separated, dried over $Na_2SO_4$ and solvent in vacuo. The residue was purified by column chromatography using a eluent of 0-100% EtOAc in petroleum ether reached via a gradient to give benzyl 4-[2-chloro-6-[(1-tetrahydropyran-2-ylindazol-4-yl)carbamoyl]pyrimidin-4-yl]piperazine-1-carboxylate (212 mg, 0.37 mmol, 73% yield) as a yellow oil.

UPLC-MS (ES+, Method 2): 2.08 min, m/z 576.4 $[M+H]^+$.

Step 2—benzyl 4-[2-[[(2S)-1-methylpyrrolidin-2-yl] methoxy]-6-[(1-tetrahydropyran-2-ylindazol-4-yl) carbamoyl]pyrimidin-4-yl]piperazine-1-carboxylate To benzyl 4-[2-chloro-6-[(1-tetrahydropyran-2-ylindazol-4-yl)carbamoyl]pyrimidin-4-yl]piperazine-1-carboxylate (212 mg, 0.37 mmol) in a microwave vial was added 1,4-dioxane (5 mL) followed by the addition of (S)-(−)-1-methyl-2-pyrrolidinemethanol (0.22 mL, 1.85 mmol), $Cs_2CO_3$ (360 mg, 1.11 mmol) and DIPEA (0.51 mL, 2.94 mmol). The reaction was heated in the microwave at 170° C. for 3 hours. The solvent was removed in vacuo and the residue dissolved in EtOAc (100 mL) and washed with brine (100 mL). The organic phase was separated, dried over $Na_2SO_4$ and solvent removed in vacuo. The residue was purified by column chromatography using an eluent of 0-10% MeOH in DCM reached via a gradient to give benzyl 4-[2-[[(2S)-1-methylpyrrolidin-2-yl]methoxy]-6-[(1-tetrahydropyran-2-ylindazol-4-yl)carbamoyl]pyrimidin-4-yl] piperazine-1-carboxylate (55 mg, 0.08 mmol, 23% yield) as a colourless oil.

UPLC-MS (ES+, Method 2): 1.59 min, m/z 655.5 $[M+H]^+$.

Step 3—2-[[(2S)-1-methylpyrrolidin-2-yl]methoxy]-6-piperazin-1-yl-N-(1-tetrahydropyran-2-ylindazol-4-yl)pyrimidine-4-carboxamide Benzyl 4-[2-[[(2S)-1-methylpyrrolidin-2-yl]methoxy]-6-[(1-tetrahydropyran-2-ylindazol-4-yl)carbamoyl]pyrimidin-4-yl]piperazine-1-carboxylate (55 mg, 0.084 mmol) was dissolved in EtOAc (5 mL) followed by the addition of palladium, 10 wt. % on carbon powder, dry (10 mg) under a nitrogen atmosphere. After 3 cycles of vacuum/$H_2$, the reaction was left stirring under an $H_2$ atmosphere for 18 hours. The reaction was then filtered through celite, washed with $NH_3$ in MeOH (10 mL) and solvent removed in vacuo to give 2-[[(2S)-1-methylpyrrolidin-2-yl]methoxy]-6-piperazin-1-yl-N-(1-tetrahydropyran-2-ylindazol-4-yl)pyrimidine-4-carboxamide (40 mg, 0.08 mmol, 91% yield) as a pale yellow solid, which was used in the next step without further purification.

UPLC-MS (ES+, Method 2): 1.18 min, m/z 521.4 $[M+H]^+$.

Step 4—2-[[(2S)-1-methylpyrrolidin-2-yl]methoxy]-6-(4-prop-2-enoylpiperazin-1-yl)-N-(1-tetrahydropyran-2-ylindazol-4-yl)pyrimidine-4-carboxamide Acryloyl chloride (0.01 mL, 0.09 mmol) and 2-[[(2S)-1-methylpyrrolidin-2-yl]methoxy]-6-piperazin-1-yl-N-(1-tetrahydropyran-2-ylindazol-4-yl)pyrimidine-4-carboxamide (40 mg, 0.08 mmol) were dissolved in DCM (4 mL) followed by the addition of DIPEA (0.04 mL, 0.24 mmol). The reaction was stirred for 5 minutes. A solution 2M $K_2CO_3$ (5 mL) was added to the reaction and the mixture allowed to stir for 20 minutes. DCM (10 mL) was added and the organic layer separated, dried over $Na_2SO_4$ and solvent removed in vacuo. The residue was purified by column chromatography using an eluent of 0-10% MeOH in DCM reached via a gradient to give 2-[[(2S)-1-methylpyrrolidin-2-yl]methoxy]-6-(4-prop-2-enoylpiperazin-1-yl)-N-(1-tetrahydropyran-2-ylindazol-4-yl)pyrimidine-4-carboxamide (30 mg, 0.05 mmol, 68% yield) as a pale yellow oil.

UPLC-MS (ES+, Method 2): 1.32 min, m/z 575.5 $[M+H]^+$.

Step 5—N-(1H-indazol-4-yl)-2-[[(2S)-1-methylpyrrolidin-2-yl]methoxy]-6-(4-prop-2-enoylpiperazin-1-yl)pyrimidine-4-carboxamide 2-[[(2S)-1-methylpyrrolidin-2-yl]methoxy]-6-(4-prop-2-enoylpiperazin-1-yl)-N-(1-tetrahydropyran-2-ylindazol-4-yl)pyrimidine-4-carboxamide (30 mg, 0.05 mmol) was dissolved in DCM (4 mL) and MeOH (0.50 mL). HCl (4M in 1,4-dioxane-0.1 mL, 0.42 mmol) was added and the reaction was left stirring at 40° C. for 4 hours. Solvent was removed in vacuo and the residue purified by preparative LC-MS to give N-(1H-indazol-4-yl)-2-[[(2S)-1-methylpyrrolidin-2-yl] methoxy]-6-(4-prop-2-enoylpiperazin-1-yl)pyrimidine-4-carboxamide (Example 22) (17 mg, 0.04 mmol, 68% yield) as a white solid.

UPLC-MS (ES+, Method 1): 2.41 min, m/z 491.4 $[M+H]^+$.

$^1$H-NMR (400 MHz, DMSO-$d_6$): δ/ppm: 13.19 (1H, br s), 10.47 (1H, s), 8.10 (1H, s), 7.64-7.59 (1H, m), 7.39-7.35 (2H, m), 7.16 (1H, s), 6.84 (1H, dd, J=16.8 Hz, 10.4 Hz), 6.16 (1H, dd, J=16.8 Hz, 2.0 Hz), 5.73 (1H, dd, J=10.4 Hz, 2.0 Hz), 4.48 (1H, dd, J=10.8 Hz, 4.4 Hz), 4.27 (1H, dd, J=10.8 Hz, 6.4 Hz), 3.80-3.64 (8H, m), 3.06-2.94 (1H, m), 2.70-2.58 (1H, m), 2.39 (3H, s), 2.27-2.18 (1H, m), 2.06-1.90 (1H, m), 1.83-1.59 (3H, m).

Example 23

N-(3-hydroxy-1-naphthyl)-2-[[(2S)-1-methylpyrrolidin-2-yl]methoxy]-6-[(1S,4S)-2-prop-2-enoyl-2,5-diazabicyclo[2.2.1]heptan-5-yl]pyrimidine-4-carboxamide

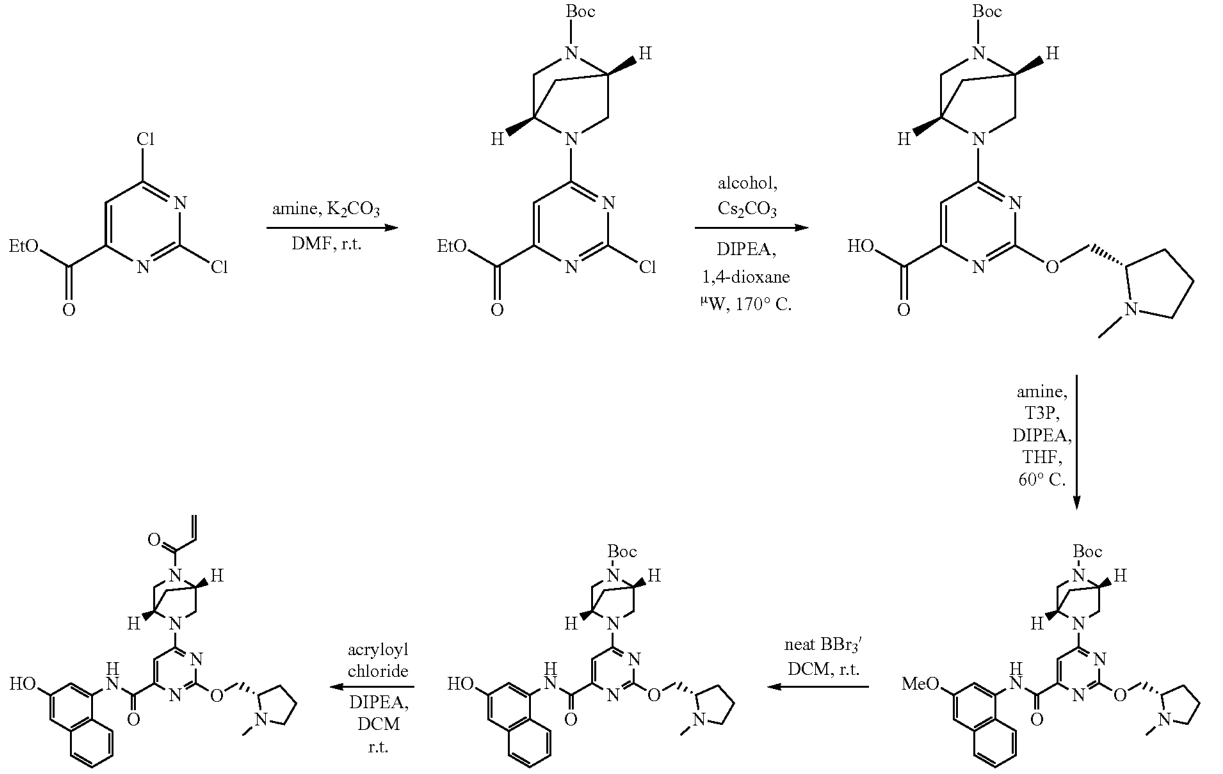

tert-butyl (1S,4S)-5-(2-chloro-6-ethoxycarbonyl-pyrimidin-4-yl)-2,5-diazabicyclo[2.2.1]heptane-2-carboxylate Step 1

(1S,4S)-2-boc-2,5-diazabicyclo[2.2.1]heptane (202 mg, 1.02 mmol) was added to a stirred mixture of ethyl 2,6-dichloropyrimidine-4-carboxylate (250 mg, 1.13 mmol), potassium carbonate (782 mg, 5.66 mmol) and DMF (10 mL) at room temperature under a nitrogen atmosphere. After 2 hours the reaction was complete by LCMS. The reaction was poured into water (100 mL) and extracted with EtOAc (2×100 mL). The combined organic layers were dried over sodium sulfate and purified by column chromatography using an eluent of 0-100% EtOAc in petroleum ether to give tert-butyl (1S,4S)-5-(2-chloro-6-ethoxycarbonyl-pyrimidin-4-yl)-2,5-diazabicyclo[2.2.1]heptane-2-carboxylate (300 mg, 0.78 mmol, 69% yield) as a yellow solid.

UPLC-MS (ES+, short acidic): 1.74 min, m/z 384.2, 386.2 [M+H]+.

6-[(1S,4S)-2-tert-butoxycarbonyl-2,5-diazabicyclo[2.2.1]heptan-5-yl]-2-[[(2S)-1-methylpyrrolidin-2-yl]methoxy]pyrimidine-4-carboxylic acid Step 2 tert-butyl (1S,4S)-5-(2-chloro-6-ethoxycarbonyl-pyrimidin-4-yl)-2,5-diazabicyclo[2.2.1]heptane-2-carboxylate (300 mg, 0.78 mmol), (S)-(−)-1-methyl-2-pyrrolidinemethanol (0.19 mL, 1.57 mmol), cesium carbonate (511 mg, 1.57 mmol), N,N-diisopropylethylamine (0.27 mL, 1.57 mmol) and 1,4-dioxane (5 mL) were combined in a microwave vial. The vial was sealed and stirred and heated to 170° C. in the microwave for 3 hours. The reaction was filtered to removed base and the filter cake washed with DCM (10 mL). The filtrate was concentrated in vacuo and the residue purified by reverse phase chromatography using an eluent of 0-100% MeCN in $H_2O$ (both with 0.1% formic acid additive) to give 6-[(1S,4S)-2-tert-butoxycarbonyl-2,5-diazabicyclo[2.2.1]heptan-5-yl]-2-[[(2S)-1-methylpyrrolidin-2-yl]methoxy]pyrimidine-4-carboxylic acid (180 mg, 0.41 mmol, 53% yield) as a yellow oil.

UPLC-MS (ES+, short acidic): 1.12 min, 434.4 [M+H]+.

tert-butyl (1S,4S)-5-[6-[(3-methoxy-1-naphthyl)carbamoyl]-2-[[(2S)-1-methylpyrrolidin-2-yl]methoxy]pyrimidin-4-yl]-2,5-diazabicyclo[2.2.1]heptane-2-carboxylate Step 3

6-[(1S,4S)-2-tert-butoxycarbonyl-2,5-diazabicyclo[2.2.1]heptan-5-yl]-2-[[(2S)-1-methylpyrrolidin-2-yl]methoxy]pyrimidine-4-carboxylic acid (180 mg, 0.42 mmol), 3-methoxynaphthalen-1-amine (72 mg, 0.42 mmol), propylphosphonic anhydride (0.19 mL, 0.62 mmol), triethylamine (0.09 mL, 0.62 mmol) and THF (10 mL) were combined and stirred under a nitrogen atmosphere. The reaction was heated to 60° C. for 72 hours and then cooled to room temperature and concentrated in vacuo. The residue was purified by column chromatography using an eluent of 0-20% MeOH in DCM to give tert-butyl (1S,4S)-5-[6-[(3-methoxy-1-naphthyl)carbamoyl]-2-[[(2S)-1-methylpyrrolidin-2-yl]methoxy]pyrimidin-4-yl]-2,5-diazabicyclo[2.2.1]heptane-2-carboxylate (205 mg, 0.35 mmol, 84% yield) as an orange oil.

UPLC-MS (ES+, short acidic): 1.65 min, m/z 589.5 [M+H]+.

6-[(1S,4S)-2,5-diazabicyclo[2.2.1]heptan-2-yl]-N-(3-hydroxy-1-naphthyl)-2-[[(2S)-1-methylpyrrolidin-2-yl]methoxy]pyrimidine-4-carboxamide Step 4

Boron tribromide (0.18 mL, 1.04 mmol) was added to a stirred solution of tert-butyl (1S,4S)-5-[6-[(3-methoxy-1-naphthyl)carbamoyl]-2-[[(2S)-1-methylpyrrolidin-2-yl]methoxy]pyrimidin-4-yl]-2,5-diazabicyclo[2.2.1]heptane-2-carboxylate (205 mg, 0.35 mmol) and DCM (5 mL) with ice cooling under a nitrogen atmosphere. The reaction was allowed to warm to room temperature and stir for 1 hour. Enough MeOH was then slowly added until the $BBr_3$ was quenched and then the resulting mixture concentrated in vacuo to give 6-[(1S,4S)-2,5-diazabicyclo[2.2.1]heptan-2-yl]-N-(3-hydroxy-1-naphthyl)-2-[[(2S)-1-methylpyrrolidin-2-yl]methoxy]pyrimidine-4-carboxamide (165 mg, 0.35 mmol, 99% yield) as a yellow solid.

UPLC-MS (ES+, short acidic): 1.23 min, m/z 475.4 [M+H]+.

N-(3-hydroxy-1-naphthyl)-2-[[(2S)-1-methylpyrrolidin-2-yl]methoxy]-6-[(1S,4S)-2-prop-2-enoyl-2,5-diazabicyclo[2.2.1]heptan-5-yl]pyrimidine-4-carboxamide Final Step:

Acryloyl chloride (0.04 mL, 0.52 mmol) was added to a stirred solution of 6-[(1S,4S)-2,5-diazabicyclo[2.2.1]heptan-2-yl]-N-(3-hydroxy-1-naphthyl)-2-[[(2S)-1-methylpyrrolidin-2-yl]methoxy]pyrimidine-4-carboxamide (165 mg, 0.35 mmol), N,N-diisopropylethylamine (0.18 mL, 1.04 mmol) and DCM (5 mL) at room temperature under a nitrogen atmosphere. After 20 minutes sat. aq. $NaHCO_3$ (50 mL) was added and stirring continued for 30 minutes. DCM (50 mL) was then added and the organic layer separated, dried over sodium sulfate and concentrated in vacuo. The residue was purified by column chromatography using an eluent of 0-10% MeOH in DCM to give N-(3-hydroxy-1-naphthyl)-2-[[(2S)-1-methylpyrrolidin-2-yl]methoxy]-6-[(1S,4S)-2-prop-2-enoyl-2,5-diazabicyclo[2.2.1]heptan-5-yl]pyrimidine-4-carboxamide (15 mg, 0.03 mmol, 8% yield) as a light orange solid.

UPLC-MS (ES+, final purity): 2.69 min, m/z 529.4 [M+H]+

1H NMR (400 MHz, DMSO-d6) δ/ppm: 10.60 (1H, s), 9.91 (1H, s), 7.82-7.74 (2H, m), 7.65-7.57 (1H, m), 7.49-7.43 (1H, m), 7.38-7.31 (1H, m), 7.19-7.07 (2H, m), 6.85-6.74 (1H, m), 6.19-6.14 (1H, m), 5.75-5.66 (1H, m), 5.19-4.87 (2H, m), 4.67-4.51 (1H, m), 3.76-3.35 (5H, m), 2.56-2.51 (6H, m), 2.11-1.96 (3H, m), 1.91-1.71 (3H, m).

Example 24

6-[(3S)-3-(cyanomethyl)-4-prop-2-enoyl-piperazin-1-yl]-N-(3-hydroxy-1-naphthyl)-2-phenyl-pyrimidine-4-carboxamide

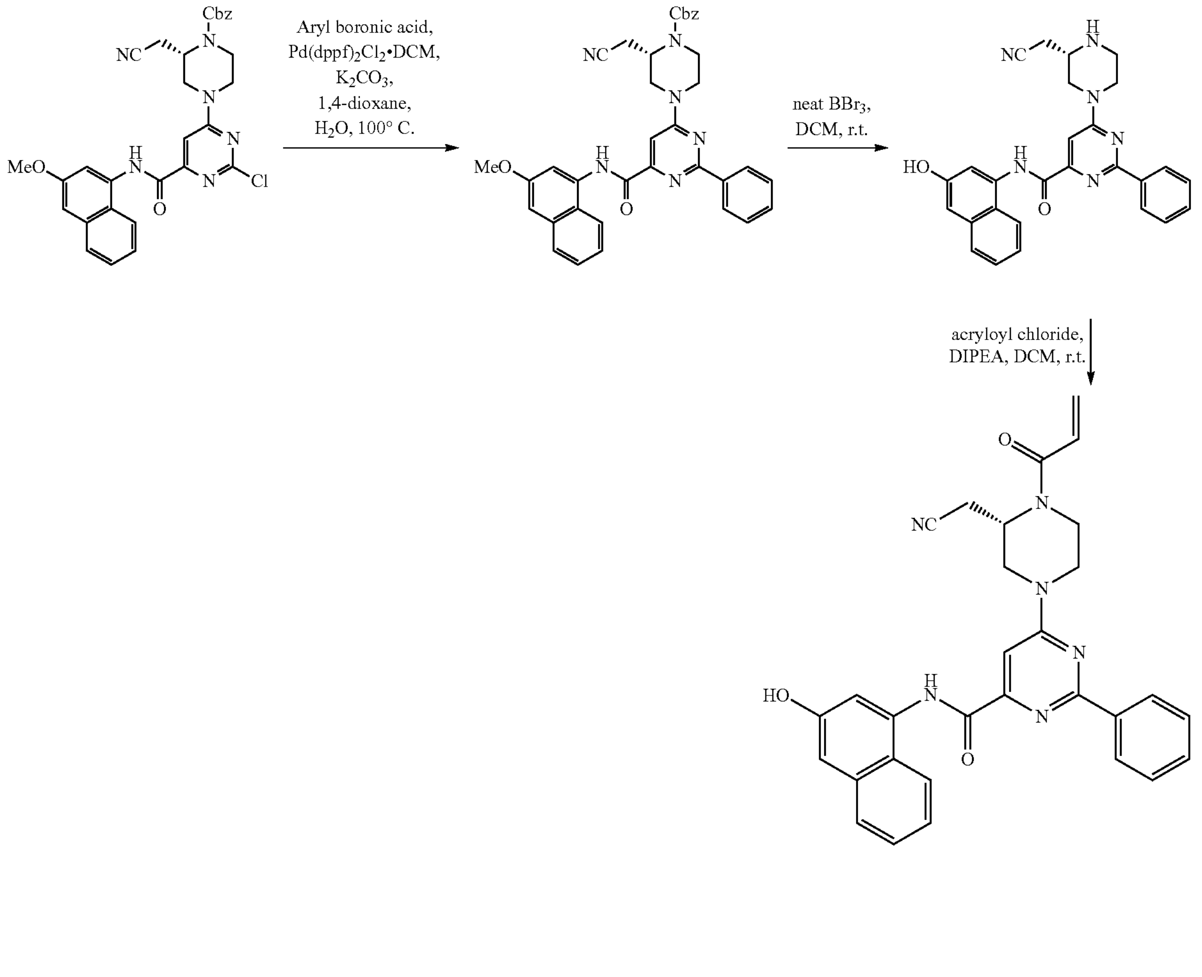

benzyl (2S)-2-(cyanomethyl)-4-[6-[(3-methoxy-1-naphthyl)carbamoyl]-2-phenyl-pyrimidin-4-yl]piperazine-1-carboxylate Step 1

A solution of benzyl (S)-4-(2-chloro-6-((3-methoxynaphthalen-1-yl)carbamoyl)pyrimidin-4-yl)-2-(cyanomethyl) piperazine-1-carboxylate (300 mg), phenylboronic acid (96.3 mg), Pd(dppf)Cl2 (35.5 mg) and $K_2CO_3$ (218 mg) in 10 mL dioxane and 2.5 mL water was heated to 110° C. under $N_2$ and stirred at 110° C. overnight. Solvent was then removed the, and the crude product was purified by flash column to afford benzyl (2S)-2-(cyanomethyl)-4-[6-[(3-methoxy-1-naphthyl)carbamoyl]-2-phenyl-pyrimidin-4-yl] piperazine-1-carboxylate (305 mg, 95%) as a yellow solid.

UPLC-MS (ES+, Method D): 4.67 min, m/z 613.5 $[M+H]^+$.

6-[(3S)-3-(cyanomethyl)piperazin-1-yl]-N-(3-hydroxy-1-naphthyl)-2-phenyl-pyrimidine-4-carboxamide Step 2

To a solution of benzyl (S)-2-(cyanomethyl)-4-(6-((3-methoxynaphthalen-1-yl)carbamoyl)-2-(((1-methyl-1H-pyrazol-4-yl)methyl)amino)pyrimidin-4-yl)piperazine-1-carboxylate (220 mg) in 1 mL DCM was added $BBr_3$ (322 mg) in 30 mL of DCM and the reaction stirred at r.t. for 10 min. The reaction was then quenched by water and extracted with DCM. Solvent was then removed in vacuo and the crude product was purified by flash column to afford 6-[(3S)-3-(cyanomethyl)piperazin-1-yl]-N-(3-hydroxy-1-naphthyl)-2-phenyl-pyrimidine-4-carboxamide (166 mg, 100%) as a yellow solid.

UPLC-MS (ES+, Method F): 1.70 min, m/z 465.1 $[M+H]^+$.

6-[(3S)-3-(cyanomethyl)-4-prop-2-enoyl-piperazin-1-yl]-N-(3-hydroxy-1-naphthyl)-2-phenyl-pyrimidine-4-carboxamide Last Step To a solution of (S)-6-(3-(cyanomethyl)piperazin-1-yl)-N-(3-hydroxynaphthalen-1-yl)-2-phenylpyrimidine-4-carboxamide (20 mg) and DIPEA (17 mg) in DMF (2 mL) at 0° C. was added acryloyl chloride (6 mg) dropwise and the reaction was stirred for 5 minutes. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-phenyl-pyrimidine-4-carboxamide (19 mg, 86%) as a yellow solid.

UPLC-MS (ES+, Method E): 3.23 min, m/z 519.3 $[M+H]^+$.

1H-NMR (400 MHz, DMSO-d6) δ/ppm: 10.98 (1H, s), 9.92 (1H, s), 8.71-6.59 (2H, m), 7.87-7.76 (2H, m), 7.62-7.30 (7H, m), 7.48-7.35 (1H, m), 6.98-6.75 (1H, m), 6.23-6.19 (1H, m), 5.81-5.79 (1H, m), 4.99-4.70 (2H, m), 4.49-4.40 (1H, m), 4.18-4.09 (1H, m), 3.64-3.45 (2H, m), 3.25-2.90 (3H, m).

Example 25

Scheme as in Example 24, using 3-pyridylboronicacid instead of phenylboronic acid 6-[(3S)-3-(cyanomethyl)-4-prop-2-enoyl-piperazin-1-yl]-N-(3-hydroxy-1-naphthyl)-2-(3-pyridyl)pyrimidine-4-carboxamide benzyl (2S)-2-(cyanomethyl)-4-[6-[(3-methoxy-1-naphthyl)carbamoyl]-2-(3-pyridyl)pyrimidin-4-yl] piperazine-1-carboxylate Step 1

A solution of benzyl (S)-4-(2-chloro-6-((3-methoxynaphthalen-1-yl)carbamoyl)pyrimidin-4-yl)-2-(cyanomethyl) piperazine-1-carboxylate (300 mg), pyridin-3-ylboronic acid (80 mg), Pd(dppf)$Cl_2$ (40 mg) and $K_2CO_3$ (220 mg) in dioxane (10 mL) and water (2.5 mL) was heated at 110° C. under $N_2$ and stirred at 110° C. overnight. Solvent was then removed in vacuo and the crude product was purified by flash column chromatography to give benzyl (2S)-2-(cyanomethyl)-4-[6-[(3-methoxy-1-naphthyl)carbamoyl]-2-(3-pyridyl)pyrimidin-4-yl]piperazine-1-carboxylate (300 mg, 93%) as a yellow solid.

UPLC-MS (ES+, Method D): 3.70 min, m/z 614.3 [M+H]+.

6-[(3S)-3-(cyanomethyl)piperazin-1-yl]-N-(3-hydroxy-1-naphthyl)-2-(3-pyridyl)pyrimidine-4-carboxamide Step 2

To a solution of (S)-6-(3-(cyanomethyl)piperazin-1-yl)-N-(3-hydroxynaphthalen-1-yl)-2-(pyridin-3-yl)pyrimidine-4-carboxamide (250 mg) in DCM (1 mL) was added $BBr_3$ (407 mg) in 30 mL, then the reaction was stirred at rt for 10 minutes. The reaction was quenched by water and extracted with DCM. The organic layer was dried over sodium sulfate and solvent removed in vacuo. The residue was purified by flash column to afford 6-[(3S)-3-(cyanomethyl)piperazin-1-yl]-N-(3-hydroxy-1-naphthyl)-2-(3-pyridyl)pyrimidine-4-carboxamide (140 mg, 74%) as a yellow solid.

UPLC-MS (ES+, Method F): 1.30 min, m/z 466.1 $[M+H]^+$.

6-[(3S)-3-(cyanomethyl)-4-prop-2-enoyl-piperazin-1-yl]-N-(3-hydroxy-1-naphthyl)-2-(3-pyridyl)pyrimidine-4-carboxamide Last Step To a solution of (S)-6-(3-(cyanomethyl)piperazin-1-yl)-N-(3-hydroxynaphthalen-1-yl)-2-(pyridin-3-yl)pyrimidine-4-carboxamide (14 mg) and 12 mg DIPEA in 2 mL DMF at 0° C. was added acryloyl chloride (4 mg) dropwise, then the reaction was stirred for 5 min. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-(3-pyridyl)pyrimidine-4-carboxamide (15 mg, 95%) as a yellow solid.

UPLC-MS (ES+, Method E): 3.40 min, m/z 520.3 [M+H]+.

1H-NMR (400 MHz, DMSO-d6) δ/ppm: 11.00 (1H, s), 9.92 (1H, br s), 9.86-9.84 (1H, m), 9.05-9.05 (1H, m), 9.78-9.76 (1H, m), 7.84-7.82 (1H, m), 7.78-7.76 (1H, m), 7.65-7.62 (1H, m), 7.53-7.43 (3H, m), 7.36-7.32 (1H, m), 7.12-7.11 (1H, m), 6.98-6.82 (1H, m), 6.23-6.19 (1H, m), 5.82-5.78 (1H, m), 5.04-4.78 (2H, m), 4.49-4.42 (1H, m), 4.16-4.08 (1H, m), 3.68-3.48 (2H, m), 3.18-3.12 (1H, m), 3.07-2.92 (2H, m).

Example 26

Scheme as in Example 24, using 4-pyridylboronicacid instead of phenylboronic acid benzyl (2S)-2-(cyanomethyl)-4-[6-[(3-methoxy-1-naphthyl)carbamoyl]-2-(4-pyridyl)pyrimidin-4-yl]piperazine-1-carboxylate benzyl (2S)-2-(cyanomethyl)-4-[6-[(3-methoxy-1-naphthyl)carbamoyl]-2-(4-pyridyl)pyrimidin-4-yl] piperazine-1-carboxylate Step 1

A solution of benzyl (S)-4-(2-chloro-6-((3-methoxynaphthalen-1-yl)carbamoyl)pyrimidin-4-yl)-2-(cyanomethyl) piperazine-1-carboxylate (300 mg), pyridin-4-ylboronic acid (80 mg), Pd(dppf)$Cl_2$ (40 mg) and $K_2CO_3$ (220 mg) in dioxane (10 mL) and water (2.5 mL) was heated at 110° C. under $N_2$ and stirred overnight. Solvent was then removed in vacuo and the crude product was purified by flash column chromatography to give benzyl (2S)-2-(cyanomethyl)-4-[6-[(3-methoxy-1-naphthyl)carbamoyl]-2-(4-pyridyl)pyrimidin-4-yl]piperazine-1-carboxylate (240 mg, 74%) as a yellow solid.

UPLC-MS (ES+, Method D): 3.47 min, m/z 614.3 [M+H]+.

6-[(3S)-3-(cyanomethyl)piperazin-1-yl]-N-(3-hydroxy-1-naphthyl)-2-(4-pyridyl)pyrimidine-4-carboxamide Step 2

To a solution of benzyl (S)-2-(cyanomethyl)-4-(6-((3-methoxynaphthalen-1-yl)carbamoyl)-2-(pyridin-4-yl)pyrimidin-4-yl)piperazine-1-carboxylate (190 mg) in DCM (1 mL) was added $BBr_3$ (307 mg) in DCM (30 mL), then the reaction was stirred at r.t. for 10 min. The reaction was quenched by water, extracted by DCM. Solvent was then removed in vacuo and the crude product was purified by flash column give 6-[(3S)-3-(cyanomethyl)piperazin-1-yl]-N-(3-hydroxy-1-naphthyl)-2-(4-pyridyl)pyrimidine-4-carboxamide, (120 mg, 83%) as a yellow solid.

UPLC-MS (ES+, Method F): 1.30 min, m/z 466.1 $[M+H]^+$.

6-[(3S)-3-(cyanomethyl)-4-prop-2-enoyl-piperazin-1-yl]-N-(3-hydroxy-1-naphthyl)-2-(4-pyridyl)pyrimidine-4-carboxamide Final Step:

To a solution of (S)-6-(3-(cyanomethyl)piperazin-1-yl)-N-(3-hydroxynaphthalen-1-yl)-2-(pyridin-4-yl)pyrimidine-4-carboxamide (15 mg) and DIPEA (12 mg) in DMF (2 mL) at 0° C. was added acryloyl chloride (4 mg) dropwise, then the reaction was stirred for 5 min. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-(4-pyridyl)pyrimidine-4-carboxamide (14 mg, 82%) as a yellow solid.

UPLC-MS (ES+, Method E): 2.93 min, m/z 520.3 $[M+H]^+$.

1H-NMR (400 MHz, DMSO-d6) δ/ppm: 11.00 (1H, s), 8.82-8.78 (2H, m), 8.60-8.55 (2H, m), 8.47-8.41 (1H, m), 7.85-7.83 (1H, m), 7.79-7.77 (1H, m), 7.52-7.4 (3H, m), 7.37-7.31 (1H, m), 7.11 (1H, s), 6.98-6.82 (1H, m), 6.22-6.17 (1H, m), 5.82-5.78 (1H, m), 5.06-4.78 (2H, m), 4.51-4.40 (1H, m), 4.16-4.07 (1H, m), 3.67-3.50 (2H, m), 3.18-3.12 (1H, m), 3.08-2.92 (2H, m).

Example 27

6-[(3S)-3-(cyanomethyl)-4-prop-2-enoyl-piperazin-1-yl]-N-(3-hydroxy-1-naphthyl)-2-[2-(4-methylpiperazin-1-yl)ethylamino]pyrimidine-4-carboxamide

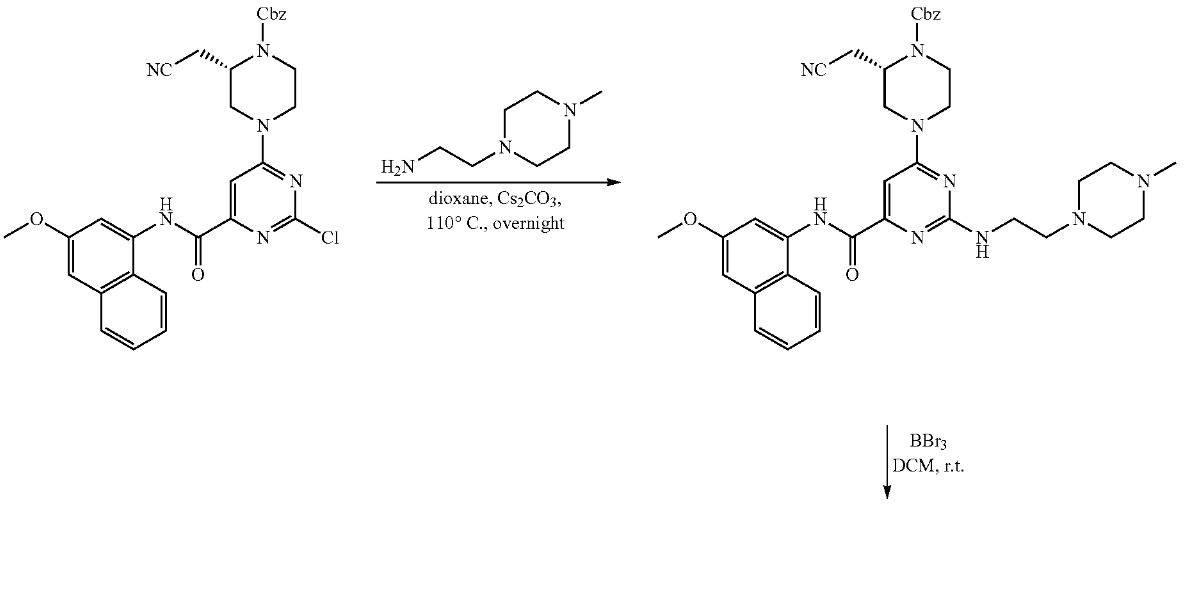

-continued

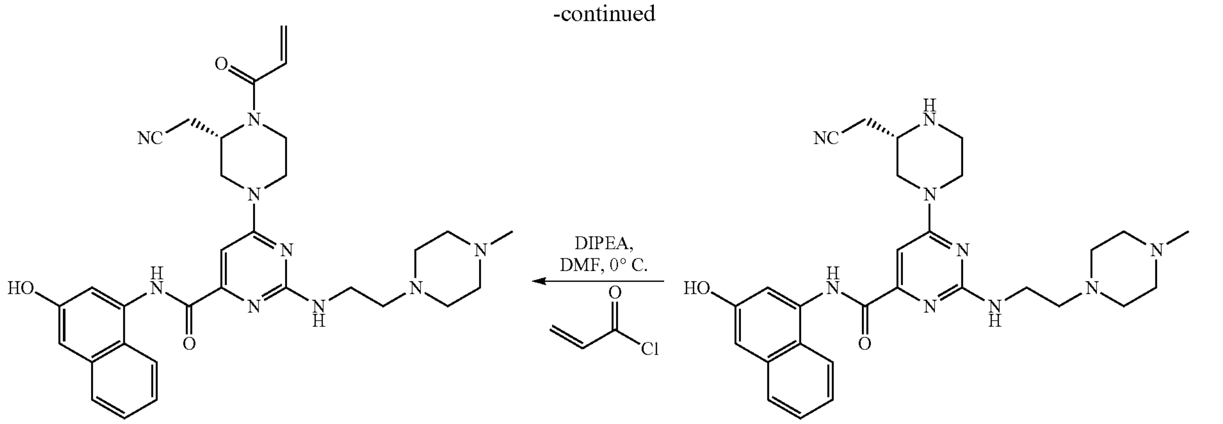

benzyl (2S)-2-(cyanomethyl)-4-[6-[(3-methoxy-1-naphthyl)carbamoyl]-2-[2-(4-methylpiperazin-1-yl)ethylamino]pyrimidin-4-yl]piperazine-1-carboxylate Step 1

To benzyl (2S)-4-[2-chloro-6-[(3-methoxy-1-naphthyl)carbamoyl]pyrimidin-4-yl]-2-(cyanomethyl)piperazine-1-carboxylate (200 mg, 0.35 mmol, 1.0 eq) was added 1,4-dioxane (10 mL) followed by the addition of 2-(4-methyl-piperazin-1-yl)-ethylamine (251 mg, 1.75 mmol, 5.0 eq), $Cs_2CO_3$ (342 mg, 1.05 mmol, 3.0 eq) and DIPEA (362 mg, 2.80 mmol, 8.0 eq). The reaction was stirred at 110° C. overnight. Solvent was then removed in vacuo and the residue was dissolved in EtOAc (100 mL) and washed with brine (100 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[6-[(3-methoxy-1-naphthyl)carbamoyl]-2-[2-(4-methylpiperazin-1-yl)ethylamino]pyrimidin-4-yl]piperazine-1-carboxylate (210 mg, 88%).

UPLC-MS (ES+, Method B): 1.83 min, m/z 678.0 [M+H]+.

6-[(3S)-3-(cyanomethyl)piperazin-1-yl]-N-(3-hydroxy-1-naphthyl)-2-[2-(4-methylpiperazin-1-yl)ethylamino]pyrimidine-4-carboxamide Step 2 benzyl (2S)-2-(cyanomethyl)-4-[6-[(3-methoxy-1-naphthyl)carbamoyl]-2-[2-(4-methylpiperazin-1-yl)ethylamino]pyrimidin-4-yl]piperazine-1-carboxylate (210 mg, 0.31 mmol, 1.0 eq) was dissolved in DCM (20 mL) followed by the addition of boron tribromide (0.2 mL). After 5 mins, MeOH (20 mL) was added and solvent removed in vacuo. The residue was purified by column chromatography using an eluent of 0-10% MeOH in DCM reached via a gradient to give 6-[(3S)-3-(cyanomethyl)piperazin-1-yl]-N-(3-hydroxy-1-naphthyl)-2-[2-(4-methylpiperazin-1-yl)ethylamino]pyrimidine-4-carboxamide (150 mg, 91%).

UPLC-MS (ES+, Method B): 0.89 min, m/z 530.0 [M+H]+.

6-[(3S)-3-(cyanomethyl)-4-prop-2-enoyl-piperazin-1-yl]-N-(3-hydroxy-1-naphthyl)-2-[2-(4-methylpiperazin-1-yl)ethylamino]pyrimidine-4-carboxamide Last Step Acryloyl chloride (8 mg, 0.09 mmol, 1.0 eq) and 6-[(3S)-3-(cyanomethyl)piperazin-1-yl]-N-(3-hydroxy-1-naphthyl)-2-[2-(4-methylpiperazin-1-yl)ethylamino]pyrimidine-4-carboxamide (50 mg, 0.09 mmol, 1.0 eq) were dissolved in DMF (2 mL) followed by the addition of DIPEA (37 mg, 0.28 mmol, 3.0 eq). The reaction was left stirring for 5 mins at 0° C. Solvent was then removed in vacuo and the residue was purified by Prep-HPLC to give 6-[(3S)-3-(cyanomethyl)-4-prop-2-enoyl-piperazin-1-yl]-N-(3-hydroxy-1-naphthyl)-2-[2-(4-methylpiperazin-1-yl)ethylamino]pyrimidine-4-carboxamide (4 mg, 7%) as a white solid.

UPLC-MS (ES+, Method B): 0.95 min, m/z 584.0 $[M+H]^+$

1H-NMR (400 MHz, DMSO-d6) δ/ppm: 10.78 (1H, s), 8.30 (1H, s), 8.01-7.76 (2H, m), 7.75-7.73 (1H, m), 7.49-7.44 (1H, m), 7.38-7.32 (1H, m), 7.20-6.78 (3H, m), 6.21-6.17 (1H, m), 5.79-5.77 (1H, m), 4.92-4.78 (1H, m), 4.52-3.98 (4H, m), 3.80-3.25 (9H, m), 3.20-2.80 (4H, m), 2.36-2.25 (3H, m), 2.14 (3H, s), 1× exchangeable proton not seen.

Example 28

6-[(3S)-3-(cyanomethyl)-4-prop-2-enoyl-piperazin-1-yl]-N-(3-hydroxy-1-naphthyl)-2-(2-morpholinoethylamino)pyrimidine-4-carboxamide

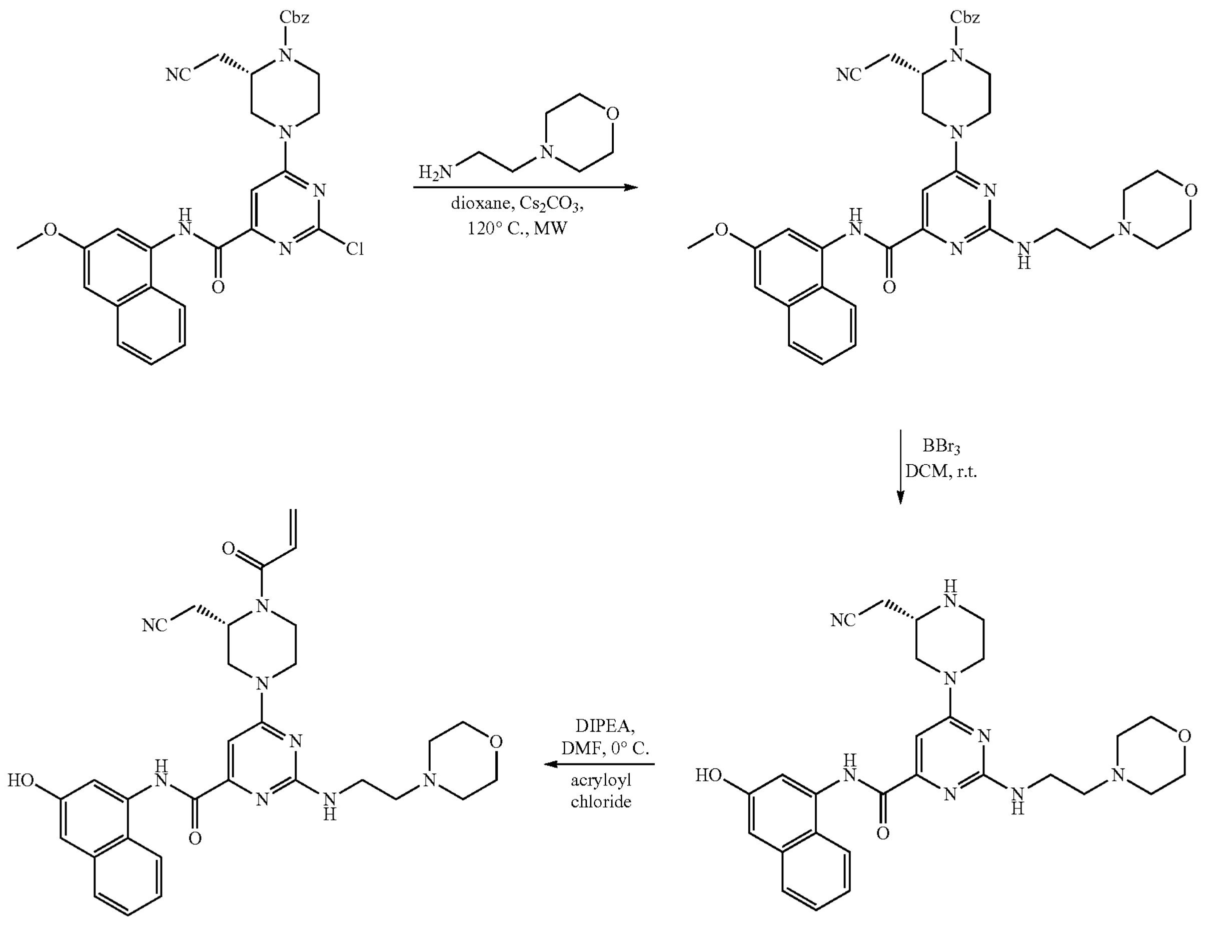

benzyl (2S)-2-(cyanomethyl)-4-[6-[(3-methoxy-1-naphthyl)carbamoyl]-2-(2-morpholinoethylamino)pyrimidin-4-yl]piperazine-1-carboxylate Step 1

To benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) in a microwave vial was added 1,4-dioxane (20 mL) followed by the addition of 4-(2-aminoethyl)morpholine (342 mg, 2.63 mmol, 5.0 eq), $Cs_2CO_3$ (513 mg, 4.58 mmol, 3.0 eq) and DIPEA (543 mg, 4.20 mmol, 8.0 eq). The reaction was heated at the microwave at 130° C. for 2 hours. The solvent was then removed in vacuo and the residue was dissolved in EtOAc (200 mL) and washed with brine (200 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[6-[(3-methoxy-1-naphthyl)carbamoyl]-2-(2-morpholinoethylamino)pyrimidin-4-yl]piperazine-1-carboxylate (210 mg, 90%) as a dark yellow oil.

UPLC-MS (ES+, Method F): 1.87 min, m/z 665.3 [M+H]+.

6-[(3S)-3-(cyanomethyl)piperazin-1-yl]-N-(3-hydroxy-1-naphthyl)-2-(2-morpholinoethylamino)pyrimidine-4-carboxamide Step 2 benzyl (2S)-2-(cyanomethyl)-4-[6-[(3-methoxy-1-naphthyl)carbamoyl]-2-(2-morpholinoethylamino)pyrimidin-4-yl]piperazine-1-carboxylate (210 mg, 0.31 mmol, 1.0 eq) was dissolved in DCM (20 mL) followed by the addition of boron tribromide (0.18 mL). After 5 mins, MeOH (20 mL) was added and solvent removed in vacuo. Solvent was then removed in vacuo and the residue was purified by column chromatography using an eluent of 0-10% MeOH in DCM reached via a gradient to give 6-[(3S)-3-(cyanomethyl)piperazin-1-yl]-N-(3-hydroxy-1-naphthyl)-2-(2-morpholinoethylamino)pyrimidine-4-carboxamide (80 mg, 49%).

UPLC-MS (ES+, Method B): 0.92 min, m/z 517.0 [M+H]+.

6-[(3S)-3-(cyanomethyl)-4-prop-2-enoyl-piperazin-1-yl]-N-(3-hydroxy-1-naphthyl)-2-(2-morpholinoethylamino)pyrimidine-4-carboxamide Last Step Acryloyl chloride (9 mg, 0.09 mmol, 1.0 eq) and 6-[(3S)-3-(cyanomethyl)piperazin-1-yl]-N-(3-hydroxy-1-naphthyl)-2-(2-morpholinoethylamino)pyrimidine-4-carboxamide (50 mg, 0.09 mmol, 1.0 eq) were dissolved in DMF (2 mL) followed by the addition of DIPEA (37 mg, 0.29 mmol, 3.0 eq). The reaction was left stirring for 5 mins at 0° C. Solvent was then removed in vacuo and the residue was purified by prep-HPLC to give 6-[(3S)-3-(cyanomethyl)-4-prop-2-enoyl-piperazin-1-yl]-N-(3-hydroxy-1-naphthyl)-2-(2-morpholinoethylamino)pyrimidine-4-carboxamide (4 mg, 7%) as a white solid.

UPLC-MS (ES+, Method B): 1.02 min, m/z 571.0 $[M+H]^+$.

1H-NMR (400 MHz, DMSO-d6) δ/ppm: 10.81 (1H, s), 9.91 (1H, s), 8.03-7.80 (2H, m), 7.79-7.77 (1H, m), 7.52-7.48 (1H, m), 7.43-7.36 (1H, m), 7.24-6.76 (4H, m), 6.25-6.20 (1H, m), 5.82-5.79 (1H, m), 4.96-4.80 (1H, m), 4.50-4.40 (3H, m), 3.70-3.50 (7H, m), 3.25-3.79 (4H, m), 2.62-2.55 (2H, m), 2.49-2.35 (4H, m).

Example 29

6-[(3S)-3-(cyanomethyl)-4-prop-2-enoyl-piperazin-1-yl]-2-[2-(dimethylamino)ethylamino]-N-(3-hydroxy-1-naphthyl)pyrimidine-4-carboxamide

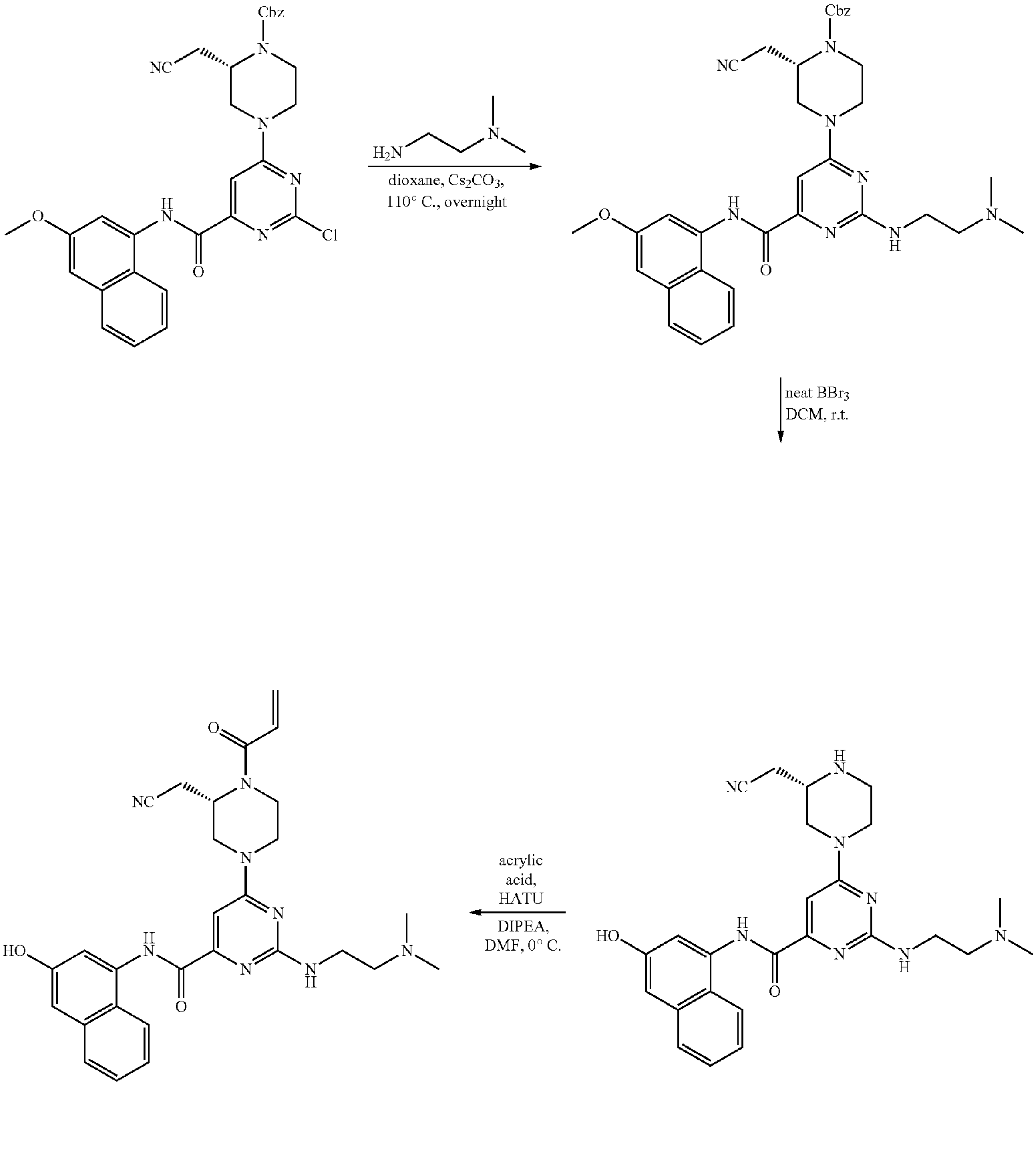

benzyl (2S)-2-(cyanomethyl)-4-[2-[2-(dimethylamino)ethylamino]-6-[(3-methoxy-1-naphthyl)carbamoyl]pyrimidin-4-yl]piperazine-1-carboxylate Step 1

To benzyl (2S)-4-[2-chloro-6-[(3-methoxy-1-naphthyl)carbamoyl]pyrimidin-4-yl]-2-(cyanomethyl)piperazine-1-carboxylate (200 mg, 0.35 mmol, 1.0 eq) was added 1,4-dioxane (10 mL) followed by the addition of N,N-dimethylethylenediamine (154 mg, 1.75 mmol, 5.0 eq), $Cs_2CO_3$ (342 mg, 1.05 mmol, 3.0 eq) and DIPEA (362 mg, 2.8 mmol, 8.0 eq). The reaction was stirred at 110° C. overnight. Solvent was then removed in vacuo and the residue was dissolved in EtOAc (100 mL) and washed with brine (100 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[2-[2-(dimethylamino)ethylamino]-6-[(3-methoxy-1-naphthyl)carbamoyl]pyrimidin-4-yl]piperazine-1-carboxylate (210 mg, 96%).

UPLC-MS (ES+, Method A): 0.91 min, m/z 622.9 [M+H]+.

6-[(3S)-3-(cyanomethyl)piperazin-1-yl]-2-[2-(dimethylamino)ethylamino]-N-(3-hydroxy-1-naphthyl)pyrimidine-4-carboxamide Step 2 benzyl (2S)-2-(cyanomethyl)-4-[2-[2-(dimethylamino)ethylamino]-6-[(3-methoxy-1-naphthyl)carbamoyl]pyrimidin-4-yl]piperazine-1-carboxylate (210 mg, 0.33 mmol, 1.0 eq) was dissolved in DCM (20 mL) followed by the addition of boron tribromide (0.26 mL). After 5 mins, MeOH (20 mL) was added and solvent removed in vacuo. The residue purified by column chromatography using an eluent of 0-10% MeOH in DCM reached via a gradient to give 6-[(3S)-3-(cyanomethyl)piperazin-1-yl]-2-[2-(dimethylamino)ethylamino]-N-(3-hydroxy-1-naphthyl)pyrimidine-4-carboxamide (120 mg, 75%).

UPLC-MS (ES+, Method B): 0.92 min, m/z 475.0 [M+H]+.

6-[(3S)-3-(cyanomethyl)-4-prop-2-enoyl-piperazin-1-yl]-2-[2-(dimethylamino)ethylamino]-N-(3-hydroxy-1-naphthyl)pyrimidine-4-carboxamide Last Step Acryloyl chloride (9 mg, 0.10 mmol, 1.0 eq) and 6-[(3S)-3-(cyanomethyl)piperazin-1-yl]-2-[2-(dimethylamino)ethylamino]-N-(3-hydroxy-1-naphthyl)pyrimidine-4-carboxamide (50 mg, 0.10 mmol, 1.0 eq) were dissolved in DMF (1 mL) followed by the addition of DIPEA (41 mg, 0.32 mmol, 3.0 eq). The reaction was left stirring for 5 mins at 0° C. Solvent was then removed in vacuo and the residue was purified by Prep-HPLC to give 6-[(3S)-3-(cyanomethyl)-4-prop-2-enoyl-piperazin-1-yl]-2-[2-(dimethylamino)ethylamino]-N-(3-hydroxy-1-naphthyl)pyrimidine-4-carboxamide (6 mg, 11%) as a grey solid.

UPLC-MS (ES+, Method B): 0.99 min, m/z 529.0 $[M+H]^+$.

1H-NMR (400 MHz, DMSO-d6) δ/ppm: 10.80 (1H, s), 8.25 (1H, s), 8.05-7.79 (2H, m), 7.77-7.75 (1H, m), 7.50-7.46 (1H, m), 7.40-7.34 (1H, m), 7.24-6.75 (4H, m), 6.24-6.19 (1H, m), 5.81-5.78 (1H, m), 4.96-4.77 (1H, m), 4.55-4.00 (3H, m), 3.65-2.80 (7H, m), 2.60-2.52 (2H, m), 2.30-2.25 (6H, m).

Example 30

6-[(3S)-3-(cyanomethyl)-4-prop-2-enoyl-piperazin-1-yl]-N-(3-hydroxy-1-naphthyl)-2-[2-(1-methylpyrrolidin-2-yl)ethylamino]pyrimidine-4-carboxamide

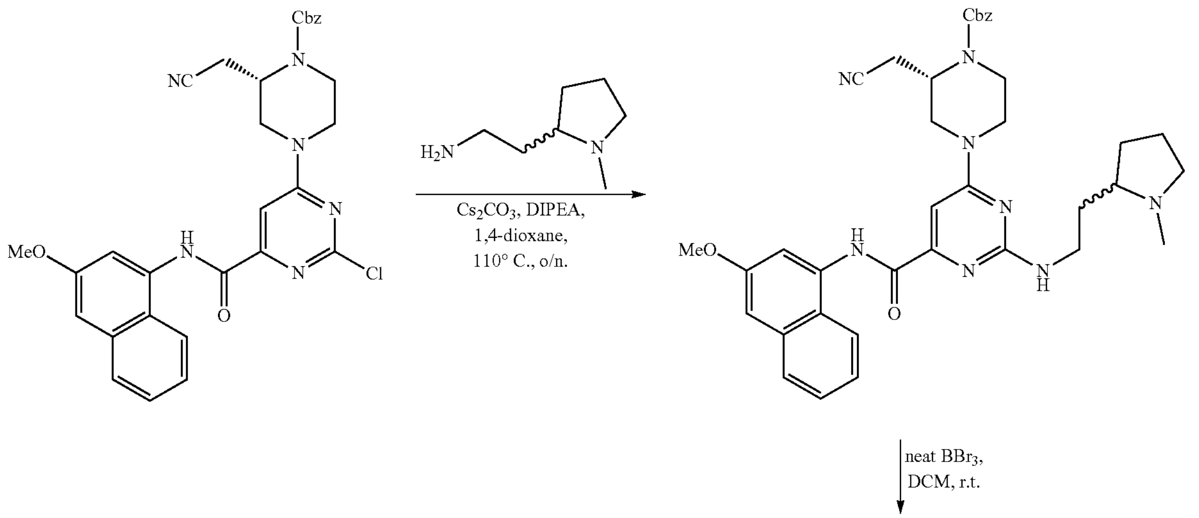

-continued

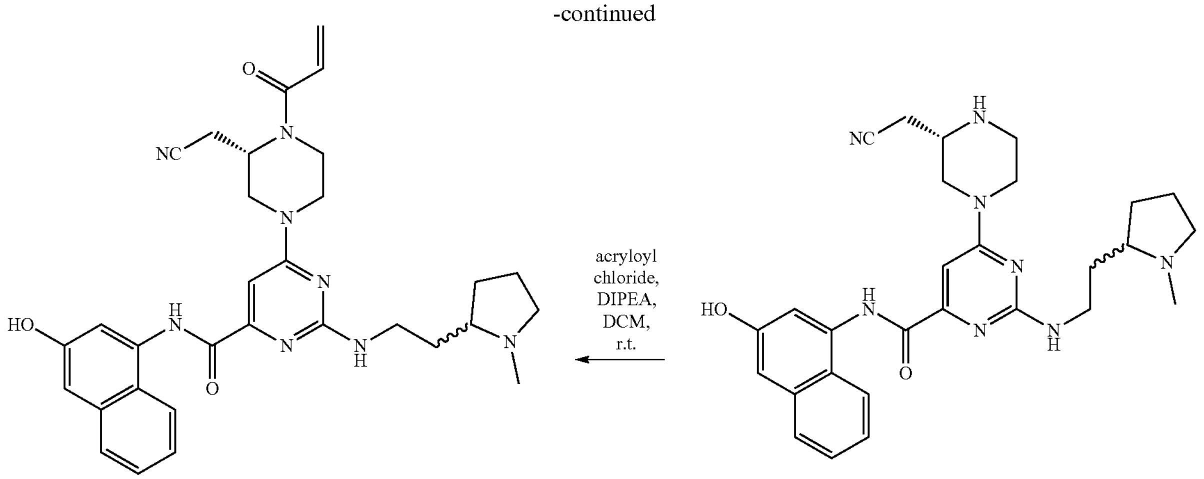

benzyl (2S)-2-(cyanomethyl)-4-[6-[(3-methoxy-1-naphthyl)carbamoyl]-2-[2-(1-methylpyrrolidin-2-yl)ethylamino]pyrimidin-4-yl]piperazine-1-carboxylate First Step:

A solution of benzyl (S)-4-(2-chloro-6-((3-methoxynaphthalen-1-yl)carbamoyl)pyrimidin-4-yl)-2-(cyanomethyl)piperazine-1-carboxylate (300 mg), 2-(1-methylpyrrolidin-2-yl)ethan-1-amine (202 mg), $Cs_2CO_3$ (515 mg) and DIPEA (543 mg) in dioxane (2 mL) was heated to 110° C. under $N_2$ and stirred at 110° C. overnight. Solvent was removed in vacuo and the crude product was purified by flash column to afford the benzyl (2S)-2-(cyanomethyl)-4-[6-[(3-methoxy-1-naphthyl)carbamoyl]-2-[2-(1-methylpyrrolidin-2-yl)ethylamino]pyrimidin-4-yl]piperazine-1-carboxylate (240 mg, 70%) as a yellow solid.

UPLC-MS (ES+, Method E): 3.00 min, m/z 663.5 [M+H]+.

6-[(3S)-3-(cyanomethyl)piperazin-1-yl]-N-(3-hydroxy-1-naphthyl)-2-[2-(1-methylpyrrolidin-2-yl)ethylamino]pyrimidine-4-carboxamide Step 2

To a solution of benzyl (2S)-2-(cyanomethyl)-4-(6-((3-methoxynaphthalen-1-yl)carbamoyl)-2-((2-(1-methylpyrrolidin-2-yl)ethyl)amino)pyrimidin-4-yl)piperazine-1-carboxylate (30 mg) in DCM (1 mL) was added $BBr_3$ (44 mg) in DCM (4 mL), then the reaction was stirred at rt for 10 min. The reaction was then quenched by water and extracted by DCM. The organic layer was dried over sodium sulfate and solvent removed in vacuo to give 6-[(3S)-3-(cyanomethyl)piperazin-1-yl]-N-(3-hydroxy-1-naphthyl)-2-[2-(1-methylpyrrolidin-2-yl)ethylamino]pyrimidine-4-carboxamide (23 mg, 100%).

UPLC-MS (ES+, Method F): 0.63 min, m/z 515.2 [M+H]+.

6-[(3S)-3-(cyanomethyl)-4-prop-2-enoyl-piperazin-1-yl]-N-(3-hydroxy-1-naphthyl)-2-[2-(1-methylpyrrolidin-2-yl)ethylamino]pyrimidine-4-carboxamide Final Step:

To a solution of 6-[(3S)-3-(cyanomethyl)piperazin-1-yl]-N-(3-hydroxy-1-naphthyl)-2-[2-(1-methylpyrrolidin-2-yl)ethylamino]pyrimidine-4-carboxamide (40 mg, 0.08 mmol, 1.0 eq) in dry-DMF was added acryloyl chloride (7 mg, 0.08 mmol, 1.0 eq) and N,N-diisopropylethylamine (30 mg, 0.23 mmol, 3.0 eq), the mixture was stirred at 0° C. under $N_2$ for 30 minutes. Solvent was then removed in vacuo and the residue purified by prep-HPLC to give 6-[(3S)-3-(cyanomethyl)-4-prop-2-enoyl-piperazin-1-yl]-N-(3-hydroxy-1-naphthyl)-2-[2-(1-methylpyrrolidin-2-yl)ethylamino]pyrimidine-4-carboxamide (8 mg, 33%) as a yellow solid.

UPLC-MS (ES+, Method E): 2.63 min, m/z 569.4 $[M+H]^+$.

1H-NMR (400 MHz, DMSO-d6) δ/ppm: 10.77 (1H, s), 8.22 (1H, s), 8.02-7.77 (2H, m), 7.75-7.73 (1H, m), 7.48-7.44 (1H, m), 7.45-7.05 (2H, m), 7.02-7.00 (1H, m), 6.88-6.70 (2H, m), 6.21-6.16 (1H, m), 5.79-5.76 (1H, m), 4.91-4.77 (1H, m), 4.48-4.20 (4H, m), 4.09-4.03 (2H, m), 3.06-2.88 (5H, m), 2.46-2.20 (5H, m), 2.05-2.95 (2H, m), 1.72-1.50 (4H, m).

Example 31

6-[(3S)-3-(cyanomethyl)-4-prop-2-enoyl-piperazin-1-yl]-N-(3-hydroxy-1-naphthyl)-2-(2-pyridyl)pyrimidine-4-carboxamide benzyl (2S)-2-(cyanomethyl)-4-[6-[(3-methoxy-1-naphthyl)carbamoyl]-2-(2-pyridyl)pyrimidin-4-yl]piperazine-1-carboxylate Scheme as in Example 24, using 2-pyridylboronicacid instead of phenylboronic acid Step 1

A solution of benzyl (S)-4-(2-chloro-6-((3-methoxynaphthalen-1-yl)carbamoyl)pyrimidin-4-yl)-2-(cyanomethyl)piperazine-1-carboxylate (20 mg), 2-(tetra-tert-butyl-15-stannyl)pyridine (15 mg), KF (6 mg) and $Pd(PPh_3)_4$ (4 mg) in toluene (2 mL) was heated to 110° C. under $N_2$ and stirred overnight. Solvent was then removed in vacuo and the residue purified by column chromatography to give benzyl (2S)-2-(cyanomethyl)-4-[6-[(3-methoxy-1-naphthyl)carbamoyl]-2-(2-pyridyl)pyrimidin-4-yl]piperazine-1-carboxylate (21 mg, 100%)

UPLC-MS (ES+, Method F): 2.37 min, m/z 614.3 [M+H]+.

6-[(3S)-3-(cyanomethyl)piperazin-1-yl]-N-(3-hydroxy-1-naphthyl)-2-(2-pyridyl)pyrimidine-4-carboxamide Step 2

To a solution of benzyl (2S)-2-(cyanomethyl)-4-[6-[(3-methoxy-1-naphthyl)carbamoyl]-2-(2-pyridyl)pyrimidin-4-yl]piperazine-1-carboxylate (30 mg, 0.05 mmol, 1.0 eq) in dry-DCM was added $BBr_3$ (122 mg, 0.49 mmol, 10.0 eq), the mixture was stirred at rt under $N_2$ for 10 minutes. MeOH (20 mL) was added and solvent removed in vacuo. The residue purified by column chromatography using an eluent of 0-10% MeOH in DCM reached via a gradient to give 6-[(3S)-3-(cyanomethyl)piperazin-1-yl]-N-(3-hydroxy-1-naphthyl)-2-(2-pyridyl)pyrimidine-4-carboxamide, (23 mg, 100%).

UPLC-MS (ES+, Method G): 3.10 min, m/z 446.3 [M+H]+.

6-[(3S)-3-(cyanomethyl)-4-prop-2-enoyl-piperazin-1-yl]-N-(3-hydroxy-1-naphthyl)-2-(2-pyridyl)pyrimidine-4-carboxamide Last Step To a solution of 6-[(3S)-3-(cyanomethyl)piperazin-1-yl]-N-(3-hydroxy-1-naphthyl)-2-(2-pyridyl)pyrimidine-4-carboxamide (15 mg, 0.03 mmol, 1.0 eq) in dry-DMF was added acryloyl chloride (3 mg, 0.03 mmol, 1.0 eq) and N,N-diisopropylethylamine (12 mg, 0.10 mmol, 3.0 eq), the mixture was stirred at 0° C. under $N_2$ for 30 minutes. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-(2-pyridyl)pyrimidine-4-carboxamide (5 mg, 29%) as a yellow solid.

UPLC-MS (ES+, Method E): 3.20 min, m/z 520.3 $[M+H]^+$.

1H-NMR (400 MHz, DMSO-d6) δ/ppm: 8.95-8.85 (2H, m), 8.28-8.24 (1H, m), 7.92-7.90 (1H, m), 7.80-7.77 (2H, m), 7.60-7.7 (2H, m), 7.51-7.47 (1H, m), 7.40-7.36 (1H, m), 7.13 (1H, s), 7.02-6.89 (1H, m), 6.26-6.22 (1H, m), 5.84-5.82 (1H, m), 5.07-4.91 (2H, m), 4.55-4.45 (1H, m), 4.20-4.20 (1H, m), 3.28-3.19 (2H, m), 3.04-2.99 (3H, m), 2×exchangeable protons not seen.

Example 32

6-[(3S)-3-(cyanomethyl)-4-prop-2-enoyl-piperazin-1-yl]-N-(3-hydroxy-1-naphthyl)-2-(1-methylindazol-6-yl)pyrimidine-4-carboxamide

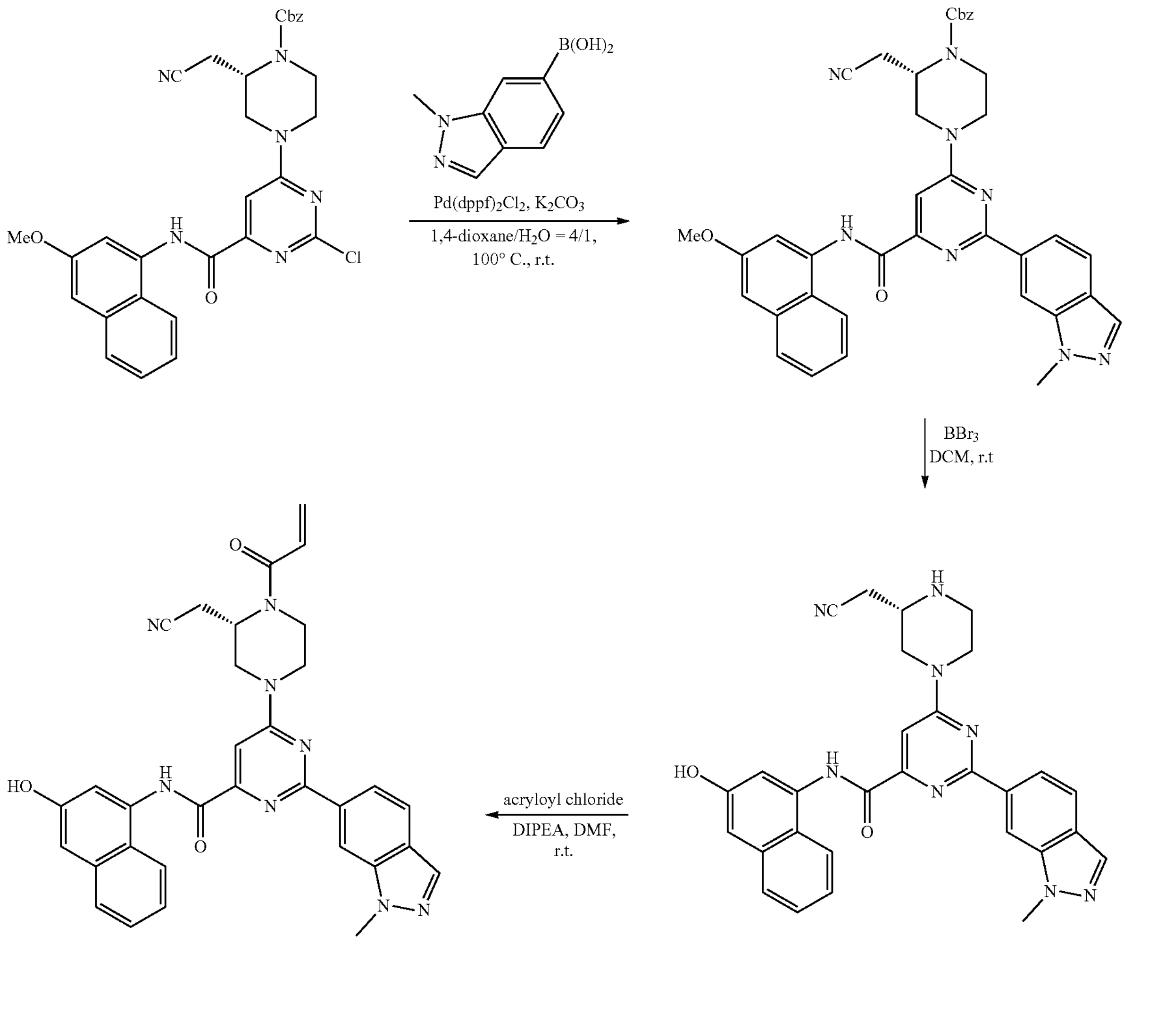

benzyl (2S)-2-(cyanomethyl)-4-[6-[(3-methoxy-1-naphthyl)carbamoyl]-2-(1-methylindazol-6-yl)pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl) piperazine-1-carboxylate (300 mg, 0.52 mmol, 1.0 eq) in 1,4-dioxane (4 mL) and water (1 mL) was added 1-methyl-1H-indazole-6-boronic acid (111 mg, 0.63 mmol, 1.2 eq), Pd(dppf)$Cl_2$ (38 mg, 0.05 mmol, 0.1eq) and $K_2CO_3$ (218 mg, 1.58 mmol, 3.0 eq) and the mixture was stirred and heated at 100° C. under $N_2$ overnight. The mixture was diluted with water (100 mL) and extracted with EtOAc (150 mL×3). The combined organic layers were dried over $Na_2SO_4$ and concentrated in vacuo. The residue was purified by silica gel column (DCM/MeOH=30/1,V/V) to give benzyl (2S)-2-(cyanomethyl)-4-[6-[(3-methoxy-1-naphthyl)carbamoyl]-2-(1-methylindazol-6-yl)pyrimidin-4-yl]piperazine-1-carboxylate (251 mg, 72%)

UPLC-MS (ES+, Method D): 4.37 min, m/z 667.4 [M+H]+.

6-[(3S)-3-(cyanomethyl)piperazin-1-yl]-N-(3-hydroxy-1-naphthyl)-2-(1-methylindazol-6-yl)pyrimidine-4-carboxamide Step 2

To a solution of benzyl (2S)-2-(cyanomethyl)-4-[6-[(3-methoxy-1-naphthyl)carbamoyl]-2-(1-methylindazol-6-yl) pyrimidin-4-yl]piperazine-1-carboxylate (100 mg, 0.15 mmol, 1.0 eq) in dry-DCM was added $BBr_3$ (451 mg, 1.80 mmol, 10.0 eq), the mixture was stirred at rt under $N_2$ for 10 minutes. MeOH (20 mL) was added and solvent removed in vacuo. The residue purified by column chromatography using an eluent of 0-10% MeOH in DCM reached via a gradient to give 6-[(3S)-3-(cyanomethyl)piperazin-1-yl]-N-(3-hydroxy-1-naphthyl)-2-(1-methylindazol-6-yl)pyrimidine-4-carboxamide (45 mg, 50%).

UPLC-MS (ES+, Method G): 3.63 min, m/z 519.3 [M+H]+.

6-[(3S)-3-(cyanomethyl)-4-prop-2-enoyl-piperazin-1-yl]-N-(3-hydroxy-1-naphthyl)-2-(1-methylindazol-6-yl)pyrimidine-4-carboxamide Last Step To a solution of 6-[(3S)-3-(cyanomethyl)piperazin-1-yl]-N-(3-hydroxy-1-naphthyl)-2-(1-methylindazol-6-yl)pyrimidine-4-carboxamide (15 mg, 0.03 mmol, 1.0 eq) in dry-DMF (1 mL) was added acryloyl chloride (3 mg, 0.03 mmol, 1.0 eq) and N,N-diisopropylethylamine (11 mg, 0.09 mmol, 3.0 eq), the mixture was stirred at 0° C. under $N_2$ for 30 minutes. Solvent was then removed in vacuo and the residue purified by prep-HPLC to give 6-[(3S)-3-(cyanomethyl)-4-prop-2-enoyl-piperazin-1-yl]-N-(3-hydroxy-1-naphthyl)-2-(1-methylindazol-6-yl)pyrimidine-4-carboxamide (4 mg, 25%) as a light yellow solid.

UPLC-MS (ES+, Method E): 4.03 min, m/z 573.3 [M+H]+.

1H-NMR (400 MHz, DMSO-d6) δ/ppm: 11.05 (1H, s), 9.97 (1H, s), 8.92 (1H, s), 8.45-8.43 (1H, m), 8.13 (1H, s), 7.94-7.87 (2H, m), 7.79-7.76 (1H, m), 7.64 (1H, s), 7.49-7.36 (3H, m), 7.11 (1H, s), 6.97-6.79 (1H, m), 6.23-6.19 (1H, m), 5.81-5.79 (1H, m), 5.02-4.86 (1H, m), 4.52-4.44 (1H, m), 4.21-4.15 (4H, m), 3.70-3.54 (2H, m), 3.18-2.84 (4H, m).

Example 33

6-[(3S)-3-(cyanomethyl)-4-prop-2-enoyl-piperazin-1-yl]-N-(3-hydroxy-1-naphthyl)-2-(1-methylindazol-5-yl)pyrimidine-4-carboxamide

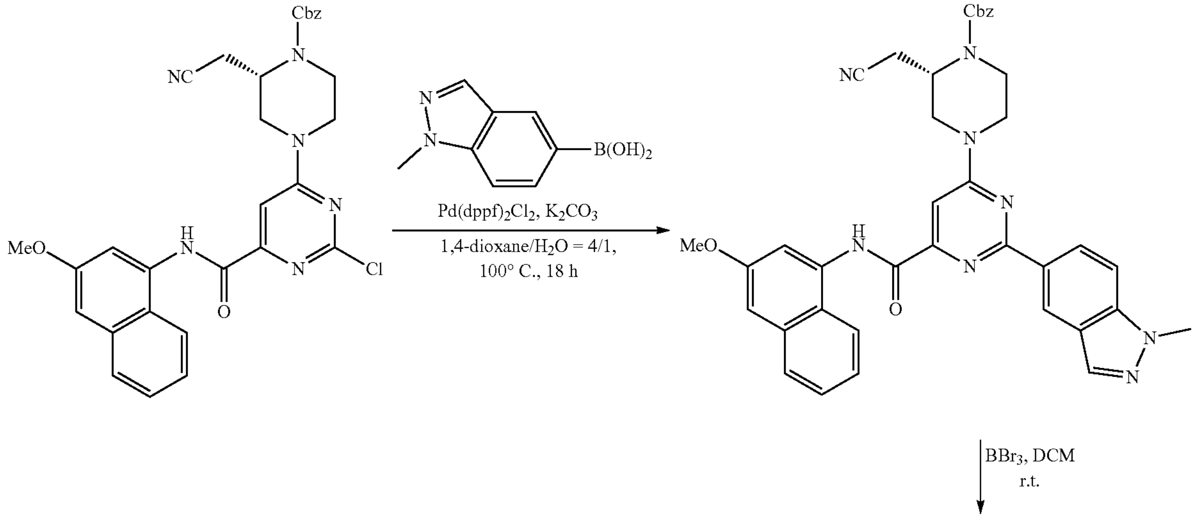

-continued

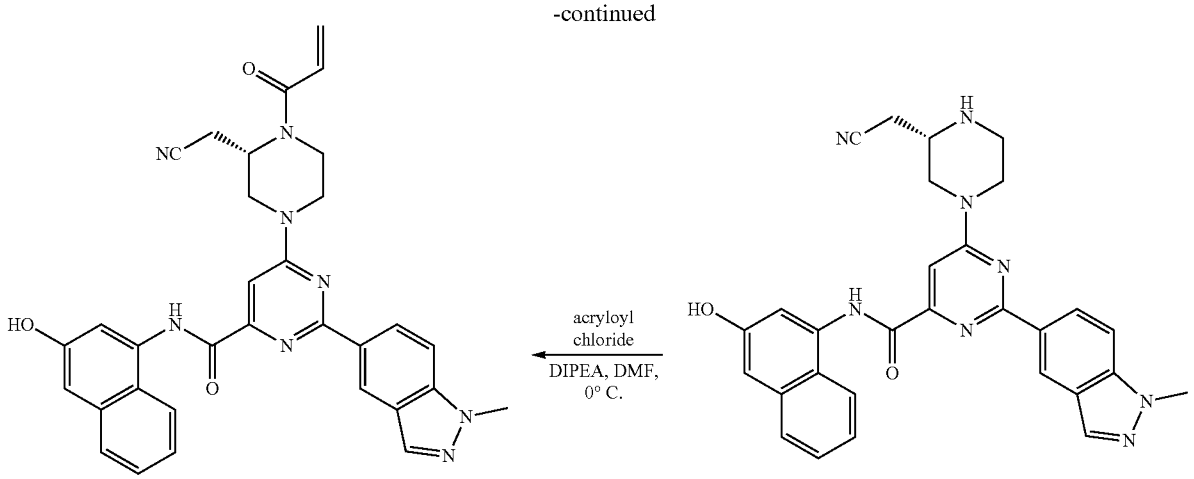

benzyl (2S)-2-(cyanomethyl)-4-[6-[(3-methoxy-1-naphthyl)carbamoyl]-2-(1-methylindazol-5-yl)pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) in 1,4-dioxane (4 mL) and water (1 mL) was added 1-methyl-1H-indazol-5-yl-5-boronic acid (111 mg, 0.63 mmol, 1.2eq), Pd(dppf)$Cl_2$ (38 mg, 0.05 mmol, 0.1eq) and $K_2CO_3$ (218 mg, 1.58 mmol, 3.0 eq) and the mixture was stirred and heated at 100° C. under $N_2$ overnight. The mixture was diluted with water (100 mL) and extracted with EtOAc (150 mL×3). The combined organic layers were dried over $Na_2SO_4$ and concentrated in vacuo. The residue was purified by silica gel column (DCM/MeOH=30/1,V/V) to give benzyl (2S)-2-(cyanomethyl)-4-[6-[(3-methoxy-1-naphthyl)carbamoyl]-2-(1-methylindazol-5-yl)pyrimidin-4-yl]piperazine-1-carboxylate (257 mg, 73%).

UPLC-MS (ES+, Method D): 4.37 min, m/z 667.4 [M+H]+.

6-[(3S)-3-(cyanomethyl)piperazin-1-yl]-N-(3-hydroxy-1-naphthyl)-2-(1-methylindazol-5-yl)pyrimidine-4-carboxamide Step 2

To a solution of benzyl (2S)-2-(cyanomethyl)-4-[6-[(3-methoxy-1-naphthyl)carbamoyl]-2-(1-methylindazol-5-yl)pyrimidin-4-yl]piperazine-1-carboxylate (274 mg) in dry-DCM (2 mL) was added $BBr_3$ (1.09 g) and the mixture stirred at rt under $N_2$ for 10 minutes. MeOH (20 mL) was added and solvent removed in vacuo. The residue purified by column chromatography using an eluent of 0-10% MeOH in DCM reached via a gradient to give 6-[(3S)-3-(cyanomethyl)piperazin-1-yl]-N-(3-hydroxy-1-naphthyl)-2-(1-methylindazol-5-yl)pyrimidine-4-carboxamide (140 mg, 65%).

UPLC-MS (ES+, Method E): 2.87 min, m/z 519.3 [M+H]+.

6-[(3S)-3-(cyanomethyl)-4-prop-2-enoyl-piperazin-1-yl]-N-(3-hydroxy-1-naphthyl)-2-(1-methylindazol-5-yl)pyrimidine-4-carboxamide Last Step To a solution of 6-[(3S)-3-(cyanomethyl)piperazin-1-yl]-N-(3-hydroxy-1-naphthyl)-2-(1-methylindazol-5-yl)pyrimidine-4-carboxamide (30 mg, 0.06 mmol, 1.0 eq) in dry-DMF was added acryloyl chloride (5 mg, 0.06 mmol, 1.0 eq) and N,N-diisopropylethylamine (22 mg, 0.17 mmol, 3.0 eq), the mixture was stirred at 0° C. under $N_2$ for 30 minutes. Solvent was then removed in vacuo and the residue purified by prep-HPLC to give 6-[(3S)-3-(cyanomethyl)-4-prop-2-enoyl-piperazin-1-yl]-N-(3-hydroxy-1-naphthyl)-2-(1-methylindazol-5-yl)pyrimidine-4-carboxamide (3 mg, 9%) as a yellow solid.

UPLC-MS (ES+, Method E): 4.00 min, m/z 573.3 [M+H]+.

1H-NMR (400 MHz, DMSO-d6) δ/ppm: 11.02 (1H, s), 9.96 (1H, s), 9.12 (1H, s), 8.74-8.72 (1H, m), 8.19 (1H, s), 7.89-7.87 (1H, m), 7.79-7.74 (2H, m), 7.57 (1H, s), 7.49-7.37 (3H, m), 7.11 (1H, s), 6.98-6.74 (1H, m), 6.24-6.20 (1H, m), 5.82-5.79 (1H, m), 5.02-4.84 (1H, m), 4.54-4.48 (1H, m), 4.15-4.08 (4H, m), 3.71-3.50 (2H, m), 3.25-2.98 (4H, m).

Example 34
6-[(3S)-3-(cyanomethyl)-4-prop-2-enoyl-piperazin-1-yl]-N-(3-hydroxy-1-naphthyl)-2-[[(2R)-1-methylpyrrolidin-2-yl]methoxy]pyrimidine-4-carboxamide
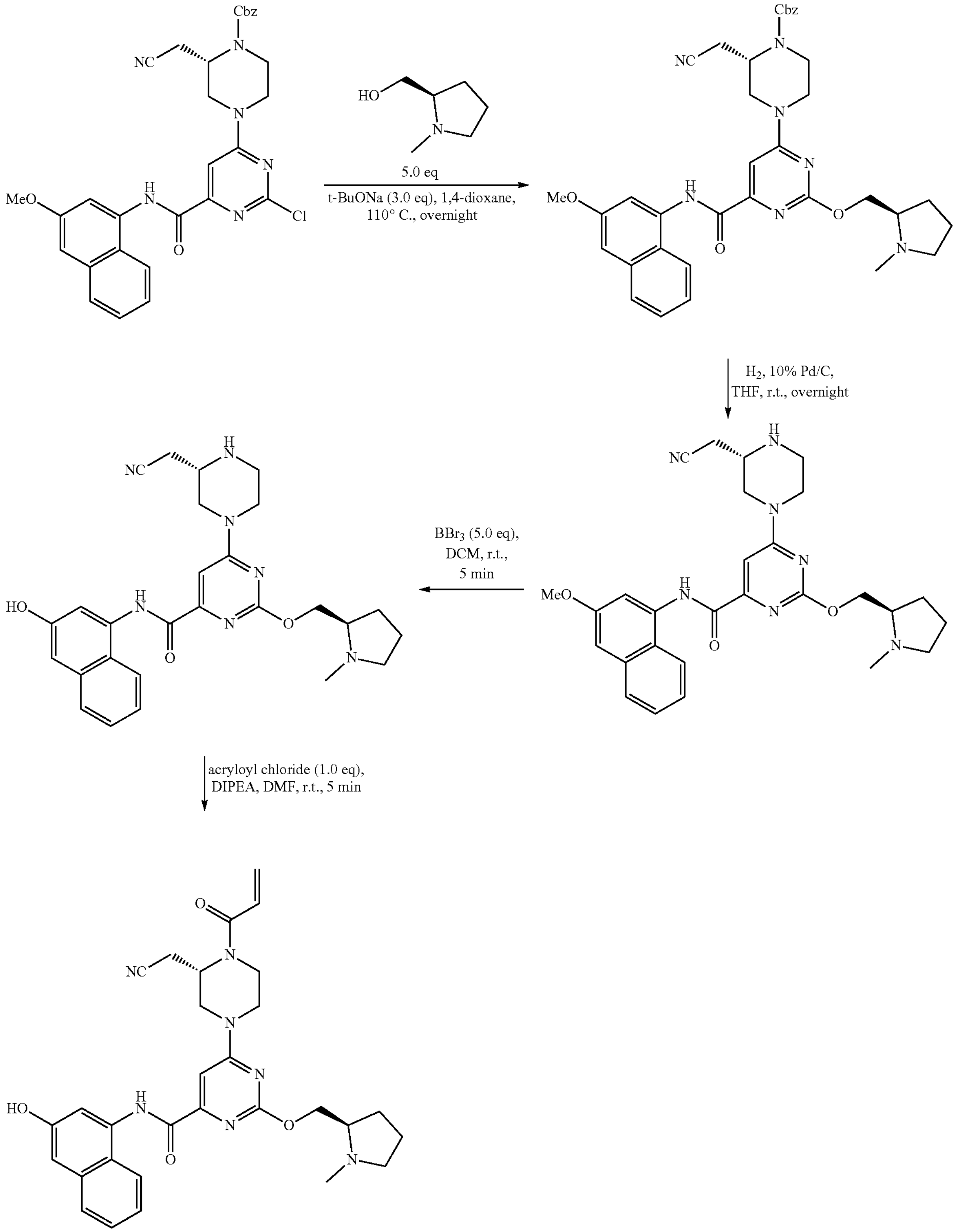

benzyl (2S)-2-(cyanomethyl)-4-[6-[(3-methoxy-1-naphthyl)carbamoyl]-2-[[(2R)-1-methylpyrrolidin-2-yl]methoxy]pyrimidin-4-yl]piperazine-1-carboxylate Step 1

To benzyl (2S)-4-[2-chloro-6-[(3-methoxy-1-naphthyl)carbamoyl]pyrimidin-4-yl]-2-(cyanomethyl)piperazine-1-carboxylate (200 mg, 0.35 mmol, 1.0 eq) was added 1,4-dioxane (10 mL) followed by the addition of [(2R)-1-methylpyrrolidin-2-yl]methanol (201 mg, 1.75 mmol, 5.0 eq) and sodium tert-butoxide (101 mg, 1.05 mmol, 3.0 eq). The reaction was stirred at 110° C. overnight. Solvent was then removed in vacuo and the residue was dissolved in EtOAc (100 mL) and washed with brine (100 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[6-[(3-methoxy-1-naphthyl)carbamoyl]-2-[[(2R)-1-methylpyrrolidin-2-yl]methoxy]pyrimidin-4-yl]piperazine-1-carboxylate (160 mg, 70%).

UPLC-MS (ES+, Method F): 0.93 min, m/z 649.9 [M+H]+.

6-[(3S)-3-(cyanomethyl)piperazin-1-yl]-N-(3-methoxy-1-naphthyl)-2-[[(2R)-1-methylpyrrolidin-2-yl]methoxy]pyrimidine-4-carboxamide Step 2 benzyl (2S)-2-(cyanomethyl)-4-[6-[(3-methoxy-1-naphthyl)carbamoyl]-2-[[(2R)-1-methylpyrrolidin-2-yl]methoxy]pyrimidin-4-yl]piperazine-1-carboxylate (100 mg, 0.15 mmol, 1.0 eq) was dissolved in THF (2 mL) followed by the addition of palladium, 10 wt. % on carbon powder, (50 mg, 1.54 mmol, 10.0 eq) under a nitrogen atmosphere. The reaction was fitted with a $H_2$ balloon and subjected to 3×vacuum/$H_2$ cycles and then left to stir under an $H_2$ atmosphere for 12 hours. The reaction was filtered through celite, washed with DCM (100 mL) and solvent removed in vacuo to give 6-[(3S)-3-(cyanomethyl)piperazin-1-yl]-N-(3-methoxy-1-naphthyl)-2-[[(2R)-1-methylpyrrolidin-2-yl]methoxy]pyrimidine-4-carboxamide (79 mg, 100%).

UPLC-MS (ES+, Method B: 0.82 min, m/z 516.0 [M+H]+.

6-[(3S)-3-(cyanomethyl)piperazin-1-yl]-N-(3-hydroxy-1-naphthyl)-2-[[(2R)-1-methylpyrrolidin-2-yl]methoxy]pyrimidine-4-carboxamide Step 3

6-[(3S)-3-(cyanomethyl)piperazin-1-yl]-N-(3-methoxy-1-naphthyl)-2-[[(2R)-1-methylpyrrolidin-2-yl]methoxy]pyrimidine-4-carboxamide (100 mg, 0.19 mmol, 1.0 eq) was dissolved in DCM (10 mL) followed by the addition of boron tribromide (0.09 mL). After 5 mins, MeOH (50 mL) was added and solvent removed in vacuo. The residue was purified by column chromatography using an eluent of 0-10% MeOH in DCM reached via a gradient to give 6-[(3S)-3-(cyanomethyl)piperazin-1-yl]-N-(3-hydroxy-1-naphthyl)-2-[[(2R)-1-methylpyrrolidin-2-yl]methoxy]pyrimidine-4-carboxamide (40 mg, 41%).

UPLC-MS (ES+, Method B): 0.57 min, m/z 502.0 [M+H]+.

6-[(3S)-3-(cyanomethyl)-4-prop-2-enoyl-piperazin-1-yl]-N-(3-hydroxy-1-naphthyl)-2-[[(2R)-1-methylpyrrolidin-2-yl]methoxy]pyrimidine-4-carboxamide Final Step:

Acryloyl chloride (4 mg, 0.04 mmol, 1.0 eq) and 6-[(3S)-3-(cyanomethyl)piperazin-1-yl]-N-(3-hydroxy-1-naphthyl)-2-[[(2R)-1-methylpyrrolidin-2-yl]methoxy]pyrimidine-4-carboxamide (20 mg, 0.04 mmol, 1.0 eq) were dissolved in DMF (2 mL) followed by the addition of DIPEA (15 mg, 0.12 mmol, 3.0 eq). The reaction was left stirring for 5 min. Water (20 mL) and DCM (20 mL) were then added and the organic layer separated, dried over $Na_2SO_4$ and solvent removed in vacuo.

The residue was purified by preparative HPLC to give 6-[(3S)-3-(cyanomethyl)-4-prop-2-enoyl-piperazin-1-yl]-N-(3-hydroxy-1-naphthyl)-2-[[(2R)-1-methylpyrrolidin-2-yl]methoxy]pyrimidine-4-carboxamide (5 mg, 23%).

UPLC-MS (ES+, Method C): 1.71 min, m/z 556.0 $[M+H]^+$.

1H-NMR (400 MHz, DMSO-d6) δ/ppm: 10.62 (1H, s), 8.23 (1H, s), 7.78-7.74 (2H, m), 7.60 (1H, s), 7.46-7.43 (1H, m), 7.34-7.30 (1H, m), 7.20-7.11 (1H, m), 7.06-7.03 (1H, m), 6.95-6.78 (1H, m), 6.22-6.17 (1H, m), 5.80-5.77 (1H, m), 4.95-4.75 (1H, m), 4.50-4.05 (5H, m), 3.08-2.91 (5H, m), 2.64-2.55 (2H, m), 2.45 (3H, s), 2.24-2.22 (1H, m), 2.08-1.97 (1H, m), 1.73-1.65 (3H, m).

Example 35
6-[(3S)-3-(cyanomethyl)-4-prop-2-enoyl-piperazin-1-yl]-N-(3-hydroxy-1-naphthyl)-2-[(2-methylpyrazol-3-yl)methoxy]pyrimidine-4-carboxamide
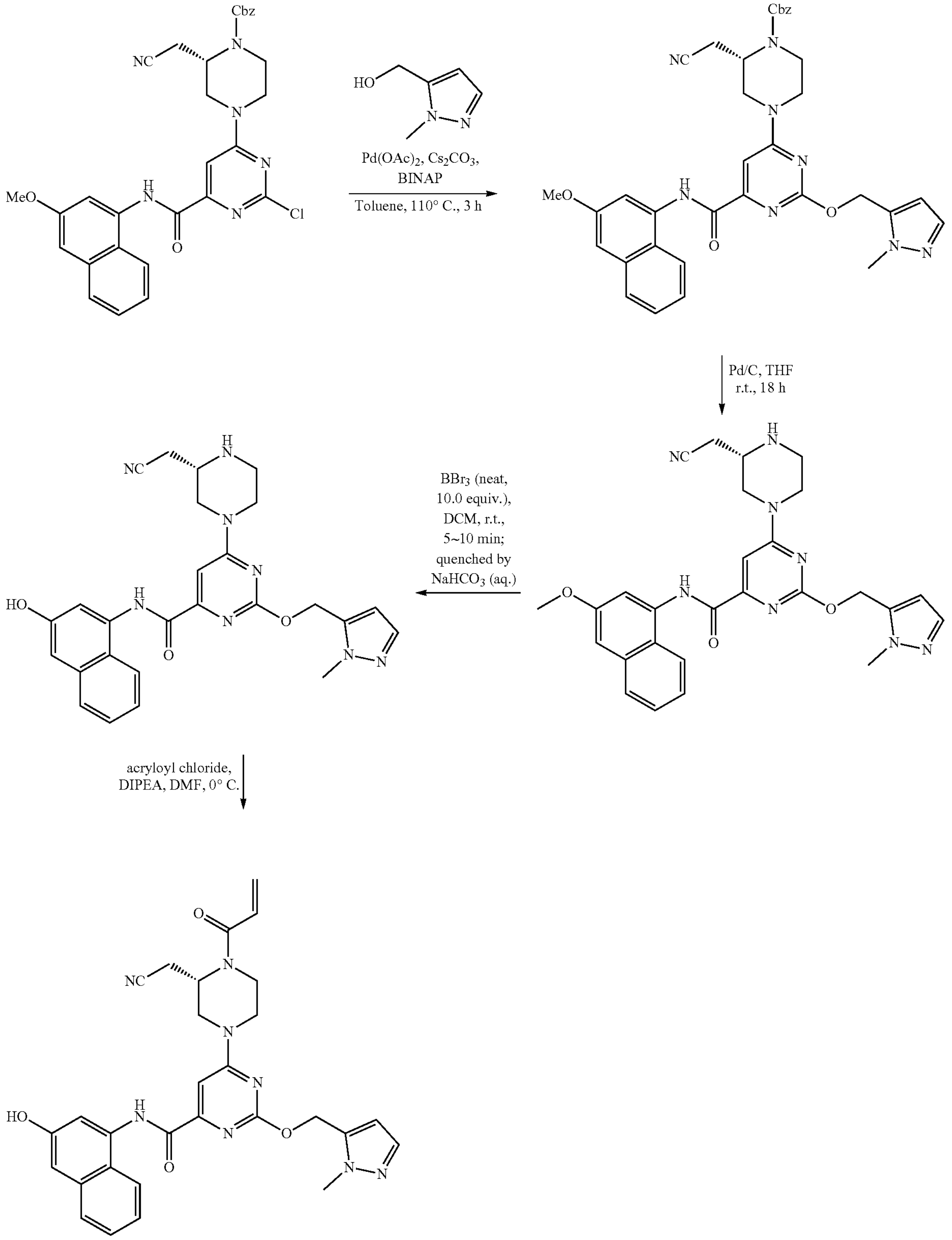

benzyl (2S)-2-(cyanomethyl)-4-[6-[(3-methoxy-1-naphthyl)carbamoyl]-2-[(2-methylpyrazol-3-yl) methoxy]pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl) piperazine-1-carboxylate (300 mg, 0.52 mmol, 1.0 eq) in toluene was added (2-methylpyrazol-3-yl)methanol (177 mg, 1.58 mmol, 3.0 eq), $Pd(OAc)_2$ (12 mg, 0.05 mmol, 0.1 eq), $Cs_2CO_3$ (513 mg, 1.58 mmol, 3.0 eq) and BINAP (65 mg, 0.10 mmol, 0.2eq) and the mixture was stirred and heated at 110° C. under $N_2$ for 3 hours. The mixture was concentrated in vacuo and the residue purified by silica gel column (DCM/MeOH=120/1,V/V) to give benzyl (2S)-2-(cyanomethyl)-4-[6-[(3-methoxy-1-naphthyl)carbamoyl]-2-[(2-methylpyrazol-3-yl)methoxy]pyrimidin-4-yl]piperazine-1-carboxylate (220 mg, 65%).

UPLC-MS (ES+, Method D): 3.63 min, m/z 647.4 [M+H]+.

6-[(3S)-3-(cyanomethyl)piperazin-1-yl]-N-(3-methoxy-1-naphthyl)-2-[(2-methylpyrazol-3-yl) methoxy]pyrimidine-4-carboxamide Step 2

To a solution of benzyl (2S)-2-(cyanomethyl)-4-[6-[(3-methoxy-1-naphthyl)carbamoyl]-2-[(2-methylpyrazol-3-yl) methoxy]pyrimidin-4-yl]piperazine-1-carboxylate (230 mg, 1.0 eq) in THF (6 mL) was added Pd/C (115 mg) and the mixture was stirred at r.t. under $H_2$ overnight. The mixture was then filtered and concentrated to give 6-[(3S)-3-(cyanomethyl)piperazin-1-yl]-N-(3-methoxy-1-naphthyl)-2-[(2-methylpyrazol-3-yl)methoxy]pyrimidine-4-carboxamide (182 mg, 100%).

UPLC-MS (ES+, Method D): 0.93 min, m/z 513.4 [M+H]+.

6-[(3S)-3-(cyanomethyl)piperazin-1-yl]-N-(3-hydroxy-1-naphthyl)-2-[(2-methylpyrazol-3-yl) methoxy]pyrimidine-4-carboxamide Step 3

To a solution of 6-[(3S)-3-(cyanomethyl)piperazin-1-yl]-N-(3-methoxy-1-naphthyl)-2-[(2-methylpyrazol-3-yl) methoxy]pyrimidine-4-carboxamide (80 mg, 0.16 mmol, 1.0 eq) in dry-DCM (15 mL) was added $BBr_3$ (313 mg, 1.25 mmol, 8.0 eq) and the mixture was stirred at r.t. under $N_2$ for 10 minutes. The reaction was then quenched with water, the organic layer dried over sodium sulfate, concentrated in vacuo and purified by prep-TLC to give 6-[(3S)-3-(cyanomethyl)piperazin-1-yl]-N-(3-hydroxy-1-naphthyl)-2-[(2-methylpyrazol-3-yl)methoxy]pyrimidine-4-carboxamide (50 mg, 65%).

UPLC-MS (ES+, Method E): 2.66 min, m/z 499.2 [M+H]+.

6-[(3S)-3-(cyanomethyl)-4-prop-2-enoyl-piperazin-1-yl]-N-(3-hydroxy-1-naphthyl)-2-[(2-methylpyrazol-3-yl)methoxy]pyrimidine-4-carboxamide Final Step:

To a solution of 6-[(3S)-3-(cyanomethyl)piperazin-1-yl]-N-(3-hydroxy-1-naphthyl)-2-[(2-methylpyrazol-3-yl) methoxy]pyrimidine-4-carboxamide (25 mg, 0.05 mmol, 1.0 eq) in dry-DMF (1 mL) was added acryloyl chloride (4 mg, 0.05 mmol, 1.0 eq) and N,N-diisopropylethylamine (19 mg, 0.15 mmol, 3.0 eq), the mixture was stirred at 0° C. under $N_2$ for 30 minutes. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-[(2-methylpyrazol-3-yl) methoxy]pyrimidine-4-carboxamide (8 mg, 30%) as a yellow solid.

UPLC-MS (ES+, Method E): 3.43 min, m/z 553.3 $[M+H]^+$.

1H-NMR (400 MHz, DMSO-d6) δ/ppm: 10.64 (1H, s), 9.90 (1H, s), 7.77-7.73 (2H, m), 7.57-7.56 (1H, m), 7.46-7.40 (2H, m), 7.36-7.32 (1H, m), 7.23-7.28 (1H, m), 7.07 (1H, s), 6.95-6.80 (1H, m), 6.43-6.42 (1H, m), 6.22-6.17 (1H, m), 5.80-5.77 (1H, m), 5.66-5.62 (2H, m), 4.94-4.78 (1H, m), 4.49-4.40 (1H, m), 4.14-4.05 (1H, m), 3.90 (3H, s), 3.55-3.45 (2H, m), 3.25-2.95 (4H, m).

Example 36

6-[(3S)-3-(cyanomethyl)-4-prop-2-enoyl-piperazin-1-yl]-N-(3-hydroxy-1-naphthyl)-2-[(1-methylpyrazol-4-yl)methylamino]pyrimidine-4-carboxamide

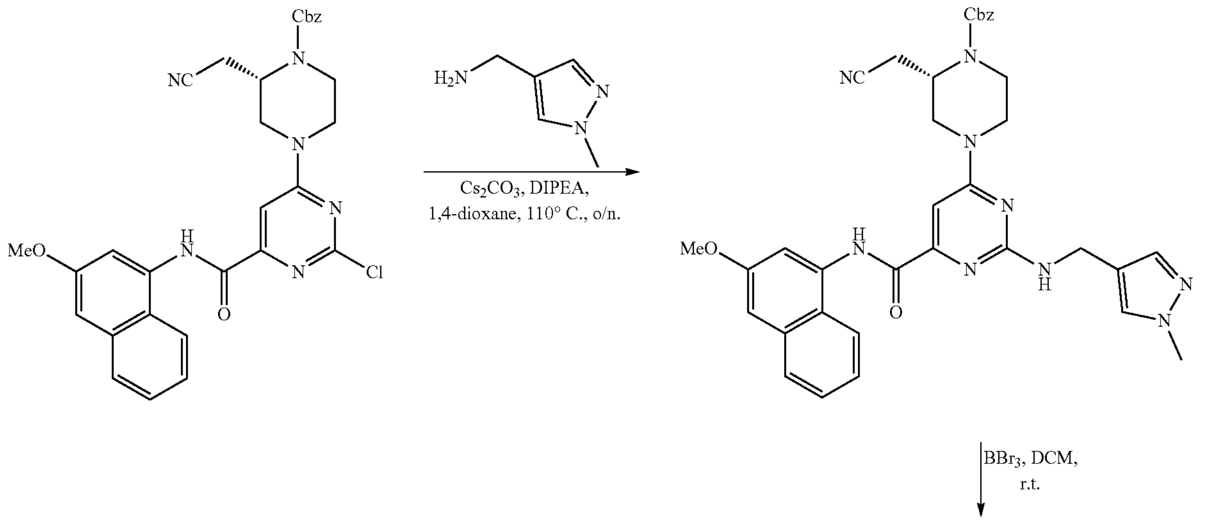

-continued

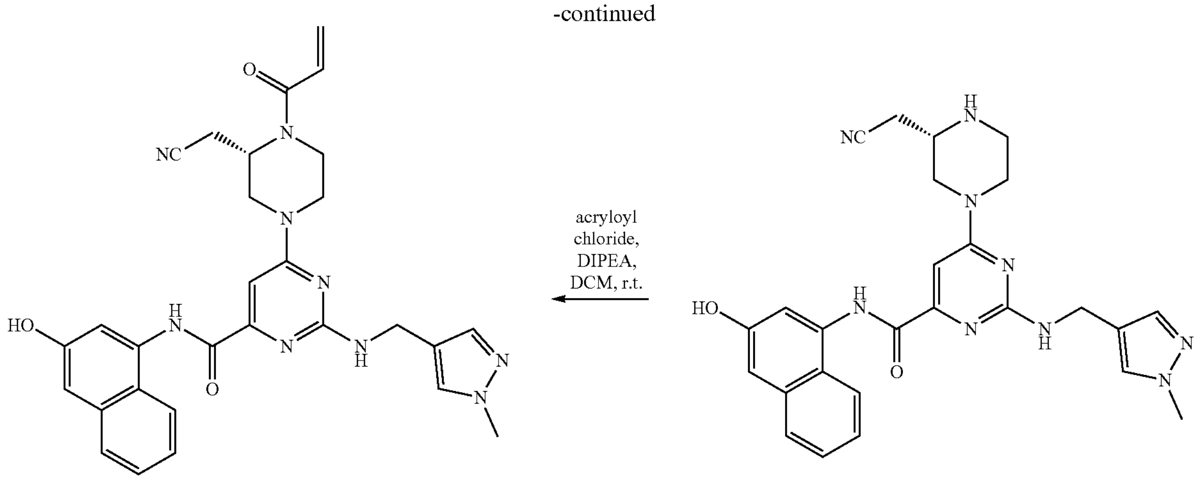

benzyl (2S)-2-(cyanomethyl)-4-[6-[(3-methoxy-1-naphthyl)carbamoyl]-2-[(1-methylpyrazol-4-yl)methylamino]pyrimidin-4-yl]piperazine-1-carboxylate Step 1

A solution of benzyl (S)-4-(2-chloro-6-((3-methoxynaphthalen-1-yl)carbamoyl)pyrimidin-4-yl)-2-(cyanomethyl)piperazine-1-carboxylate (300 mg), (1-methyl-1H-pyrazol-4-yl)methanamine (176 mg), $Cs_2CO_3$ (515 mg) and DIPEA (543 mg) in dioxane (10 mL) was heated to 110° C. under a $N_2$ atmosphere and stirred at 110° C. overnight. Solvent was then removed in vacuo and the residue purified by flash column chromatography to give benzyl (2S)-2-(cyanomethyl)-4-[6-[(3-methoxy-1-naphthyl)carbamoyl]-2-[(1-methylpyrazol-4-yl)methylamino]pyrimidin-4-yl]piperazine-1-carboxylate (260 mg, 77%) as a yellow solid.

UPLC-MS (ES+, Method E): 4.33 min, m/z 646.4 [M+H]+.

6-[(3S)-3-(cyanomethyl)piperazin-1-yl]-N-(3-hydroxy-1-naphthyl)-2-[(1-methylpyrazol-4-yl)methylamino]pyrimidine-4-carboxamide Step 2

To a solution of benzyl (S)-2-(cyanomethyl)-4-(6-((3-methoxynaphthalen-1-yl)carbamoyl)-2-(((1-methyl-1H-pyrazol-4-yl)methyl)amino)pyrimidin-4-yl)piperazine-1-carboxylate (30 mg) in DCM (1 mL) was added $BBr_3$ (44 mg) in DCM (4 mL) and the reaction stirred at rt for 10 min. The reaction was then quenched by water and extracted by DCM. The organic layer was dried over sodium sulfate and solvent removed in vacuo to give 6-[(3S)-3-(cyanomethyl)piperazin-1-yl]-N-(3-hydroxy-1-naphthyl)-2-[(1-methylpyrazol-4-yl)methylamino]pyrimidine-4-carboxamide (23 mg, 100%).

UPLC-MS (ES+, Method F): 1.27 min, m/z 498.2 [M+H]+.

6-[(3S)-3-(cyanomethyl)-4-prop-2-enoyl-piperazin-1-yl]-N-(3-hydroxy-1-naphthyl)-2-[(1-methylpyrazol-4-yl)methylamino]pyrimidine-4-carboxamide Final Step To a solution of 6-[(3S)-3-(cyanomethyl)piperazin-1-yl]-N-(3-hydroxy-1-naphthyl)-2-[(1-methylpyrazol-4-yl)methylamino]pyrimidine-4-carboxamide (20 mg, 0.04 mmol, 1.0 eq) in dry-DMF (1 mL) was added acryloyl chloride (4 mg, 0.04 mmol, 1.0 eq) and N,N-diisopropylethylamine (16 mg, 0.12 mmol, 3.0 eq) and the mixture was stirred at 0° C. under $N_2$ for 30 minutes. Solvent was then removed in vacuo and the residue purified by prep-HPLC to give 6-[(3S)-3-(cyanomethyl)-4-prop-2-enoyl-piperazin-1-yl]-N-(3-hydroxy-1-naphthyl)-2-[(1-methylpyrazol-4-yl)methylamino]pyrimidine-4-carboxamide (7 mg, 34%) as a light yellow solid.

UPLC-MS (ES+, Method E): 3.33 min, m/z 552.3 $[M+H]^+$.

1H-NMR (400 MHz, DMSO-d6) δ/ppm: 10.84 (1H, s), 9.92 (1H, s), 8.09-7.89 (2H, m), 7.77-7.75 (1H, m), 7.68-7.37 (5H, m), 7.02-7.01 (1H, m), 6.98-6.77 (2H, m), 6.24-6.19 (1H, m), 5.82-5.79 (1H, m), 4.99-4.75 (1H, m), 4.55-4.25 (5H, m), 4.13-4.06 (1H, m), 3.79 (3H, s), 3.72-3.65 (2H, m), 3.02-2.85 (2H, m).

Example 37

6-[(3S)-3-(cyanomethyl)-4-prop-2-enoyl-piperazin-1-yl]-2-[4-(2-hydroxyethyl)piperazin-1-yl]-N-(3-hydroxy-1-naphthyl)pyrimidine-4-carboxamide

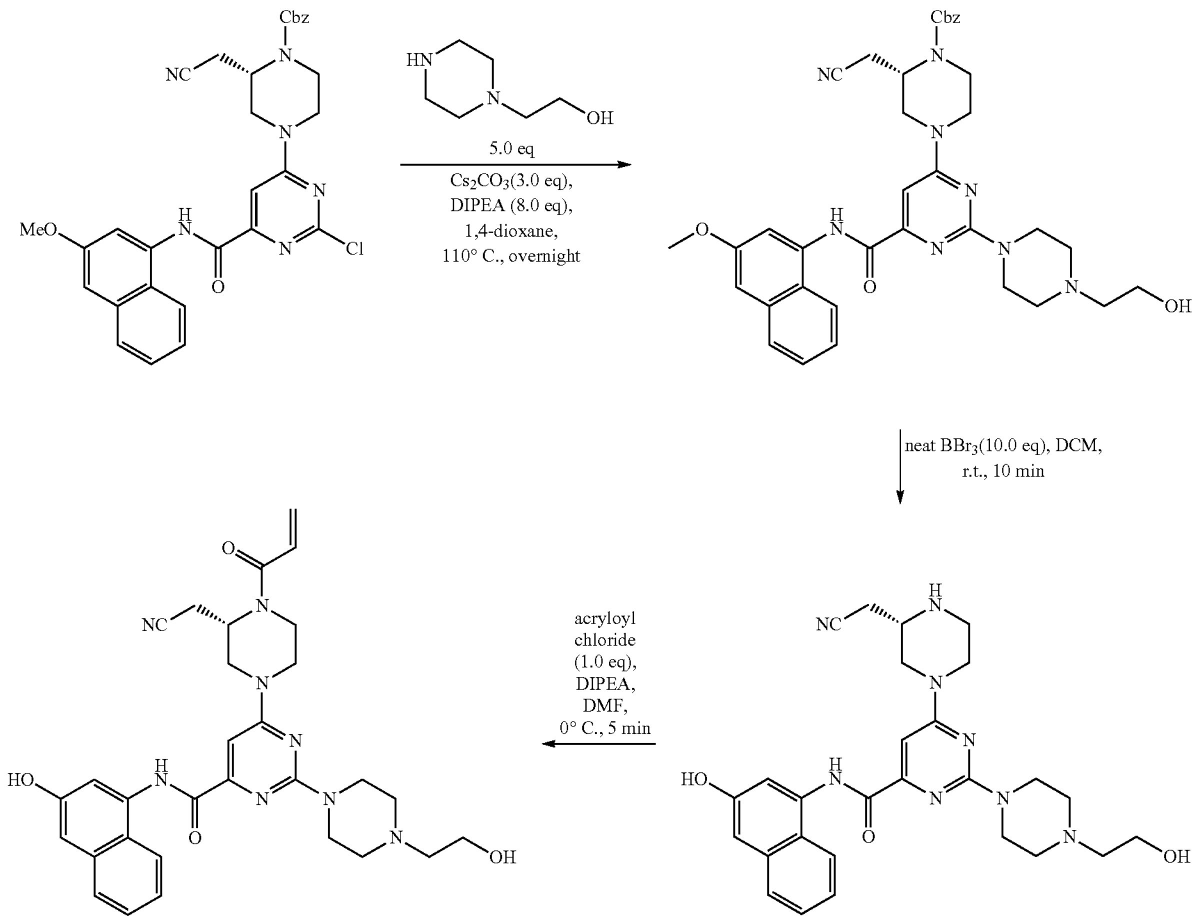

benzyl (2S)-2-(cyanomethyl)-4-[2-[4-(2-hydroxyethyl)piperazin-1-yl]-6-[(3-methoxy-1-naphthyl)carbamoyl]pyrimidin-4-yl]piperazine-1-carboxylate Step 1

To benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) was added 1,4-dioxane (30 mL) followed by the addition of 2-piperazin-1-ylethanol (342 mg, 2.63 mmol, 5.0 eq), $Cs_2CO_3$ (513 mg, 1.58 mmol, 3.0 eq) and DIPEA (543 mg, 4.20 mmol, 8.0 eq). The reaction was stirred at 110° C. overnight. The solvent was then removed in vacuo and the residue was dissolved in EtOAc (300 mL) and washed with brine (300 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[2-[4-(2-hydroxyethyl)piperazin-1-yl]-6-[(3-methoxy-1-naphthyl)carbamoyl]pyrimidin-4-yl]piperazine-1-carboxylate (270 mg, 77%).

UPLC-MS (ES+, Method A): 0.88 min, m/z 665.0 [M+H]+.

6-[(3S)-3-(cyanomethyl)piperazin-1-yl]-2-[4-(2-hydroxyethyl)piperazin-1-yl]-N-(3-hydroxy-1-naphthyl)pyrimidine-4-carboxamide Step 2 benzyl (2S)-2-(cyanomethyl)-4-[2-[4-(2-hydroxyethyl)piperazin-1-yl]-6-[(3-methoxy-1-naphthyl)carbamoyl]pyrimidin-4-yl]piperazine-1-carboxylate (270 mg, 0.41 mmol, 1.0 eq) was dissolved in DCM (20 mL) followed by the addition of boron tribromide (0.3 mL). After 5 mins, MeOH (50 mL) was added and solvent removed in vacuo. Solvent was then removed in vacuo and the residue was purified by column chromatography using an eluent of 0-10% MeOH in DCM reached via a gradient to give 6-[(3S)-3-(cyanomethyl)piperazin-1-yl]-2-[4-(2-hydroxyethyl)piperazin-1-yl]-N-(3-hydroxy-1-naphthyl)pyrimidine-4-carboxamide (209 mg, 100%).

UPLC-MS (ES+, Method B): 0.64 min, m/z 517.0 [M+H]+.

6-[(3S)-3-(cyanomethyl)-4-prop-2-enoyl-piperazin-1-yl]-2-[4-(2-hydroxyethyl)piperazin-1-yl]-N-(3-hydroxy-1-naphthyl)pyrimidine-4-carboxamide Final Step Acryloyl chloride (12 mg, 0.14 mmol, 1.0 eq) and 6-[(3S)-3-(cyanomethyl)piperazin-1-yl]-2-[4-(2-hydroxyethyl)piperazin-1-yl]-N-(3-hydroxy-1-naphthyl)pyrimidine-4-carboxamide (70 mg, 0.14 mmol, 1.0 eq) were dissolved in DMF (5 mL) followed by the addition of DIPEA (53 mg, 0.41 mmol, 3.0 eq). The reaction was left stirring for 5 min. Water (50 mL) and DCM (50 mL) were then added and the organic layer separated, dried over $Na_2SO_4$ and solvent removed in vacuo.

The residue was purified by column chromatography using an eluent of 0-10% MeOH in DCM reached via a gradient to give 6-[(3S)-3-(cyanomethyl)-4-prop-2-enoyl-piperazin-1-yl]-2-[4-(2-hydroxyethyl)piperazin-1-yl]-N-(3-hydroxy-1-naphthyl)pyrimidine-4-carboxamide (12 mg, 15%) as a yellow solid.

UPLC-MS (ES+, Method C): 1.67 min, m/z 571.0 $[M+H]^+$.

1H-NMR (400 MHz, DMSO-d6) δ/ppm: 10.67 (1H, s), 9.87 (1H, s), 7.77-7.73 (2H, m), 7.62 (1H, s), 7.46-7.42 (1H, m), 7.37-7.35 (1H, m), 7.05-7.04 (1H, m), 6.98-7.75 (2H, m), 6.21-6.17 (1H, m), 5.79-5.76 (1H, m), 4.90-4.61 (1H, m), 4.55-3.97 (5H, m), 3.92-3.76 (5H, m), 3.65-3.50 (3H, m), 3.30-3.19 (1H, m), 3.15-2.78 (3H, m), 2.48-2.38 (3H, m), 1×exchangeable proton not seen.

Example 38

6-[(3S)-3-(cyanomethyl)-4-prop-2-enoyl-piperazin-1-yl]-N-(3-hydroxy-1-naphthyl)-2-(1-methylindazol-4-yl)pyrimidine-4-carboxamide

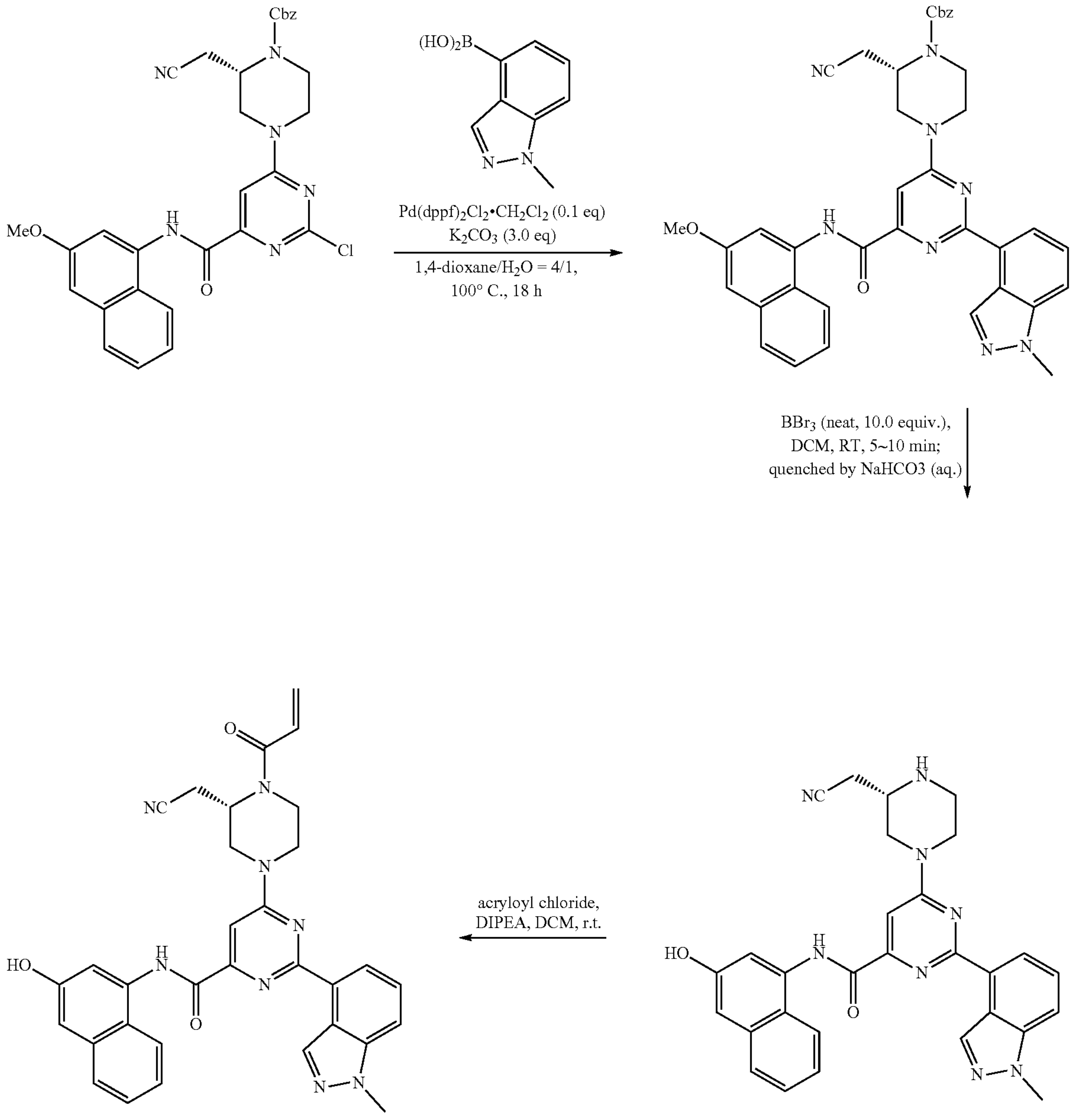

benzyl (2S)-2-(cyanomethyl)-4-[6-[(3-methoxy-1-naphthyl)carbamoyl]-2-(1-methylindazol-4-yl)pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl)piperazine-1-carboxylate (300 mg, 0.53 mmol, 1.0 eq) in 1,4-dioxane (8 mL) and water (2 mL) was added (1-methylindazol-4-yl)boronic acid (185 mg, 1.05 mmol, 2.0 eq), $Pd(dppf)Cl_2CH_2Cl_2$ (43 mg, 0.05 mmol, 0.1eq) and $K_2CO_3$ (218 mg, 1.58 mmol, 3.0 eq) and the mixture was stirred and heated at 100° C. under $N_2$ overnight. Solvent was then removed in vacuo and the residue purified by column chromatography to give benzyl (2S)-2-(cyanomethyl)-4-[6-[(3-methoxy-1-naphthyl)carbamoyl]-2-(1-methylindazol-4-yl)pyrimidin-4-yl]piperazine-1-carboxylate (180 mg, 48%).

UPLC-MS (ES+, Method D): 1.90 min, m/z 667.2 [M+H]+.

6-[(3S)-3-(cyanomethyl)piperazin-1-yl]-N-(3-hydroxy-1-naphthyl)-2-(1-methylindazol-4-yl)pyrimidine-4-carboxamide Step 2

To a solution of benzyl (2S)-2-(cyanomethyl)-4-[6-[(3-methoxy-1-naphthyl)carbamoyl]-2-(1-methylindazol-4-yl)pyrimidin-4-yl]piperazine-1-carboxylate (130 mg, 0.19 mmol, 1.0 eq) in dry-DCM (12 mL) was added $BBr_3$ (488 mg, 1.95 mmol, 10.0 eq) and the mixture was stirred at r.t. under $N_2$ for 10 minutes. The reaction was quenched by saturated $NaHCO_3$ (aq.). The mixture was extracted with DCM and the combined organic layer dried over $Na_2SO_4$ and concentrated in vacuo. The residue was purified by column chromatography using an eluent of MeOH/ammonia in DCM to give 6-[(3S)-3-(cyanomethyl)piperazin-1-yl]-N-(3-hydroxy-1-naphthyl)-2-(1-methylindazol-4-yl)pyrimidine-4-carboxamide (50 mg, 49%).

UPLC-MS (ES+, Method E): 1.30 min, m/z 519.2 [M+H]+.

6-[(3S)-3-(cyanomethyl)-4-prop-2-enoyl-piperazin-1-yl]-N-(3-hydroxy-1-naphthyl)-2-(1-methylindazol-4-yl)pyrimidine-4-carboxamide Final Step To a solution of 6-[(3S)-3-(cyanomethyl)piperazin-1-yl]-N-(3-hydroxy-1-naphthyl)-2-(1-methylindazol-4-yl)pyrimidine-4-carboxamide (15 mg, 0.03 mmol, 1.0 eq) in dry-DMF 1 mL) was added acryloyl chloride (3 mg, 0.03 mmol, 1.0 eq) and N,N-diisopropylethylamine (11 mg, 0.09 mmol, 3.0 eq), the mixture was stirred at 0° C. under $N_2$ for 30 minutes. Solvent was then removed in vacuo and the residue purified by prep-HPLC to give 6-[(3S)-3-(cyanomethyl)-4-prop-2-enoyl-piperazin-1-yl]-N-(3-hydroxy-1-naphthyl)-2-(1-methylindazol-4-yl)pyrimidine-4-carboxamide (3 mg, 19%) as a light yellow solid.

UPLC-MS (ES+, Method E): 4.00 min, m/z 573.4 [M+H]+.

1H-NMR (400 MHz, DMSO-d6) δ/ppm: 10.89 (1H, s), 9.96 (1H, s), 8.80 (1H, s), 8.52-8.50 (1H, m), 7.90-7.86 (2H, m), 7.78-7.76 (1H, m), 7.72-7.71 (1H, m), 7.61-7.57 (1H, m), 7.49-7.45 (2H, m), 7.36-7.32 (1H, m), 7.09 (1H, s), 6.99-6.80 (1H, m), 6.24-6.20 (1H, m), 5.82-5.79 (1H, m), 5.03-4.50 (2H, m), 4.22-4.11 (4H, m), 3.70-3.48 (4H, m), 3.25-2.98 (2H, m).

Example 39

6-[(3S)-3-(cyanomethyl)-4-prop-2-enoyl-piperazin-1-yl]-N-(3-hydroxy-1-naphthyl)-2-(1-methylindazol-7-yl)pyrimidine-4-carboxamide

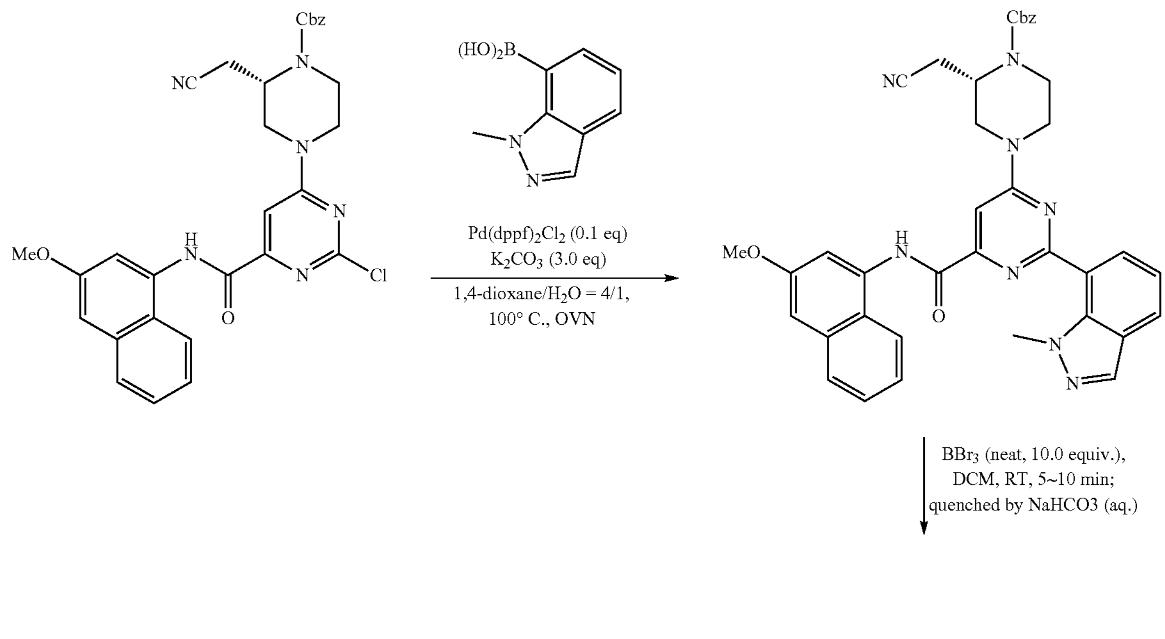

-continued

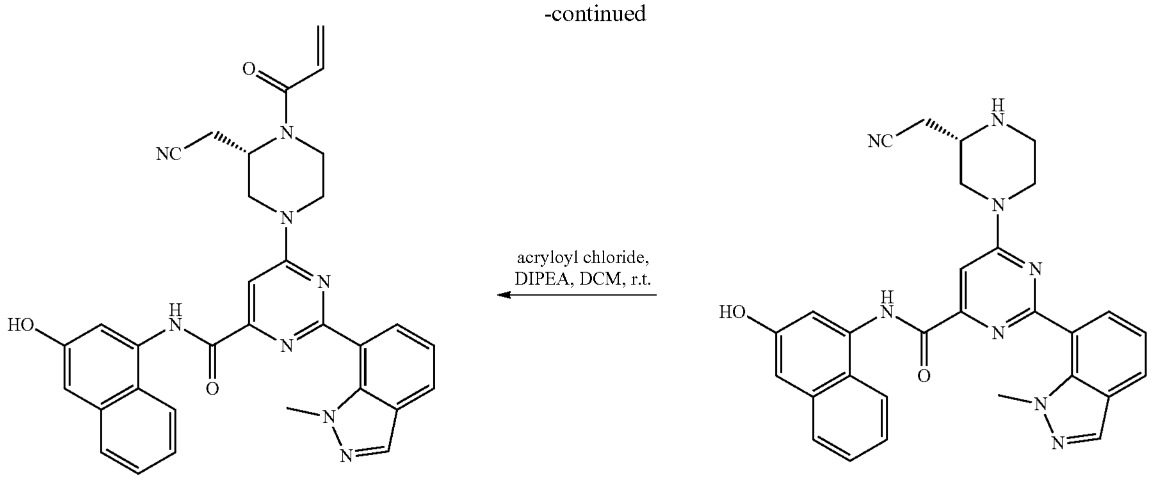

benzyl (2S)-2-(cyanomethyl)-4-[6-[(3-methoxy-1-naphthyl)carbamoyl]-2-(1-methylindazol-7-yl)pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl)piperazine-1-carboxylate (300 mg, 0.53 mmol, 1.0 eq) in 1,4-dioxane (4 mL) and water (1 mL) was added (1-methylindazol-7-yl)boronic acid (185 mg, 1.05 mmol, 2.0 eq), $Pd(dppf)Cl_2$ (38 mg, 0.05 mmol, 0.1eq) and $K_2CO_3$ (218 mg, 1.58 mmol, 3.0 eq) and the mixture was stirred and heated at 100° C. under $N_2$ overnight. Solvent was then removed in vacuo and the residue purified by column chromatography to give benzyl (2S)-2-(cyanomethyl)-4-[6-[(3-methoxy-1-naphthyl)carbamoyl]-2-(1-methylindazol-4-yl)pyrimidin-4-yl]piperazine-1-carboxylate (248 mg, 71%).

UPLC-MS (ES+, Method E): 2.57 min, m/z 667.2 [M+H]+.

6-[(3S)-3-(cyanomethyl)piperazin-1-yl]-N-(3-hydroxy-1-naphthyl)-2-(1-methylindazol-7-yl)pyrimidine-4-carboxamide Step 2

To a solution of benzyl (2S)-2-(cyanomethyl)-4-[6-[(3-methoxy-1-naphthyl)carbamoyl]-2-(1-methylindazol-7-yl)pyrimidin-4-yl]piperazine-1-carboxylate (200 mg, 0.30 mmol, 1.0 eq) in dry-DCM (20 mL) was added $BBr_3$ (752 mg, 3.0 mmol, 10.0 eq), the mixture was stirred at r.t under $N_2$ for 10 minutes and then quenched by $NaHCO_3$ (aq.). The organic layer was separated, dried over sodium sulfate and purified by prep-TLC to give 6-[(3S)-3-(cyanomethyl)piperazin-1-yl]-N-(3-hydroxy-1-naphthyl)-2-(1-methylindazol-7-yl)pyrimidine-4-carboxamide (70 mg, 46%).

UPLC-MS (ES+, Method F): 1.30 min, m/z 519.2 [M+H]+.

6-[(3S)-3-(cyanomethyl)-4-prop-2-enoyl-piperazin-1-yl]-N-(3-hydroxy-1-naphthyl)-2-(1-methylindazol-7-yl)pyrimidine-4-carboxamide Final Step To a solution of 6-[(3S)-3-(cyanomethyl)piperazin-1-yl]-N-(3-hydroxy-1-naphthyl)-2-(1-methylindazol-7-yl)pyrimidine-4-carboxamide (20 mg, 0.04 mmol, 1.0 eq) in dry-DMF (1 mL) was added acryloyl chloride (4 mg, 0.04 mmol, 1.0 eq) and N,N-diisopropylethylamine (15 mg, 0.12 mmol, 3.0 eq), the mixture was stirred at 0° C. under $N_2$ for 30 minutes. Solvent was then removed in vacuo and the residue purified by prep-HPLC to give 6-[(3S)-3-(cyanomethyl)-4-prop-2-enoyl-piperazin-1-yl]-N-(3-hydroxy-1-naphthyl)-2-(1-methylindazol-7-yl)pyrimidine-4-carboxamide (7 mg, 34%) as a light yellow solid.

UPLC-MS (ES+, Method E): 3.93 min, m/z 573.5 [M+H]+.

1H-NMR (400 MHz, DMSO-d6) δ/ppm: 10.85 (1H, s), 9.92 (1H, s), 8.23 (1H, s), 7.96-7.92 (2H, m), 7.75-7.69 (2H, m), 7.63 (1H, s), 7.54-7.50 (1H, m), 7.44-7.40 (1H, m), 7.32-7.24 (2H, m), 7.06 (1H, s), 6.98-6.80 (1H, m), 6.22-6.18 (1H, m), 5.81-5.78 (1H, m), 4.96-4.79 (1H, m), 4.55-4.20 (2H, m), 3.96 (3H, s), 3.68-3.52 (3H, m), 3.20-2.96 (3H, m).

Example 40

2-benzyl-6-[(3S)-3-(cyanomethyl)-4-prop-2-enoyl-piperazin-1-yl]-N-(3-hydroxy-1-naphthyl)pyrimidine-4-carboxamide

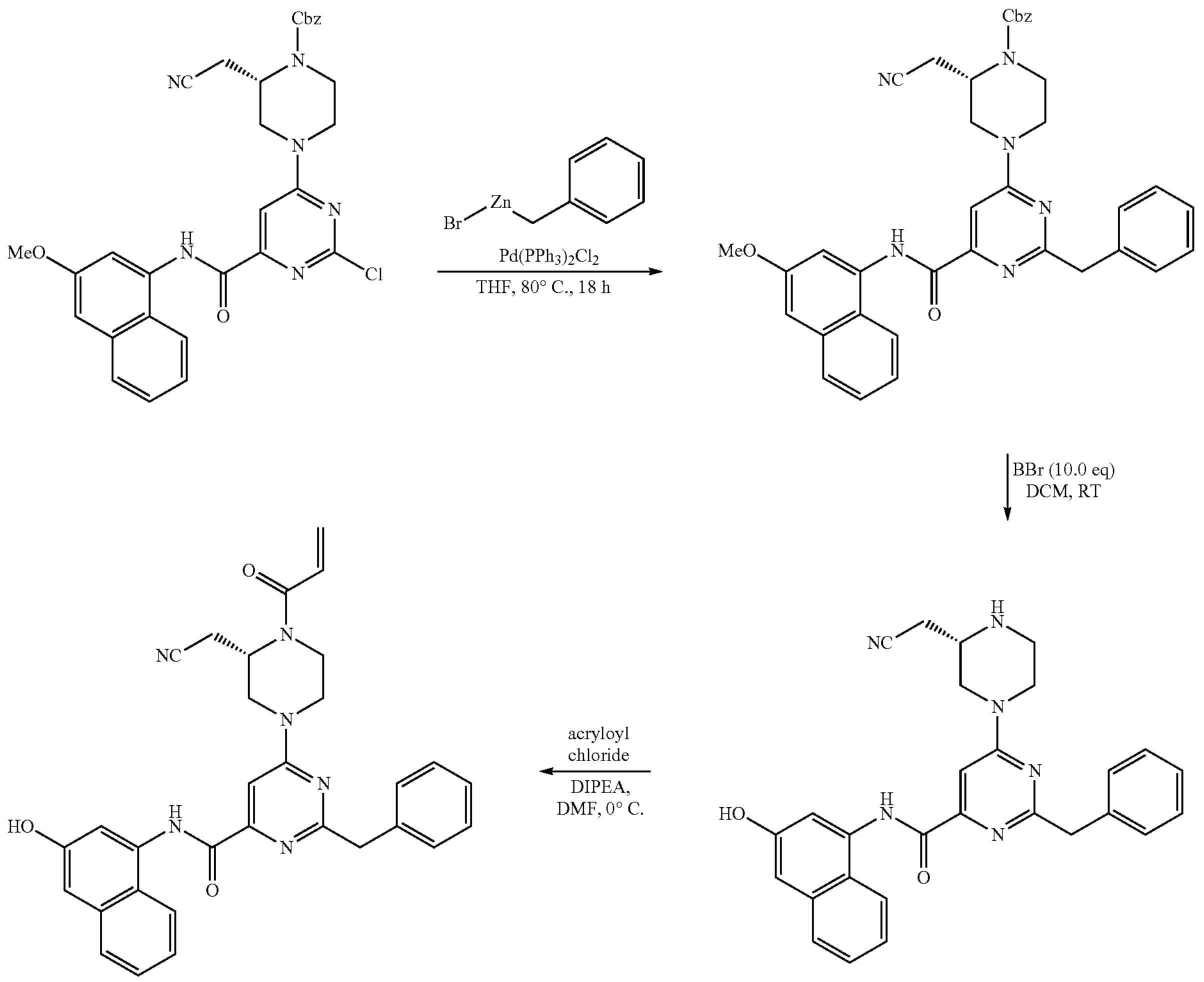

benzyl (2S)-4-[2-benzyl-6-[(3-methoxy-1-naphthyl)carbamoyl]pyrimidin-4-yl]-2-(cyanomethyl)piperazine-1-carboxylate Step 1

To a solution of benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) in THF (15 mL) was added benzyl(bromo)zinc (497 mg, 2.1 mmol, 4.0 eq), $Pd(PPh_3)Cl_2$ (37 mg, 0.05 mmol, 0.1eq) and the mixture was stirred and heated at 80° C. under $N_2$ overnight. The mixture was concentrated in vacuo and the residue purified by silica gel column (DCM/MeOH=120/1, V/V) to give benzyl (2S)-4-[2-benzyl-6-[(3-methoxy-1-naphthyl)carbamoyl]pyrimidin-4-yl]-2-(cyanomethyl)piperazine-1-carboxylate (240 mg, 69%).

UPLC-MS (ES+, Method D): 4.70 min, m/z 626.4 [M+H]+

2-benzyl-6-[(3S)-3-(cyanomethyl)piperazin-1-yl]-N-(3-hydroxy-1-naphthyl)pyrimidine-4-carboxamide Step 2

To a solution of benzyl (2S)-4-[2-benzyl-6-[(3-methoxy-1-naphthyl)carbamoyl]pyrimidin-4-yl]-2-(cyanomethyl)piperazine-1-carboxylate (190 mg, 0.30 mmol, 1.0 eq) in dry-DCM was added $BBr_3$ (608 mg, 2.42 mmol, 8.0 eq), the mixture was stirred at RT under $N_2$ for 10 minutes. The reaction was then quenched with water, the organic layer dried over sodium sulfate, concentrated in vacuo and purified by prep-TLC to give benzyl (2S)-4-[2-benzyl-6-[(3-methoxy-1-naphthyl)carbamoyl]pyrimidin-4-yl]-2-(cyanomethyl)piperazine-1-carboxylate (60 mg, 41%).

UPLC-MS (ES+, Method E): 3.00 min, m/z 479.3 [M+H]+

2-benzyl-6-[(3S)-3-(cyanomethyl)-4-prop-2-enoyl-piperazin-1-yl]-N-(3-hydroxy-1-naphthyl)pyrimidine-4-carboxamide Final Step To a solution of 2-benzyl-6-[(3S)-3-(cyanomethyl)piperazin-1-yl]-N-(3-hydroxy-1-naphthyl)pyrimidine-4-carboxamide (30 mg, 0.06 mmol, 1.0 eq) in dry-DMF (1 mL) was added acryloyl chloride (6 mg, 0.06 mmol, 1.0 eq) and N,N-diisopropylethylamine (24 mg, 0.19 mmol, 3.0 eq), the mixture was stirred at 0° C. under $N_2$ for 30 minutes. Solvent was then removed in vacuo and the residue purified by column chromatography to give 2-benzyl-6-[(3S)-3-(cyanomethyl)-4-prop-2-enoyl-piperazin-1-yl]-N-(3-hydroxy-1-naphthyl)pyrimidine-4-carboxamide (8 mg, 24%) as a yellow solid.

UPLC-MS (ES+, Method E): 4.37 min, m/z 533.3 [M+H]+.

1H-NMR (400 MHz, DMSO-d6) δ/ppm: 10.73 (1H, s), 9.90 (1H, s), 7.93 (1H, s), 7.75-7.73 (1H, m), 7.50-7.26 (9H, m), 7.01 (1H, s), 6.99-6.78 (1H, m), 6.22-6.17 (1H, m), 5.80-5.78 (1H, m), 4.98-4.76 (1H, m), 4.48-4.41 (1H, m), 4.18 (2H, s), 4.14-4.07 (1H, m), 3.55-3.44 (2H, m), 3.25-2.86 (4H, m).

Example 41

6-[(3S)-3-(cyanomethyl)-4-prop-2-enoyl-piperazin-1-yl]-N-(3-hydroxy-1-naphthyl)-2-[(2-methylpyrazol-3-yl)methylamino]pyrimidine-4-carboxamide

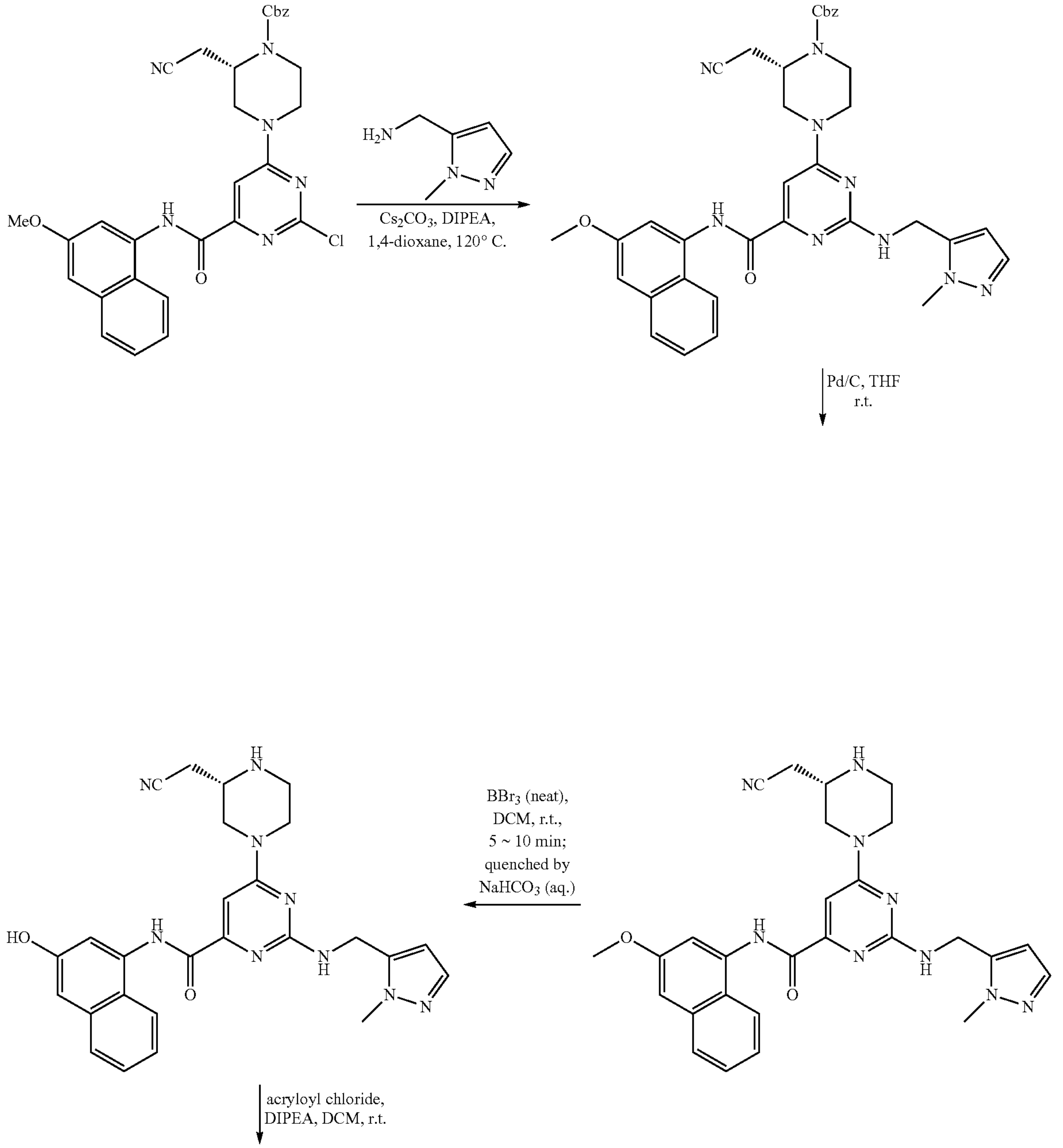

-continued

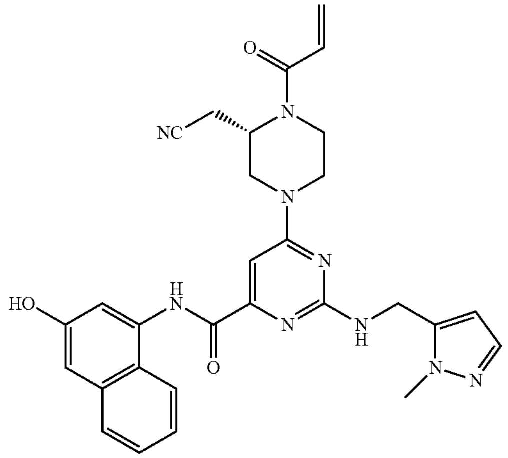

benzyl (2S)-2-(cyanomethyl)-4-[6-[(3-methoxy-1-naphthyl)carbamoyl]-2-[(2-methylpyrazol-3-yl)methylamino]pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) in 1,4-dioxane (15 mL) was added (2-methylpyrazol-3-yl)methanamine (292 mg, 2.63 mmol, 5.0 eq), $Cs_2CO_3$ (512 mg, 1.58 mmol, 3.0 eq) and DIPEA (542 mg, 4.20 mmol, 8.0 eq) and the mixture was stirred and heated at 120° C. under $N_2$ overnight. Solvent was then removed in vacuo and the residue purified by column chromatography to give benzyl (2S)-4-[2-benzyl-6-[(3-methoxy-1-naphthyl)carbamoyl]pyrimidin-4-yl]-2-(cyanomethyl)piperazine-1-carboxylate (190 mg, 56%).

UPLC-MS (ES+, Method E): 3.57 min, m/z 646.4 [M+H]+

6-[(3S)-3-(cyanomethyl)piperazin-1-yl]-N-(3-methoxy-1-naphthyl)-2-[(2-methylpyrazol-3-yl)methylamino]pyrimidine-4-carboxamide Step 2

To a solution of benzyl (2S)-2-(cyanomethyl)-4-[6-[(3-methoxy-1-naphthyl)carbamoyl]-2-[(2-methylpyrazol-3-yl)methylamino]pyrimidin-4-yl]piperazine-1-carboxylate (190 mg, 1.0 eq) in THF (6 mL) was added Pd/C (95 mg) and the mixture was stirred at r.t. under $H_2$ overnight. The mixture was filtered through celite and concentrated in vacuo to give 6-[(3S)-3-(cyanomethyl)piperazin-1-yl]-N-(3-methoxy-1-naphthyl)-2-[(2-methylpyrazol-3-yl)methylamino]pyrimidine-4-carboxamide (130 mg, 87%).

UPLC-MS (ES+, Method E): 2.83 min, m/z 512.3 [M+H]+

Step 3

To a solution of 6-[(3S)-3-(cyanomethyl)piperazin-1-yl]-N-(3-methoxy-1-naphthyl)-2-[(2-methylpyrazol-3-yl)methylamino]pyrimidine-4-carboxamide (100 mg, 0.19 mmol, 1.0 eq) in dry-DCM (15 mL) was added $BBr_3$ (245 mg, 0.98 mmol, 5.0 eq), the mixture was stirred at RT under $N_2$ for 10 minutes and quenched by $NaHCO_3$ (aq.). The organic layer was separated, dried over sodium sulfate and purified by prep-TLC to give 6-[(3S)-3-(cyanomethyl)piperazin-1-yl]-N-(3-hydroxy-1-naphthyl)-2-[(2-methylpyrazol-3-yl)methylamino]pyrimidine-4-carboxamide (60 mg, 61%).

UPLC-MS (ES+, Method E): 2.67 min, m/z 498.3 [M+H]+.

2-benzyl-6-[(3S)-3-(cyanomethyl)-4-prop-2-enoyl-piperazin-1-yl]-N-(3-hydroxy-1-naphthyl)pyrimidine-4-carboxamide Final Step To a solution of 6-[(3S)-3-(cyanomethyl)piperazin-1-yl]-N-(3-hydroxy-1-naphthyl)-2-[(2-methylpyrazol-3-yl)methylamino]pyrimidine-4-carboxamide (30 mg, 0.06 mmol, 1.0 eq) in dry-DMF was added acryloyl chloride (5 mg, 0.06 mmol, 1.0 eq) and N,N-diisopropylethylamine (23 mg, 0.18 mmol, 3.0 eq), the mixture was stirred at 0° C. under $N_2$ for 30 minutes. Solvent was then removed in vacuo and the residue purified by column chromatography to give 2-benzyl-6-[(3S)-3-(cyanomethyl)-4-prop-2-enoyl-piperazin-1-yl]-N-(3-hydroxy-1-naphthyl)pyrimidine-4-carboxamide (13 mg, 39%) as a yellow solid.

UPLC-MS (ES+, Method E): 3.43 min, m/z 552.3 [M+H]+.

1H-NMR (400 MHz, DMSO-d6) δ/ppm: 10.75 (1H, s), 9.89 (1H, s), 8.02-9.96 (1H, m), 7.74-7.70 (2H, m), 7.60-7.26 (4H, m), 7.01-7.00 (1H, m), 7.96-7.75 (2H, m), 6.22-6.17 (1H, m), 5.80-5.77 (1H, m), 4.93-4.60 (5H, m), 4.14-4.02 (1H, m), 3.85 (3H, s), 6.65-3.50 (2H, m), 3.08-2.75 (3H, m).

Example 42
6-[(3S)-3-(cyanomethyl)-4-prop-2-enoyl-piperazin-1-yl]-N-(3-hydroxy-1-naphthyl)-2-[(1-methylpyrazol-4-yl)methoxy]pyrimidine-4-carboxamide
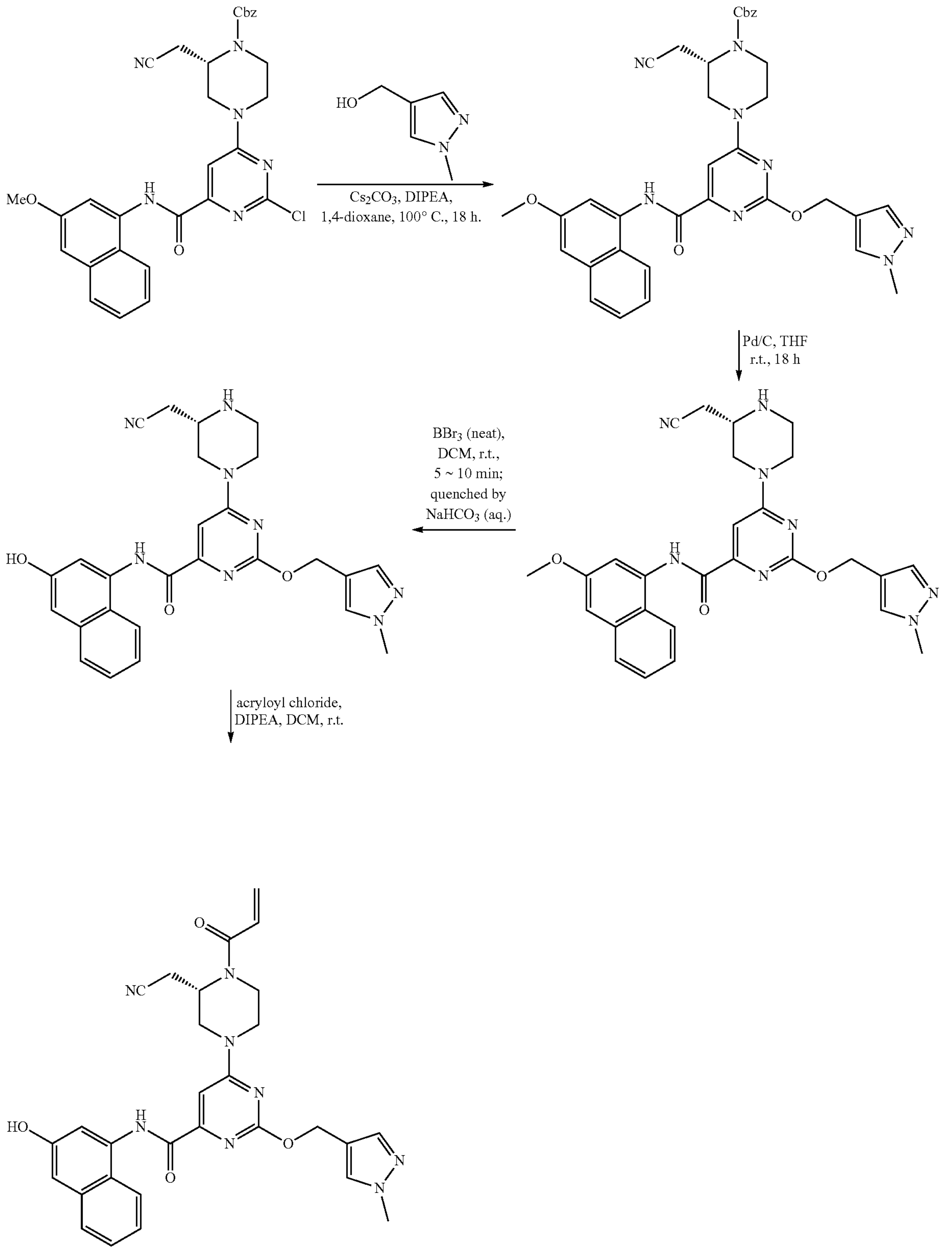

benzyl (2S)-2-(cyanomethyl)-4-[6-[(3-methoxy-1-naphthyl)carbamoyl]-2-[(2-methylpyrazol-3-yl)methoxy]pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) in toluene (15 mL) was added (1-methyl-1H-pyrazol-4-yl)methanol (177 mg, 1.58 mmol, 3.0 eq), $Pd(OAc)_2$ (12 mg, 0.05 mmol, 0.1eq), $Cs_2CO_3$ (513 mg, 1.58 mmol, 3.0 eq) and BINAP (65 mg, 0.10 mmol, 0.2eq) and the mixture was stirred and heated at 110° C. under $N_2$ for 3 hours. Solvent was then removed in vacuo and the residue purified by column chromatography to give benzyl (2S)-2-(cyanomethyl)-4-[6-[(3-methoxy-1-naphthyl)carbamoyl]-2-[(2-methylpyrazol-3-yl)methoxy]pyrimidin-4-yl]piperazine-1-carboxylate (260 mg, 77%).

UPLC-MS (ES+, Method D): 3.57 min, m/z 647.5 [M+H]+

6-[(3S)-3-(cyanomethyl)piperazin-1-yl]-N-(3-methoxy-1-naphthyl)-2-[(1-methylpyrazol-4-yl)methoxy]pyrimidine-4-carboxamide Step 2

To a solution of benzyl (2S)-2-(cyanomethyl)-4-[6-[(3-methoxy-1-naphthyl)carbamoyl]-2-[(1-methylpyrazol-4-yl)methoxy]pyrimidin-4-yl]piperazine-1-carboxylate (260 mg, 1.0 eq) in THF (6 mL) was added Pd/C (130 mg) and the mixture was stirred at r.t. under $H_2$ overnight. The mixture was then filtered through celite and the filtrate concentrated to give 6-[(3S)-3-(cyanomethyl)piperazin-1-yl]-N-(3-methoxy-1-naphthyl)-2-[(1-methylpyrazol-4-yl)methoxy]pyrimidine-4-carboxamide (190 mg, 92%).

UPLC-MS (ES+, Method D): 3.57 min, m/z 513.5 [M+H]+

6-[(3S)-3-(cyanomethyl)piperazin-1-yl]-N-(3-hydroxy-1-naphthyl)-2-[(1-methylpyrazol-4-yl)methoxy]pyrimidine-4-carboxamide Step 3

To a solution of 6-[(3S)-3-(cyanomethyl)piperazin-1-yl]-N-(3-methoxy-1-naphthyl)-2-[(1-methylpyrazol-4-yl)methoxy]pyrimidine-4-carboxamide (160 mg, 0.31 mmol, 1.0 eq) in dry-DCM (20 mL) was added $BBr_3$ (391 mg, 1.56 mmol, 5.0 eq), the mixture was stirred at RT under $N_2$ for 10 minutes, then was quenched by $NaHCO_3$ (aq.). The organic layer was separated, dried over sodium sulfate and purified by prep-TLC to give 6-[(3S)-3-(cyanomethyl)piperazin-1-yl]-N-(3-hydroxy-1-naphthyl)-2-[(1-methylpyrazol-4-yl)methoxy]pyrimidine-4-carboxamide (40 mg, 26%).

UPLC-MS (ES+, Method D): 2.63 min, m/z 499.3 [M+H]+.

6-[(3S)-3-(cyanomethyl)-4-prop-2-enoyl-piperazin-1-yl]-N-(3-hydroxy-1-naphthyl)-2-[(1-methylpyrazol-4-yl)methoxy]pyrimidine-4-carboxamide Final Step To a solution of 6-[(3S)-3-(cyanomethyl)piperazin-1-yl]-N-(3-hydroxy-1-naphthyl)-2-[(1-methylpyrazol-4-yl)methoxy]pyrimidine-4-carboxamide (20 mg, 0.04 mmol, 1.0 eq) in dry-DMF (1 mL) was added acryloyl chloride (4 mg, 0.04 mmol, 1.0 eq) and N,N-diisopropylethylamine (15 mg, 0.12 mmol, 3.0 eq), the mixture was stirred at 0° C. under $N_2$ for 30 minutes. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-[(1-methylpyrazol-4-yl)methoxy]pyrimidine-4-carboxamide (6 mg, 27%).

UPLC-MS (ES+, Method D): 3.53 min, m/z 553.3 [M+H]+.

1H-NMR (400 MHz, DMSO-d6) δ/ppm: 10.63 (1H, s), 9.89 (1H, s), 7.83 (1H, s), 7.77-7.73 (2H, m), 7.64-7.62 (1H, m), 7.56-7.54 (1H, m), 7.46-7.42 (1H, m), 7.35-7.31 (1H, m), 7.22-7.13 (1H, m), 7.06-7.05 (1H, m), 6.91-6.83 (1H, m), 6.22-6.17 (1H, m), 5.80-5.75 (1H, m), 5.41-5.38 (2H, m), 4.94-4.78 (1H, m), 4.55-4.35 (1H, m), 4.13-4.05 (1H, m), 3.83 (3H, s), 3.60-3.45 (3H, m), 3.14-2.80 (3H, m).

Example 43

6-[(3S)-3-(cyanomethyl)-4-prop-2-enoyl-piperazin-1-yl]-N-(3-hydroxy-1-naphthyl)-2-[(1-methyl-3-piperidyl)methylamino]pyrimidine-4-carboxamide

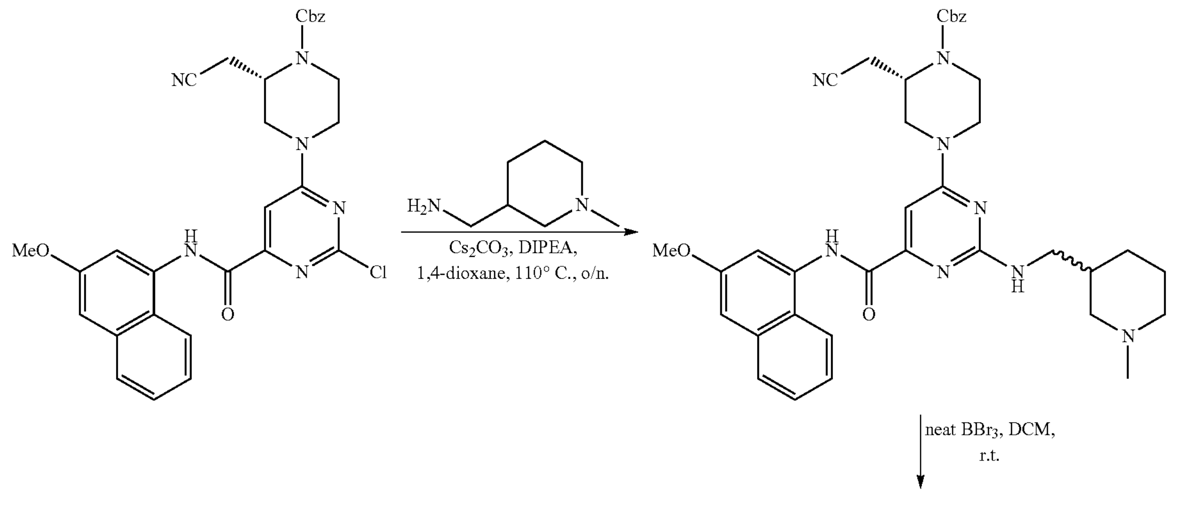

-continued

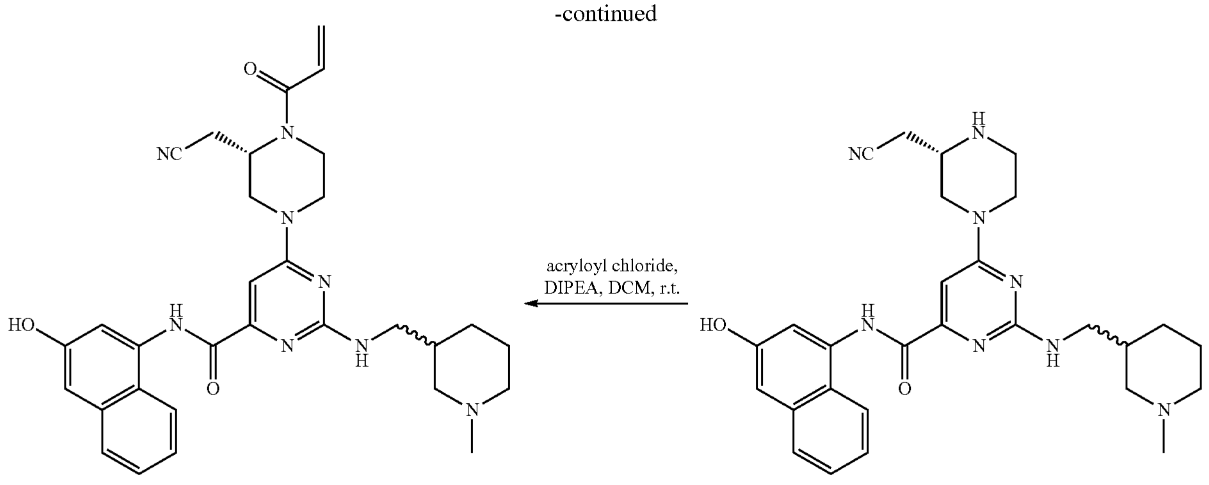

benzyl (2S)-2-(cyanomethyl)-4-[6-[(3-methoxy-1-naphthyl)carbamoyl]-2-[(1-methyl-3-piperidyl)methylamino]pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl) piperazine-1-carboxylate (300 mg, 0.52 mmol, 1.0 eq) in 1,4-dioxane (15 mL) was added (1-methyl-3-piperidyl) methanamine (337 mg, 2.63 mmol, 5.0 eq), $CS_2CO_3$ (512 mg, 1.58 mmol, 3.0 eq) and DIPEA (542 mg, 4.20 mmol, 8.0 eq) and the mixture was stirred and heated at 100° C. under $N_2$ overnight. The mixture was diluted with water (100 mL) and extracted with EtOAc (150 mL×3). The combined organic layers were dried over $Na_2SO_4$ and concentrated in vacuo and the residue purified by silica gel column (DCM/MeOH=100/1,V/V) to give 6-[(3S)-3-(cyanomethyl)piperazin-1-yl]-N-(3-hydroxy-1-naphthyl)-2-[(1-methylpyrazol-4-yl)methoxy]pyrimidine-4-carboxamide (220 mg, 63%).

UPLC-MS (ES+, Method D): 0.93 min, m/z 663.5 [M+H]+

6-[(3S)-3-(cyanomethyl)piperazin-1-yl]-N-(3-hydroxy-1-naphthyl)-2-[(1-methyl-3-piperidyl)methylamino]pyrimidine-4-carboxamide Step 2

To a solution of benzyl (2S)-2-(cyanomethyl)-4-[6-[(3-methoxy-1-naphthyl)carbamoyl]-2-[(1-methyl-3-piperidyl) methylamino]pyrimidin-4-yl]piperazine-1-carboxylate (210 mg, 0.32 mmol, 1.0 eq) in dry-DCM was added $BBr_3$ (635 mg, 2.53 mmol, 8.0 eq), the mixture was stirred at RT under $N_2$ for 10 minutes then was quenched by $NaHCO_3$ (aq.). The organic layer was separated, dried over sodium sulfate and purified by prep-TLC to give 6-[(3S)-3-(cyanomethyl)piperazin-1-yl]-N-(3-hydroxy-1-naphthyl)-2-[(1-methyl-3-piperidyl)methylamino]pyrimidine-4-carboxamide (30 mg, 18%).

UPLC-MS (ES+, Method E): 1.73 min, m/z 515.4 [M+H]+

6-[(3S)-3-(cyanomethyl)-4-prop-2-enoyl-piperazin-1-yl]-N-(3-hydroxy-1-naphthyl)-2-[(1-methyl-3-piperidyl)methylamino]pyrimidine-4-carboxamide Final Step To a solution of 6-[(3S)-3-(cyanomethyl)piperazin-1-yl]-N-(3-hydroxy-1-naphthyl)-2-[(1-methyl-3-piperidyl)methylamino]pyrimidine-4-carboxamide (15 mg, 0.03 mmol, 1.0 eq) in dry-DMF was added acryloyl chloride (3 mg, 0.03 mmol, 1.0 eq) and N,N-diisopropylethylamine (11 mg, 0.09 mmol, 3.0 eq), the mixture was stirred at 0° C. under $N_2$ for 30 minutes. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-[(1-methyl-3-piperidyl)methylamino] pyrimidine-4-carboxamide (7 mg, 47%).

UPLC-MS (ES+, Method E): 3.26 min, m/z 569.3 $[M+H]^+$.

1H-NMR (400 MHz, DMSO-d6) δ/ppm: 10.84-10.78 (1H, m), 8.01-8.00 (1H, m), 7.93-7.86 (1H, m), 7.76-7.73 (1H, m), 7.49-7.45 (1H, m), 7.36-7.16 (2H, m), 7.00 (1H, s), 7.95-7.60 (2H, m), 6.21-6.17 (1H, m), 5.79-5.76 (1H, m), 4.93-4.79 (1H, m), 4.45-4.28 (2H, m), 4.10-4.04 (1H, m), 3.06-2.52 (6H, m), 2.20-1.55 (9H, m), 1.48-0.95 (4H, m), 1×exchangeable not seen.

Example 44
2-[[(2S)-1-benzylpyrrolidin-2-yl]methylamino]-6-[(3S)-3-(cyanomethyl)-4-prop-2-enoyl-piperazin-1-yl]-N-(3-hydroxy-1-naphthyl)pyrimidine-4-carboxamide
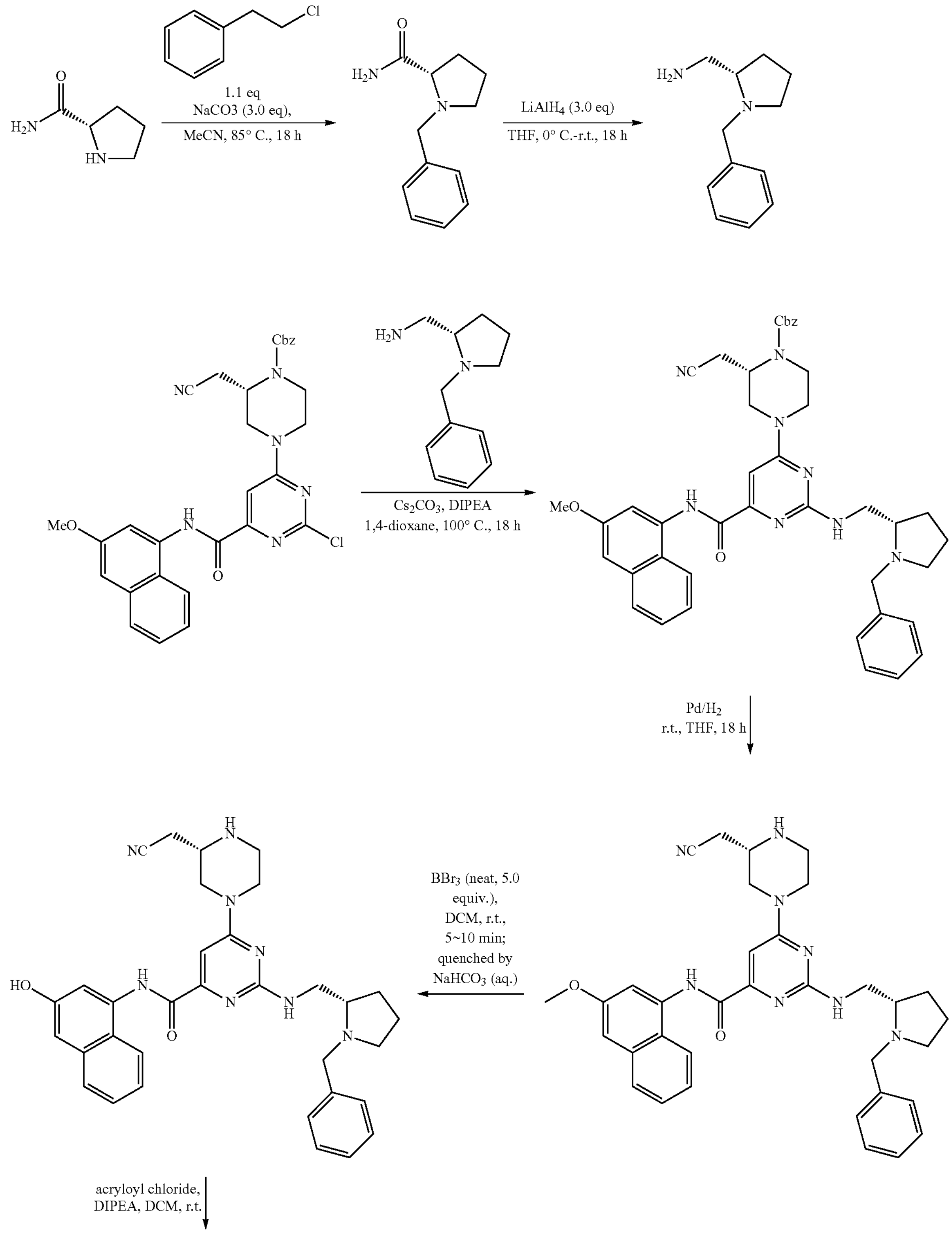

-continued

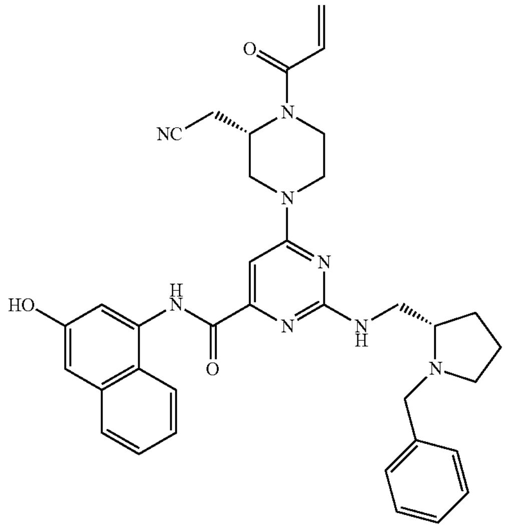 [SMILES: C=CC(=O)N1CCN(c2cc(C(=O)Nc3cc(O)cc4ccccc34)nc(NC[C@@H]3CCCN3Cc3ccccc3)n2)C[C@@H]1CC#N]

1-benzylpyrrolidine-2-carboxamide

Intermediate Step 1

To a solution of pyrrolidine-2-carboxamide (1 g, 8.76 mmol, 1.0 eq) in MeCN (20 mL) was added benzyl chloride (1.22 g, 9.64 mmol, 1.1 eq) and $NaHCO_3$ (2.21 g, 26.28 mmol, 3.0 eq) and the mixture was stirred and heated at 85° C. under $N_2$ overnight. The reaction was poured into water and extracted with EtOAc. The organic layer was separated, dried over sodium sulfate and concentrated in vacuo. The residue was purified by column chromatography to give 1-benzylpyrrolidine-2-carboxamide (1.8 g, 100%).

UPLC-MS (ES+, Method E): 0.67 min, m/z 205.2 [M+H]+

[(2S)-1-benzylpyrrolidin-2-yl]methanamine

Intermediate Step 2

To a solution of (2S)-1-benzylpyrrolidine-2-carboxamide (200 mg, 0.98 mmol, 1.0 eq) in THF was added $LiAlH_4$ (2.94 mL, 3.0 eq), the mixture was stirred at 0° C. under $N_2$ overnight. The reaction was quenched with water, dried over sodium sulfate and the filtrate concentrated in vacuo. The residue was purified by column chromatography to give [(2S)-1-benzylpyrrolidin-2-yl]methanamine (110 mg, 59%).

UPLC-MS (ES+, short acidic): 0.60 min, m/z 191.2 [M+H]+ benzyl (2S)-4-[2-[[(2S)-1-benzylpyrrolidin-2-yl] methylamino]-6-[(3-methoxy-1-naphthyl)carbamoyl] pyrimidin-4-yl]-2-(cyanomethyl)piperazine-1-carboxylate Step 1

To a solution of benzyl (2S)-4-[2-chloro-6-[(3-methoxy-1-naphthyl)carbamoyl]pyrimidin-4-yl]-2-(cyanomethyl) piperazine-1-carboxylate (300 mg, 0.52 mmol, 1.0 eq) in 1,4-dioxane (15 mL) was added[(2S)-1-benzylpyrrolidin-2-yl]methanamine (500 mg, 2.63 mmol, 5.0 eq), $Cs_2CO_3$ (512 mg, 1.58 mmol, 3.0 eq) and DIPEA (542 mg, 4.2 mmol, 8.0 eq) and the mixture was stirred and heated at 100° C. under $N_2$ overnight. The mixture was diluted with water (100 mL) and extracted with EtOAc (150 mL×3). The combined organic layers were dried over $Na_2SO_4$ and concentrated in vacuo. The residue was purified by silica gel column (DCM/MeOH=100/1,V/V) to give benzyl (2S)-4-[2-[[(2S)-1-benzylpyrrolidin-2-yl]methylamino]-6-[(3-methoxy-1-naphthyl)carbamoyl]pyrimidin-4-yl]-2-(cyanomethyl) piperazine-1-carboxylate (270 mg, 71%).

UPLC-MS (ES+, Method D): 0.77 min, m/z 725.5 [M+H]+ 2-[[(2S)-1-benzylpyrrolidin-2-yl]methylamino]-6-[(3S)-3-(cyanomethyl)piperazin-1-yl]-N-(3-methoxy-1-naphthyl)pyrimidine-4-carboxamide Step 2

To a solution of benzyl (2S)-4-[2-[[(2S)-1-benzylpyrrolidin-2-yl]methylamino]-6-[(3-methoxy-1-naphthyl)carbamoyl]pyrimidin-4-yl]-2-(cyanomethyl)piperazine-1-carboxylate (210 mg, 1.0 eq) in THF (6 mL) was added Pd/C (95 mg) and the mixture was stirred at r.t. under $H_2$ overnight. The mixture was filtered through celite and concentrated in vacuo to give benzyl (2S)-4-[2-[[(2S)-1-benzylpyrrolidin-2-yl]methylamino]-6-[(3-methoxy-1-naphthyl)carbamoyl]pyrimidin-4-yl]-2-(cyanomethyl)piperazine-1-carboxylate (170 mg, 95%).

UPLC-MS (ES+, Method E): 2.47 min, m/z 591.4 [M+H]+.

2-[[(2S)-1-benzylpyrrolidin-2-yl]methylamino]-6-[(3S)-3-(cyanomethyl)piperazin-1-yl]-N-(3-hydroxy-1-naphthyl)pyrimidine-4-carboxamide Step 3

To a solution of 2-[[(2S)-1-benzylpyrrolidin-2-yl]methylamino]-6-[(3S)-3-(cyanomethyl)piperazin-1-yl]-N-(3-methoxy-1-naphthyl)pyrimidine-4-carboxamide (140 mg, 0.24 mmol, 1.0 eq) in dry-DCM was added $BBr_3$ (297 mg, 1.18 mmol, 5.0 eq), the mixture was stirred at RT under $N_2$ for 10 minutes and quenched by $NaHCO_3$ (aq.). The organic layer was separated, dried over sodium sulfate and purified by prep-TLC to give 2-[[(2S)-1-benzylpyrrolidin-2-yl]methylamino]-6-[(3S)-3-(cyanomethyl)piperazin-1-yl]-N-(3-hydroxy-1-naphthyl)pyrimidine-4-carboxamide (60 mg, 44%).

UPLC-MS (ES+, Method E): 2.30 min, m/z 577.4 [M+H]+.

2-[[(2S)-1-benzylpyrrolidin-2-yl]methylamino]-6-[(3S)-3-(cyanomethyl)-4-prop-2-enoyl-piperazin-1-yl]-N-(3-hydroxy-1-naphthyl)pyrimidine-4-carboxamide Final Step To a solution of 2-[[(2S)-1-benzylpyrrolidin-2-yl]methylamino]-6-[(3S)-3-(cyanomethyl)-4-prop-2-enoyl-piperazin-1-yl]-N-(3-hydroxy-1-naphthyl)pyrimidine-4-carboxamide (30 mg, 0.05 mmol, 1.0 eq) in dry-DMF (2 mL) was added acryloyl chloride (5 mg, 0.05 mmol, 1.0 eq) and N,N-diisopropylethylamine (20 mg, 0.16 mmol, 3.0 eq), the mixture was stirred at 0° C. under $N_2$ for 30 minutes. Solvent was then removed in vacuo and the residue purified by column chromatography to give 2-[[(2S)-1-benzylpyrrolidin-2-yl]methylamino]-6-[(3S)-3-(cyanomethyl)-4-prop-2-enoyl-piperazin-1-yl]-N-(3-hydroxy-1-naphthyl)pyrimidine-4-carboxamide (11 mg, 33%).

UPLC-MS (ES+, Method E): 2.73 min, m/z 631.4 [M+H]+.

1H-NMR (400 MHz, DMSO-d6) δ/ppm: 10.76 (1H, s), 9.90 (1H, s), 7.94-7.82 (2H, m), 7.75-7.73 (1H, m), 7.50-7.22 (8H, m), 7.02-7.00 (1H, m), 6.90-6.76 (2H, m), 6.21-6.16 (1H, m), 5.79-5.75 (1H, m), 4.94-4.75 (1H, m), 4.55-4.02 (4H, m), 3.80-3.49 (2H, m), 3.30-2.75 (7H, m), 2.30-2.20 (1H, m), 2.03-1.80 (1H, m), 1.75-1.58 (4H, m).

Example 45

6-[(3S)-3-(cyanomethyl)-4-prop-2-enoyl-piperazin-1-yl]-N-(3-hydroxy-1-naphthyl)-2-[(1-methylpyrrolidin-2-yl)methylamino]pyrimidine-4-carboxamide

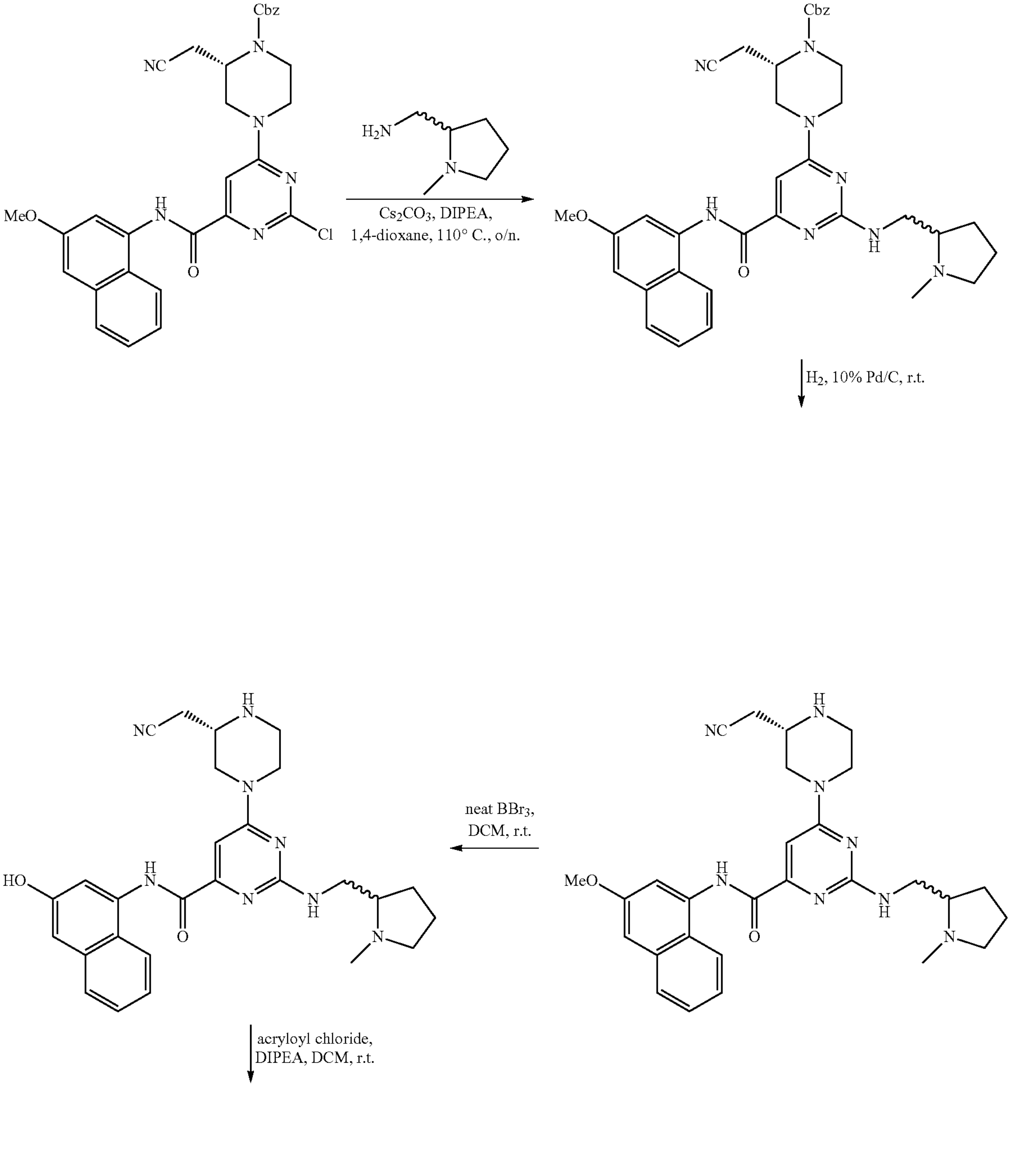

-continued

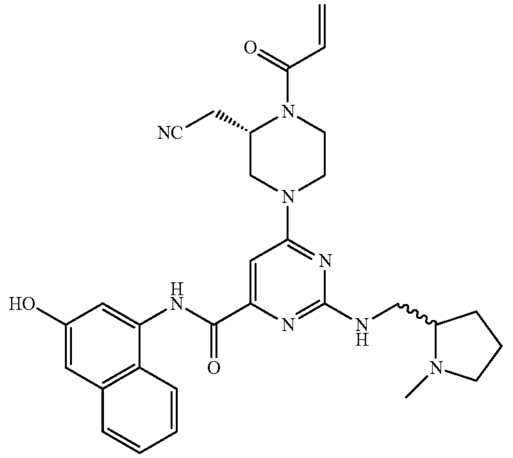

benzyl (2S)-2-(cyanomethyl)-4-[6-[(3-methoxy-1-naphthyl)carbamoyl]-2-[(1-methylpyrrolidin-2-yl)methylamino]pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl)piperazine-1-carboxylate (258 mg, 0.45 mmol, 1.0 eq) in 1,4-dioxane (15 mL) was added (1-methylpyrrolidin-2-yl)methanamine (155 mg, 1.35 mmol, 3.0 eq), $Cs_2CO_3$ (440 mg, 1.35 mmol, 3.0 eq) and DIPEA (466 mg, 3.61 mmol, 8.0 eq) and the mixture was stirred and heated at 110° C. under $N_2$ overnight. The mixture was diluted with water (100 mL) and extracted with EtOAc (150 mL×3). The combined organic layers were dried over $Na_2SO_4$ and concentrated in vacuo. The residue was purified by silica gel column (DCM/MeOH=100/1,V/V) to give benzyl (2S)-2-(cyanomethyl)-4-[6-[(3-methoxy-1-naphthyl)carbamoyl]-2-[(1-methylpyrrolidin-2-yl)methylamino]pyrimidin-4-yl]piperazine-1-carboxylate (200 mg, 68%).

UPLC-MS (ES+, Method D): 0.97 min, m/z 649.5 [M+H]+

6-[(3S)-3-(cyanomethyl)piperazin-1-yl]-N-(3-methoxy-1-naphthyl)-2-[(1-methylpyrrolidin-2-yl)methylamino]pyrimidine-4-carboxamide Step 2

To a solution of benzyl (2S)-2-(cyanomethyl)-4-[6-[(3-methoxy-1-naphthyl)carbamoyl]-2-[(1-methylpyrrolidin-2-yl)methylamino]pyrimidin-4-yl]piperazine-1-carboxylate (195 mg, 1.0 eq) in THF (6 mL) was added Pd/C (98 mg) and the mixture was stirred at r.t. under $H_2$ overnight. The mixture was filtered through celite and concentrated in vacuo to give 6-[(3S)-3-(cyanomethyl)piperazin-1-yl]-N-(3-methoxy-1-naphthyl)-2-[(1-methylpyrrolidin-2-yl)methylamino]pyrimidine-4-carboxamide (140 mg, 91%).

UPLC-MS (ES+, Method E): 2.43 min, m/z 515.4 [M+H]+.

6-[(3S)-3-(cyanomethyl)piperazin-1-yl]-N-(3-hydroxy-1-naphthyl)-2-[(1-methylpyrrolidin-2-yl)methylamino]pyrimidine-4-carboxamide Step 3

To a solution of 6-[(3S)-3-(cyanomethyl)piperazin-1-yl]-N-(3-methoxy-1-naphthyl)-2-[(1-methylpyrrolidin-2-yl)methylamino]pyrimidine-4-carboxamide (109 mg, 0.21 mmol, 1.0 eq) in dry-DCM was added $BBr_3$ (265 mg, 1.06 mmol, 5.0 eq), the mixture was stirred at RT under N for 10 minutes and quenched by $NaHCO_3$ (aq.). The organic layer was separated, dried over sodium sulfate and purified by prep-TLC to give 2-[[(2S)-1-benzylpyrrolidin-2-yl]methylamino]-6-[(3S)-3-(cyanomethyl)piperazin-1-yl]-N-(3-hydroxy-1-naphthyl)pyrimidine-4-carboxamide (50 mg, 47%).

UPLC-MS (ES+, Method E): 1.07 min, m/z 501.3 [M+H]+

6-[(3S)-3-(cyanomethyl)-4-prop-2-enoyl-piperazin-1-yl]-N-(3-hydroxy-1-naphthyl)-2-[(1-methylpyrrolidin-2-yl)methylamino]pyrimidine-4-carboxamide Final Step To a solution of 6-[(3S)-3-(cyanomethyl)piperazin-1-yl]-N-(3-hydroxy-1-naphthyl)-2-[(1-methylpyrrolidin-2-yl)methylamino]pyrimidine-4-carboxamide (30 mg, 0.06 mmol, 1.0 eq) in dry-DMF was added acryloyl chloride (5 mg, 0.06 mmol, 1.0 eq) and N,N-diisopropylethylamine (23 mg, 0.18 mmol, 3.0 eq), the mixture was stirred at 0° C. under $N_2$ for 30 minutes. Solvent was then removed in vacuo and the residue purified by column chromatography to give 2-[[(2S)-1-benzylpyrrolidin-2-yl]methylamino]-6-[(3S)-3-(cyanomethyl)-4-prop-2-enoyl-piperazin-1-yl]-N-(3-hydroxy-1-naphthyl)pyrimidine-4-carboxamide (7 mg, 23%) as a light yellow solid.

UPLC-MS (ES+, Method E): 2.60 min, m/z 555.3 $[M+H]^+$.

1H-NMR (400 MHz, DMSO-d6) δ/ppm: 10.74 (1H, s), 9.91 (1H, s), 7.93-7.83 (2H, m), 7.76-7.74 (1H, m), 7.48-7.46 (1H, m), 7.44-7.35 (1H, m), 7.20-7.16 (1H, m), 7.04-7.00 (1H, m), 6.90-6.79 (2H, m), 6.22-6.17 (1H, m), 5.80-5.75 (1H, m), 4.92-4.78 (1H, m), 4.55-4.42 (2H, m), 4.08-3.99 (1H, m), 3.75-3.65 (2H, m), 3.08-2.75 (3H, m), 2.68-2.52 (3H, m), 2.48-2.44 (3H, m), 2.20-2.25 (1H, m), 2.02-1.92 (1H, m), 1.78-1.65 (4H, m).

Example 46
6-[(3S)-3-(cyanomethyl)-4-prop-2-enoyl-piperazin-1-yl]-2-[[(2S)-1-(2-hydroxyethyl)pyrrolidin-2-yl]methylamino]-N-(3-hydroxy-1-naphthyl)pyrimidine-4-carboxamide
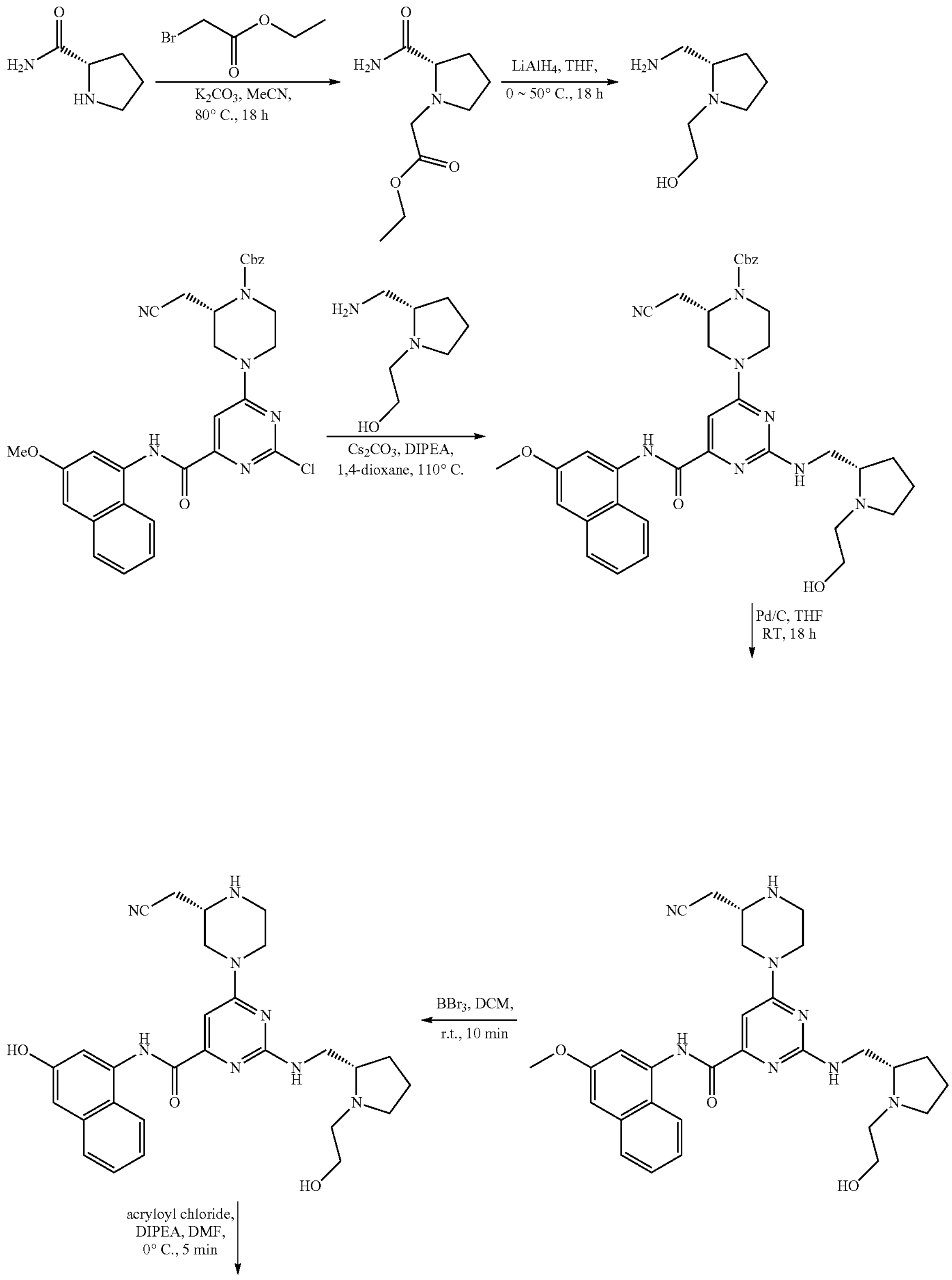

-continued

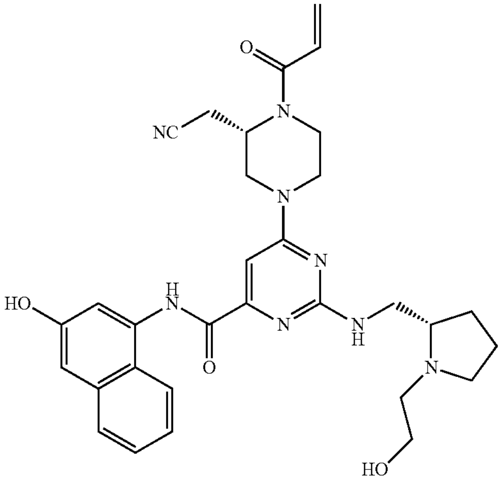

ethyl 2-[(2S)-2-carbamoylpyrrolidin-1-yl]acetate

Intermediate Step 1

To (2S)-pyrrolidine-2-carboxamide (1.0 g, 8.76 mmol, 1.0 eq) was added MeCN (100 mL) followed by the addition of ethyl bromoacetate (7.31 g, 43.80 mmol, 5.0 eq) and $K_2CO_3$ (3.63 g, 26.28 mmol, 3.0 eq). The reaction was stirred at 80° C. overnight. Solvent was then removed in vacuo and the residue purified by column chromatography using an eluent of 0-5% MeOH in DCM reached via a gradient to give ethyl 2-[(2S)-2-carbamoylpyrrolidin-1-yl]acetate (1.2 g, 68%).

UPLC-MS (ES+, Method C): 0.37 min, m/z 201.0 [M+H]+

2-[(2S)-2-(aminomethyl)pyrrolidin-1-yl]ethanol

Intermediate Step 2 ethyl 2-[(2S)-2-carbamoylpyrrolidin-1-yl]acetate (1.1 g, 5.49 mmol, 1.0 eq) was dissolved in THF (150 mL). The reaction was left stirring at 0° C., then $LiAlH_4$ (1M in THF) (27.50 mL, 27.47 mmol, 5.0 eq) was added slowly. The reaction was left stirring at 50° C. overnight. Water (27.5 mL) was added slowly, then 15% NaOH aq (27.5 mL) was added slowly at 0° C. Then solvent removed in vacuo. The residue was purified by column chromatography using an eluent of 0-10% MeOH in DCM reached via a gradient to give 2-[(2S)-2-(aminomethyl)pyrrolidin-1-yl]ethanol (500 mg, 63%).

UPLC-MS (ES+, Method C): 0.34 min, m/z 145.1 [M+H]+ benzyl (2S)-2-(cyanomethyl)-4-[2-[[(2S)-1-(2-hydroxyethyl)pyrrolidin-2-yl]methylamino]-6-[(3-methoxy-1-naphthyl)carbamoyl]pyrimidin-4-yl]piperazine-1-carboxylate Step 1

To benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) was added 1,4-dioxane (10 mL) followed by the addition of 2-[(2S)-2-(aminomethyl)pyrrolidin-1-yl]ethanol (379 mg, 2.63 mmol, 5.0 eq), $Cs_2CO_3$ (513 mg, 1.58 mmol, 3.0 eq) and DIPEA (543 mg, 4.20 mmol, 8.0 eq). The reaction was stirred at 110° C. overnight. Solvent was then removed in vacuo and the residue was dissolved in EtOAc (200 mL) and washed with brine (200 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[2-[[(2S)-1-(2-hydroxyethyl)pyrrolidin-2-yl]methylamino]-6-[(3-methoxy-1-naphthyl)carbamoyl]pyrimidin-4-yl]piperazine-1-carboxylate (200 mg, 56%).

UPLC-MS (ES+, Method A): 0.93 min, m/z 679.0 [M+H]+

6-[(3S)-3-(cyanomethyl)piperazin-1-yl]-2-[[(2S)-1-(2-hydroxyethyl)pyrrolidin-2-yl]methylamino]-N-(3-methoxy-1-naphthyl)pyrimidine-4-carboxamide Step 2

To a solution of benzyl (2S)-2-(cyanomethyl)-4-[2-[[(2S)-1-(2-hydroxyethyl)pyrrolidin-2-yl]methylamino]-6-[(3-methoxy-1-naphthyl)carbamoyl]pyrimidin-4-yl]piperazine-1-carboxylate (190 mg, 1.0 eq) in THF (6 mL) was added Pd/C (95 mg) and the mixture was stirred at r.t. under $H_2$ overnight. The mixture was filtered through celite and concentrated in vacuo to give 6-[(3S)-3-(cyanomethyl)piperazin-1-yl]-N-(3-methoxy-1-naphthyl)-2-[(1-methylpyrrolidin-2-yl)methylamino]pyrimidine-4-carboxamide (150 mg, 99%).

UPLC-MS (ES+, Method E): 2.30 min, m/z 545.4 [M+H]+

6-[(3S)-3-(cyanomethyl)piperazin-1-yl]-2-[[(2S)-1-(2-hydroxyethyl)pyrrolidin-2-yl]methylamino]-N-(3-hydroxy-1-naphthyl)pyrimidine-4-carboxamide Step 3

To a solution of 6-[(3S)-3-(cyanomethyl)piperazin-1-yl]-2-[[(2S)-1-(2-hydroxyethyl)pyrrolidin-2-yl]methylamino]-N-(3-methoxy-1-naphthyl)pyrimidine-4-carboxamide (118 mg, 0.22 mmol, 1.0 eq) in dry-DCM (15 mL) was added $BBr_3$ (271 mg, 0.22 mmol, 5.0 eq), the mixture was stirred at r.t. under $N_2$ for 10 minutes and quenched by sat. aq. $NaHCO_3$. The organic layer was separated, dried over sodium sulfate and purified by prep-TLC to give 6-[(3S)-3-(cyanomethyl)piperazin-1-yl]-2-[[(2S)-1-(2-hydroxyethyl)pyrrolidin-2-yl]methylamino]-N-(3-hydroxy-1-naphthyl)pyrimidine-4-carboxamide (50 mg, 43%).

UPLC-MS (ES+, Method E): 0.63 min, m/z 531.3 [M+H]+

6-[(3S)-3-(cyanomethyl)-4-prop-2-enoyl-piperazin-1-yl]-2-[[(2S)-1-(2-hydroxyethyl)pyrrolidin-2-yl]methylamino]-N-(3-hydroxy-1-naphthyl)pyrimidine-4-carboxamide Final Step To a solution of 6-[(3S)-3-(cyanomethyl)piperazin-1-yl]-2-[[(2S)-1-(2-hydroxyethyl)pyrrolidin-2-yl]methylamino]-N-(3-hydroxy-1-naphthyl)pyrimidine-4-carboxamide (15 mg, 0.03 mmol, 1.0 eq) in dry-DMF (1 mL) was added acryloyl chloride (3 mg, 0.03 mmol, 1.0 eq) and N,N-diisopropylethylamine (11 mg, 0.08 mmol, 3.0 eq), the mixture was stirred at 0° C. under $N_2$ for 30 minutes. Solvent was then removed in vacuo and the residue purified by column chromatography to give 6-[(3S)-3-(cyanomethyl)-4-prop-2-enoyl-piperazin-1-yl]-2-[[(2S)-1-(2-hydroxyethyl)pyrrolidin-2-yl]methylamino]-N-(3-hydroxy-1-naphthyl)pyrimidine-4-carboxamide (9 mg, 56%).

UPLC-MS (ES+, Method E): 2.53 min, m/z 585.3 $[M+H]^+$.

1H-NMR (400 MHz, DMSO-d6) δ/ppm: 10.75 (1H, s), 9.89 (1H, s), 7.94-7.85 (2H, m), 7.75-7.73 (1H, m), 7.48-7.44 (1H, m), 7.39-7.35 (1H, m), 7.18-7.12 (1H, m), 7.01 (1H, s), 6.95-6.76 (2H, m), 6.22-6.17 (1H, m), 5.80-5.77 (1H, m), 4.93-4.77 (1H, m), 4.51-4.30 (4H, m), 4.08-4.05 (1H, m), 3.60-3.45 (5H, m), 3.20-3.89 (5H, m), 2.79-2.71 (1H, m), 2.43-2.27 (1H, m), 1.90-1.80 (1H, m), 1.75-1.55 (3H, m), 1×exchangeable not seen.

Example 47

6-[(3S)-3-(cyanomethyl)-4-prop-2-enoyl-piperazin-1-yl]-N-(3-hydroxy-1-naphthyl)-2-[2-(1-methylpyrrolidin-2-yl)ethoxy]pyrimidine-4-carboxamide

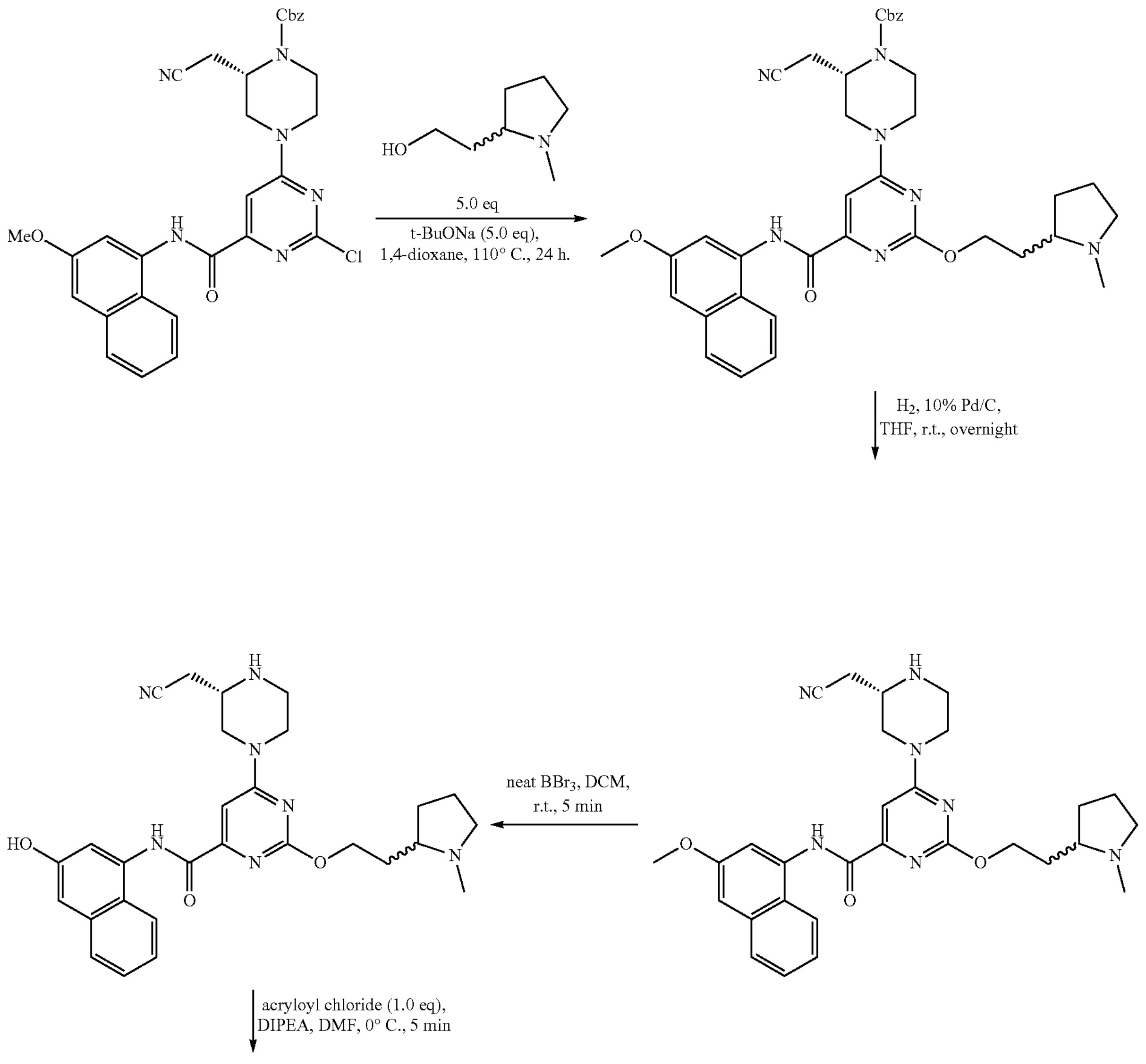

-continued

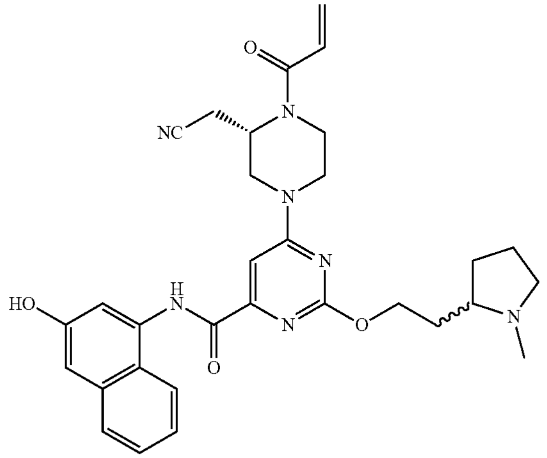

benzyl (2S)-2-(cyanomethyl)-4-[6-[(3-methoxy-1-naphthyl)carbamoyl]-2-[(1-methyl-2-piperidyl)methoxy]pyrimidin-4-yl]piperazine-1-carboxylate Step 1

To benzyl (2S)-4-[2-chloro-6-[(3-methoxy-1-naphthyl)carbamoyl]pyrimidin-4-yl]-2-(cyanomethyl)piperazine-1-carboxylate (300 mg, 0.53 mmol, 1.0 eq) was added 1,4-dioxane (30 mL) followed by the addition of 2-(1-methylpyrrolidin-2-yl)ethanol (340 mg, 2.63 mmol, 5.0 eq) and sodium tert-butoxide (252 mg, 2.63 mmol, 5.0 eq). The reaction was stirred at 110° C. overnight. Solvent was then removed in vacuo and the residue was dissolved in EtOAc (200 mL) and washed with brine (200 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[6-[(3-methoxy-1-naphthyl)carbamoyl]-2-[2-(1-methylpyrrolidin-2-yl)ethoxy]pyrimidin-4-yl]piperazine-1-carboxylate ( ).

UPLC-MS (ES+, Method A): 1.05 min, m/z 665.0 [M+H]+

6-[(3S)-3-(cyanomethyl)piperazin-1-yl]-N-(3-methoxy-1-naphthyl)-2-[(1-methyl-2-piperidyl)methoxy]pyrimidine-4-carboxamide Step 2 benzyl (2S)-2-(cyanomethyl)-4-[6-[(3-methoxy-1-naphthyl)carbamoyl]-2-[2-(1-methylpyrrolidin-2-yl)ethoxy]pyrimidin-4-yl]piperazine-1-carboxylate (120 mg, 0.18 mmol, 1.0 eq) was dissolved in THF (10 mL) followed by the addition of palladium, 10 wt. % on carbon powder, (50 mg, 1.81 mmol, 10.0 eq) under a nitrogen atmosphere. The reaction was fitted with a $H_2$ balloon and subjected to 3×vacuum/$H_2$ cycles and then left to stir under an $H_2$ atmosphere for 12 hours. The reaction was filtered through celite, washed with DCM (200 mL) and solvent removed in vacuo to give 6-[(3S)-3-(cyanomethyl)piperazin-1-yl]-N-(3-methoxy-1-naphthyl)-2-[2-(1-methylpyrrolidin-2-yl)ethoxy]pyrimidine-4-carboxamide (95 mg, 100%).

UPLC-MS (ES+, Method A): 0.35 min, m/z 530.0 [M+H]+ benzyl (2S)-2-(cyanomethyl)-4-[6-[(3-methoxy-1-naphthyl)carbamoyl]-2-[[(2R)-4-methylmorpholin-2-yl]methoxy]pyrimidin-4-yl]piperazine-1-carboxylate Step 3

6-[(3S)-3-(cyanomethyl)piperazin-1-yl]-N-(3-methoxy-1-naphthyl)-2-[2-(1-methylpyrrolidin-2-yl)ethoxy]pyrimidine-4-carboxamide (100 mg, 0.19 mmol, 1.0 eq) was dissolved in DCM (10 mL) followed by the addition of boron tribromide (0.1 mL). After 5 mins, MeOH (50 mL) was added and solvent removed in vacuo. The residue was purified by column chromatography using an eluent of 0-10% MeOH in DCM reached via a gradient to give 6-[(3S)-3-(cyanomethyl)piperazin-1-yl]-N-(3-hydroxy-1-naphthyl)-2-[2-(1-methylpyrrolidin-2-yl)ethoxy]pyrimidine-4-carboxamide (30 mg, 31%).

UPLC-MS (ES+, Method C): 1.26 min, m/z 516.0 [M+H]+

6-[(3S)-3-(cyanomethyl)-4-prop-2-enoyl-piperazin-1-yl]-N-(3-hydroxy-1-naphthyl)-2-[2-(1-methylpyrrolidin-2-yl)ethoxy]pyrimidine-4-carboxamide Final Step Acryloyl chloride (5 mg, 0.06 mmol, 1.0 eq) and 6-[(3S)-3-(cyanomethyl)piperazin-1-yl]-N-(3-hydroxy-1-naphthyl)-2-[2-(1-methylpyrrolidin-2-yl)ethoxy]pyrimidine-4-carboxamide (30 mg, 0.06 mmol, 1.0 eq) were dissolved in DMF (1 mL) followed by the addition of DIPEA (22 mg, 0.17 mmol, 3.0 eq). The reaction was left stirring for 5 min. Water (50 mL) and DCM (50 mL) was then added and the organic layer separated, dried over $Na_2SO_4$ and solvent removed in vacuo. The residue was purified by column chromatography using an eluent of 0-10% MeOH in DCM reached via a gradient to give 6-[(3S)-3-(cyanomethyl)-4-prop-2-enoyl-piperazin-1-yl]-N-(3-hydroxy-1-naphthyl)-2-[2-(1-methylpyrrolidin-2-yl)ethoxy]pyrimidine-4-carboxamide (3 mg, 9%) as a yellow solid.

UPLC-MS (ES+, Method B): 1.96 min, m/z 570.3 $[M+H]^+$.

1H-NMR (400 MHz, DMSO-d6) δ/ppm: 10.63 (1H, s), 9.91 (1H, s), 7.79-7.68 (2H, m), 7.68-7.67 (1H, m), 7.47-7.43 (1H, m), 7.35-7.31 (1H, m), 7.21-7.09 (1H, m), 7.04 (1H, s), 6.96-7.78 (1H, m), 6.22-6.17 (1H, m), 5.80-5.77 (1H, m), 4.95-4.75 (1H, m), 4.56-4.44 (3H, m), 4.15-4.08 (1H, m), 3.60-3.47 (2H, m), 3.15-2.87 (4H, m), 2.25 (3H, s), 2.24-1.95 (5H, m), 1.76-1.50 (4H, m).

Example 48
6-[(3S)-3-(cyanomethyl)-4-prop-2-enoyl-piperazin-1-yl]-N-(3-hydroxy-1-naphthyl)-2-[(1-methyl-2-piperidyl)methoxy]pyrimidine-4-carboxamide
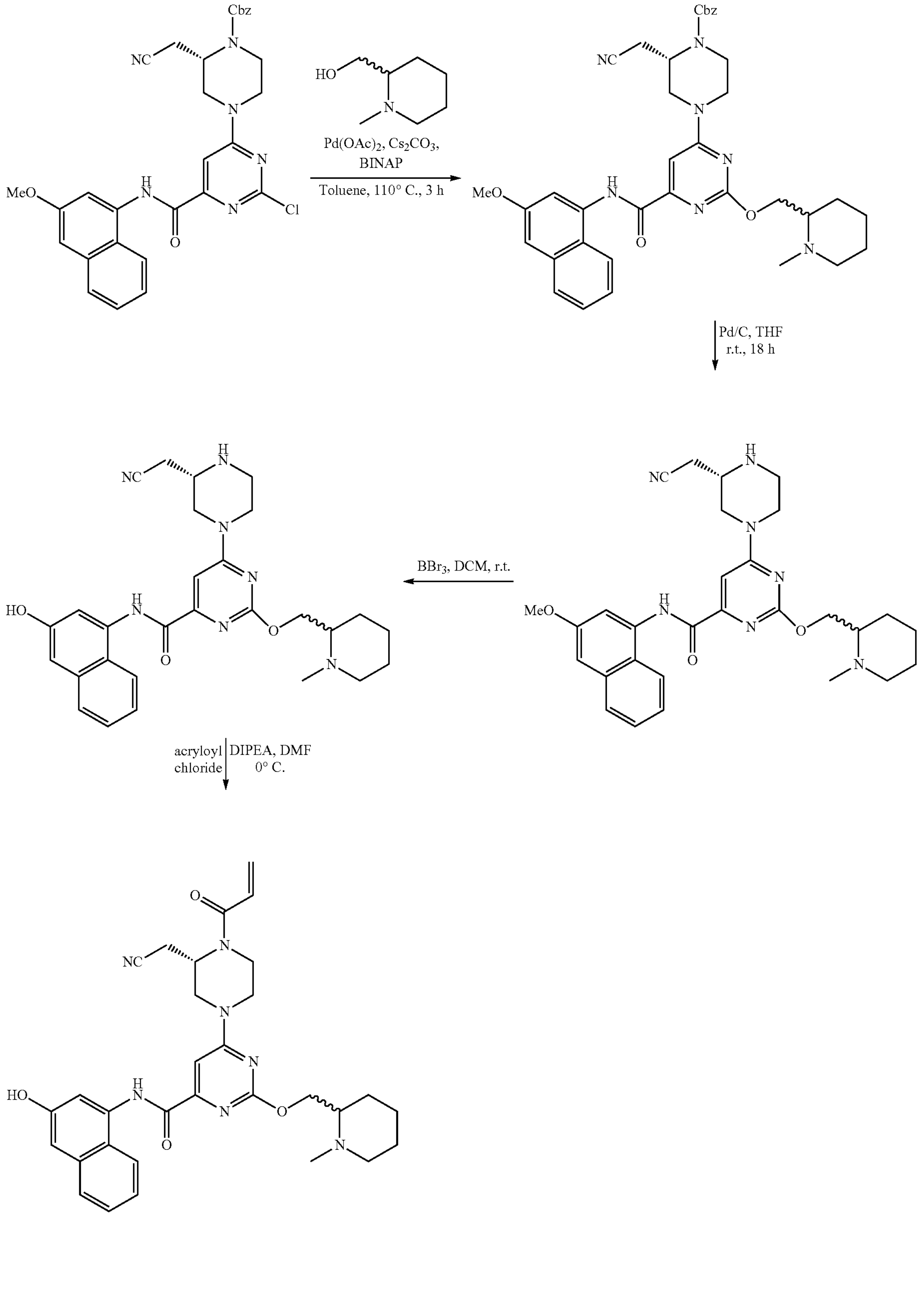

benzyl (2S)-2-(cyanomethyl)-4-[6-[(3-methoxy-1-naphthyl)carbamoyl]-2-[(1-methyl-2-piperidyl)methoxy]pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) in toluene was added (1-methyl-2-piperidyl)methanol (204 mg, 1.58 mmol, 3.0 eq), $Pd(OAc)_2$ (12 mg, 0.05 mmol, 0.1eq), $CS_2CO_3$ (513 mg, 1.58 mmol, 3.0 eq) and BINAP (65 mg, 0.10 mmol, 0.2eq) and the mixture was stirred and heated at 110° C. under $N_2$ overnight. Solvent was then removed in vacuo and the residue was dissolved in EtOAc (200 mL) and washed with brine (200 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[6-[(3-methoxy-1-naphthyl)carbamoyl]-2-[(1-methyl-2-piperidyl)methoxy]pyrimidin-4-yl]piperazine-1-carboxylate (180 mg, 52%).

UPLC-MS (ES+, Method C: 0.93 min, m/z 664.4 [M+H]+

6-[(3S)-3-(cyanomethyl)piperazin-1-yl]-N-(3-methoxy-1-naphthyl)-2-[(1-methyl-2-piperidyl)methoxy]pyrimidine-4-carboxamide Step 2

To a solution of benzyl (2S)-2-(cyanomethyl)-4-[6-[(3-methoxy-1-naphthyl)carbamoyl]-2-[(1-methyl-2-piperidyl)methoxy]pyrimidin-4-yl]piperazine-1-carboxylate (180 mg, 1.0 eq) in THF (6 mL) was added Pd/C (90 mg) and the mixture was stirred at r.t. under $H_2$ overnight. The mixture was filtered through celite and concentrated in vacuo to give 6-[(3S)-3-(cyanomethyl)piperazin-1-yl]-N-(3-methoxy-1-naphthyl)-2-[(1-methyl-2-piperidyl)methoxy]pyrimidine-4-carboxamide (143 mg, 100%).

UPLC-MS (ES+, Method E): 2.40 min, m/z 530.3 [M+H]+

6-[(3S)-3-(cyanomethyl)piperazin-1-yl]-N-(3-hydroxy-1-naphthyl)-2-[(1-methyl-2-piperidyl)methoxy]pyrimidine-4-carboxamide Step 3

To a solution of 6-[(3S)-3-(cyanomethyl)piperazin-1-yl]-N-(3-methoxy-1-naphthyl)-2-[(1-methyl-2-piperidyl)methoxy]pyrimidine-4-carboxamide (120 mg, 0.23 mmol, 1.0 eq) in dry-DCM (16 mL) was added $BBr_3$ (454 mg, 1.81 mmol, 8.0 eq), the mixture was stirred at r.t. under $N_2$ for 10 minutes and quenched by $NaHCO_3$ (aq.). The organic layer was separated, dried over sodium sulfate and purified by prep-TLC to give 6-[(3S)-3-(cyanomethyl)piperazin-1-yl]-N-(3-hydroxy-1-naphthyl)-2-[(1-methyl-2-piperidyl)methoxy]pyrimidine-4-carboxamide (60 mg, 52%).

UPLC-MS (ES+, Method E): 1.40 min, m/z 516.4 [M+H]+.

6-[(3S)-3-(cyanomethyl)-4-prop-2-enoyl-piperazin-1-yl]-N-(3-hydroxy-1-naphthyl)-2-[(1-methyl-2-piperidyl)methoxy]pyrimidine-4-carboxamide Final Step To a solution of 6-[(3S)-3-(cyanomethyl)piperazin-1-yl]-N-(3-hydroxy-1-naphthyl)-2-[(1-methyl-2-piperidyl)methoxy]pyrimidine-4-carboxamide (30 mg, 0.06 mmol, 1.0 eq) in dry-DMF (1 mL) was added acryloyl chloride (5 mg, 0.06 mmol, 1.0 eq) and N,N-diisopropylethylamine (22 mg, 0.17 mmol, 3.0 eq), the mixture was stirred at 0° C. under $N_2$ for 30 minutes. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-[(1-methyl-2-piperidyl)methoxy]pyrimidine-4-carboxamide (11 mg, 33%) as a yellow solid.

UPLC-MS (ES+, Method E): 2.63 min, m/z 570.3 $[M+H]^+$.

1H-NMR (400 MHz, DMSO-d6) δ/ppm: 10.61 (1H, s), 9.90 (1H, s), 7.80-7.74 (2H, m), 7.63-7.62 (1H, m), 7.46-7.43 (1H, m), 7.34-7.30 (1H, m), 7.21-7.14 (1H, m), 7.06 (1H, s), 6.96-7.78 (1H, m), 6.21-6.17 (1H, m), 5.80-5.77 (1H, m), 4.95-4.76 (1H, m), 4.62-4.45 (3H, m), 4.15-4.08 (1H, m), 3.60-3.51 (2H, m), 3.20-2.75 (4H, m), 2.30 (3H, s), 2.20-2.05 (1H, m), 1.80-1.70 (1H, m), 1.60-1.20 (7H, m)

Example 49

6-[(3S)-3-(cyanomethyl)-4-prop-2-enoyl-piperazin-1-yl]-N-(3-hydroxy-1-naphthyl)-2-[(1-methyl-2-piperidyl)methylamino]pyrimidine-4-carboxamide

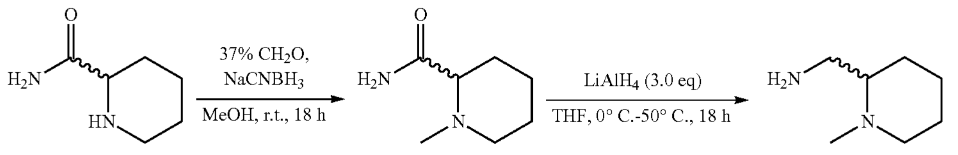

-continued
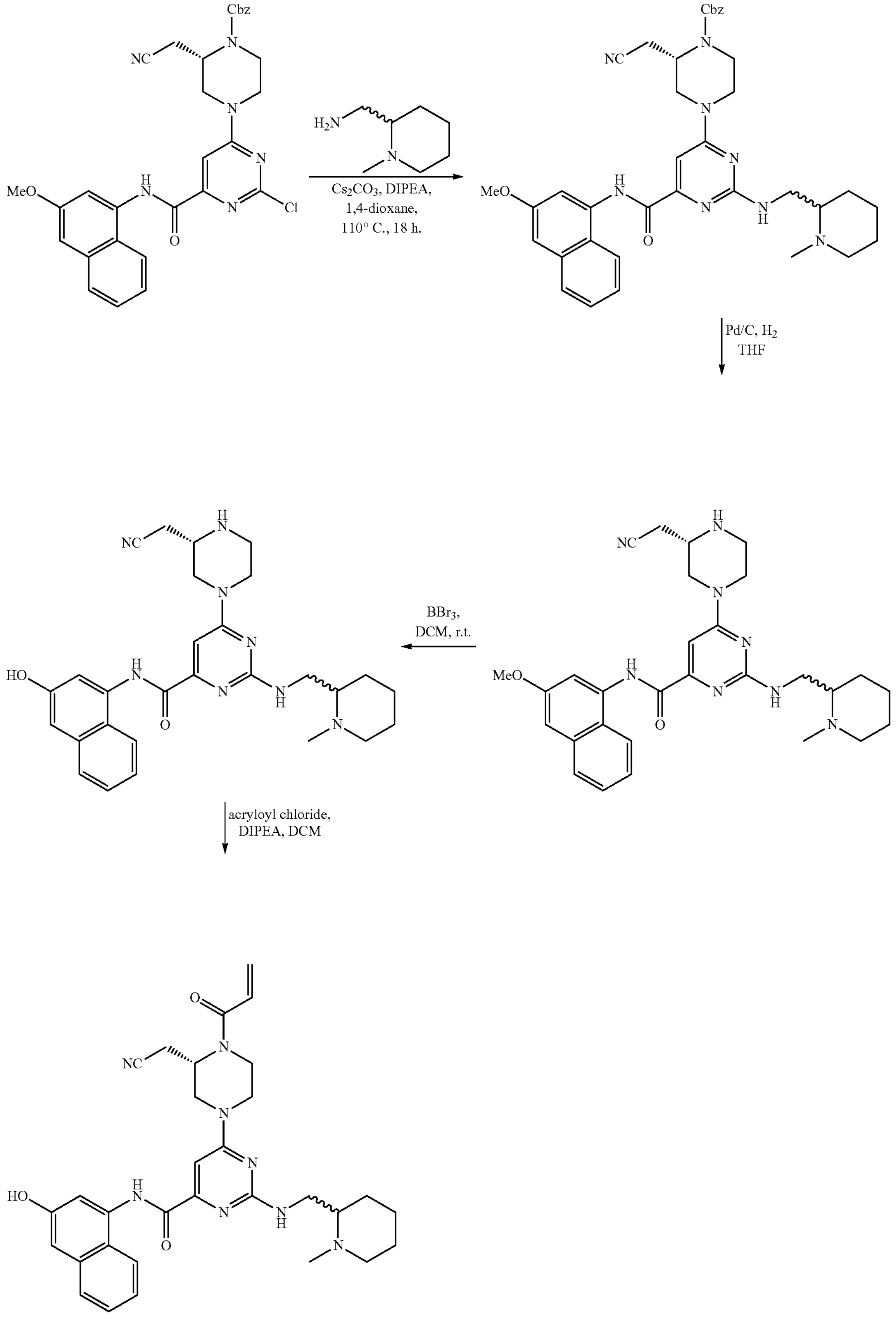

1-methylpiperidine-2-carboxamide

Intermediate Step 1

To a solution of piperidine-2-carboxamide (1.0 g, 7.80 mmol, 1.0 eq) in methanol (35 mL) was added 37% formaldehyde (585 mg, 19.5 mmol, 2.5eq), the mixture was added sodium cyanoborohydride (1.23 g, 19.5 mmol, 2.5eq) after 16 hours. The mixture was stirred at r.t. for 3 hours. Solvent was then removed in vacuo and the residue purified by column chromatography to give 1-methylpiperidine-2-carboxamide (800 mg, 73%).

UPLC-MS (ES+, Method C): 0.34 min, m/z 143.1 [M+H]+.

(1-methyl-2-piperidyl)methanamine

Intermediate Step 2

To a solution of 1-methylpiperidine-2-carboxamide (600 mg, 0.70 mmol, 1.0 eq) was added $LiAlH_4$ (1M, 12.6 mL, 3.0 eq) at 0° C. and the mixture was stirred at 50° C. under $N_2$ overnight. The reaction was quenched with a minimum amount of water, dried over sodium sulfate and concentrated in vacuo. The residue was purified by column chromatography to give 1-methylpiperidine-2-carboxamide; (170 mg, 31%).

UPLC-MS (ES+, Method C): 0.34 min, m/z 129.2 [M+H]+ benzyl (2S)-2-(cyanomethyl)-4-[6-[(3-methoxy-1-naphthyl)carbamoyl]-2-[(1-methyl-2-piperidyl)methylamino]pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl) piperazine-1-carboxylate (300 mg, 0.52 mmol, 1.0 eq) in 1,4-dioxane was added (1-methyl-2-piperidyl)methanamine (202 mg, 1.58 mmol, 3.0 eq), $Cs_2CO_3$ (512 mg, 1.58 mmol, 3.0 eq) and DIPEA (542 mg, 4.20 mmol, 8.0 eq) and the mixture was stirred and heated at 110° C. under $N_2$ overnight. Solvent was then removed in vacuo and the residue purified by column chromatography to give benzyl (2S)-2-(cyanomethyl)-4-[6-[(3-methoxy-1-naphthyl)carbamoyl]-2-[(1-methyl-2-piperidyl)methylamino]pyrimidin-4-yl]piperazine-1-carboxylate (270 mg, 77%).

UPLC-MS (ES+, Method D): 0.97 min, m/z 663.4 [M+H]+

6-[(3S)-3-(cyanomethyl)piperazin-1-yl]-N-(3-methoxy-1-naphthyl)-2-[(1-methyl-2-piperidyl) methylamino]pyrimidine-4-carboxamide Step 2

To a solution of benzyl (2S)-2-(cyanomethyl)-4-[6-[(3-methoxy-1-naphthyl)carbamoyl]-2-[(1-methyl-2-piperidyl) methylamino]pyrimidin-4-yl]piperazine-1-carboxylate (270 mg, 1.0 eq) in THF (6 mL) was added Pd/C (135 mg) and the mixture was stirred at r.t. under $H_2$ overnight. The mixture was filtered through celite and concentrated in vacuo benzyl (2S)-2-(cyanomethyl)-4-[6-[(3-methoxy-1-naphthyl)carbamoyl]-2-[(1-methyl-2-piperidyl)methylamino]pyrimidin-4-yl]piperazine-1-carboxylate (215 mg, 100%).

UPLC-MS (ES+, Method E): 2.40 min, m/z 529.4 [M+H]+

6-[(3S)-3-(cyanomethyl)piperazin-1-yl]-N-(3-hydroxy-1-naphthyl)-2-[(1-methyl-2-piperidyl)methylamino]pyrimidine-4-carboxamide Step 3

To a solution of 6-[(3S)-3-(cyanomethyl)piperazin-1-yl]-N-(3-methoxy-1-naphthyl)-2-[(1-methyl-2-piperidyl)methylamino]pyrimidine-4-carboxamide (180 mg, 0.34 mmol, 1.0 eq) in dry-DCM (25 mL) was added $BBr_3$ (512 mg, 2.04 mmol, 6.0 eq), the mixture was stirred at r.t. under $N_2$ for 10 minutes and quenched by $NaHCO_3$ (aq.). The organic layer was separated, dried over sodium sulfate and purified by prep-TLC to give 6-[(3S)-3-(cyanomethyl)piperazin-1-yl]-N-(3-hydroxy-1-naphthyl)-2-[(1-methyl-2-piperidyl)methylamino]pyrimidine-4-carboxamide (90 mg, 51%).

UPLC-MS (ES+, Method E): 1.40 min, m/z 515.3 [M+H]+

6-[(3S)-3-(cyanomethyl)-4-prop-2-enoyl-piperazin-1-yl]-N-(3-hydroxy-1-naphthyl)-2-[(1-methyl-2-piperidyl)methylamino]pyrimidine-4-carboxamide Final Step To a solution of 6-[(3S)-3-(cyanomethyl)piperazin-1-yl]-N-(3-hydroxy-1-naphthyl)-2-[(1-methyl-2-piperidyl)methylamino]pyrimidine-4-carboxamide (50 mg, 0.10 mmol, 1.0 eq) in dry-DMF was added acryloyl chloride (9 mg, 0.10 mmol, 1.0 eq) and N,N-diisopropylethylamine (38 mg, 0.29 mmol, 3.0 eq), the mixture was stirred at 0° C. under $N_2$ for 30 minutes. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-[(1-methyl-2-piperidyl)methylamino] pyrimidine-4-carboxamide (15 mg, 27%) as a yellow solid.

UPLC-MS (ES+, Method E): 2.77 min, m/z 569.3 $[M+H]^+$.

1H-NMR (400 MHz, DMSO-d6) δ/ppm: 10.72 (1H, s), 9.84 (1H, s), 7.90 (2H, s), 7.75-7.73 (1H, m), 7.48-7.44 (1H, m), 7.37-7.34 (1H, m), 7.02 (1H, s), 6.98-6.75 (3H, m), 6.21-6.17 (1H, m), 5.79-5.76 (1H, m), 4.91-4.77 (1H, m), 4.49-4.02 (3H, m), 4.28-4.24 (1H, m), 3.19 (3H, s), 2.92-2.77 (3H, m), 2.40-2.02 (5H, m), 1.76-1.64 (2H, m), 1.52-1.11 (5H, m).

Example 50
6-[(3S)-3-(cyanomethyl)-4-prop-2-enoyl-piperazin-1-yl]-N-(3-hydroxy-1-naphthyl)-2-[(1-methyl-3-piperidyl)methoxy]pyrimidine-4-carboxamide
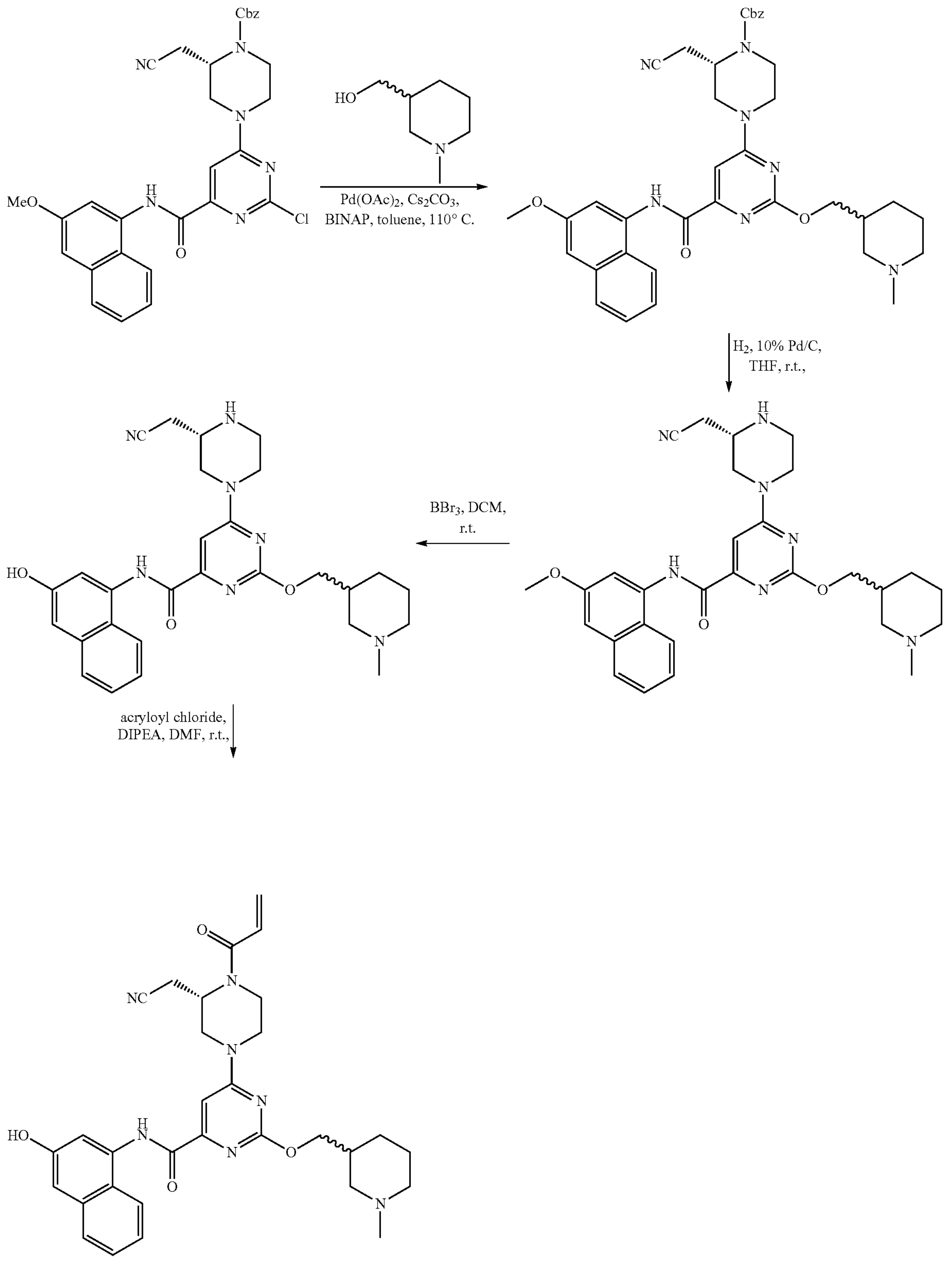

benzyl (2S)-2-(cyanomethyl)-4-[6-[(3-methoxy-1-naphthyl)carbamoyl]-2-[(1-methyl-3-piperidyl)methoxy]pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) in toluene was added 3-(hydroxymethyl)-1-methylpiperidine (204 mg, 1.58 mmol, 3.0 eq), $Pd(OAc)_2$ (12 mg, 0.05 mmol, 0.1eq), $Cs_2CO_3$ (513 mg, 1.58 mmol, 3.0 eq) and BINAP (65 mg, 0.10 mmol, 0.2eq) and the mixture was stirred and heated at 110° C. under $N_2$ overnight. Solvent was then removed in vacuo and the residue purified by column chromatography to give benzyl (2S)-2-(cyanomethyl)-4-[6-[(3-methoxy-1-naphthyl)carbamoyl]-2-[(1-methyl-3-piperidyl)methoxy]pyrimidin-4-yl]piperazine-1-carboxylate (160 mg, 46%).

UPLC-MS (ES+, Method C): 0.67 min, m/z 664.4 [M+H]+

6-[(3S)-3-(cyanomethyl)piperazin-1-yl]-N-(3-methoxy-1-naphthyl)-2-[(1-methyl-3-piperidyl)methoxy]pyrimidine-4-carboxamide Step 2

To a solution of benzyl (2S)-2-(cyanomethyl)-4-[6-[(3-methoxy-1-naphthyl)carbamoyl]-2-[(1-methyl-3-piperidyl)methoxy]pyrimidin-4-yl]piperazine-1-carboxylate (160 mg, 1.0 eq) in THF (6 mL) was added Pd/C (80 mg) and the mixture was stirred at r.t under $H_2$ overnight. The mixture was filtered through celite and concentrated in vacuo to give 6-[(3S)-3-(cyanomethyl)piperazin-1-yl]-N-(3-methoxy-1-naphthyl)-2-[(1-methyl-3-piperidyl)methoxy]pyrimidine-4-carboxamide (127 mg, 100%).

UPLC-MS (ES+, Method E): 2.40 min, m/z 530.5 [M+H]+

6-[(3S)-3-(cyanomethyl)piperazin-1-yl]-N-(3-hydroxy-1-naphthyl)-2-[(1-methyl-3-piperidyl)methoxy]pyrimidine-4-carboxamide Step 3

To a solution of 6-[(3S)-3-(cyanomethyl)piperazin-1-yl]-N-(3-methoxy-1-naphthyl)-2-[(1-methyl-3-piperidyl)methoxy]pyrimidine-4-carboxamide (110 mg, 0.21 mmol, 1.0 eq) in dry-DCM was added $BBr_3$ (416 mg, 1.66 mmol, 8.0 eq), the mixture was stirred at r.t under $N_2$ for 10 minutes and quenched by $NaHCO_3$ (aq.). The organic layer was separated, dried over sodium sulfate and purified by prep-TLC to give 6-[(3S)-3-(cyanomethyl)piperazin-1-yl]-N-(3-methoxy-1-naphthyl)-2-[(1-methyl-3-piperidyl)methoxy]pyrimidine-4-carboxamide (40 mg, 37%).

UPLC-MS (ES+, Method E): 1.57 min, m/z 516.4 [M+H]+

6-[(3S)-3-(cyanomethyl)-4-prop-2-enoyl-piperazin-1-yl]-N-(3-hydroxy-1-naphthyl)-2-[(1-methyl-3-piperidyl)methoxy]pyrimidine-4-carboxamide Final Step To a solution of 6-[(3S)-3-(cyanomethyl)piperazin-1-yl]-N-(3-hydroxy-1-naphthyl)-2-[(1-methyl-3-piperidyl)methoxy]pyrimidine-4-carboxamide (30 mg, 0.06 mmol, 1.0 eq) in dry-DMF (2 mL) was added Acryloyl chloride (5 mg, 0.06 mmol, 1.0 eq) and N,N-diisopropylethylamine (22 mg, 0.17 mmol, 3.0 eq), the mixture was stirred at 0° C. under $N_2$ for 30 minutes. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-[(1-methyl-3-piperidyl)methoxy]pyrimidine-4-carboxamide (8 mg, 24%).

UPLC-MS (ES+, Method E): 2.63 min, m/z 570.4 [M+H]+.

1H-NMR (400 MHz, DMSO-d6) δ/ppm: 10.62 (1H, s), 9.90 (1H, s), 7.80-7.74 (2H, m), 7.66 (1H, s), 7.47-7.43 (1H, m), 7.35-7.31 (1H, m), 7.18-7.12 (1H, m), 7.05 (1H, s), 6.96-6.78 (1H, m), 6.22-6.17 (1H, m), 5.80-5.77 (1H, m), 4.95-4.72 (1H, m), 4.48-4.02 (4H, m), 3.62-3.45 (1H, m), 3.14-2.75 (5H, m), 2.72-2.65 (1H, m), 2.21 (3H, s), 2.20-2.14 (1H, m), 1.97-1.45 (6H, m), 1.16-1.04 (1H, m).

Example 51

6-[(3S)-3-(cyanomethyl)-4-prop-2-enoyl-piperazin-1-yl]-2-[[(2S)-1-ethylpyrrolidin-2-yl]methoxy]-N-(3-hydroxy-1-naphthyl)pyrimidine-4-carboxamide

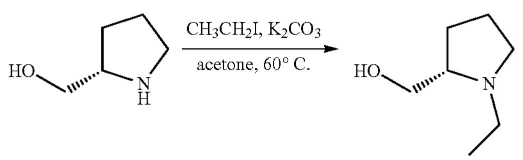

-continued
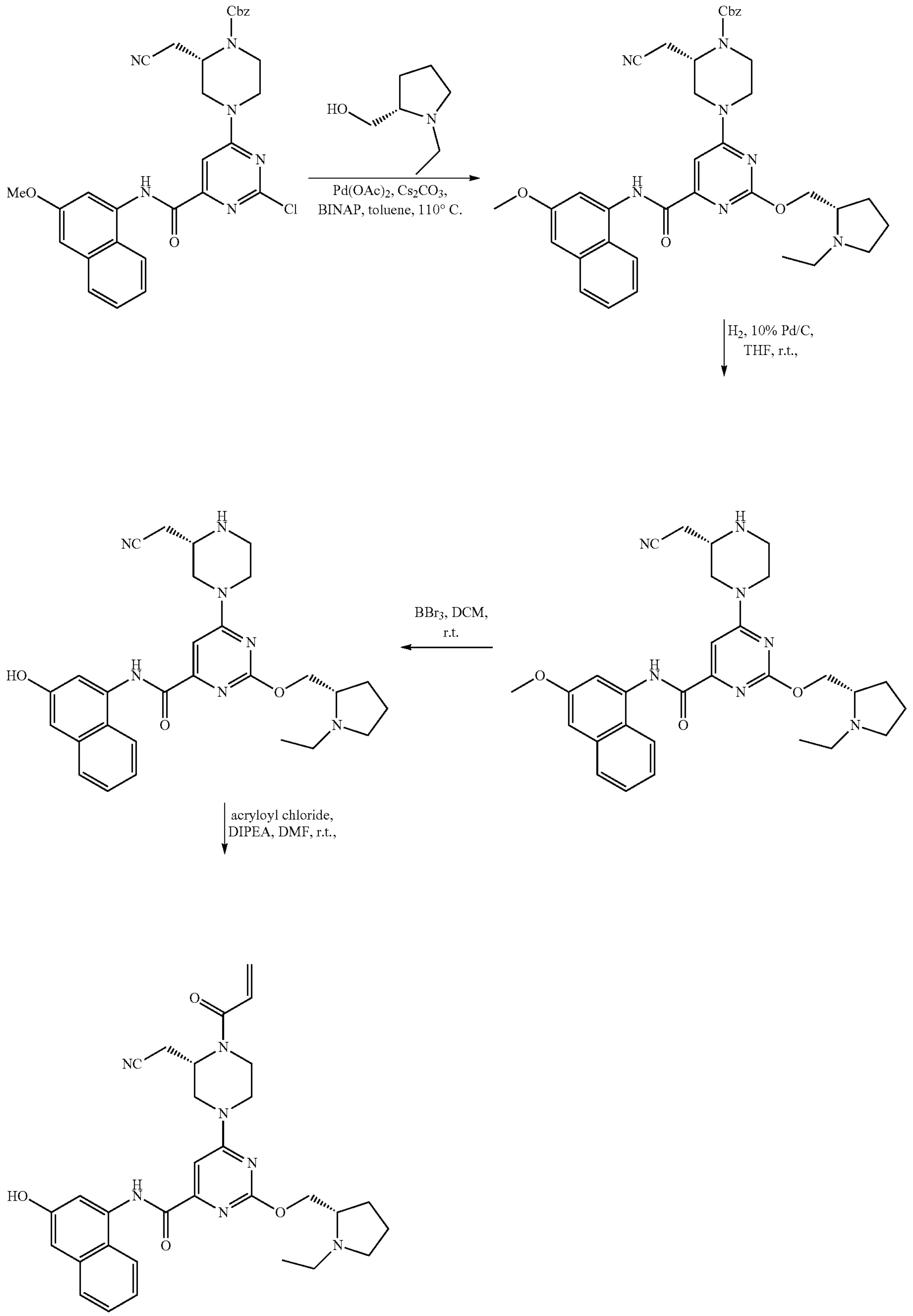

[(2S)-1-ethylpyrrolidin-2-yl]methanol

Intermediate Step 1

To [(2S)-pyrrolidin-2-yl]methanol (1.0 g, 9.89 mmol, 1.0 eq) was added acetone (50 mL) followed by the addition of Iodoethane (7.71 g, 49.43 mmol, 5.0 eq) and $K_2CO_3$ (4.09 g, 29.66 mmol, 3.0 eq). The reaction was stirred at 60° C. overnight. The solvent was then removed in vacuo and the residue purified by column chromatography using an eluent of 0-5% MeOH in DCM reached via a gradient to give [(2S)-1-ethylpyrrolidin-2-yl]methanol (350 mg, 27%).

UPLC-MS (ES+, Method C): 0.33 min, m/z 130.2 [M+H]+ benzyl (2S)-2-(cyanomethyl)-4-[2-[[(2S)-1-ethylpyrrolidin-2-yl]methoxy]-6-[(3-methoxy-1-naphthyl)carbamoyl]pyrimidin-4-yl]piperazine-1-carboxylate Step 1

To benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) was added toluene (10 mL) followed by the addition of [(2S)-1-ethylpyrrolidin-2-yl]methanol (340 mg, 2.63 mmol, 5.0 eq), $Cs_2CO_3$ (513 mg, 1.58 mmol, 3.0 eq), $Pd(OAc)_2$ (12 mg, 0.052 mmol, 0.1eq) and BINAP (65 mg, 0.11 mmol, 0.2eq). The reaction was stirred at 110° C. overnight. Solvent was then removed in vacuo and the residue was dissolved in EtOAc (300 mL) and washed with brine (300 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[2-[[(2S)-1-ethylpyrrolidin-2-yl]methoxy]-6-[(3-methoxy-1-naphthyl)carbamoyl]pyrimidin-4-yl]piperazine-1-carboxylate (300 mg, 86%).

UPLC-MS (ES+, Method A): 1.13 min, m/z 664.3 [M+H]+

6-[(3S)-3-(cyanomethyl)piperazin-1-yl]-2-[[(2S)-1-ethylpyrrolidin-2-yl]methoxy]-N-(3-methoxy-1-naphthyl)pyrimidine-4-carboxamide Step 2

Benzyl (2S)-2-(cyanomethyl)-4-[2-[[(2S)-1-ethylpyrrolidin-2-yl]methoxy]-6-[(3-methoxy-1-naphthyl)carbamoyl]pyrimidin-4-yl]piperazine-1-carboxylate (300 mg, 0.45 mmol, 1.0 eq) was dissolved in THF (30 mL) followed by the addition of palladium, 10 wt. % on carbon powder, (150 mg, 4.52 mmol, 10.0 eq) under a nitrogen atmosphere. The reaction was fitted with a $H_2$ balloon and subjected to 3×vacuum/$H_2$ cycles and then left to stir under an $H_2$ atmosphere for 12 hours. The reaction was filtered through celite, washed with DCM (200 mL) and solvent removed in vacuo to give 6-[(3S)-3-(cyanomethyl)piperazin-1-yl]-2-[[(2S)-1-ethylpyrrolidin-2-yl]methoxy]-N-(3-methoxy-1-naphthyl)pyrimidine-4-carboxamide (239 mg, 100%).

UPLC-MS (ES+, Method B): 1.01 min, m/z 530.3 [M+H]+

6-[(3S)-3-(cyanomethyl)piperazin-1-yl]-2-[[(2S)-1-ethylpyrrolidin-2-yl]methoxy]-N-(3-hydroxy-1-naphthyl)pyrimidine-4-carboxamide Step 3

6-[(3S)-3-(cyanomethyl)piperazin-1-yl]-2-[[(2S)-1-ethylpyrrolidin-2-yl]methoxy]-N-(3-methoxy-1-naphthyl)pyrimidine-4-carboxamide (240 mg, 0.45 mmol, 1.0 eq) was dissolved in DCM (10 mL) followed by the addition of boron tribromide (0.3 mL). After 5 mins, MeOH (10 mL) was added and solvent removed in vacuo. The residue was purified by column chromatography using an eluent of 0-10% MeOH in DCM reached via a gradient to give 6-[(3S)-3-(cyanomethyl)piperazin-1-yl]-2-[[(2S)-1-ethylpyrrolidin-2-yl]methoxy]-N-(3-hydroxy-1-naphthyl)pyrimidine-4-carboxamide (70 mg, 30%).

UPLC-MS (ES+, Method C): 1.49 min, m/z 516.3 [M+H]+

6-[(3S)-3-(cyanomethyl)-4-prop-2-enoyl-piperazin-1-yl]-2-[[(2S)-1-ethylpyrrolidin-2-yl]methoxy]-N-(3-hydroxy-1-naphthyl)pyrimidine-4-carboxamide Final Step Acryloyl chloride (9 mg, 0.10 mmol, 1.0 eq) and 6-[(3S)-3-(cyanomethyl)piperazin-1-yl]-2-[[(2S)-1-ethylpyrrolidin-2-yl]methoxy]-N-(3-hydroxy-1-naphthyl)pyrimidine-4-carboxamide (50 mg, 0.10 mmol, 1.0 eq) were dissolved in DMF (3 mL) followed by the addition of DIPEA (38 mg, 0.30 mmol, 3.0 eq). Water (50 mL) and DCM (50 mL) was then added and the organic layer separated, dried over $Na_2SO_4$ and solvent removed in vacuo. The residue was purified by column chromatography using an eluent of 0-10% MeOH in DCM reached via a gradient to give 6-[(3S)-3-(cyanomethyl)-4-prop-2-enoyl-piperazin-1-yl]-2-[[(2S)-1-ethylpyrrolidin-2-yl]methoxy]-N-(3-hydroxy-1-naphthyl)pyrimidine-4-carboxamide (25 mg, 45%)

UPLC-MS (ES+, Method C): 1.83 min, m/z 570.3 [M+H]+.

1H-NMR (400 MHz, DMSO-d6) δ/ppm: 10.62 (1H, s), 9.88 (1H, s), 7.80-7.73 (2H, m), 7.63 (1H, s), 7.47-7.43 (1H, m), 7.34-7.30 (1H, m), 7.17-7.12 (1H, m), 7.05 (1H, s), 6.95-6.79 (1H, m), 6.22-6.17 (1H, m), 5.80-5.77 (1H, m), 4.95-4.72 (1H, m), 4.48-4.02 (5H, m), 3.60-3.46 (1H, m), 3.10-2.77 (7H, m), 2.32-2.26 (1H, m), 2.20-2.15 (1H, m), 1.97-1.83 (1H, m), 1.74-1.63 (3H, m), 1.04 (3H, t, J=7.2 Hz).

Example 52
6-[(3S)-3-(cyanomethyl)-4-prop-2-enoyl-piperazin-1-yl]-N-(3-hydroxy-1-naphthyl)-2-[[(2R)-4-methyl-morpholin-2-yl]methoxy]pyrimidine-4-carboxamide
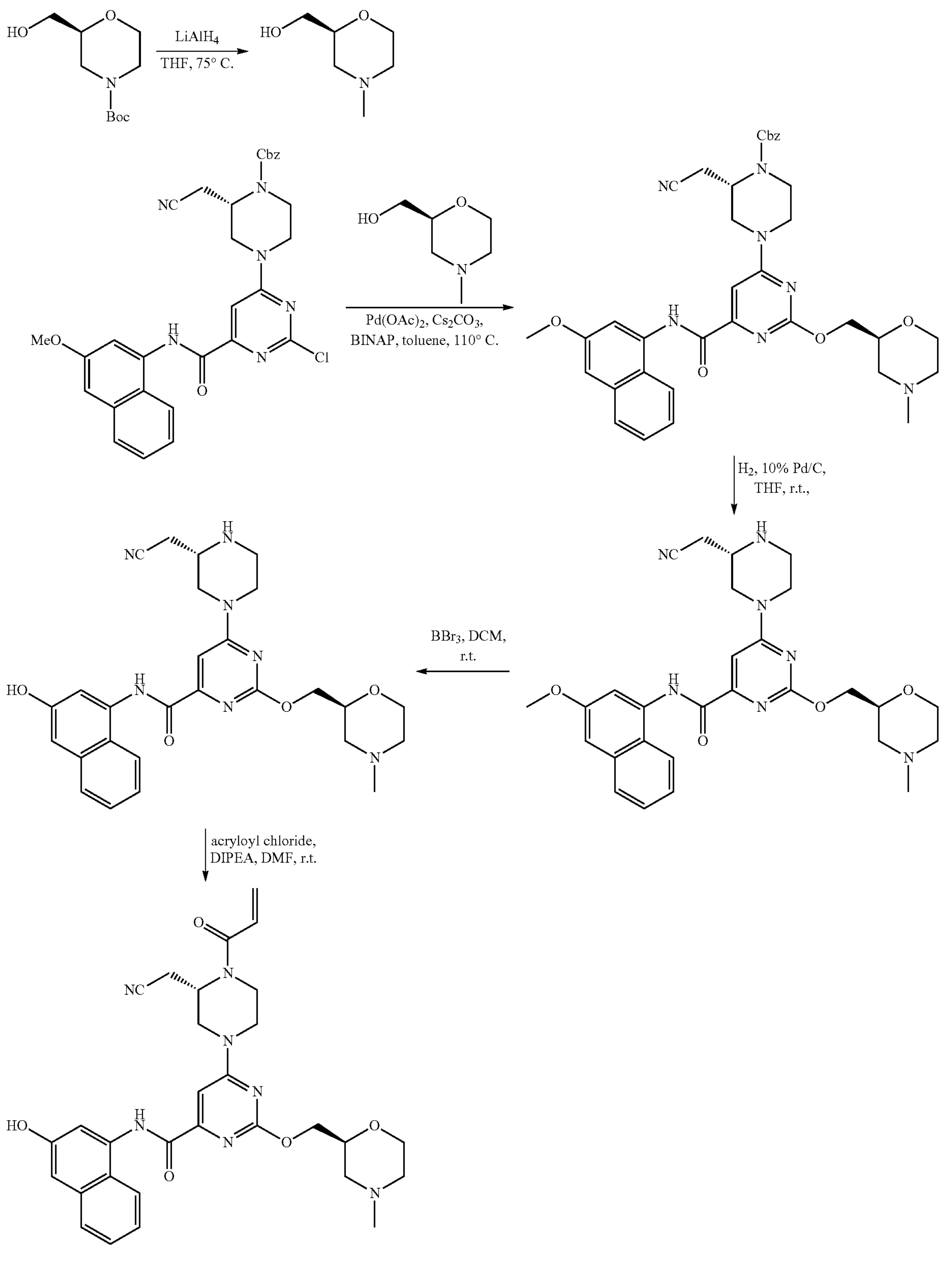

[(2R)-4-methylmorpholin-2-yl]methanol

Intermediate Step 1

To a solution of tert-butyl-(2R)-2-(hydroxymethyl)morpholin-4-carboxylat (730 mg, 3.36 mmol, 1.0 eq) was added $LiAlH_4$ (1M, 10.1 mL, 3.0 eq) at 0° C. and the mixture was stirred at 75° C. under $N_2$ overnight. The reaction was then quenched with the minimum amount of water, dried over sodium sulfate and solvent removed in vacuo. The residue was purified by column chromatography to give [(2R)-4-methylmorpholin-2-yl]methanol (340 mg, 77%).

UPLC-MS (ES+, Method C): 1.40 min, m/z 132.1 [M+H]+ benzyl (2S)-2-(cyanomethyl)-4-[6-[(3-methoxy-1-naphthyl)carbamoyl]-2-[[(2R)-4-methylmorpholin-2-yl]methoxy]pyrimidin-4-yl]piperazine-1-carboxylate Step 1

To a solution of benzyl (2S)-4-[2-chloro-6-[(3-methoxy-1-naphthyl)carbamoyl]pyrimidin-4-yl]-2-(cyanomethyl) piperazine-1-carboxylate (300 mg, 0.52 mmol, 1.0 eq) in toluene was added [(2R)-4-methylmorpholin-2-yl]methanol (207 mg, 1.58 mmol, 3.0 eq), $Pd(OAc)_2$ (12 mg, 0.05 mmol, 0.1eq), $Cs_2CO_3$ (513 mg, 1.58 mmol, 3.0 eq) and BINAP (65 mg, 0.10 mmol, 0.2eq) and the mixture was stirred and heated at 110° C. under $N_2$ overnight. Solvent was then removed in vacuo and the residue purified by column chromatography to give benzyl (2S)-2-(cyanomethyl)-4-[6-[(3-methoxy-1-naphthyl)carbamoyl]-2-[[(2R)-4-methylmorpholin-2-yl]methoxy]pyrimidin-4-yl]piperazine-1-carboxylate (250 mg, 71%).

UPLC-MS (ES+, Method D): 0.67 min, m/z 666.4 [M+H]+

6-[(3S)-3-(cyanomethyl)piperazin-1-yl]-N-(3-methoxy-1-naphthyl)-2-[[(2R)-4-methylmorpholin-2-yl]methoxy]pyrimidine-4-carboxamide Step 2

To a solution of benzyl (2S)-2-(cyanomethyl)-4-[6-[(3-methoxy-1-naphthyl)carbamoyl]-2-[[(2R)-4-methylmorpholin-2-yl]methoxy]pyrimidin-4-yl]piperazine-1-carboxylate (250 mg, 1.0 eq) in THF (6 mL) was added Pd/C (125 mg) and the mixture was stirred at r.t. under $H_2$ overnight. The reaction mixture was then filtered through celite and concentrated in vacuo to give 6-[(3S)-3-(cyanomethyl)piperazin-1-yl]-N-(3-methoxy-1-naphthyl)-2-[[(2R)-4-methylmorpholin-2-yl]methoxy]pyrimidine-4-carboxamide (190 mg, 95%)

UPLC-MS (ES+, Method E): 2.30 min, m/z 532.3 [M+H]+.

6-[(3S)-3-(cyanomethyl)piperazin-1-yl]-N-(3-hydroxy-1-naphthyl)-2-[[(2R)-4-methylmorpholin-2-yl]methoxy]pyrimidine-4-carboxamide Step 3

To a solution of 6-[(3S)-3-(cyanomethyl)piperazin-1-yl]-N-(3-methoxy-1-naphthyl)-2-[[(2R)-4-methylmorpholin-2-yl]methoxy]pyrimidine-4-carboxamide (155 mg, 0.29 mmol, 1.0 eq) in dry-DCM (20 mL) was added $BBr_3$ (438 mg, 1.75 mmol, 6.0 eq), the mixture was stirred at r.t. under $N_2$ for 10 minutes and quenched by $NaHCO_3$ (aq.). The organic layer was separated, dried over sodium sulfate and purified by prep-TLC to give 6-[(3S)-3-(cyanomethyl)piperazin-1-yl]-N-(3-hydroxy-1-naphthyl)-2-[[(2R)-4-methylmorpholin-2-yl]methoxy]pyrimidine-4-carboxamide (60 mg, 40%).

UPLC-MS (ES+, Method E): 1.10 min, m/z 518.3 [M+H]+

6-[(3S)-3-(cyanomethyl)-4-prop-2-enoyl-piperazin-1-yl]-N-(3-hydroxy-1-naphthyl)-2-[[(2R)-4-methylmorpholin-2-yl]methoxy]pyrimidine-4-carboxamide Final Step To a solution of 6-[(3S)-3-(cyanomethyl)piperazin-1-yl]-N-(3-hydroxy-1-naphthyl)-2-[[(2R)-4-methylmorpholin-2-yl]methoxy]pyrimidine-4-carboxamide (40 mg, 0.08 mmol, 1.0 eq) in dry-DMF (2 mL) was added acryloyl chloride (7 mg, 0.08 mmol, 1.0 eq) and N,N-diisopropylethylamine (30 mg, 0.23 mmol, 3.0 eq), the mixture was stirred at 0° C. under $N_2$ for 30 minutes. Solvent was then removed in vacuo and the residue purified by column chromatography to give 6-[(3S)-3-(cyanomethyl)-4-prop-2-enoyl-piperazin-1-yl]-N-(3-hydroxy-1-naphthyl)-2-[[(2R)-4-methylmorpholin-2-yl] methoxy]pyrimidine-4-carboxamide (16 mg, 36%).

UPLC-MS (ES+, Method E): 2.63 min, m/z 572.3 [M+H]+.

1H-NMR (400 MHz, DMSO-d6) δ/ppm: 10.61 (1H, s), 9.89 (1H, s), 7.80-7.74 (2H, m), 7.61 (1H, s), 7.47-7.43 (1H, m), 7.36-7.32 (1H, m), 7.17-7.13 (1H, m), 7.06 (1H, s), 6.96-6.80 (1H, m), 6.21-6.17 (1H, m), 5.80-5.77 (1H, m), 4.93-4.76 (1H, m), 4.52-4.30 (4H, m), 4.12-4.03 (1H, m), 3.88-3.82 (2H, m), 3.59-3.35 (3H, m), 3.20-2.83 (4H, m), 2.72-2.68 (1H, m), 2.23 (3H, s), 2.20-1.95 (2H, m).

Example 53

6-[(3S)-3-(cyanomethyl)-4-prop-2-enoyl-piperazin-1-yl]-2-[[(2S)-1-(2-hydroxyethyl)pyrrolidin-2-yl] methoxy]-N-(3-hydroxy-1-naphthyl)pyrimidine-4-carboxamide

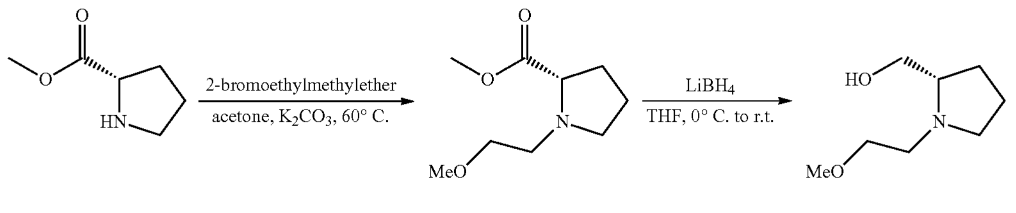

-continued
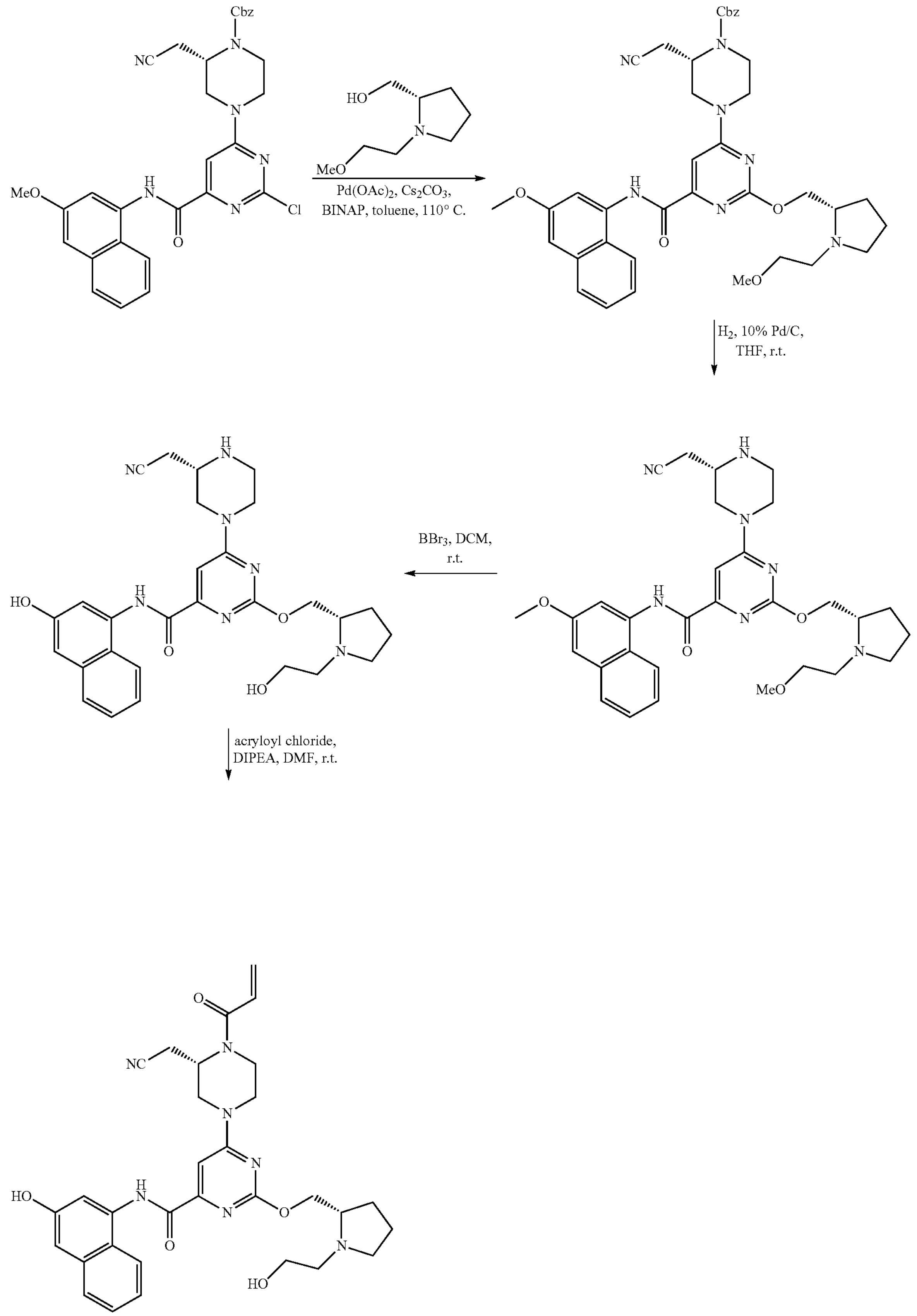

methyl (2S)-1-(2-methoxyethyl)pyrrolidine-2-carboxylate

Intermediate Step 1

To methyl (2S)-pyrrolidine-2-carboxylate (1 g, 7.74 mmol, 1.0 eq) was added acetone (20 mL) followed by the addition of 2-bromoethyl methyl ether (2.15 g, 15.48 mmol, 2.0 eq) and $K_2CO_3$ (3.20 g, 23.23 mmol, 3.0 eq). The reaction was stirred at 60° C. for overnight. Solvent was then removed in vacuo. The residue was purified by column chromatography using an eluent of 0-5% MeOH in DCM reached via a gradient to give methyl (2S)-1-(2-methoxyethyl)pyrrolidine-2-carboxylate (800 mg, 55%).

UPLC-MS (ES+, Method C): 2.63 min, m/z 572.3 [M+H]+.

[(2S)-1-(2-methoxyethyl)pyrrolidin-2-yl]methanol

Intermediate Step 2 methyl (2S)-1-(2-methoxyethyl)pyrrolidine-2-carboxylate (600 mg, 3.20 mmol, 1.0 eq) was dissolved in THF (20 mL). The reaction was stirred at 0° C., then $LiBH_4$ (2M in THF) (6 mL, 12.82 mmol, 4.0 eq) was added slowly. The reaction was left stirring overnight. MeOH (5 mL) was added and solvent removed in vacuo. The residue was purified by column chromatography using an eluent of 0-10% MeOH in DCM reached via a gradient to give [(2S)-1-(2-methoxyethyl)pyrrolidin-2-yl]methanol (250 mg, 50%).

UPLC-MS (ES+, Method C): 0.34 min, m/z 160.1 [M+H]+.

benzyl (2S)-2-(cyanomethyl)-4-[2-[[(2S)-1-(2-methoxyethyl)pyrrolidin-2-yl]methoxy]-6-[(3-methoxy-1-naphthyl)carbamoyl]pyrimidin-4-yl]piperazine-1-carboxylate Step 1:

To benzyl (2S)-4-[2-chloro-6-[(3-methoxy-1-naphthyl)carbamoyl]pyrimidin-4-yl]-2-(cyanomethyl)piperazine-1-carboxylate (300 mg, 0.52 mmol, 1.0 eq) was added toluene (10 mL) followed by the addition of [(2S)-1-(2-methoxyethyl)pyrrolidin-2-yl]methanol (251 mg, 1.58 mmol, 3.0 eq), $Cs_2CO_3$ (513 mg, 1.58 mmol, 3.0 eq), $Pd(OAc)_2$ (12 mg, 0.05 mmol, 0.1eq) and BINAP (65 mg, 0.11 mmol, 0.2eq). The reaction was stirred at 110° C. for 3 h. Solvent was then removed in vacuo and the residue was dissolved in EtOAc (300 mL) and washed with brine (300 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[2-[[(2S)-1-(2-methoxyethyl)pyrrolidin-2-yl]methoxy]-6-[(3-methoxy-1-naphthyl)carbamoyl]pyrimidin-4-yl]piperazine-1-carboxylate (200 mg, 55%).

UPLC-MS (ES+, Method A): 1.11 min, m/z 694.2 [M+H]+.

6-[(3S)-3-(cyanomethyl)piperazin-1-yl]-2-[[(2S)-1-(2-methoxyethyl)pyrrolidin-2-yl]methoxy]-N-(3-methoxy-1-naphthyl)pyrimidine-4-carboxamide Step 2 benzyl (2S)-2-(cyanomethyl)-4-[2-[[(2S)-1-(2-methoxyethyl)pyrrolidin-2-yl]methoxy]-6-[(3-methoxy-1-naphthyl)carbamoyl]pyrimidin-4-yl]piperazine-1-carboxylate (200 mg, 0.29 mmol, 1.0 eq) was dissolved in THF (20 mL) followed by the addition of palladium, 10 wt. % on carbon powder (100 mg, 2.88 mmol, 10.0 eq) under a nitrogen atmosphere. The reaction was fitted with a $H_2$ balloon and subjected to 3×vacuum/$H_2$ cycles and then left to stir under an $H_2$ atmosphere for 12 hours. The reaction was then filtered through celite, washed with DCM (300 mL) and solvent removed in vacuo to give 6-[(3S)-3-(cyanomethyl)piperazin-1-yl]-2-[[(2S)-1-(2-methoxyethyl)pyrrolidin-2-yl]methoxy]-N-(3-methoxy-1-naphthyl)pyrimidine-4-carboxamide (161 mg, 100%).

UPLC-MS (ES+, Method B): 0.32 min, m/z 560.3 [M+H]+.

6-[(3S)-3-(cyanomethyl)piperazin-1-yl]-2-[[(2S)-1-(2-hydroxyethyl)pyrrolidin-2-yl]methoxy]-N-(3-hydroxy-1-naphthyl)pyrimidine-4-carboxamide Step 3

6-[(3S)-3-(cyanomethyl)piperazin-1-yl]-2-[[(2S)-1-(2-methoxyethyl)pyrrolidin-2-yl]methoxy]-N-(3-methoxy-1-naphthyl)pyrimidine-4-carboxamide (160 mg, 0.28 mmol, 1.0 eq) was dissolved in DCM (10 mL) followed by the addition of boron tribromide (0.17 mL). After 5 mins, MeOH (10 mL) was added and solvent removed in vacuo. The residue was purified by column chromatography using an eluent of 0-10% MeOH in DCM reached via a gradient to give 6-[(3S)-3-(cyanomethyl)piperazin-1-yl]-2-[[(2S)-1-(2-hydroxyethyl)pyrrolidin-2-yl]methoxy]-N-(3-hydroxy-1-naphthyl)pyrimidine-4-carboxamide (60 mg, 39%).

UPLC-MS (ES+, Method B): 0.39 min, m/z 532.3 [M+H]+.

6-[(3S)-3-(cyanomethyl)-4-prop-2-enoyl-piperazin-1-yl]-2-[[(2S)-1-(2-hydroxyethyl)pyrrolidin-2-yl]methoxy]-N-(3-hydroxy-1-naphthyl)pyrimidine-4-carboxamide Final Step Acryloyl chloride (5 mg, 0.06 mmol, 1.0 eq) and 6-[(3S)-3-(cyanomethyl)piperazin-1-yl]-2-[[(2S)-1-(2-hydroxyethyl)pyrrolidin-2-yl]methoxy]-N-(3-hydroxy-1-naphthyl)pyrimidine-4-carboxamide (30 mg, 0.06 mmol, 1.0 eq) were dissolved in DMF (2 mL) followed by the addition of DIPEA (22 mg, 0.17 mmol, 3.0 eq). The reaction was left stirring for 5 min. Water (50 mL) and DCM (50 mL) were then added and the organic layer separated, dried over $Na_2SO_4$ and solvent removed in vacuo. The residue was purified by column chromatography using an eluent of 0-10% MeOH in DCM reached via a gradient to give 6-[(3S)-3-(cyanomethyl)-4-prop-2-enoyl-piperazin-1-yl]-2-[[(2S)-1-(2-hydroxyethyl)pyrrolidin-2-yl]methoxy]-N-(3-hydroxy-1-naphthyl)pyrimidine-4-carboxamide (10 mg, 30%).

UPLC-MS (ES+, Method C): 1.82 min, m/z 586.3 [M+H]+.

1H-NMR (400 MHz, DMSO-d6) δ/ppm: 10.64 (1H, s), 9.89 (1H, s), 7.81-7.74 (2H, m), 7.67-7.64 (1H, m), 7.49-7.44 (1H, m), 7.38-7.33 (1H, m), 7.23-7.14 (1H, m), 7.09-7.06 (1H, m), 6.93-6.82 (1H, m), 6.25-6.17 (1H, m), 5.83-5.76 (1H, m), 5.00-4.73 (1H, m), 4.51-4.29 (3H, m), 4.29-4.21 (2H, m), 4.15-4.04 (1H, m), 3.59-3.40 (3H, m), 3.15-2.88 (6H, m), 2.51-2.44 (1H, m), 2.35-2.25 (1H, m), 2.03-1.89 (1H, m), 1.78-1.62 (3H, m), 1×exchangeable H not seen.

Example 54
6-[(3S)-3-(cyanomethyl)-4-prop-2-enoyl-piperazin-1-yl]-N-(3-hydroxy-1-naphthyl)-2-[[(2S)-1-isopropylpyrrolidin-2-yl]methoxy]pyrimidine-4-carboxamide
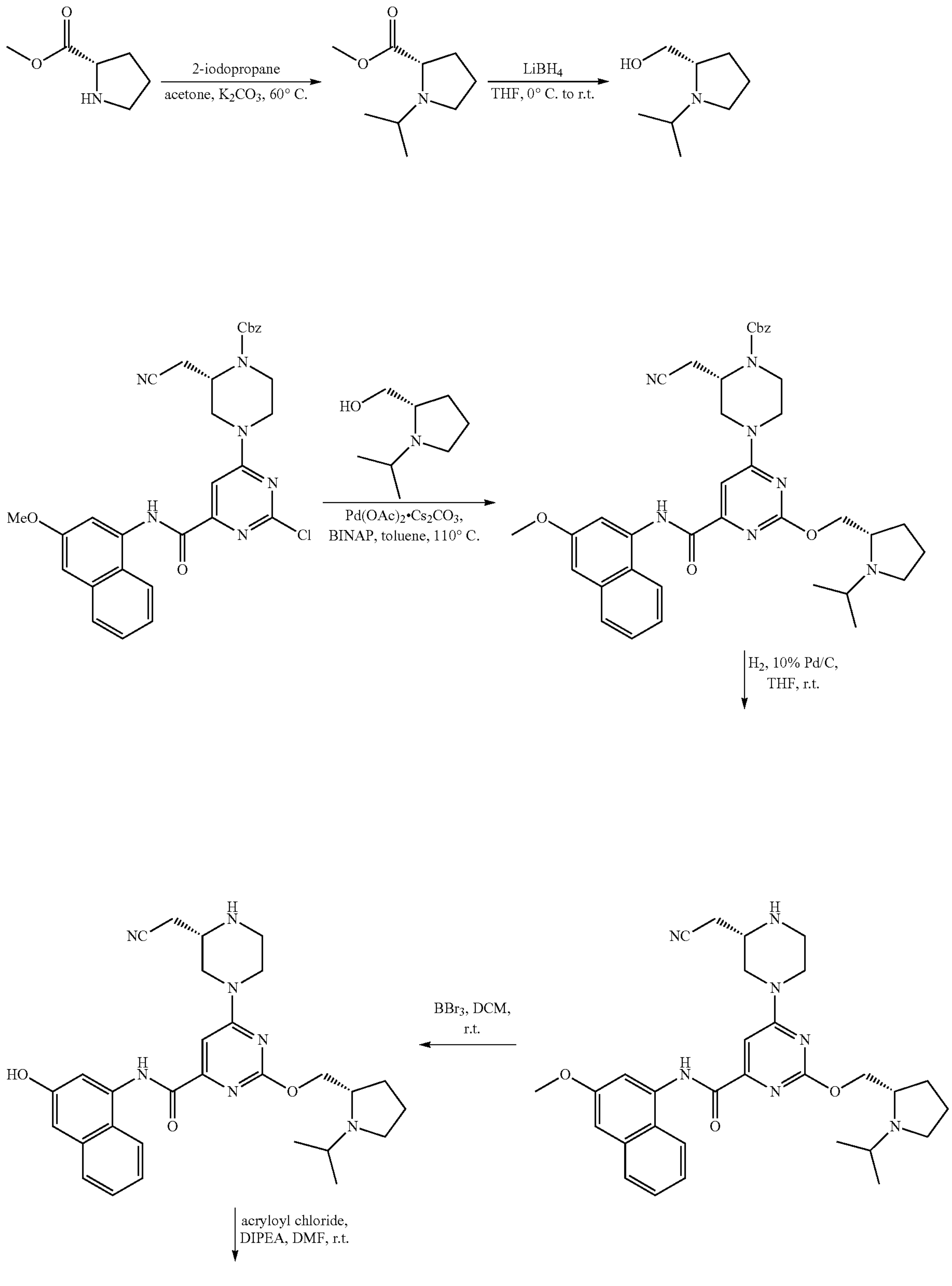

-continued

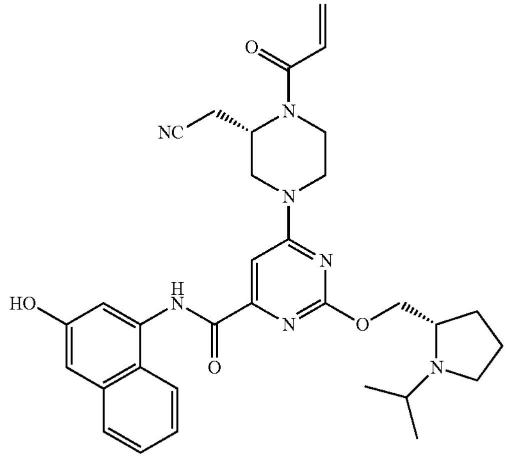

methyl (2S)-1-isopropylpyrrolidine-2-carboxylate

Intermediate Step 1

To methyl (2S)-pyrrolidine-2-carboxylate (2 g, 15.48 mmol, 1.0 eq) was added acetone (50 mL) followed by the addition of 2-iodopropane (7.90 g, 46.45 mmol, 3.0 eq) and $K_2CO_3$ (6.41 g, 46.45 mmol, 3.0 eq). The reaction was stirred at 60° C. overnight. Solvent was then removed in vacuo. The residue was purified by column chromatography using an eluent of 0-5% MeOH in DCM reached via a gradient to give methyl (2S)-1-isopropylpyrrolidine-2-carboxylate (1.1 g, 41%).

UPLC-MS (ES+, Method C): 0.34 min, m/z 171.1 [M+H]+.

[(2S)-1-isopropylpyrrolidin-2-yl]methanol

Intermediate Step 2

Methyl (2S)-1-isopropylpyrrolidine-2-carboxylate (1.1 g, 5.84 mmol, 1.0 eq) was dissolved in THF (50 mL). The reaction was left stirring at 0° C., then $LiBH_4$ (2M in THF) (6 mL, 11.68 mmol, 2.0 eq) was added slowly. The reaction was left stirring overnight. MeOH (5 mL) was then added and solvent removed in vacuo. The residue was purified by column chromatography using an eluent of 0-10% MeOH in DCM reached via a gradient to give [(2S)-1-isopropylpyrrolidin-2-yl]methanol (350 mg, 41%).

UPLC-MS (ES+, Method C): 0.34 min, m/z 144.2 [M+H]+.

benzyl (2S)-2-(cyanomethyl)-4-[2-[[(2S)-1-isopropylpyrrolidin-2-yl]methoxy]-6-[(3-methoxy-1-naphthyl)carbamoyl]pyrimidin-4-yl]piperazine-1-carboxylate Step 1

To benzyl (2S)-4-[2-chloro-6-[(3-methoxy-1-naphthyl) carbamoyl]pyrimidin-4-yl]-2-(cyanomethyl)piperazine-1-carboxylate (300 mg, 0.52 mmol, 1.0 eq) was added toluene (10 mL) followed by the addition of [(2S)-1-isopropylpyrrolidin-2-yl]methanol (226 mg, 1.58 mmol, 3.0 eq), $Cs_2CO_3$ (513 mg, 1.58 mmol, 3.0 eq), $Pd(OAc)_2$ (12 mg, 0.05 mmol, 0.1eq) and BINAP (65 mg, 0.10 mmol, 0.2eq). The reaction was stirred at 110° C. for 3 h. Solvent was then removed in vacuo and the residue was dissolved in EtOAc (300 mL) and washed with brine (300 mL). The organic phase was separated, dried over $Na_2SO_4$ and the solvent removed in vacuo. The residue was purified by column chromatography using an eluent of 0-5% MeOH in DCM reached via a gradient to give benzyl (2S)-2-(cyanomethyl)-4-[2-[[(2S)-1-isopropylpyrrolidin-2-yl]methoxy]-6-[(3-methoxy-1-naphthyl)carbamoyl]pyrimidin-4-yl]piperazine-1-carboxylate (200 mg, 56%).

UPLC-MS (ES+, Method A): 1.19 min, m/z 678.3 [M+H]+.

6-[(3S)-3-(cyanomethyl)piperazin-1-yl]-2-[[(2S)-1-isopropylpyrrolidin-2-yl]methoxy]-N-(3-methoxy-1-naphthyl)pyrimidine-4-carboxamide Step 2 benzyl (2S)-2-(cyanomethyl)-4-[2-[[(2S)-1-isopropylpyrrolidin-2-yl]methoxy]-6-[(3-methoxy-1-naphthyl)carbamoyl]pyrimidin-4-yl]piperazine-1-carboxylate (200 mg, 0.29 mmol, 1.0 eq) was dissolved in THF (20 mL) followed by the addition of palladium, 10 wt. % on carbon powder (100 mg, 2.95 mmol, 10.0 eq) under a nitrogen atmosphere. The reaction was fitted with a $H_2$ balloon and subjected to 3×vacuum/$H_2$ cycles and then left to stir under an $H_2$ atmosphere for 12 hours. The reaction was filtered through celite, washed with DCM (200 mL) and solvent removed in vacuo to give 6-[(3S)-3-(cyanomethyl)piperazin-1-yl]-2-[[(2S)-1-isopropylpyrrolidin-2-yl]methoxy]-N-(3-methoxy-1-naphthyl)pyrimidine-4-carboxamide (160 mg, 100%).

UPLC-MS (ES+, Method B): 0.32 min, m/z 544.3 [M+H]+.

6-[(3S)-3-(cyanomethyl)piperazin-1-yl]-N-(3-hydroxy-1-naphthyl)-2-[[(2S)-1-isopropylpyrrolidin-2-yl]methoxy]pyrimidine-4-carboxamide Step 3

6-[(3S)-3-(cyanomethyl)piperazin-1-yl]-2-[[(2S)-1-isopropylpyrrolidin-2-yl]methoxy]-N-(3-methoxy-1-naphthyl) pyrimidine-4-carboxamide (160 mg, 0.29 mmol, 1.0 eq) was dissolved in DCM (50 mL) followed by the addition of boron tribromide (0.2 ml). After 5 mins, MeOH (10 mL) was added and solvent removed in vacuo. The residue was purified by column chromatography using an eluent of 0-10% MeOH in DCM reached via a gradient to give 6-[(3S)-3-(cyanomethyl)piperazin-1-yl]-N-(3-hydroxy-1-naphthyl)-2-[[(2S)-1-isopropylpyrrolidin-2-yl]methoxy]pyrimidine-4-carboxamide (40 mg, 26%).

UPLC-MS (ES+, Method C): 1.49 min, m/z 530.3 [M+H]+.

6-[(3S)-3-(cyanomethyl)-4-prop-2-enoyl-piperazin-1-yl]-N-(3-hydroxy-1-naphthyl)-2-[[(2S)-1-isopropylpyrrolidin-2-yl]methoxy]pyrimidine-4-carboxamide Final Step Acryloyl chloride (5 mg, 0.06 mmol, 1.0 eq) and 6-[(3S)-3-(cyanomethyl)piperazin-1-yl]-N-(3-hydroxy-1-naphthyl)-2-[[(2S)-1-isopropylpyrrolidin-2-yl]methoxy]pyrimidine-4-carboxamide (30 mg, 0.06 mmol, 1.0 eq) were dissolved in DMF (2 mL) followed by the addition of DIPEA (22 mg, 0.17 mmol, 3.0 eq). The reaction was left stirring for 5 min. Water (50 mL) and DCM (50 mL) was then added and the organic layer separated, dried over $Na_2SO_4$ and solvent removed in vacuo. The residue was purified by column chromatography using an eluent of 0-10% MeOH in DCM reached via a gradient to give 6-[(3S)-3-(cyanomethyl)-4-prop-2-enoyl-piperazin-1-yl]-N-(3-hydroxy-1-naphthyl)-2-[[(2S)-1-isopropylpyrrolidin-2-yl]methoxy]pyrimidine-4-carboxamide (15 mg, 45%).

UPLC-MS (ES+, Method C): 1.67 min, m/z 584.4 [M+H]+.

1H-NMR (400 MHz, DMSO-d6) δ/ppm: 10.68 (1H, s), 9.95 (1H, s), 7.87-7.79 (2H, m), 7.73-7.68 (1H, m), 7.53-7.49 (1H, m), 7.41-7.36 (1H, m), 7.26-7.18 (1H, m), 7.13-7.10 (1H, m), 7.01-6.86 (1H, m), 6.29-6.22 (1H, m), 5.87-5.82 (1H, m), 5.05-4.77 (1H, m), 4.51-4.34 (3H, m), 4.25-4.09 (2H, m), 3.68-3.47 (1H, m), 3.25-2.89 (6H, m), 1.96-1.72 (4H, m), 1.36-1.27 (2H, m), 1.13 (3H, d, J=6.8 Hz), 1.05 (3H, d, J=6.8 Hz).

Compound Depletion Assay Method

Lyophilized human K-RAS (12 Cys) protein (His tag) and human K-RAS (12 Asp) protein (His tag) were purchased from Stratech and reconstituted at 30 μM in water. The protein concentration of K-RAS G12C and K-RAS G12D was adjusted to 20 μM in K-RAS Assay Buffer (20 mM HEPES pH 7.5, 150 mM NaCl, 1 mM $MgCl_2$). A 49 μl aliquot of protein solution was transferred to 1.5 ml eppendorfs and incubated at room temperature for 10 minutes. A 1 μl aliquot of compound solution in DMSO was added to the protein solutions in the 1.5 ml eppendorfs to initiate the reaction, with a final assay compound concentration of 8 μM. Reactions were agitated at 25° C., 700 rpm. At each time point (0, 30, 180, 360, 1440 minutes), 10 μl of the reaction mixture was removed, added to 30 μl quench solution (0.3% formic acid, 75 nM propranolol in acetonitrile) to stop the reaction and stored at 4° C. Once all reactions were quenched, the samples were centrifuged at 16000 g for 10 minutes to pellet the protein and salts. A 10 μl aliquot of supernatant containing compound was diluted in 50:50 acetonitrile:$H_2O$ in a 96 well plate. The plates were heat sealed and the samples analysed by LC-MS/MS to determine the concentration of compound remaining in the samples. To determine the reaction progress, the compound signal was normalized to the internal standard signal (propranolol). The decrease in free compound concentration is shown as a percentage over time, with the percent engagement at time zero fixed at one hundred percent. Compound is assumed to be completely depleted when no longer detectable with a double blank sample as reference.

TABLE 1

Compound depletion assay data

| Compound ID | 30 min Category | 3 hr Category | 6 hr Category | 24 hr Category | Protein |
|---|---|---|---|---|---|
| Example 01 | | A | | B | G12C |
| Example 02 | | B | | B | G12C |
| Example 03 | B | C | C | C | G12C |
| Example 04 | | A | | A | G12C |
| Example 05 | | A | | A | G12C |
| Example 06 | | A | | A | G12C |
| Example 07 | | A | | A | G12C |
| Example 08 | B | C | C | C | G12C |
| Example 09 | | A | A | B | G12C |
| Example 10 | | A | | A | G12C |
| Example 11 | A | A | | A | G12C |
| Example 12 | | A | | A | G12C |
| Example 13 | | A | | A | G12C |
| Example 14 | | A | | A | G12C |
| Example 15 | | A | | A | G12C |
| Example 16 | | A | | A | G12C |
| Example 17 | | A | | A | G12C |
| Example 18 | | A | | A | G12C |
| Example 19 | | A | | A | G12C |
| Example 20 | | A | | A | G12C |
| Example 21 | | A | | A | G12C |
| Example 22 | | A | | A | G12C |
| Example 23 | A | A | A | | G12C |
| Example 24 | A | A | A | | G12C |
| Example 25 | A | A | A | | G12C |
| Example 26 | A | A | A | | G12C |
| Example 27 | A | B | C | | G12C |
| Example 28 | A | A | B | | G12C |
| Example 29 | A | B | C | | G12C |
| Example 30 | B | C | C | | G12C |
| Example 31 | A | B | B | | G12C |
| Example 32 | A | A | A | | G12C |
| Example 23 | A | A | A | | G12C |
| Example 34 | B | C | C | | G12C |
| Example 35 | B | C | C | | G12C |
| Example 36 | A | A | B | | G12C |
| Example 37 | B | C | C | | G12C |
| Example 38 | A | A | A | | G12C |
| Example 39 | A | B | B | | G12C |
| Example 40 | A | A | A | | G12C |
| Example 41 | A | B | B | | G12C |
| Example 42 | B | C | C | | G12C |
| Example 43 | B | C | C | | G12C |
| Example 44 | A | B | B | | G12C |
| Example 45 | B | C | C | | G12C |
| Example 46 | B | C | C | | G12C |
| Example 47 | C | C | C | | G12C |
| Example 48 | C | C | C | | G12C |
| Example 49 | B | C | C | | G12C |
| Example 50 | C | C | C | | G12C |
| Example 51 | C | C | C | | G12C |
| Example 52 | C | C | C | | G12C |
| Example 53 | C | C | C | | G12C |
| Example 54 | C | C | C | | G12C |
| Example 01 | | A | | A | G12D |
| Example 02 | | A | | A | G12D |
| Example 03 | | A | | A | G12D |
| Example 04 | | A | | A | G12D |
| Example 05 | | A | | A | G12D |
| Example 06 | | A | | A | G12D |
| Example 07 | | A | | A | G12D |
| Example 08 | A | A | A | A | G12D |
| Example 09 | A | A | A | A | G12D |
| Example 10 | | A | | A | G12D |
| Example 11 | | A | | A | G12D |
| Example 12 | | A | | A | G12D |
| Example 13 | | A | | A | G12D |
| Example 14 | | A | | A | G12D |
| Example 15 | | A | | A | G12D |
| Example 16 | | A | | A | G12D |

TABLE 1-continued

| Compound depletion assay data | | | | | |
|---|---|---|---|---|---|
| Compound ID | 30 min Category | 3 hr Category | 6 hr Category | 24 hr Category | Protein |
| Example 17 | | A | | A | G12D |
| Example 18 | | A | | A | G12D |
| Example 19 | | A | | A | G12D |
| Example 20 | | A | | A | G12D |
| Example 21 | | A | | A | G12D |
| Example 22 | | A | | A | G12D |
| Example 23 | A | A | A | | G12D |
| Example 24 | A | A | A | | G12D |
| Example 25 | A | A | A | | G12D |
| Example 26 | A | A | A | | G12D |
| Example 27 | A | A | A | | G12D |
| Example 28 | A | A | A | | G12D |
| Example 29 | A | A | A | | G12D |
| Example 30 | A | A | A | | G12D |
| Example 31 | A | A | A | | G12D |
| Example 32 | A | A | A | | G12D |
| Example 23 | A | A | A | | G12D |
| Example 34 | A | A | A | | G12D |
| Example 35 | A | A | A | | G12D |
| Example 36 | A | A | A | | G12D |
| Example 37 | A | A | A | | G12D |
| Example 38 | A | A | A | | G12D |
| Example 39 | A | A | A | | G12D |
| Example 40 | A | A | A | | G12D |
| Example 41 | A | A | A | | G12D |
| Example 42 | A | A | A | | G12D |
| Example 43 | A | A | A | | G12D |
| Example 44 | A | A | A | | G12D |
| Example 45 | A | A | A | | G12D |
| Example 46 | A | A | A | | G12D |
| Example 47 | A | A | A | | G12D |
| Example 48 | A | A | A | | G12D |
| Example 49 | A | A | A | | G12D |
| Example 50 | A | A | A | | G12D |
| Example 51 | A | A | A | | G12D |
| Example 52 | A | A | A | | G12D |
| Example 53 | A | A | A | | G12D |
| Example 54 | A | A | A | | G12D |

Data Categories:

A—≥70% compound remaining at timepoint

B—30%-70% compound remaining at timepoint

C—≤30% compound remaining at timepoint

The invention is further described by the following numbered embodiments:

1. A compound of formula (I):

(I)

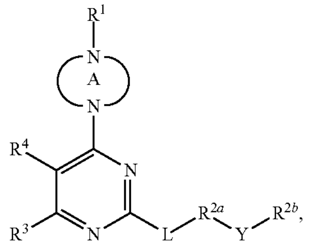

wherein:

ring A is a 4-12 membered heterocyclic ring, optionally substituted with one or more substituents selected from the group consisting of halo, hydroxyl, cyano, oxo, $C_{1-4}$-alkyl, $C_{2-4}$-alkynyl, $C_{1-4}$-heteroalkyl, $C_{3-8}$-cycloalkyl, —$C_{0-4}$-alkyl-C(O)N($R^{6d}$)$_2$, —$C_{0-4}$-alkyl-C(O)O$R^{6d}$;

and/or wherein two substituents on the same atom of ring A may form a 3- to 5-membered ring together with the carbon atom on which they are attached;

and/or wherein two substituents on adjacent atoms of ring A may form a 3- to 6-membered ring together with the carbon atoms on which they are attached;

wherein the $C_{1-4}$-alkyl, $C_{2-4}$-alkynyl, $C_{1-4}$-heteroalkyl or $C_{3-8}$-cycloalkyl may be optionally substituted with one or more substituents selected from the group consisting of halo, hydroxy, —O$R^{6d}$, cyano and oxo;

$R^1$ is selected from the group consisting of

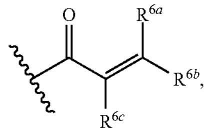
,
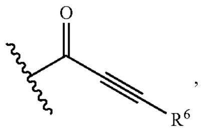
,
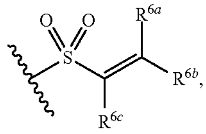
and
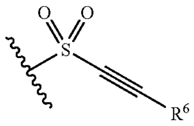
;

L is selected from the group consisting of a direct bond, —N($R^{6d}$)—, —C(O)N($R^{6d}$)—, —S($O_2$)N($R^{6d}$)— and —O—;

$R^{2a}$ is a direct bond, $C_{1-4}$-alkylene, $C_{1-4}$-heteroalkylene, $C_{3-8}$-cycloalkylene, 3- to 8-membered heterocycloalkylene, 6- to 10-membered aryl, or 5- to 10-membered heteroaryl, wherein the $C_{1-4}$-alkylene, $C_{1-4}$-heteroalkylene, $C_{3-8}$-cycloalkylene, 3- to 8-membered heterocycloalkylene, 6- to 10-membered aryl, or 5- to 10-membered heteroaryl each is optionally substituted with one or more substituents selected from the group consisting of halo, hydroxyl, carboxyl, —O$R^{6d}$, oxo, cyano, $C_{3-8}$-cycloalkyl, $C_{1-4}$-alkyl, $C_{1-4}$-heteroalkyl, 3- to 8-membered heterocycloalkyl;

Y is selected from the group consisting of a direct bond, unsubstituted or substituted $C_{1-4}$-alkyl, unsubstituted or substituted $C_{1-4}$-alkylene, unsubstituted or substituted $C_{1-4}$-heteroalkyl, —N($R^{6d}$)—, —N$R^{6d}$C(O)—, —C(O)N$R^{6d}$—, —N$R^{6d}$C(O)N$R^{6d}$—, —S($O_2$)N$R^{6d}$—, and —N$R^{6d}$S(O)$_2$—;

$R^{2b}$ is H, $C_{1-4}$-alkyl, $C_{1-4}$-heteroalkyl, $C_{3-8}$-cycloalkyl, 3- to 8-membered heterocycloalkyl, 6- to 10-membered aryl, or 5- to 10-membered heteroaryl, wherein the $C_{1-4}$-alkyl, $C_{1-4}$-heteroalkyl, $C_{3-8}$-cycloalkyl, 3- to 8-membered heterocycloalkyl, 6- to 10-membered aryl, or 5- to 10-membered heteroaryl is each optionally substituted with one or more substituents selected from the group consisting of halo, hydroxyl, carboxyl, —O$R^{6d}$, oxo, cyano, —N($R^{6d}$)$_2$, $C_{3-8}$-cycloalkyl, $C_{1-4}$-alkyl, $C_{1-4}$-heteroalkyl, and 3- to 8-membered heterocycloalkyl;

$R^3$ is

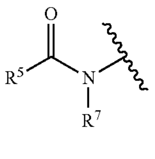
or
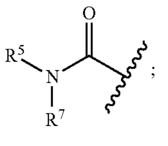
;

$R^4$ is H, $C_{1-6}$-alkyl, $C_{1-6}$-heteroalkyl, $C_{1-6}$-haloalkyl, $C_{3-8}$-cycloalkyl, 3- to 8-membered heterocycloalkyl, $—OC_{1-6}$-haloalkyl, $—NH(C_{1-6}$-alkyl) or $—N(C_{1-6}$-alkyl$)_2$, wherein the $C_{1-6}$-alkyl, $C_{1-6}$-heteroalkyl, $C_{1-6}$-haloalkyl, $C_{3-8}$-cycloalkyl, 3- to 8-membered heterocycloalkyl, or $—OC_{1-6}$-haloalkyl is each optionally substituted with one or more substituents selected from the group consisting of $C_{1-4}$-alkyl, $C_{1-4}$-heteroalkyl, halo, cyano, hydroxyl, ether, $—N(R^{6d})_2$, $C_{3-8}$-cycloalkyl, 3- to 8-membered heterocycloalkyl.

$R^5$ is H, $C_{1-6}$-alkyl, $C_{1-6}$-heteroalkyl, $C_{3-8}$-cycloalkyl, 3- to 8-membered heterocycloalkyl, 6- to 10-membered aryl, or 5- to 10-membered heteroaryl, wherein the $C_{1-6}$-alkyl, $C_{1-6}$-heteroalkyl, $C_{3-8}$-cycloalkyl, 3- to 8-membered heterocycloalkyl, 6- to 10-membered aryl, or 5- to 10-membered heteroaryl is each optionally substituted with one or more substituents selected from the group consisting of halo, hydroxyl, carboxyl, cyano, $—OR^{6d}$, $—N(R^{6d})_2$, $C_{3-8}$-cycloalkyl, $C_{1-4}$-alkyl, $C_{1-4}$-heteroalkyl, 3- to 8-membered heterocycloalkyl, 6-membered aryl, and 5- to 6-membered heteroaryl, or an $R^5$ and $R^7$ taken together with the atom to which they are attached form a 5- or 6-membered monocyclic ring system or a bicyclic system, wherein the bicyclic system is a 9- or 10-membered heterocyclic ring system;

$R^6$, $R^{6a}$ and $R^{6b}$ are each independently H, halo, cyano, $C_{1-6}$-alkyl, $C_{1-6}$-heteroalkyl, $C_{3-8}$-cycloalkyl, 3- to 8-membered heterocycloalkyl, $C_{3-8}$-aryl, or $C_{3-8}$-heteroaryl, wherein the $C_{1-6}$-alkyl, $C_{1-6}$-heteroalkyl, $C_{3-8}$-cycloalkyl, 3- to 8-membered heterocycloalkyl, $C_{3-8}$-aryl, or $C_{3-8}$-heteroaryl each is optionally substituted with one or more substituents selected from halo, hydroxy, cyano, $—N(R^{6d})_2$, $—OR^{6d}$, $C_{1-4}$-alkyl, 3- to 8-membered heterocycloalkyl and $C_{1-4}$-heteroalkyl;

$R^{6c}$ is H, halo, cyano, $C_{1-6}$-alkyl, $C_{1-6}$-heteroalkyl, $C_{3-8}$-cycloalkyl, or 3- to 8-membered heterocycloalkyl, wherein the $C_{1-6}$-alkyl, $C_{1-6}$-heteroalkyl, $C_{3-8}$-cycloalkyl, or 3- to 8-membered heterocycloalkyl is each optionally substituted with one or more substituents selected from halo, cyano, $—OR^{6d}$, hydroxy and $C_{1-4}$-heteroalkyl;

$R^{6d}$ is independently at each occurrence selected from the group consisting of H, cyano, $C_{1-6}$-alkyl, $C_{1-6}$-heteroalkyl, $C_{3-8}$-cycloalkyl, and 3- to 8-membered heterocycloalkyl; and $R^7$ is H, $C_{1-6}$-alkyl, $C_{1-6}$-heteroalkyl, or $C_{3-8}$-cycloalkyl, wherein the $C_{1-6}$-alkyl, $C_{1-6}$-heteroalkyl, or $C_{3-8}$-cycloalkyl is each optionally substituted with one or more substituents selected from the group consisting of halo, cyano, hydroxyl, carboxyl, $—OR^{6d}$, $—N(R^{6d})_2$, $C_{3-8}$-cycloalkyl, $C_{1-4}$-alkyl, $C_{1-4}$-heteroalkyl, and 3- to 8-membered heterocycloalkyl.

2. The compound of embodiment 1, wherein ring A is a 4- to 8-membered heterocyclic ring, optionally substituted with one or more substituents selected from the group consisting of halo, hydroxyl, $C_{1-4}$-alkyl, and $C_{1-4}$-heteroalkyl, wherein the $C_{1-4}$-alkyl and $C_{1-4}$-heteroalkyl is optionally substituted with one or more substituents selected from the group consisting of halo, hydroxy, and cyano.

2a. The compound of embodiment 1 or 2, wherein ring A is a 6- or 7-membered heterocyclic ring, optionally substituted with one or more substituents selected from the group consisting of halo, hydroxyl, $C_{1-4}$-alkyl, and $C_{1-4}$-heteroalkyl, wherein the $C_{1-4}$-alkyl and $C_{1-4}$-heteroalkyl is optionally substituted with one or more substituents selected from the group consisting of halo, hydroxy, and cyano.

3. The compound of embodiment 1 or 2, wherein ring A is an optionally substituted 6-membered heterocyclic ring.

4. The compound of embodiment any one of embodiments 1-3, wherein ring A is an optionally substituted piperazinyl ring.

5. The compound of any preceding embodiment, wherein ring A is selected from the group consisting of:

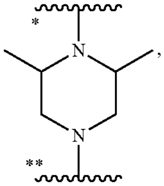, 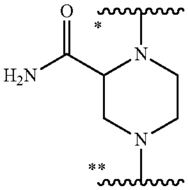, 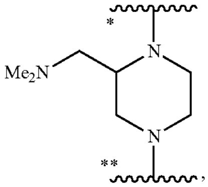, 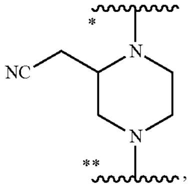, 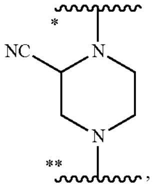, 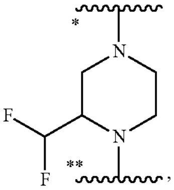, 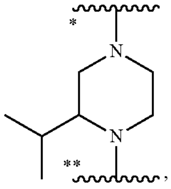, 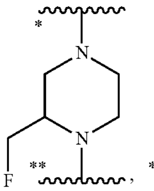, 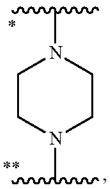, 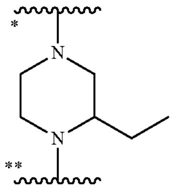, 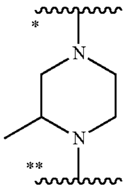 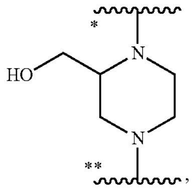 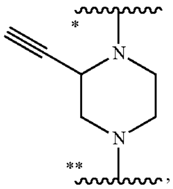, 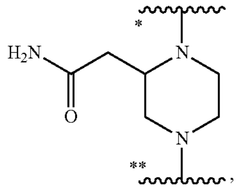, 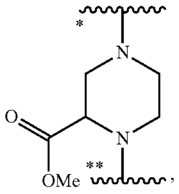, 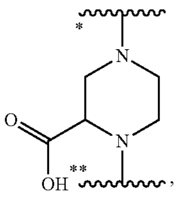, 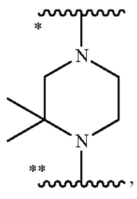, 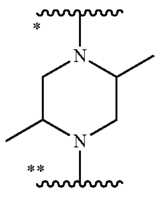, 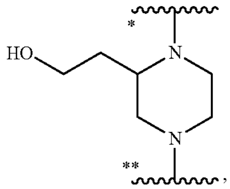 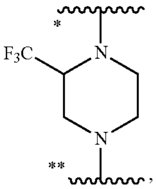, -continued

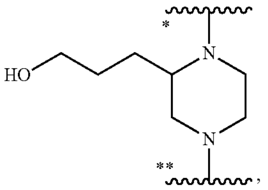

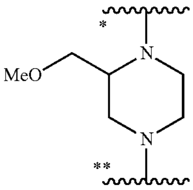,

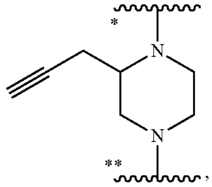,

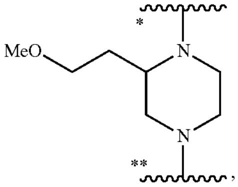,

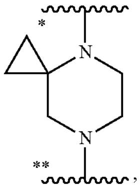,

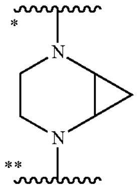,

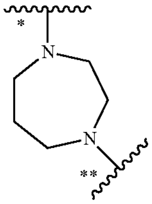, and

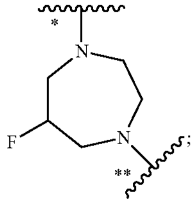;

wherein the * indicates a bond between the nitrogen atom of ring A containing the *, and $R^1$; and the  indicates a bond between the nitrogen atom of ring A containing the , and the pyrimidyl group of formula (I);

or wherein the * indicates a bond between the nitrogen atom of ring A containing the *, and the pyrimidyl group of formula (I); and the ** indicates a bond between the nitrogen atom of ring A containing the * and $R^1$.

6. The compound of any preceding embodiment, wherein ring A is

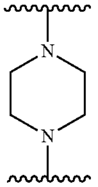

or

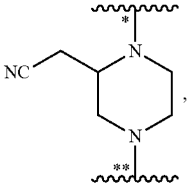, wherein the * indicates a bond between the nitrogen atom of ring A containing the * and $R^1$; and the  indicates a bond between the nitrogen atom of ring A containing the  and the pyrimidyl group of formula (I).

7. The compound of any preceding embodiment, wherein $R^1$ is

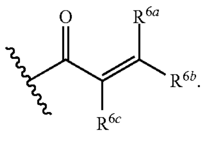

7a. The compound of embodiment 7, wherein $R^{6c}$ is H or F.

7b. The compound of embodiment 7 or 7a, wherein $R^{6a}$ and $R^{6b}$ are H.

8. The compound of any preceding embodiments, wherein $R^1$ is

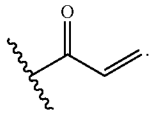 [SMILES: *C(=O)C=C]

9. The compound of any preceding embodiment, wherein L is selected from the group consisting of a direct bond, —N($R^{6d}$)—, and —O—.

9a. The compound of any preceding embodiment, wherein L is —N($R^{6d}$)— or —O—.

9b. The compound of any preceding embodiment, wherein $R^{6d}$ is H or $C_{1-6}$ alkyl.

10. The compound of any preceding embodiment, wherein $R^{2a}$ is selected from the group consisting of $C_{1-6}$ alkyl, 3- to 8-membered heterocycloalkyl and 5- to 6-membered heteroaryl.

10a. The compound of any preceding embodiment, wherein $R^{2a}$ is $C_{1-6}$ alkyl.

11. The compound of any preceding embodiment, wherein Y is selected from the group consisting of a direct bond, —N($R^{6d}$)—, and —O—.

11a. The compound of any preceding embodiment, wherein Y is a direct bond.

12. The compound of any preceding embodiment, wherein $R^{2b}$ is selected from the group consisting of H, $C_{1-4}$-alkyl, $C_{1-4}$-heteroalkyl, 5- to 6-membered heterocycloalkyl and 5- to 6-membered heteroaryl.

12a. The compound of any preceding embodiment, wherein $R^{2b}$ is 5- to 6-membered heterocycloalkyl or 5- to 6-membered heteroaryl.

13. The compound of any preceding embodiment, wherein -L-$R^{2a}$—Y—$R^{2b}$ is selected from the group consisting of:

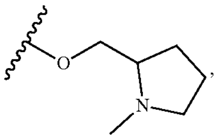,

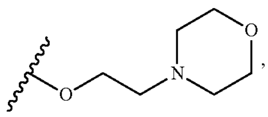,

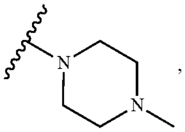,

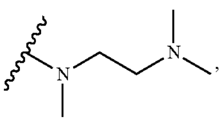,

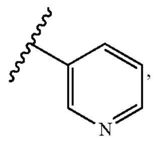,

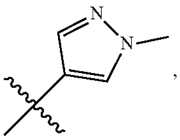, and

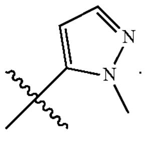

14. The compound of any preceding embodiment, wherein $R^3$ is

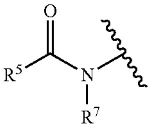

or

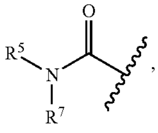

, wherein $R^5$ is 6- to 10-membered aryl or 5- to 10-membered heteroaryl, and $R^7$ is H or $C_{1-6}$ alkyl.

14a. The compound of any preceding embodiment, wherein $R^3$ is selected from the group consisting of:

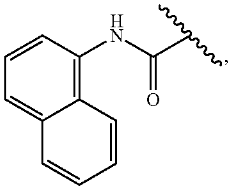

,

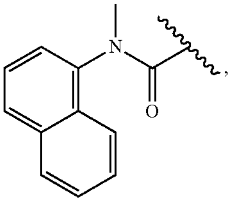

,

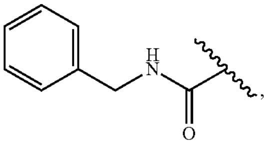

,

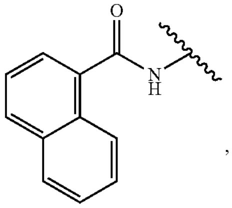

,

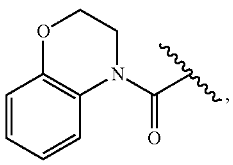

,

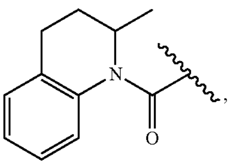

,

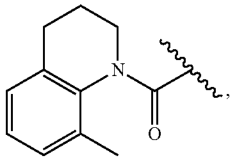

,

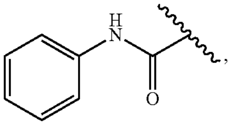

,

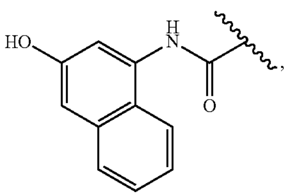

,

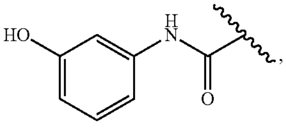

,

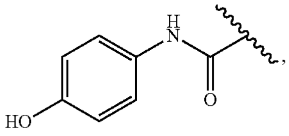

,

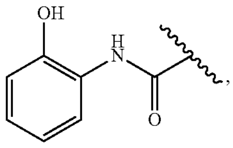

,

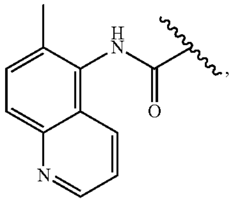

, and

-continued

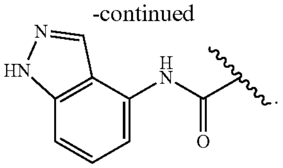

.

15. The compound of any preceding embodiment, wherein $R^4$ is H, halo, $C_{1-6}$-alkyl, $C_{1-3}$ haloalkyl, $-OC_{1-6}$ alkyl, $-OC_{1-3}$ haloalkyl, $-CH_2-OC_{1-6}$ alkyl, $-NH(C_{1-6}$-alkyl) or $-N(C_{1-6}\text{-alkyl})_2$.

15a. The compound of any preceding embodiment, wherein $R^4$ is H.

16. The compound of embodiment 1, having the structure:

(IIIb)

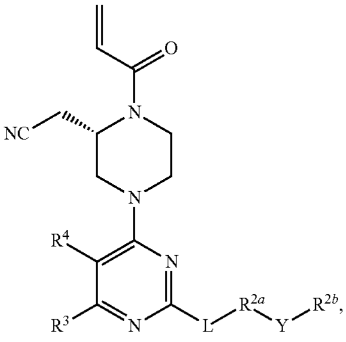

or a pharmaceutically acceptable salt or stereoisomer thereof.

16a. The compound of embodiment 16, wherein L is $-N(R^{6d})-$ or $-O-$.

16b. The compound of embodiment 16 or 16a, wherein $R^{2a}$ is $C_{1-6}$ alkylene.

16c. The compound of embodiment 16b, wherein the $C_{1-6}$ alkylene is $-CH_2-$ or $-CH_2CH_2-$.

16d. The compound of any one of embodiments 16-16c, wherein Y is a direct bond.

16e. The compound of any one of embodiments 16-16d, wherein $R^{2b}$ is a heterocyclyl or heteroaryl.

16f. The compound of any one of embodiments 16-16e, wherein $R^{2b}$ is a heterocyclyl.

16g. The compound of embodiment 16e, wherein the heteroaryl is a 5-membered heteroaryl.

16h. The compound of embodiment 16g, wherein the heteroaryl is an optionally substituted pyrazole.

16i. The compound of embodiment 16e or 16f, wherein the heterocyclyl is a 5- or 6-membered heterocyclyl.

16j. The compound of embodiment 16e or 16f, wherein the heterocyclyl is pyrrolidinyl, piperidinyl, or morpholinyl.

16k. The compound of embodiment 16e or 16f, wherein the heterocyclyl is pyrrolidinyl.

16l. The compound of any one of embodiments 16-16k, wherein $R^3$ is

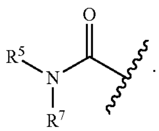

.

16m. The compound of 16l, wherein $R^5$ is a 6- to 10-membered aryl or 6- to 10-membered heteroaryl, each of which is optionally substituted with one or more substituents selected from the group consisting of halo, hydroxyl, carboxyl, cyano, —$OR^{6d}$, —$N(R^{6d})_2$, or $C_{1-4}$-alkyl; and $R^7$ is H or $C_{1-6}$ alkyl.

16n. The compound of embodiment 16m, wherein $R^5$ is 6- to 10-membered aryl, optionally substituted with one or more substituents selected from the group consisting of halo, hydroxyl, carboxyl, cyano, —$OR^{6d}$, —$N(R^{6d})_2$, or $C_{1-4}$-alkyl.

16o. The compound of any one of embodiments 16l-16n, wherein $R^7$ is H.

16p. The compound of any one of embodiments 16-16o, wherein $R^3$ is

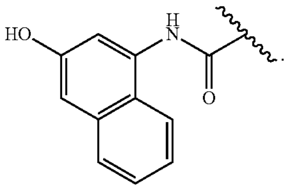 [SMILES: *C(=O)Nc1cc(O)cc2ccccc12]

16q. The compound of any one of embodiments 16-16p, wherein $R^4$ is H, halo, $C_{1-6}$-alkyl, $C_{1-3}$ haloalkyl, —$OC_{1-6}$ alkyl, —$OC_{1-3}$ haloalkyl, —$CH_2$—$OC_{1-6}$ alkyl, —NH($C_{1-6}$-alkyl) or —$N(C_{1-6}\text{-alkyl})_2$.

16r. The compound of any one of embodiments 16-16q, wherein $R^4$ is F, Cl, —OMe, —OEt, $CF_3$, $CF_2H$, $CH_2F$, —$CH_2OMe$, $CH_3$, —$OCF_3$, —$NMe_2$, or —NHMe.

17. The compound of any one of embodiments 1-15, wherein the compound of formula (I) is selected from the group consisting of:

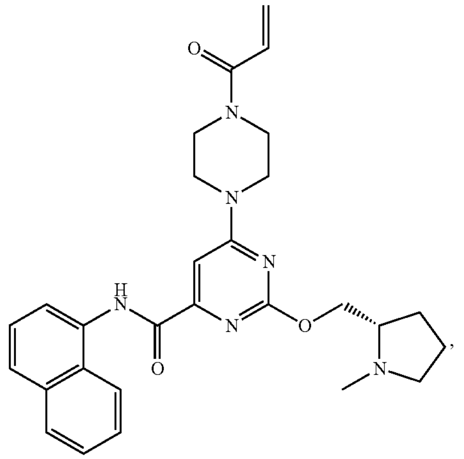

-continued

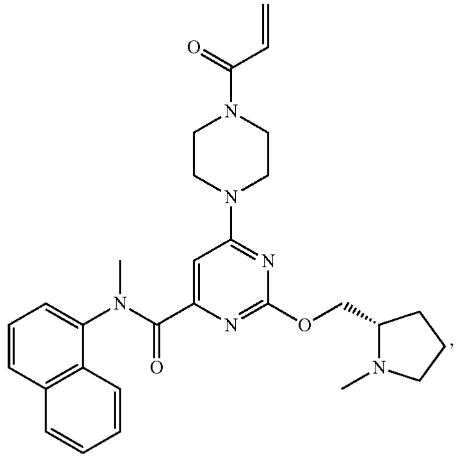

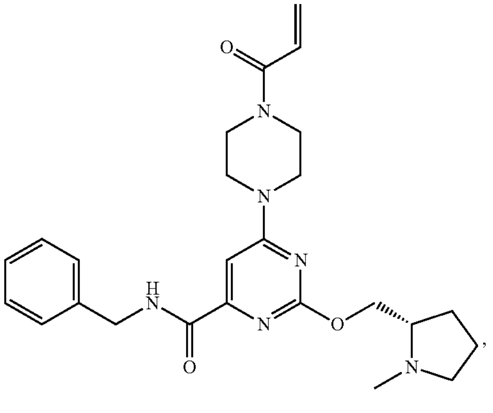

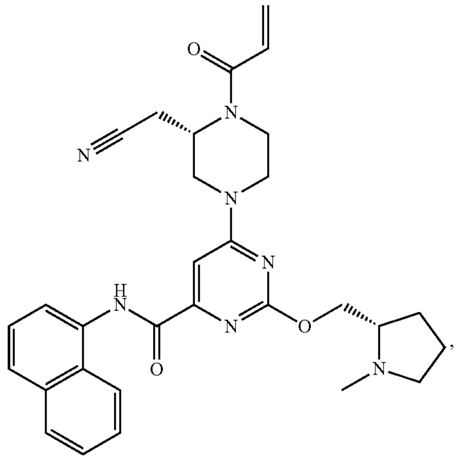

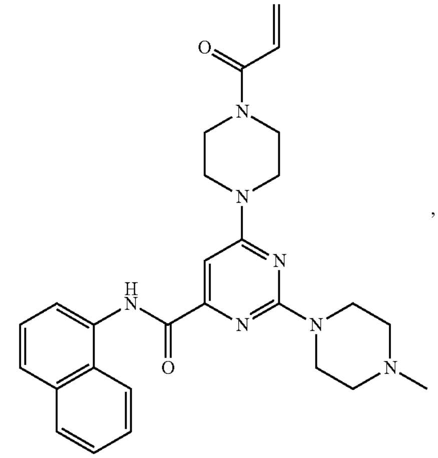
,
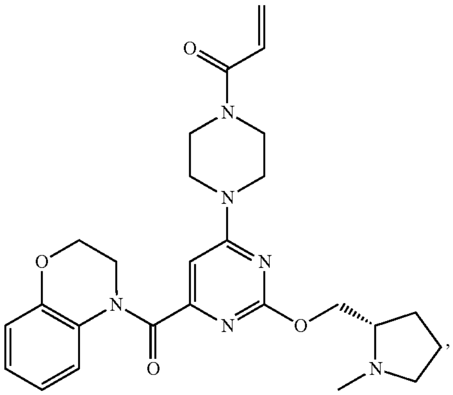
,
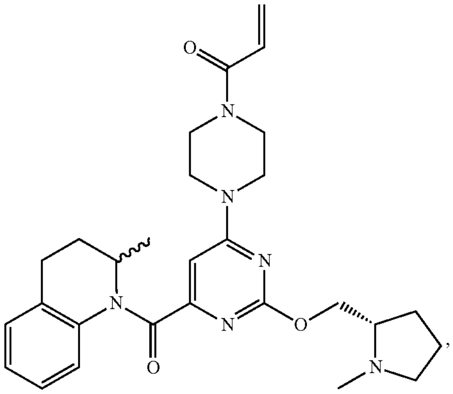
,
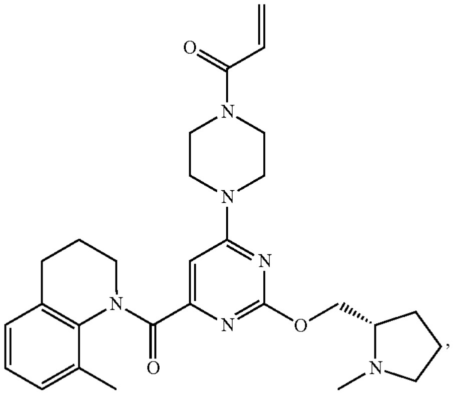
,
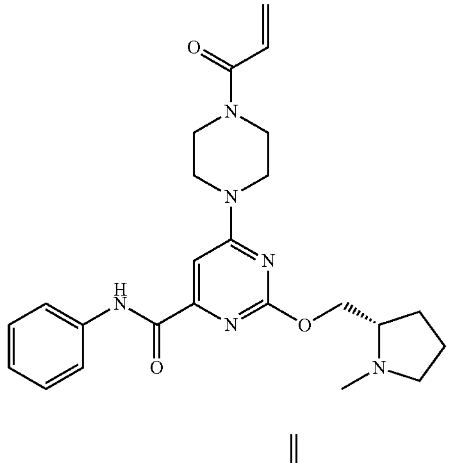
,
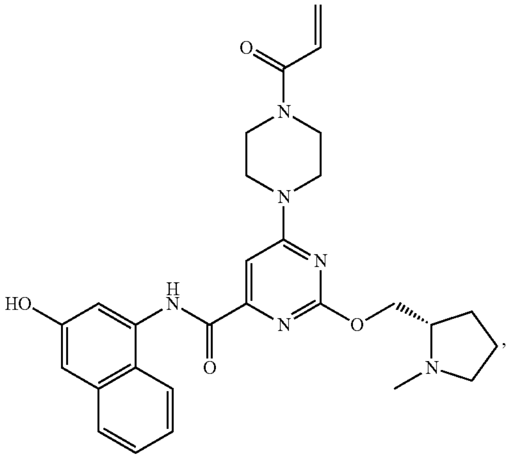
,
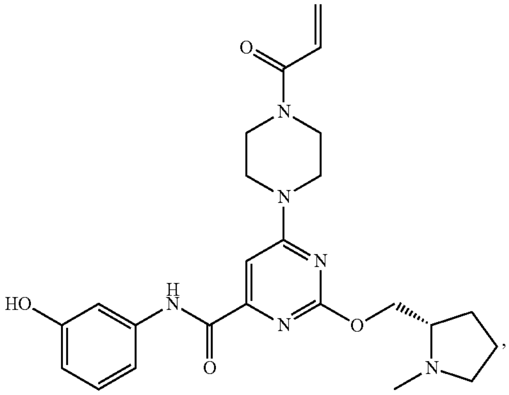
,
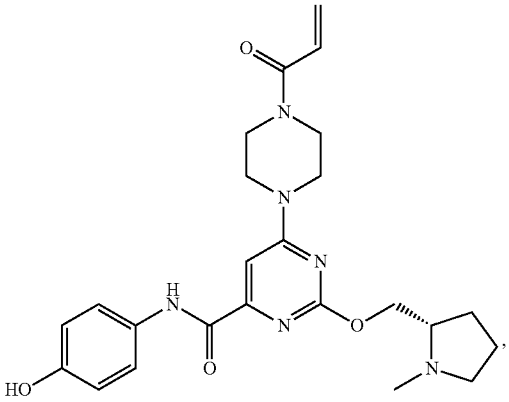
, -continued
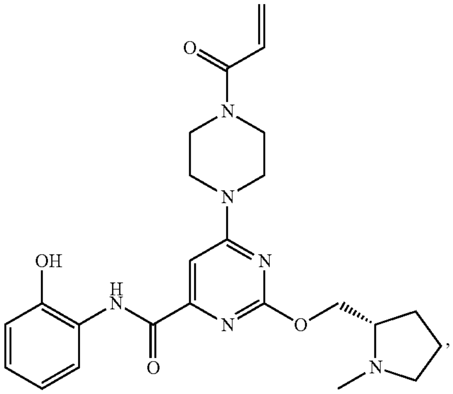
,
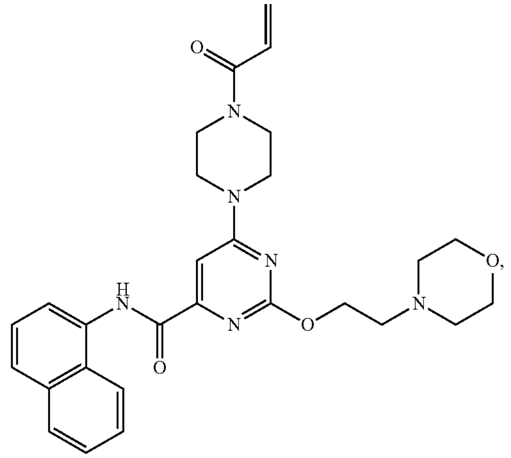
,
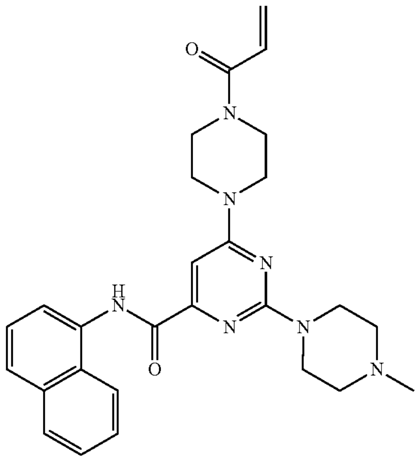
,
-continued
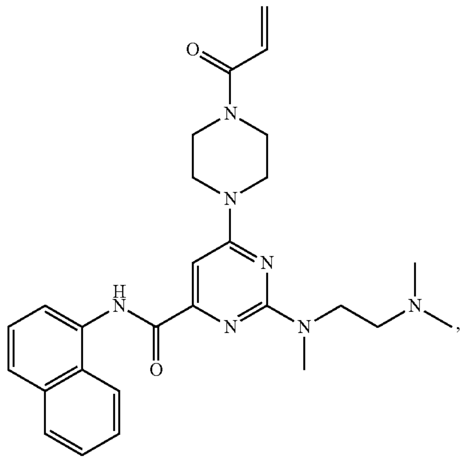
,
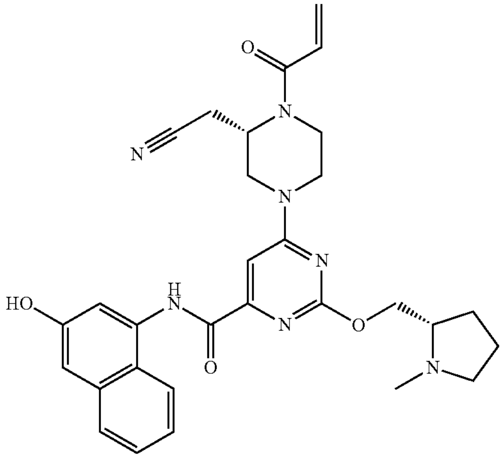
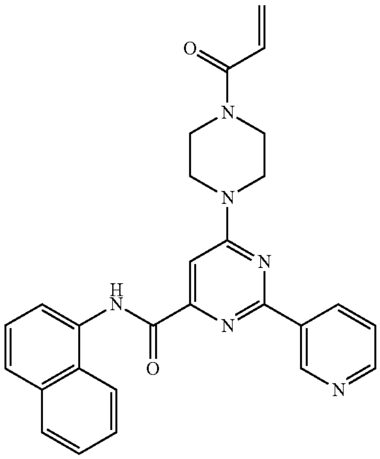
, -continued
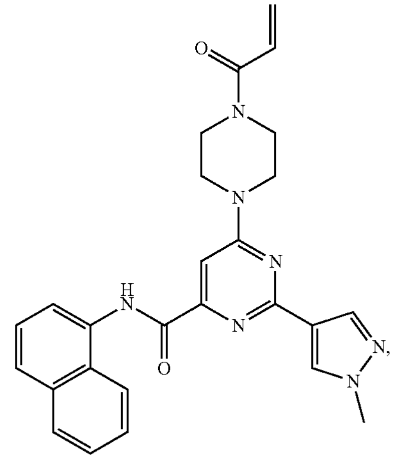
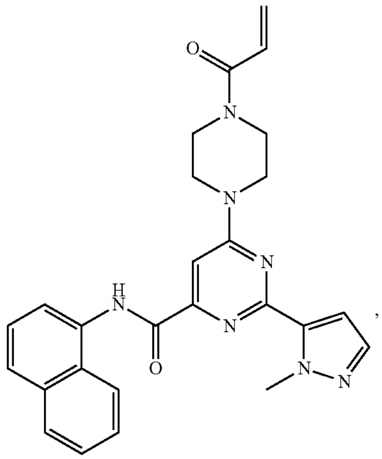
,
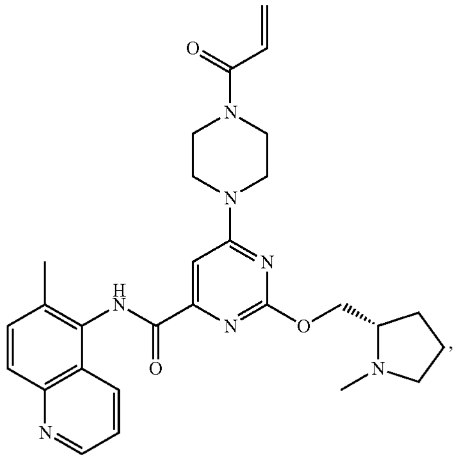
, and
-continued
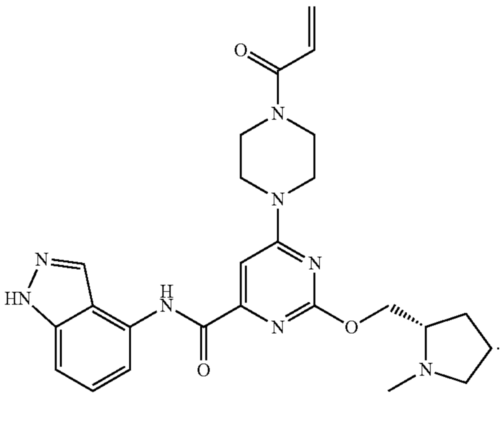
17a. The compound of any one of embodiments 1-15, wherein the compound of formula (I) is selected from the group consisting of:
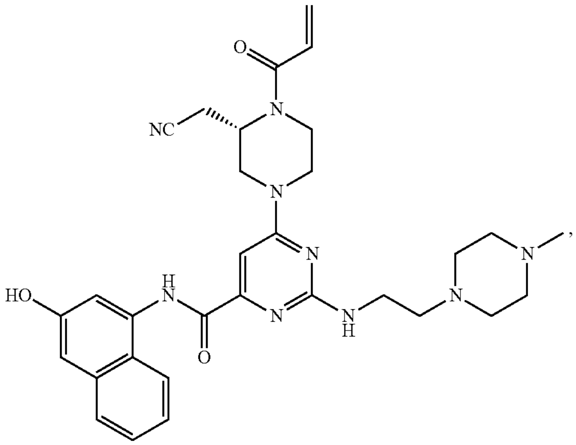
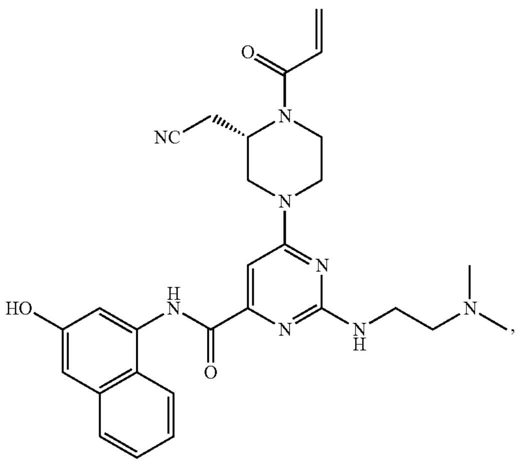

-continued
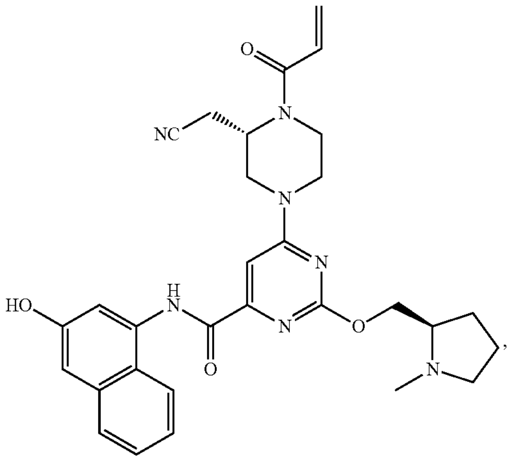,
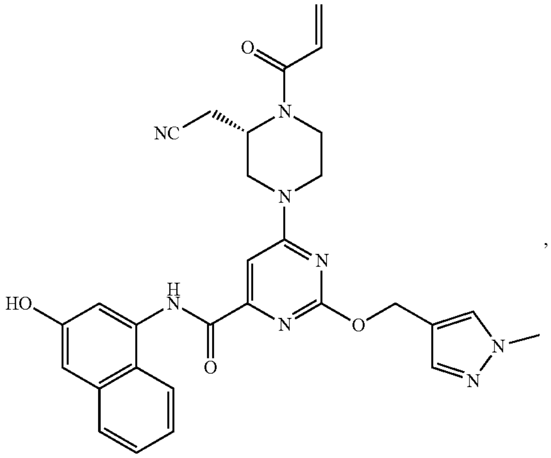,
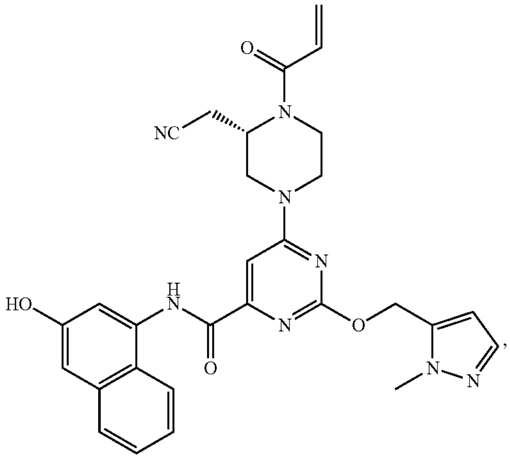,
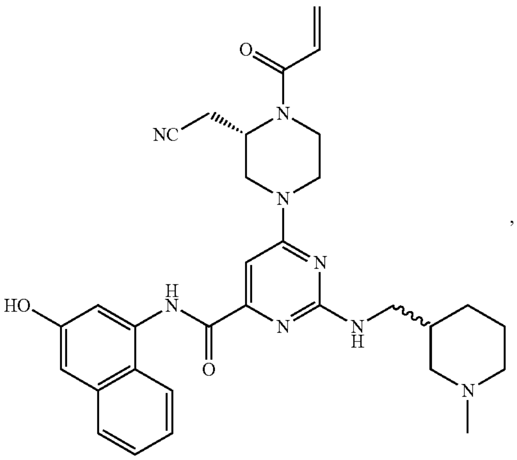,
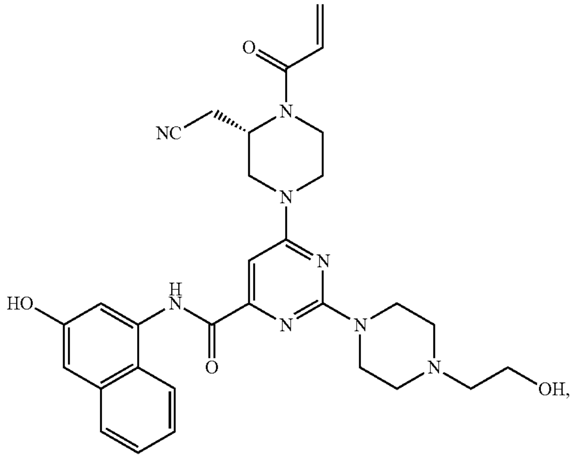
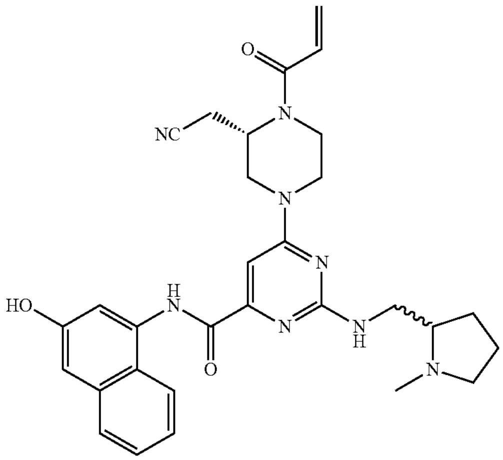, -continued
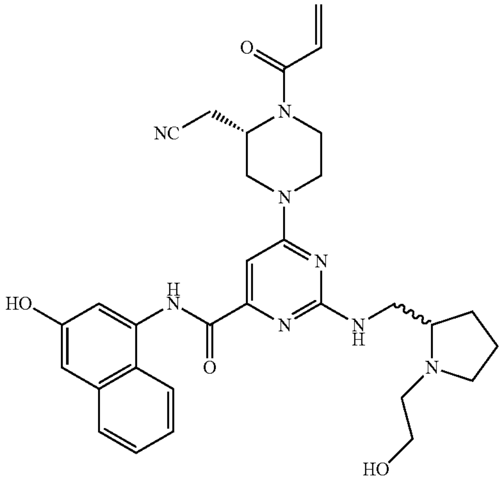
,
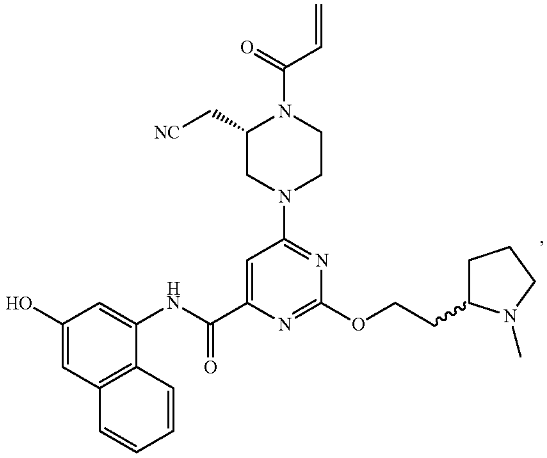
,
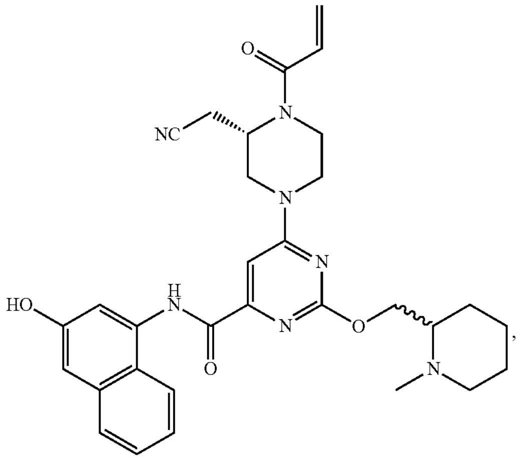
,
-continued
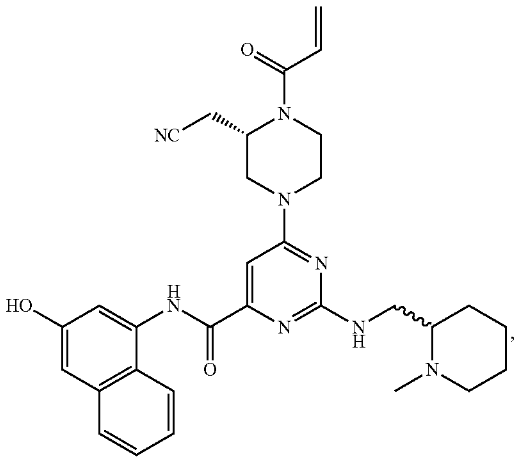
,
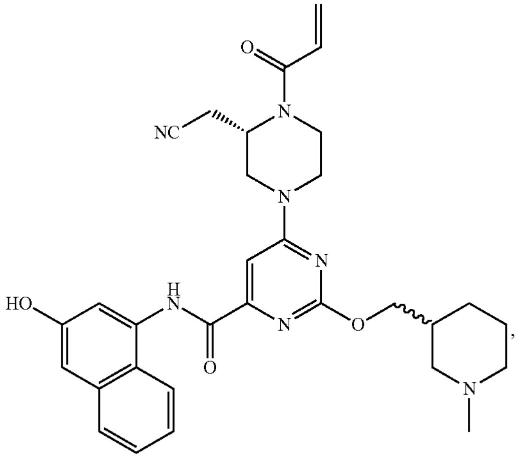
,
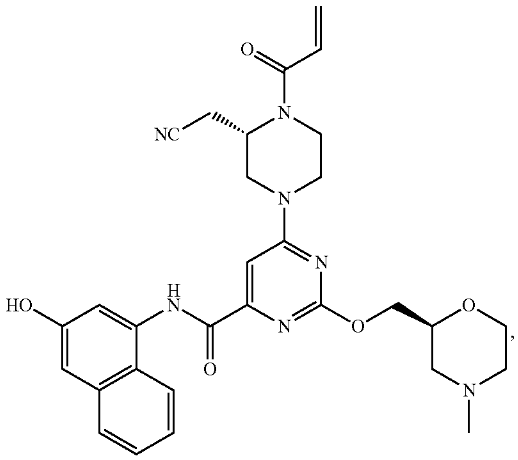
, -continued

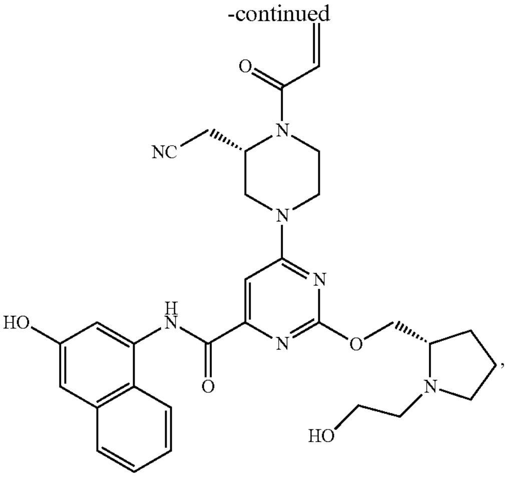

, and

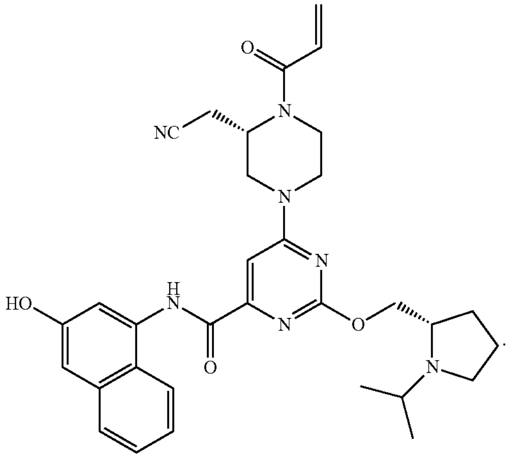 [SMILES: C=CC(=O)N1CCN(c2cc(C(=O)Nc3cc(O)cc4ccccc34)nc(OC[C@@H]3CCCN3C(C)C)n2)C[C@@H]1CC#N]

18. A pharmaceutical composition comprising a compound of any one of embodiments 1-17a and a pharmaceutically acceptable excipient.

18a. The pharmaceutical composition of embodiment 18, further comprising an additional pharmaceutically active agent.

18b. The pharmaceutical composition of embodiment 18a, wherein the additional pharmaceutically active agent is an anti-inflammatory agent, an anti-fibrotic agent, a chemotherapeutic, an anti-cancer agent, an immunosuppressant, an anti-tumour vaccine, a cytokine therapy, or a tyrosine kinase inhibitor.

19. The compound of any one of the preceding embodiments, for use as a medicament.

20. The compound for use of any one of embodiments 1-17a, wherein the compound is for use in the inhibition of KRAS proteins.

21. The compound for use of any of one embodiments 1-17a, for use in the treatment of a condition which can be modulated by inhibition of KRAS proteins.

22. The compound for use of embodiment 21, wherein the condition modulated by inhibition of KRAS proteins is cancer.

23. The compound for use of any one of embodiments 20-22, wherein the condition treatable by the inhibition of KRAS proteins is selected from the group consisting of sarcoma, melanoma, skin cancer, haematological tumors, lymphoma, carcinoma, and leukemia.

24. The compound for use of any one of embodiments 20-22, wherein the condition is selected from the group consisting of cervical cancer, multiple myeloma, stomach cancer, bladder cancer, uterine cancer, esophageal squamous cell carcinoma, gastric cancer, glioblastomas, astrocytomas; retinoblastoma, osteosarcoma, chondosarcoma, Ewing's sarcoma, rabdomysarcoma, Wilm's tumor, basal cell carcinoma, non-small cell lung cancer, brain tumour, hormone refractory prostate cancer, prostate cancer, metastatic breast cancer, breast cancer, metastatic pancreatic cancer, pancreatic cancer, colorectal cancer, head and neck squamous cell carcinoma and cancer of the head and neck.

25. The compound for use of any one of embodiments 20-22, wherein the condition is selected from the group consisting of lung cancer, esophageal cancer, colorectal cancer, stomach cancer, bladder cancer, hepatocellular cancer, uterine cancer, cervical cancer, pancreatic cancer and ovarian cancer.

26. A method of treating a condition modulated by inhibition of KRAS proteins in a subject in need thereof, the method comprising administering a therapeutically effective amount of a compound according to any one of embodiments 1-17a or the pharmaceutical composition of any one of embodiments 18-18b to the subject.

27. The method of embodiment 26, wherein the condition is selected from the group consisting of cancer, sarcoma, melanoma, skin cancer, haematological tumors, lymphoma, carcinoma, and leukemia.

28. The method of embodiment 26, wherein the condition is selected from the group consisting of cervical cancer, multiple myeloma, stomach cancer, bladder cancer and uterine cancer. esophageal squamous cell carcinoma, gastric cancer, glioblastomas, astrocytomas; retinoblastoma, osteosarcoma, chondosarcoma, Ewing's sarcoma, rabdomysarcoma, Wilm's tumor, basal cell carcinoma, non-small cell lung cancer, brain tumour, hormone refractory prostate cancer, prostate cancer, metastatic breast cancer, breast cancer, metastatic pancreatic cancer, pancreatic cancer, colorectal cancer, cervical cancer, head and neck squamous cell carcinoma and cancer of the head and neck.

29. The method of any one of embodiments 26-28, wherein the condition is associated with a KRAS mutation.

30. The method of embodiment 29, wherein the KRAS mutation is a G12C mutation.

INCORPORATION BY REFERENCE

All references, articles, publications, patents, patent publications, and patent applications cited herein within the above text are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

What is claimed is:

1. A compound of formula (I):

(I)

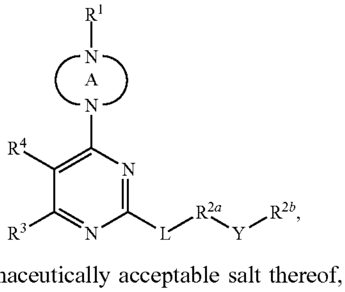

or a pharmaceutically acceptable salt thereof, wherein:

ring A is a 4-12 membered heterocyclic ring, optionally substituted with one or more substituents selected from the group consisting of halo, hydroxyl, cyano, oxo, $C_{1-4}$-alkyl, $C_{2-4}$-alkynyl, $C_{1-4}$-heteroalkyl, $C_{3-8}$-cycloalkyl, -$C_{0-4}$-alkyl-C(O)N($R^{6d}$)$_2$, and —$C_{0-4}$-alkyl-C(O)O$R^{6d}$;

and/or wherein two substituents on the same atom of ring A may form a 3- to 5-membered ring together with the carbon atom on which they are attached;

and/or wherein two substituents on adjacent atoms of ring A may form a 3- to 6-membered ring together with the carbon atoms on which they are attached;

wherein the $C_{1-4}$-alkyl, $C_{2-4}$-alkynyl, $C_{1-4}$-heteroalkyl or $C_{3-8}$-cycloalkyl may be optionally substituted with one or more substituents selected from the group consisting of halo, hydroxy, —O$R^{6d}$, cyano, and oxo;

$R^1$ is selected from the group consisting of

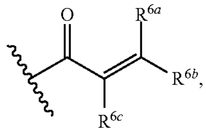
,
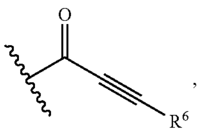
,

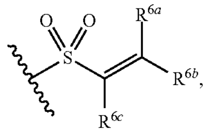
and
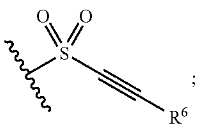
;

L is selected from the group consisting of a direct bond, -N($R^{6d}$)-, -C(O)N($R^{6d}$)—, —S($O_2$)N($R^{6d}$)-, and —O—;

$R^{2a}$ is a direct bond, $C_{1-4}$-alkylene, $C_{1-4}$-heteroalkylene, $C_{3-8}$-cycloalkylene, 3- to 8-membered heterocycloalkylene, 6- to 10-membered aryl, or 5- to 10-membered heteroaryl, wherein the $C_{1-4}$-alkylene, $C_{1-4}$-heteroalkylene, $C_{3-8}$-cycloalkylene, 3- to 8-membered heterocycloalkylene, 6- to 10-membered aryl, or 5- to 10-membered heteroaryl each is optionally substituted with one or more substituents selected from the group consisting of halo, hydroxyl, carboxyl, -O$R^{6d}$, oxo, cyano, $C_{3-8}$-cycloalkyl, $C_{1-4}$-alkyl, $C_{1-4}$-heteroalkyl, and 3- to 8-membered heterocycloalkyl;

Y is selected from the group consisting of a direct bond, unsubstituted or substituted $C_{1-4}$-alkyl, unsubstituted or substituted $C_{1-4}$-alkylene, unsubstituted or substituted $C_{1-4}$-heteroalkyl, —N($R^{6d}$)—, —N$R^{6d}$C(O)—, —C(O)N$R^{6d}$—, —N$R^{6d}$C(O)N$R^{6d}$—, -S($O_2$)N$R^{6d}$—, and —N$R^{6d}$S(O)$_2$—;

$R^{2b}$ is H, $C_{1-4}$-alkyl, $C_{1-4}$-heteroalkyl, $C_{3-8}$-cycloalkyl, 3- to 8-membered heterocycloalkyl, 6- to 10-membered aryl, or 5- to 10-membered heteroaryl, wherein the $C_{1-4}$-alkyl, $C_{1-4}$-heteroalkyl, $C_{3-8}$-cycloalkyl, 3- to 8-membered heterocycloalkyl, 6- to 10-membered aryl, or 5-to 10-membered heteroaryl is each optionally substituted with one or more substituents selected from the group consisting of halo, hydroxyl, carboxyl, —O$R^{6d}$, oxo, cyano, -N($R^{6d}$)$_2$, $C_{3-8}$-cycloalkyl, $C_{1-4}$-alkyl, $C_{1-4}$-heteroalkyl, and 3- to 8-membered heterocycloalkyl;

$R^3$ is

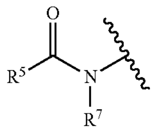
or
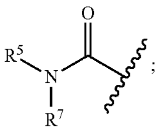
;

$R^4$ is H, $C_{1-6}$-alkyl, $C_{1-6}$-heteroalkyl, $C_{1-6}$-haloalkyl, $C_{3-8}$-cycloalkyl, 3- to 8-membered heterocycloalkyl, —O$C_{1-6}$-haloalkyl, —NH($C_{1-6}$-alkyl), or —N($C_{1-6}$-alkyl)$_2$, wherein the $C_{1-6}$-alkyl, $C_{1-6}$-heteroalkyl, $C_{1-6}$-haloalkyl, $C_{3-8}$-cycloalkyl, 3- to 8-membered heterocycloalkyl, or —O$C_{1-6}$-haloalkyl is each optionally substituted with one or more substituents selected from the group consisting of $C_{1-4}$-alkyl, $C_{1-4}$-heteroalkyl, halo, cyano, hydroxyl, ether, —N($R^{6d}$)$_2$, and $C_{3-8}$-cycloalkyl, 3- to 8-membered heterocycloalkyl, $R^5$ is H, $C_{1-6}$-alkyl, $C_{1-6}$-heteroalkyl, $C_{3-8}$-cycloalkyl, 3- to 8-membered heterocycloalkyl, 6- to 10-membered aryl, or 5- to 10-membered heteroaryl, wherein the $C_{1-6}$-alkyl, $C_{1-6}$-heteroalkyl, $C_{3-8}$-cycloalkyl, 3- to 8-membered heterocycloalkyl, 6- to 10-membered aryl, or 5- to 10-membered heteroaryl is each optionally substituted with one or more substituents selected from the group consisting of halo, hydroxyl, carboxyl, cyano, —O$R^{6d}$, —N($R^{6d}$)$_2$, $C_{3-8}$-cycloalkyl, $C_{1-4}$-alkyl, $C_{1-4}$-heteroalkyl, 3- to 8-membered heterocycloalkyl, 6-membered aryl, and 5- to 6-membered heteroaryl, or an $R^5$ and $R^7$ taken together with the atom to which they are attached form a 5- or 6-membered monocyclic ring system or a bicyclic system, wherein the bicyclic system is a 9- or 10-membered heterocyclic ring system;

$R^6$, $R^{6a}$ and $R^{6b}$ are each independently H, halo, cyano, $C_{1-6}$-alkyl, $C_{1-6}$-heteroalkyl, $C_{3-8}$-cycloalkyl, 3- to 8-membered heterocycloalkyl, $C_{3-8}$-aryl, or $C_{3-8}$-heteroaryl, wherein the $C_{1-6}$-alkyl, $C_{1-6}$-heteroalkyl, $C_{3-8}$-cycloalkyl, 3- to 8-membered heterocycloalkyl, $C_{3-8}$-aryl, or $C_{3-8}$-heteroaryl each is optionally substituted with one or more substituents selected from halo, hydroxy, cyano, —N($R^{6d}$)$_2$, —O$R^{6d}$, $C_{1-4}$-alkyl, 3- to 8-membered heterocycloalkyl, and $C_{1-4}$-heteroalkyl;

$R^{6c}$ is H, halo, cyano, $C_{1-6}$-alkyl, $C_{1-6}$-heteroalkyl, $C_{3-8}$-cycloalkyl, or 3- to 8-membered heterocycloalkyl, wherein the $C_{1-6}$-alkyl, $C_{1-6}$-heteroalkyl, $C_{3-8}$-cycloalkyl, or 3- to 8-membered heterocycloalkyl is each optionally substituted with one or more substituents selected from halo, cyano, —O$R^{6d}$, hydroxy, and $C_{1-4}$-heteroalkyl;

$R^{6d}$ is independently at each occurrence selected from the group consisting of H, cyano, $C_{1-6}$-alkyl, $C_{1-6}$-heteroalkyl, $C_{3-8}$-cycloalkyl, and 3- to 8-membered heterocycloalkyl; and $R^7$ is H, $C_{1-6}$-alkyl, $C_{1-6}$-heteroalkyl, or $C_{3-8}$-cycloalkyl, wherein the $C_{1-6}$-alkyl, $C_{1-6}$-heteroalkyl, or $C_{3-8}$-cycloalkyl is each optionally substituted with one or more substituents selected from the group consisting of halo, cyano, hydroxyl, carboxyl, —O$R^{6d}$, —N($R^{6d}$)$_2$, $C_{3-8}$-cycloalkyl, $C_{1-4}$-alkyl, $C_{1-4}$-heteroalkyl, and 3- to 8-membered heterocycloalkyl.

2. The compound of claim 1, wherein ring A is a 6- or 7-membered heterocyclic ring, optionally substituted with one or more substituents selected from the group consisting of halo, hydroxyl, $C_{1-4}$-alkyl, and $C_{1-4}$-heteroalkyl, wherein the $C_{1-4}$-alkyl and $C_{1-4}$-heteroalkyl are optionally substituted with one or more substituents selected from the group consisting of halo, hydroxy, and cyano.

3. The compound of claim 1, wherein ring A is selected from the group consisting of:

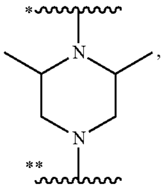, 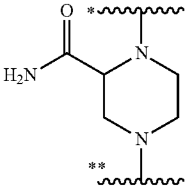, 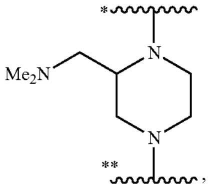, 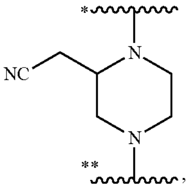, 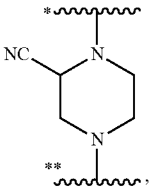, 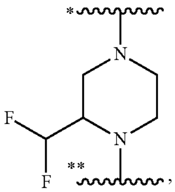, 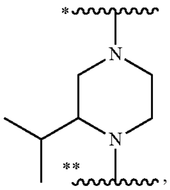, 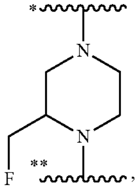, 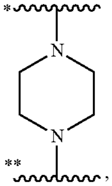, 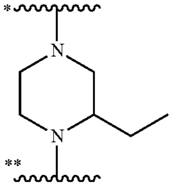, 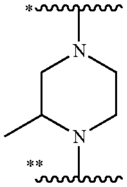, 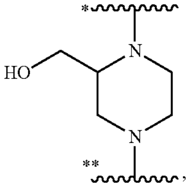, 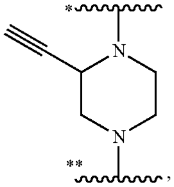, 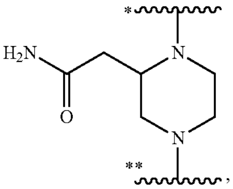, 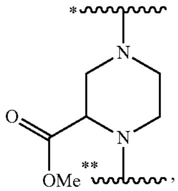, 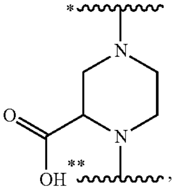, 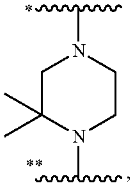, 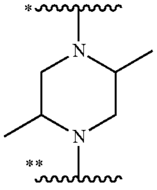, 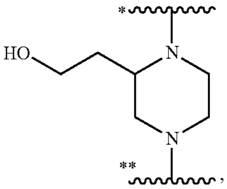, 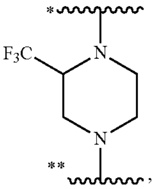, -continued

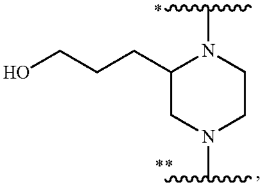, 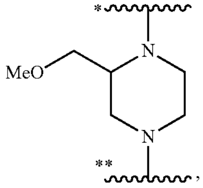, 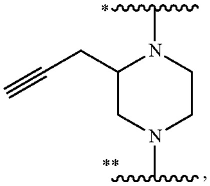, 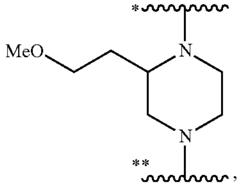, 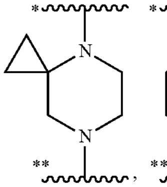, 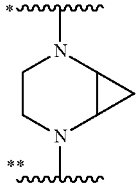, 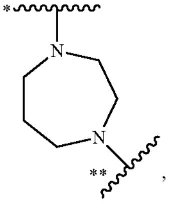, and 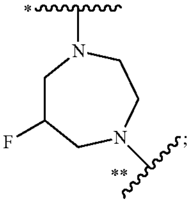;

wherein the * indicates a bond between the nitrogen atom of ring A containing the* and $R^1$; and the  indicates a bond between the nitrogen atom of ring A containing the  and the pyrimidyl group of formula (I);

or wherein the * indicates a bond between the nitrogen atom of ring A containing the* and the pyrimidyl group of formula (I); and the ** indicates a bond between the nitrogen atom of ring A containing the * and $R^1$.

4. The compound of claim 3, wherein ring A is

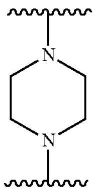 or 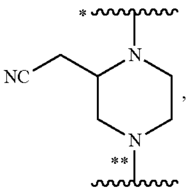, wherein the * indicates a bond between the nitrogen atom of ring A containing the * and $R^1$; and the  indicates a bond between the nitrogen atom of ring A containing the  and the pyrimidyl group of formula (I).

5. The compound of claim 3, wherein $R^1$ is

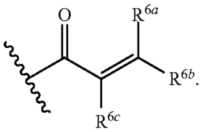

6. The compound of claim 5, wherein $R^1$ is

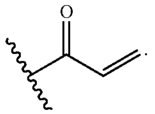 [SMILES: *C(=O)C=C]

7. The compound of claim 5, wherein L is selected from the group consisting of a direct bond, —N($R^{6d}$)—, and —O—.

8. The compound of claim 7, wherein L is —N($R^{6d}$)— or —O—.

9. The compound of claim 8, wherein Rod is H or $C_{1-6}$ alkyl.

10. The compound of claim 9, wherein $R^{2a}$ is selected from the group consisting of $C_{1-6}$ alkyl, 3- to 8-membered heterocycloalkyl and 5- to 6-membered heteroaryl.

11. The compound of claim 10, wherein Y is selected from the group consisting of a direct bond, —N($R^{6d}$)—, and —O—.

12. The compound of claim 11, wherein $R^{2b}$ is selected from the group consisting of H, $C_{1-4}$-alkyl, $C_{1-4}$-heteroalkyl, 5- to 6-membered heterocycloalkyl and 5-to 6-membered heteroaryl.

13. The compound of claim 12, wherein -L-$R^{2a}$-Y-$R^{2b}$ is selected from the group consisting of:

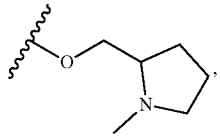,
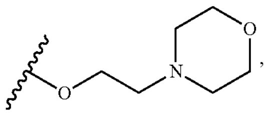,
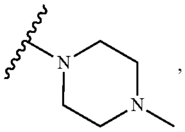,
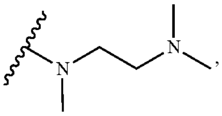,
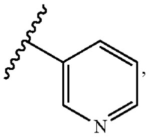,
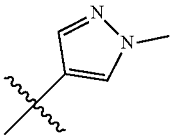, and
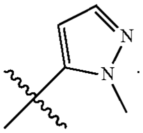.

14. The compound of claim 12, wherein $R^3$ is

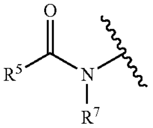 or 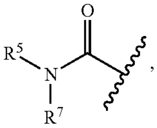, wherein $R^5$ is 6- to 10-membered aryl or 5- to 10-membered heteroaryl, and $R^7$ is H or $C_{1-6}$ alkyl.

15. The compound of claim 14, wherein $R^3$ is selected from the group consisting of:

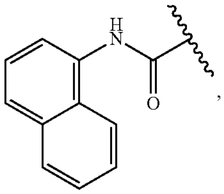,
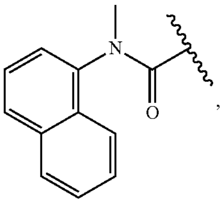,
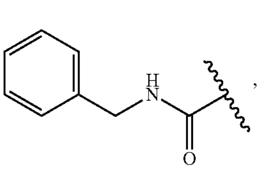,
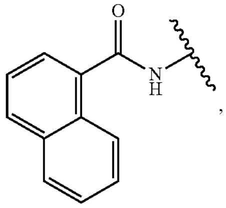,
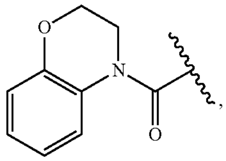,
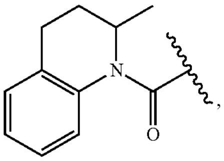,
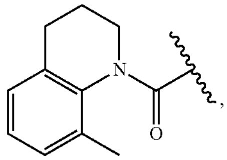,
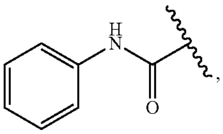,
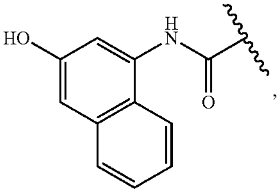,
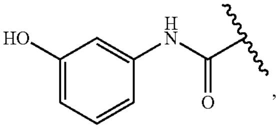,
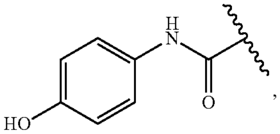,
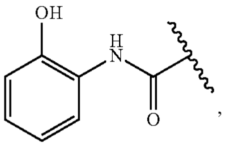,
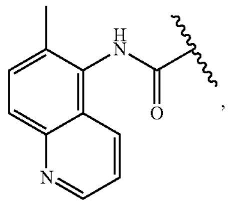, and
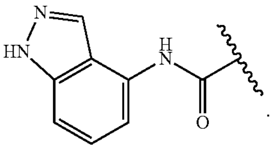.

16. The compound of claim 1, wherein $R^4$ is H, halo, $C_{1-6}$-alkyl, $C_{1-3}$ haloalkyl, —$OC_{1-6}$ alkyl, —$OCC_{1-3}$ haloalkyl, —$CH_2$—$OC_{1-6}$ alkyl, —NH($C_{1-6}$-alkyl) or —N($C_{1-6}$-alkyl)$_2$.

17. The compound of claim 16, wherein $R^4$ is H.

18. The compound of claim 1, wherein the compound of formula (I) is selected from the group consisting of:
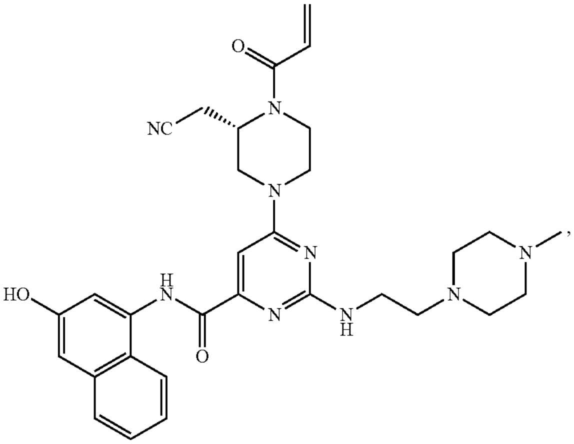
,
-continued
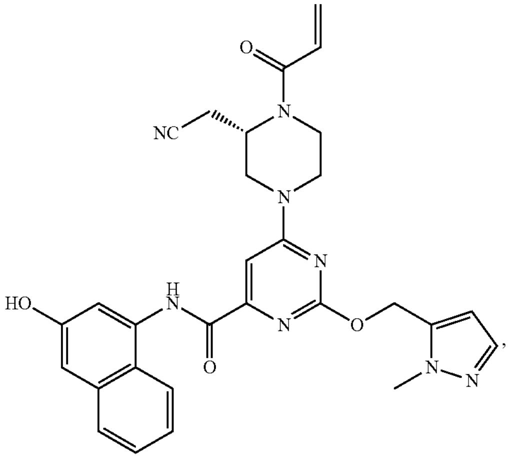
,
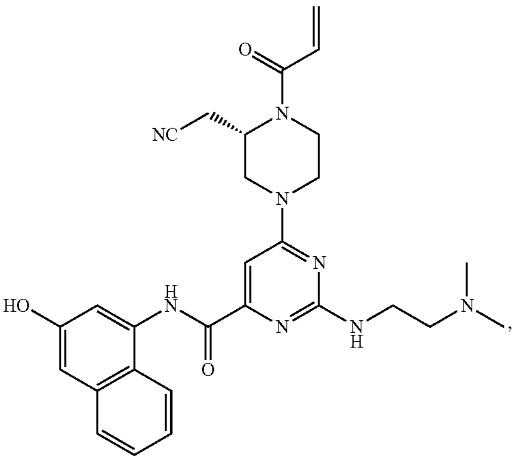
,
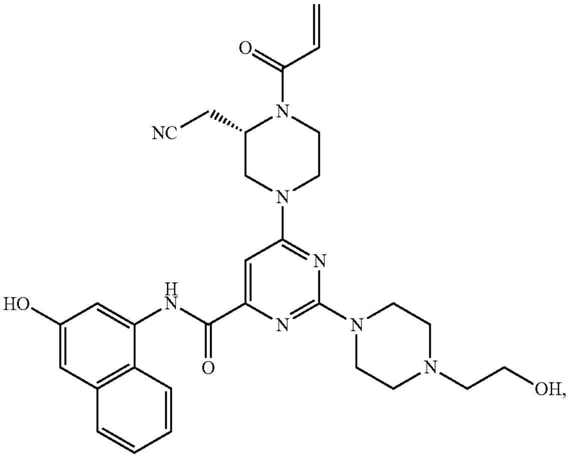
,
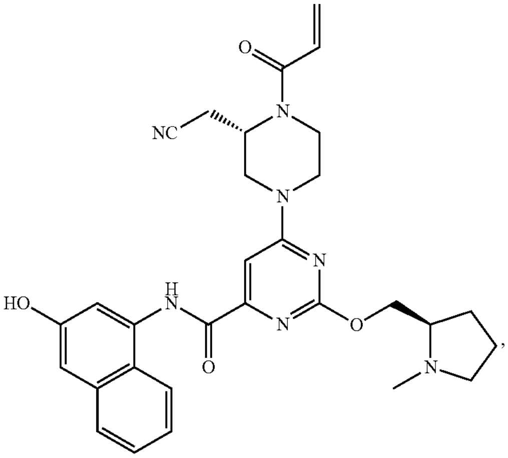
,
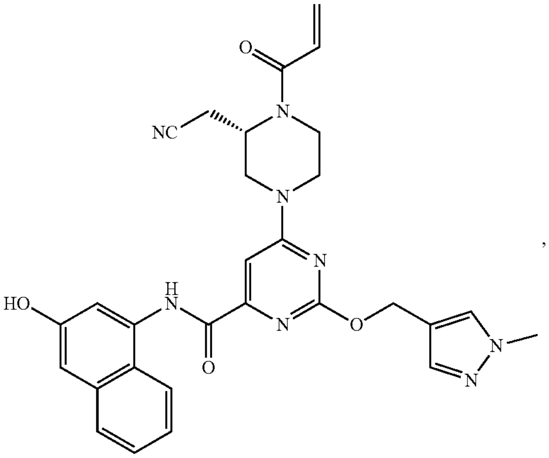
, -continued
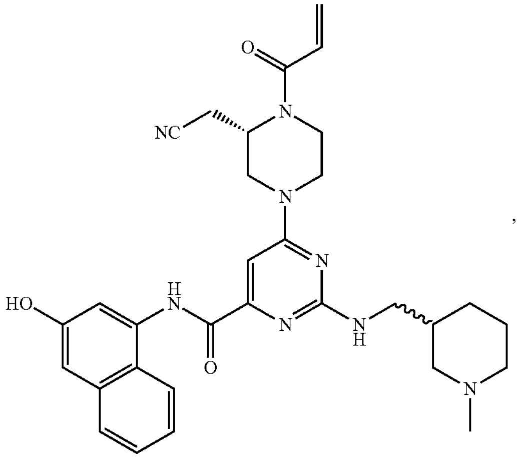
,
-continued
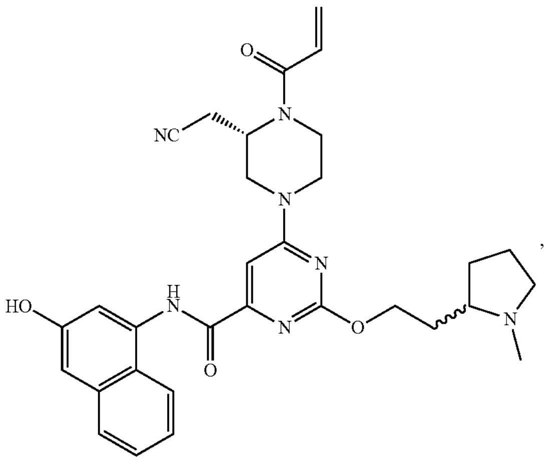
,
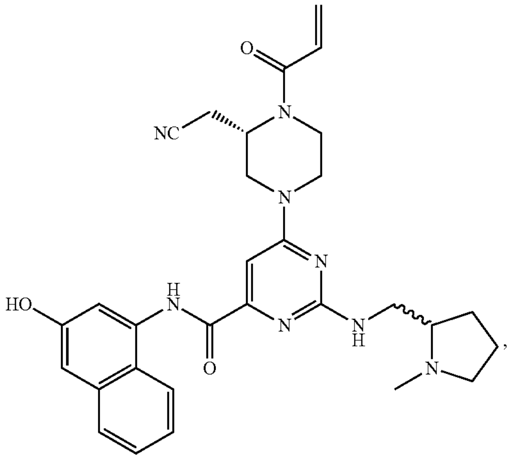
,
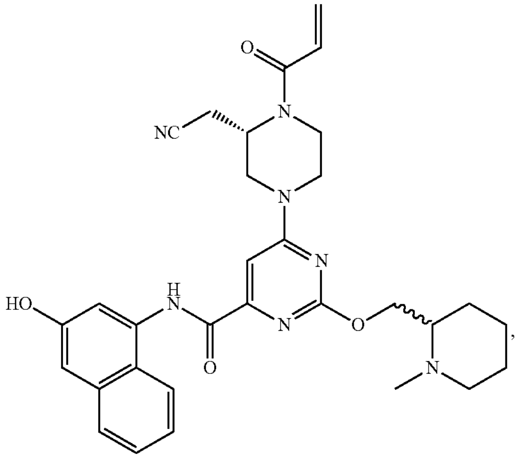
,
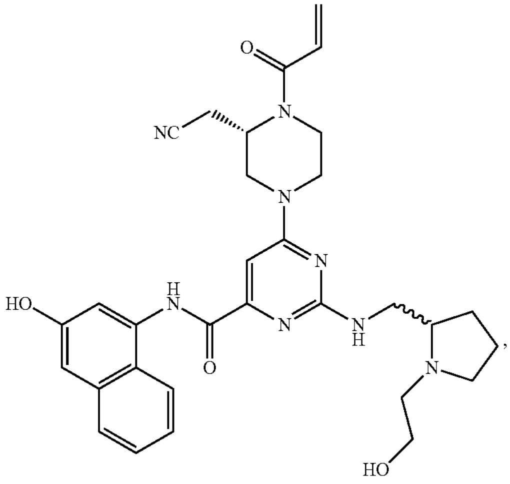
,
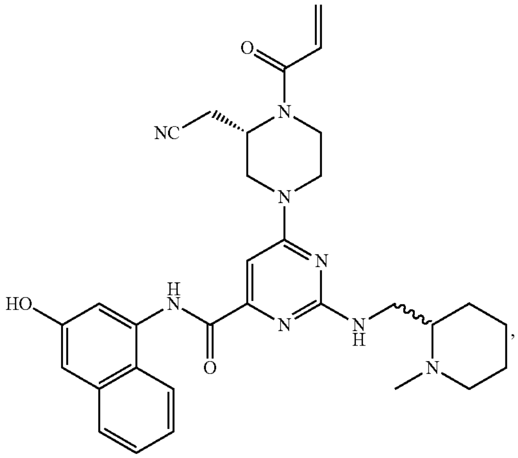
, -continued
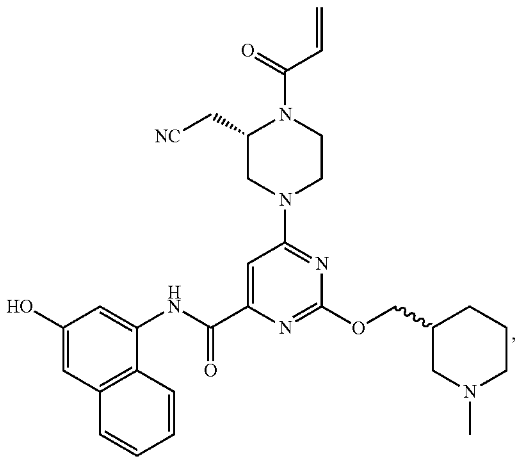
,
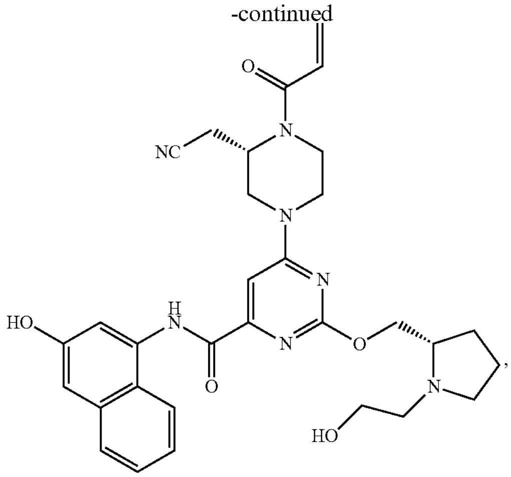
, and
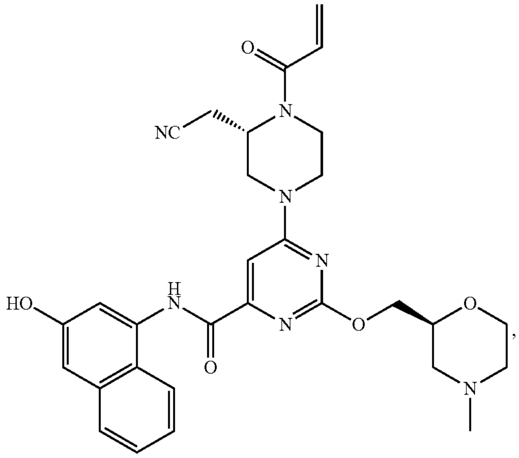
,
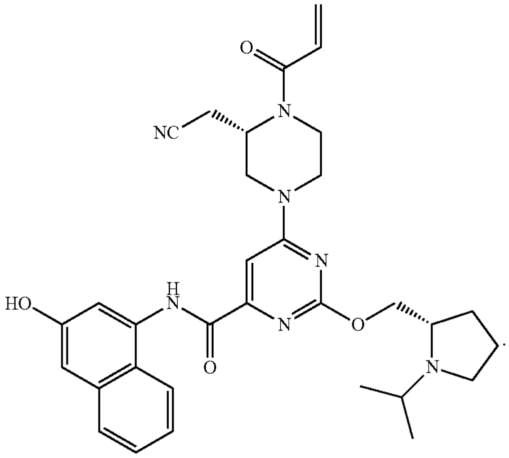 [SMILES: C=CC(=O)N1CCN(c2cc(C(=O)Nc3cc(O)cc4ccccc34)nc(OC[C@@H]3CCCN3C(C)C)n2)C[C@@H]1CC#N]
.
* * * * *